United States Patent
Deisseroth et al.

(10) Patent No.: US 10,052,383 B2
(45) Date of Patent: Aug. 21, 2018

(54) ENGINEERED LIGHT-ACTIVATED ANION CHANNEL PROTEINS AND METHODS OF USE THEREOF

(71) Applicant: The Board of Trustees of the Leland Stanford Junior University, Stanford, CA (US)

(72) Inventors: Karl A. Deisseroth, Stanford, CA (US); Soo Yeun Lee, Stanford, CA (US); Charu Ramakrishnan, San Jose, CA (US); Andre Berndt, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/126,859

(22) PCT Filed: Mar. 27, 2015

(86) PCT No.: PCT/US2015/023087
§ 371 (c)(1),
(2) Date: Sep. 16, 2016

(87) PCT Pub. No.: WO2015/148974
PCT Pub. Date: Oct. 1, 2015

(65) Prior Publication Data
US 2017/0095556 A1   Apr. 6, 2017

Related U.S. Application Data

(60) Provisional application No. 61/972,182, filed on Mar. 28, 2014.

(51) Int. Cl.
C07K 14/705 (2006.01)
C07K 19/00 (2006.01)
A61K 41/00 (2006.01)
C07K 14/47 (2006.01)
A61K 38/00 (2006.01)

(52) U.S. Cl.
CPC .......... *A61K 41/0042* (2013.01); *C07K 14/47* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 8,398,692 B2 | 3/2013 | Deisseroth et al. | |
| 8,401,609 B2 | 3/2013 | Deisseroth et al. | |
| 8,603,790 B2 | 12/2013 | Deisseroth et al. | |
| 8,696,722 B2 | 4/2014 | Deisseroth et al. | |
| 8,716,447 B2 | 5/2014 | Deisseroth et al. | |
| 8,729,040 B2 | 5/2014 | Deisseroth et al. | |
| 8,815,582 B2 | 8/2014 | Deisseroth et al. | |
| 8,834,546 B2 | 9/2014 | Deisseroth et al. | |
| 8,864,805 B2 | 10/2014 | Deisseroth et al. | |
| 8,906,360 B2 | 12/2014 | Deisseroth et al. | |
| 8,926,959 B2 | 1/2015 | Deisseroth et al. | |
| 8,932,562 B2 | 1/2015 | Deisseroth et al. | |
| 8,956,363 B2 | 2/2015 | Deisseroth et al. | |
| 8,962,589 B2 | 2/2015 | Deisseroth et al. | |
| 9,079,940 B2 | 7/2015 | Deisseroth et al. | |
| 9,084,885 B2 | 7/2015 | Deisseroth et al. | |
| 9,101,690 B2 | 8/2015 | Deisseroth et al. | |
| 9,101,759 B2 | 8/2015 | Deisseroth et al. | |
| 9,175,095 B2 | 11/2015 | Deisseroth et al. | |
| 9,187,745 B2 | 11/2015 | Deisseroth et al. | |
| 9,238,150 B2 | 1/2016 | Deisseroth et al. | |
| 9,249,200 B2 | 2/2016 | Deisseroth et al. | |
| 9,249,234 B2 | 2/2016 | Deisseroth et al. | |
| 9,271,674 B2 | 3/2016 | Deisseroth et al. | |
| 9,274,099 B2 | 3/2016 | Deisseroth et al. | |
| 9,278,159 B2 | 3/2016 | Deisseroth et al. | |
| 9,284,353 B2 | 3/2016 | Deisseroth et al. | |
| 9,308,392 B2 | 4/2016 | Deisseroth et al. | |
| 9,309,296 B2 | 4/2016 | Deisseroth et al. | |
| 9,340,589 B2 | 5/2016 | Deisseroth et al. | |
| 9,359,449 B2 | 6/2016 | Deisseroth et al. | |
| 9,360,472 B2 | 6/2016 | Deisseroth et al. | |
| 9,365,628 B2 | 6/2016 | Deisseroth et al. | |

(Continued)

FOREIGN PATENT DOCUMENTS

WO   WO 2009/119782   10/2009

OTHER PUBLICATIONS

Co-pending U.S. Appl. No. 15/008,214, filed Jan. 27, 2016.
Co-pending U.S. Appl. No. 15/059,159, filed Mar. 2, 2016.
Co-pending U.S. Appl. No. 15/095,519, filed Apr. 11, 2016.
Co-pending U.S. Appl. No. 15/147,772, filed May 5, 2016.
Co-pending U.S. Appl. No. 15/153,299, filed May 12, 2016.
Co-pending U.S. Appl. No. 15/153,305, filed May 12, 2016.
Co-pending U.S. Appl. No. 15/156,124, filed May 16, 2016.
Co-pending U.S. Appl. No. 15/194,379, filed Jun. 27, 2016.

(Continued)

*Primary Examiner* — John D Ulm
(74) *Attorney, Agent, or Firm* — Bozicevic, Field & Francis LLP; Paula A. Borden

(57) ABSTRACT

Aspects of the disclosure include compositions, devices, systems and methods for optogenetic modulation of action potentials in target cells. The subject devices include light-generating devices, control devices, and delivery devices for delivering light-responsive polypeptides, or nucleic acids encoding same, to target cells. The subject compositions and systems include light-activated polypeptides, nucleic acids comprising nucleotide sequences encoding these polypeptides, as well as expression systems that facilitate expression of these polypeptides in target cells. Also provided are methods of using the subject devices and systems to optogenetically manipulate action potentials in target cells, e.g., to treat a neurological or psychiatric condition in a human or animal subject.

27 Claims, 62 Drawing Sheets

(56) References Cited

U.S. PATENT DOCUMENTS

| | | |
|---|---|---|
| 9,394,347 B2 | 7/2016 | Deisseroth et al. |
| 2009/0112133 A1 | 4/2009 | Deisseroth et al. |
| 2009/0118800 A1 | 5/2009 | Deisseroth et al. |
| 2010/0190229 A1 | 7/2010 | Deisseroth et al. |
| 2010/0234273 A1 | 9/2010 | Deisseroth et al. |
| 2011/0159562 A1 | 6/2011 | Deisseroth et al. |
| 2011/0301529 A1 | 12/2011 | Deisseroth et al. |
| 2013/0284920 A1 | 10/2013 | Deisseroth et al. |
| 2013/0289669 A1 | 10/2013 | Deisseroth et al. |
| 2013/0317569 A1 | 11/2013 | Deisseroth et al. |
| 2013/0317575 A1 | 11/2013 | Deisseroth et al. |
| 2013/0330816 A1 | 12/2013 | Deisseroth et al. |
| 2013/0343998 A1 | 12/2013 | Deisseroth et al. |
| 2013/0347137 A1 | 12/2013 | Deisseroth et al. |
| 2014/0082758 A1 | 3/2014 | Deisseroth et al. |
| 2014/0148880 A1 | 5/2014 | Deisseroth et al. |
| 2014/0235826 A1 | 8/2014 | Deisseroth et al. |
| 2014/0271479 A1 | 9/2014 | Lammel et al. |
| 2014/0324133 A1 | 10/2014 | Deisseroth et al. |
| 2015/0040249 A1 | 2/2015 | Deisseroth et al. |
| 2015/0165227 A1 | 6/2015 | Deisseroth et al. |
| 2015/0174244 A1 | 6/2015 | Deisseroth et al. |
| 2015/0192567 A1 | 7/2015 | Chuong et al. |
| 2015/0217128 A1 | 8/2015 | Deisseroth et al. |
| 2015/0218547 A1 | 8/2015 | Deisseroth et al. |
| 2016/0015996 A1 | 1/2016 | Deisseroth et al. |
| 2016/0038761 A1 | 2/2016 | Deisseroth et al. |
| 2016/0038764 A1 | 2/2016 | Deisseroth et al. |
| 2016/0045599 A1 | 2/2016 | Deisseroth et al. |
| 2016/0096035 A1 | 4/2016 | Lundmark et al. |
| 2016/0096036 A1 | 4/2016 | Deisseroth et al. |
| 2016/0175607 A1 | 6/2016 | Deisseroth et al. |
| 2016/0194624 A1 | 7/2016 | Deisseroth et al. |
| 2016/0199663 A1 | 7/2016 | Deisseroth et al. |
| 2016/0222073 A1 | 8/2016 | Deisseroth et al. |
| 2016/0237126 A1 | 8/2016 | Deisseroth et al. |
| 2016/0287895 A1 | 10/2016 | Deisseroth et al. |
| 2016/0316730 A1 | 11/2016 | Deisseroth et al. |

OTHER PUBLICATIONS

Co-pending U.S. Appl. No. 15/214,399, filed Jul. 19, 2016.
Co-pending U.S. Appl. No. 15/214,400, filed Jul. 19, 2016.
Co-pending U.S. Appl. No. 15/214,402, filed Jul. 19, 2016.
Co-pending U.S. Appl. No. 15/214,403, filed Jul. 19, 2016.
Co-pending U.S. Appl. No. 15/229,064, filed Aug. 4, 2016.
Berndt, et al.; "Structure-Guided Transformation of Channelrhodopsin into a Light-Activated Chloride Channel"; Science; vol. 344, No. 6182, pp. 420-424 (Apr. 25, 2014).
Wietek, et al.; "Conversion of channelrhodopsin into a light-gated chloride channel"; Science; vol. 344, No. 6182, pp. 409-412 (Apr. 25, 2014).
Zorzos, et al.; "Multiwaveguide implantable probe for light delivery to sets of distributed brain targets"; Optics Letters; vol. 35, No. 24, pp. 4133-4135 (Dec. 15, 2010).

FIG. 3D
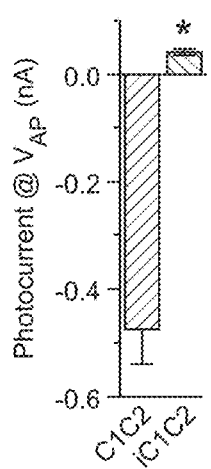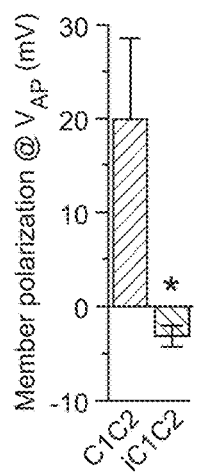
FIG. 3E
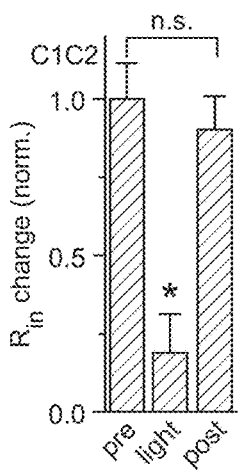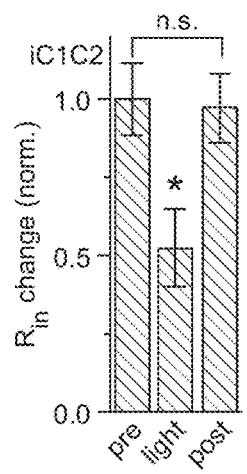
FIG. 3F
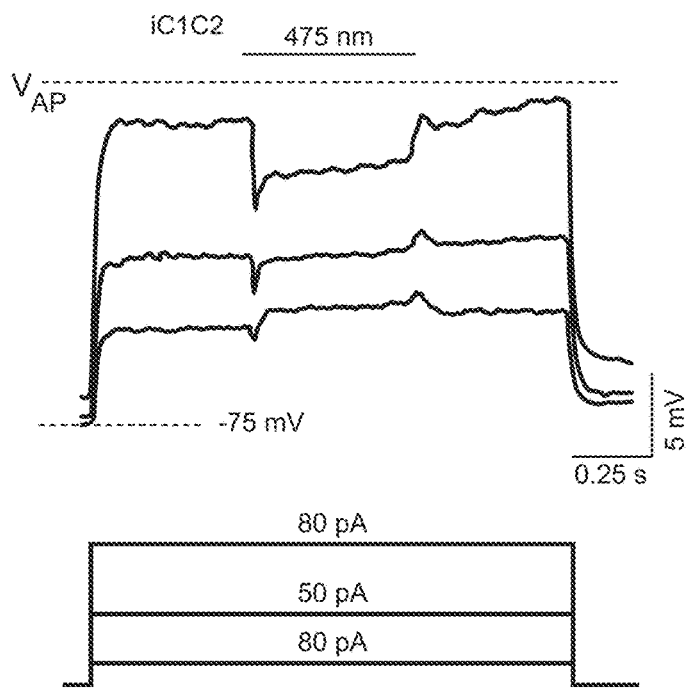

FIG. 4F
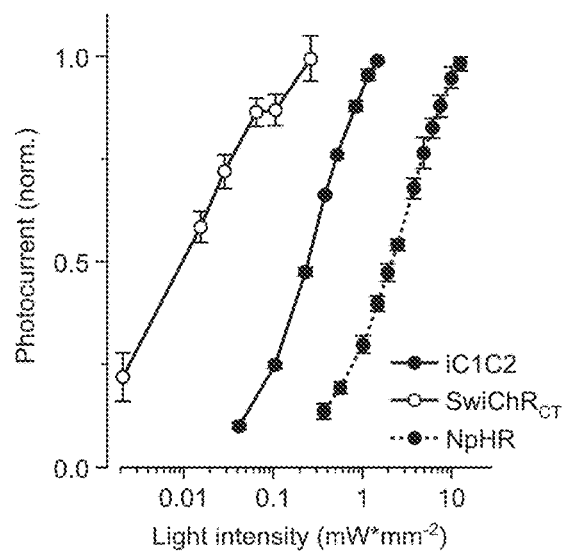
FIG. 4G
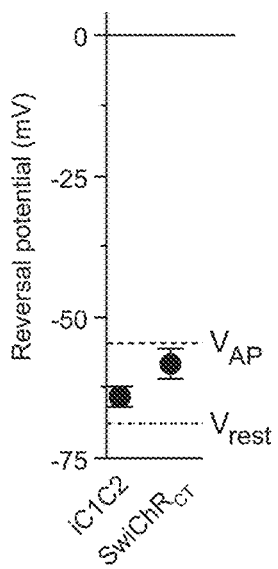
FIG. 4H
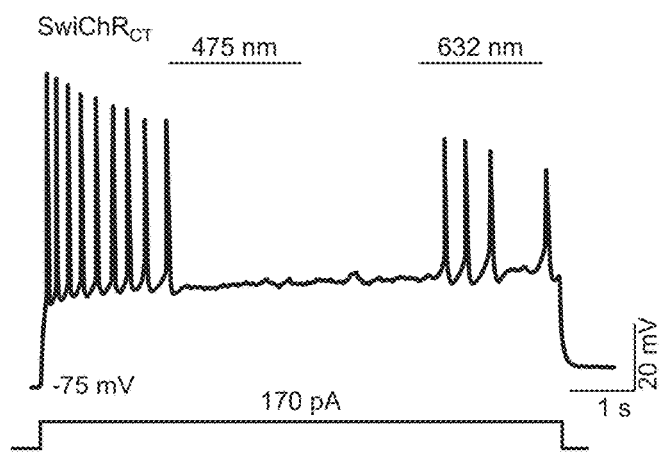
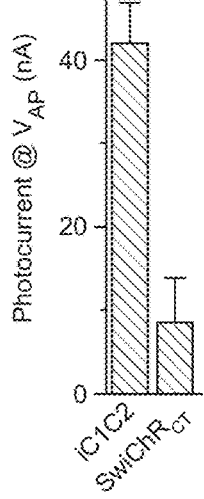

FIG. 5

```
C1C2    1   MSRRPWLLALALAVALAAGSAGASTGSDATVPVATQDGPDYVFHRAHERMLFQTSYTLENNGSVICIPNN
iC1C2   1   MSRRPWLLALALAVALAAGSAGASTGSDATVPVATQDGPDYVFHRAHERMLFQTSYTLENNGSVICIPNN
ChR2    1   ------MDYGGALSAVG----------------------------------RELLFVTNPVVVN-GSVLVPED-
                                                                              TM1

C1C2   71   GQCFCLAWLKSNGTNAEKLAANILQWITFALSALCLMFYGYQTWKSTCGWEEIYVATIEMIKFIIEYFHE
iC1C2  71   GQCFCLAWLKSNGTNAEKLAANILQWISFALSALCLMFYGYQTWKSTCGWEEIYVATISMIKFIIEYFHS
ChR2   33   -QCYCAGWIESRGTNGAQTASNVLQWLAAGFSILLLMFYAYQTWKSTCGWEEIYVCAIEMVKVILEFFFE
                           TM2                                              TM3

C1C2  141   FDEPAVIYSSNGNKTVWLRYAEWLLTCPVILIHLSNLTGLANDYNKRTMGLLVSDIGTIVWGTTAALSKG
iC1C2 141   FDEPAVIYSSNGNKTKWLRYASWLLTCPVILIRLSNLTGLANDYNKRTMGLLVSDIGTIVWGTTAALSKG
ChR2  102   FKNPSMLYLATGHRVQWLRYAEWLLTCPVILIHLSNLTGLSNDYSRRTMGLLVSDIGTIVWGATSAMATG
                                   TM4                           TM5

C1C2  211   YVRVIFFLMGLCYGIYTFFNAAKVYIEAYHTVPKGRCRQVVTGMAWLFFVSWGMFPILFILGPEGFGVLS
iC1C2 211   YVRVIFFLMGLCYGIYTFFNAAKVYIEAYHTVPKGRCRQVVTGMAWLFFVSWGMFPILFILGPEGFGVLS
ChR2  172   YVKVIFFCLGLCYGANTFFHAAKAYIEGYHTVPKGRCRQVVTGMAWLFFVSWGMFPILFILGPEGFGVLS
                                             TM6                      TM7

C1C2  281   VMGSTVGHTIIDLMSKNCWGLLGHYLRVLIHEHILIHGDIRKTTKLNIGGTEIEVETLVEDEAEAGAV
iC1C2 281   KMGSNVGHTIIDLMSKQCWGLLGHYLRVLIHEHILIHGDIRKTTKLNIGGTEIEVETLVEDEAEAGAV
ChR2  242   VYGSTVGHTIIDLMSKQCWGLLGHYLRVLIHEHILIHGDIRKTTKLNIGGTEIEVETLVEDEAEAGAV
```

FIG. 12A iC1C2 (SEQ ID NO: 1)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTCPVILIRLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV iC1C2-D195N (SEQ ID NO: 2)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTCPVILIRLSNLTGLANDYNKRTMGLLVSNIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV ibC1C2 (SEQ ID NO: 3)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTCPVILIRLSNLTG
LANDYNKRTMGLLVSDIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAV ibC1C2-D156N (SEQ ID NO: 4)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTCPVILIRLSNLTG
LANDYNKRTMGLLVSNIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAV iC1C2-C167T (SEQ ID NO: 5)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTTPVILIRLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV

FIG. 12B iC1C2-C167A (SEQ ID NO: 6)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTAPVILIRLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV iC1C2-C167S (SEQ ID NO: 7)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTSPVILIRLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV iC1C2-C167T-D195A (SEQ ID NO: 8)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTTPVILIRLSNLTGLANDYNKRTMGLLVSAIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV iC1C2-C167T-D195N (SEQ ID NO: 9)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTTPVILIRLSNLTGLANDYNKRTMGLLVSNIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV iC1C2-C167A-D195A (SEQ ID NO: 10)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTAPVILIRLSNLTGLANDYNKRTMGLLVSAIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV

FIG. 12C iC1C2-C167A-D195N (SEQ ID NO: 11)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTAPVILIRLSNLTGLANDYNKRTMGLLVSNIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV iC1C2-C167S-D195A (SEQ ID NO: 12)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTSPVILIRLSNLTGLANDYNKRTMGLLVSAIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV iC1C2-C167S-D195N (SEQ ID NO: 13)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTSPVILIRLSNLTGLANDYNKRTMGLLVSNIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV ibC1C2-C128T (SEQ ID NO: 14)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTTPVILIRLSNLTG
LANDYNKRTMGLLVSDIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAV ibC1C2-C128A (SEQ ID NO: 15)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTAPVILIRLSNLTG
LANDYNKRTMGLLVSDIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAV

FIG. 12D ibC1C2-C128S (SEQ ID NO: 16)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTTPVILIRLSNLTG
LANDYNKRTMGLLVSDIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAV ibC1C2-C128T-D156A (SEQ ID NO: 17)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTTPVILIRLSNLTG
LANDYNKRTMGLLVSAIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAV ibC1C2-C128T-D156N (SEQ ID NO: 18)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTTPVILIRLSNLTG
LANDYNKRTMGLLVSNIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAV ibC1C2-C128A-D156A (SEQ ID NO: 19)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTAPVILIRLSNLTG
LANDYNKRTMGLLVSAIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAV ibC1C2-C128A-D156N (SEQ ID NO: 20)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTAPVILIRLSNLTG
LANDYNKRTMGLLVSNIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAV

FIG. 12E ibC1C2-C128S-D156A (SEQ ID NO: 21)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTSPVILIRLSNLTG
LANDYNKRTMGLLVSAIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAV ibC1C2-C128S-D156N (SEQ ID NO: 22)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTSPVILIRLSNLTG
LANDYNKRTMGLLVSNIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAV

FIG. 13A iChR2 (SEQ ID NO: 23)

MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTCPVILIRLSNLTG
LSNDYSRRTMGLLVSDIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP iChR2-D156N (SEQ ID NO: 24)

MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTCPVILIRLSNLTG
LSNDYSRRTMGLLVSNIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP iChR2-C128T (SEQ ID NO: 25)

MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTTPVILIRLSNLTG
LSNDYSRRTMGLLVSDIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP iChR2-C128A (SEQ ID NO: 26)

MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTAPVILIRLSNLTG
LSNDYSRRTMGLLVSDIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP iChR2-C128S (SEQ ID NO: 27)

MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTSPVILIRLSNLTG
LSNDYSRRTMGLLVSDIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP

FIG. 13B iChR2-C128T-D156A (SEQ ID NO: 28)

MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTTPVILIRLSNLTG
LSNDYSRRTMGLLVSAIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP iChR2-C128T-D156N (SEQ ID NO: 29)

MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTTPVILIRLSNLTG
LSNDYSRRTMGLLVSNIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP iChR2-C128A-D156A (SEQ ID NO: 30)

MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTAPVILIRLSNLTG
LSNDYSRRTMGLLVSAIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP iChR2-C128A-D156N (SEQ ID NO: 31)

MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTAPVILIRLSNLTG
LSNDYSRRTMGLLVSNIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP iChR2-C128S-D156A (SEQ ID NO: 32)

MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTSPVILIRLSNLTG
LSNDYSRRTMGLLVSAIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP

FIG. 13C iChR2-C128S-D156N (SEQ ID NO: 33)

MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTSPVILIRLSNLTG
LSNDYSRRTMGLLVSNIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP

FIG. 14A iC1V1 (SEQ ID NO: 34)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTCPVLLIRLSNLTGLKDDYSKRTMGLLVSDVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED iC1V1-D195N (SEQ ID NO: 35)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTCPVLLIRLSNLTGLKDDYSKRTMGLLVSNVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED ibC1V1 (SEQ ID NO: 36)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTCPVLLIRLSNLTG
LKDDYSKRTMGLLVSDVGCIVWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEED ibC1V1-D156N (SEQ ID NO: 37)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTCPVLLIRLSNLTG
LKDDYSKRTMGLLVSNVGCIVWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEED iC1V1-C167T (SEQ ID NO: 38)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTTPVLLIRLSNLTGLKDDYSKRTMGLLVSDVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED

FIG. 14B iC1V1-C167A (SEQ ID NO: 39)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTAPVLLIRLSNLTGLKDDYSKRTMGLLVSDVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED iC1V1-C167S (SEQ ID NO: 40)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTSPVLLIRLSNLTGLKDDYSKRTMGLLVSDVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED iC1V1-C167T-D195A (SEQ ID NO: 41)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTTPVLLIRLSNLTGLKDDYSKRTMGLLVSAVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED iC1V1-C167T-D195N (SEQ ID NO: 42)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTTPVLLIRLSNLTGLKDDYSKRTMGLLVSNVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED iC1V1-C167A-D195A (SEQ ID NO: 43)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTAPVLLIRLSNLTGLKDDYSKRTMGLLVSAVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED

FIG. 14C iC1V1-C167A-D195N (SEQ ID NO: 44)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTAPVLLIRLSNLTGLKDDYSKRTMGLLVSNVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED iC1V1-C167S-D195A (SEQ ID NO: 45)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTSPVLLIRLSNLTGLKDDYSKRTMGLLVSAVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED iC1V1-C167S-D195N (SEQ ID NO: 46)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTSPVLLIRLSNLTGLKDDYSKRTMGLLVSNVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED ibC1V1-C128T (SEQ ID NO: 47)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTTPVLLIRLSNLTG
LKDDYSKRTMGLLVSDVGCIVWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEED ibC1V1-C128A (SEQ ID NO: 48)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTAPVLLIRLSNLTG
LKDDYSKRTMGLLVSDVGCIVWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEED

FIG. 14D ibC1V1-C128S (SEQ ID NO: 49)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTSPVLLIRLSNLTG
LKDDYSKRTMGLLVSDVGCIVWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEED ibC1V1-C128T-D156A (SEQ ID NO: 50)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTTPVLLIRLSNLTG
LKDDYSKRTMGLLVSAVGCIVWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEED ibC1V1-C128T-D156N (SEQ ID NO: 51)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTTPVLLIRLSNLTG
LKDDYSKRTMGLLVSNVGCIVWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEED ibC1V1-C128A-D156A (SEQ ID NO: 52)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTAPVLLIRLSNLTG
LKDDYSKRTMGLLVSAVGCIVWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEED ibC1V1-C128A-D156N (SEQ ID NO: 53)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTAPVLLIRLSNLTG
LKDDYSKRTMGLLVSNVGCIVWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEED

FIG. 14E

<u>ibC1V1-C128S-D156A</u> (SEQ ID NO: 54)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTSPVLLIRLSNLTG
LKDDYSKRTMGLLVSAVGCIWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEED

<u>ibC1V1-C128S-D156N</u> (SEQ ID NO: 55)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTSPVLLIRLSNLTG
LKDDYSKRTMGLLVSNVGCIWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEED

FIG. 15A iReaChR (SEQ ID NO: 56)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTCPVILIRLSNLTGLKDDYSKRTMGLLVSDVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS iReaChR-D196N (SEQ ID NO: 57)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTCPVILIRLSNLTGLKDDYSKRTMGLLVSNVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS ibReaChR (SEQ ID NO: 58)

MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTCPVILIRLSNLTG
LKDDYSKRTMGLLVSDVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
IRKKQKITIAGQEMEVETLVAEEEDKYESS ibReaChR-D156N (SEQ ID NO: 59)

MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTCPVILIRLSNLTG
LKDDYSKRTMGLLVSNVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
IRKKQKITIAGQEMEVETLVAEEEDKYESS iReaChR-C168T (SEQ ID NO: 60)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTTPVILIRLSNLTGLKDDYSKRTMGLLVSDVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS

FIG. 15B iReaChR-C168A (SEQ ID NO: 61)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTAPVILIRLSNLTGLKDDYSKRTMGLLVSDVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS iReaChR-C168S (SEQ ID NO: 62)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTSPVILIRLSNLTGLKDDYSKRTMGLLVSDVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS iReaChR-C168T-D196A (SEQ ID NO: 63)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTTPVILIRLSNLTGLKDDYSKRTMGLLVSAVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS iReaChR-C168T-D196N (SEQ ID NO: 64)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTTPVILIRLSNLTGLKDDYSKRTMGLLVSNVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS iReaChR-C168A-D196A (SEQ ID NO: 65)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTAPVILIRLSNLTGLKDDYSKRTMGLLVSAVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS

FIG. 15C iReaChR-C168A-D196N (SEQ ID NO: 66)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTAPVILIRLSNLTGLKDDYSKRTMGLLVSNVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS iReaChR-C168S-D196A (SEQ ID NO: 67)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTSPVILIRLSNLTGLKDDYSKRTMGLLVSAVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS iReaChR-C168S-D196N (SEQ ID NO: 68)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTSPVILIRLSNLTGLKDDYSKRTMGLLVSNVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS ibReaChR-C128T (SEQ ID NO: 69)

MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTTPVILIRLSNLTG
LKDDYSKRTMGLLVSDVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
IRKKQKITIAGQEMEVETLVAEEEDKYESS

FIG. 15D ibReaChR-C128A (SEQ ID NO: 70)

MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTAPVILIRLSNLTG
LKDDYSKRTMGLLVSDVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
IRKKQKITIAGQEMEVETLVAEEEDKYESS ibReaChR-C128S (SEQ ID NO: 71)

MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTSPVILIRLSNLTG
LKDDYSKRTMGLLVSDVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
IRKKQKITIAGQEMEVETLVAEEEDKYESS ibReaChR-C128T-D156A (SEQ ID NO: 72)

MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTTPVILIRLSNLTG
LKDDYSKRTMGLLVSAVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
IRKKQKITIAGQEMEVETLVAEEEDKYESS ibReaChR-C128T-D156N (SEQ ID NO: 73)

MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTTPVILIRLSNLTG
LKDDYSKRTMGLLVSNVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
IRKKQKITIAGQEMEVETLVAEEEDKYESS

FIG. 15E ibReaChR-C128A-D156A (SEQ ID NO: 74)

MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTAPVILIRLSNLTG
LKDDYSKRTMGLLVSAVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
IRKKQKITIAGQEMEVETLVAEEEDKYESS ibReaChR-C128A-D156N (SEQ ID NO: 75)

MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTAPVILIRLSNLTG
LKDDYSKRTMGLLVSNVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
IRKKQKITIAGQEMEVETLVAEEEDKYESS ibReaChR-C128S-D156A (SEQ ID NO: 76)

MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTSPVILIRLSNLTG
LKDDYSKRTMGLLVSAVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
IRKKQKITIAGQEMEVETLVAEEEDKYESS ibReaChR-C128S-D156N (SEQ ID NO: 77)

MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTSPVILIRLSNLTG
LKDDYSKRTMGLLVSNVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
IRKKQKITIAGQEMEVETLVAEEEDKYESS

FIG. 16A

C1C2 (SEQ ID NO: 78)

MSRRPWLLALALAVALAAGSAGASTGSDATVPVATQDGPDYVFHRAHERMLFQTSYTLENNGSVI
CIPNNGQCFCLAWLKSNGTNAEKLAANILQWITFALSALCLMFYGYQTWKSTCGWEEIYVATIEM
IKFIIEYFHEFDEPAVIYSSNGNKTVWLRYAEWLLTCPVILIHLSNLTGLANDYNKRTMGLLVSD
IGTIVWGTTAALSKGYVRVIFFLMGLCYGIYTFFNAAKVYIEAYHTVPKGRCRQVVTGMAWLFFV
SWGMFPILFILGPEGFGVLSVYGSTVGHTIIDLMSKNCWGLLGHYLRVLIHEHILIHGDIRKTTK
LNIGGTEIEVETLVEDEAEAGAV

ChR2 (SEQ ID NO: 79)

MDYGGALSAVGRELLFVTNPVVVNGSVLVPEDQCYCAGWIESRGTNGAQTASNVLQWLAAGFSIL
LLMFYAYQTWKSTCGWEEIYVCAIEMVKVILEFFFEFKNPSMLYLATGHRVQWLRYAEWLLTCPV
ILIHLSNLTGLSNDYSRRTMGLLVSDIGTIVWGATSAMATGYVKVIFFCLGLCYGANTFFHAAKA
YIEGYHTVPKGRCRQVVTGMAWLFFVSWGMFPILFILGPEGFGVLSVYGSTVGHTIIDLMSKNCW
GLLGHYLRVLIHEHILIHGDIRKTTKLNIGGTEIEVETLVEDEAEAGAVP

C1V1 (SEQ ID NO: 80)

MSRRPWLLALALAVALAAGSAGASTGSDATVPVATQDGPDYVFHRAHERMLFQTSYTLENNGSVI
CIPNNGQCFCLAWLKSNGTNAEKLAANILQWITFALSALCLMFYGYQTWKSTCGWEEIYVATIEM
IKFIIEYFHEFDEPAVIYSSNGNKTVWLRYAEWLLTCPVLLIHLSNLTGLKDDYSKRTMGLLVSD
VGCIWGATSAMCTGWTKILFFLISLSYGMYTYFHAAKVYIEAFHTVPKGICRELVRVMAWTFFV
AWGMFPVLFLLGTEGFGHISPYGSAIGHSILDLIAKNMWGVLGNYLRVKIHEHILLYGDIRKKQK
ITIAGQEMEVETLVAEEED

ReaChR (SEQ ID NO: 81)

MVSRRPWLLALALAVALAAGSAGASTGSDATVPVATQDGPDYVFHRAHERMLFQTSYTLENNGSV
ICIPNNGQCFCLAWLKSNGTNAEKLAANILQWVTFALSVACLGWYAYQAWRATCGWEEVYVALIE
MMKSIIEAFHEFDSPATLWLSSGNGVVWMRYGEWLLTCPVILIHLSNLTGLKDDYSKRTMGLLVS
DVGCIVWGATSAMCTGWTKILFFLISLSYGMYTYFHAAKVYIEAFHTVPKGLCRQLVRAMAWLFF
VSWGMFPVLFLLGPEGFGHISPYGSAIGHSILDLIAKNMWGVLGNYLRVKIHEHILLYGDIRKKQ
KITIAGQEMEVETLVAEEEDKYESS

Amino Acids 1-11 of ChR2 (SEQ ID NO: 82)

MDYGGALSAVG

FIG. 16B

Membrane Trafficking signal (SEQ ID NO: 83)

KSRITSEGEYIPLDQIDINV

ER export signal (SEQ ID NO: 84)

FCYENEV

Signal peptide of hChR2 (SEQ ID NO: 85)

MDYGGALSAVGRELLFVTNPVVVNGS

Signal peptide of beta2 subunit (SEQ ID NO: 86)

MAGHSNSMALFSFSLLWLCSGVLGTEF

Signal sequence 1 of nicotinic acetylcholine receptor (SEQ ID NO: 87)

MGLRALMLWLLAAAGLVRESLQG

Signal sequence 2 of nicotinic acetylcholine receptor (SEQ ID NO: 88)

MRGTPLLLVVSLFSLLQD

ER export sequence 1 (SEQ ID NO:89)

VKESL

ER export sequence 2 (SEQ ID NO:90)

VLGSL

ER export sequence 3 (SEQ ID NO:91)

NANSFCYENEVALTSK

FIG. 16C

ER export sequence 4 (SEQ ID NO:92)

FXYENE, where X is any amino acid

ER export sequence 5 (SEQ ID NO:93)

FCYENEV

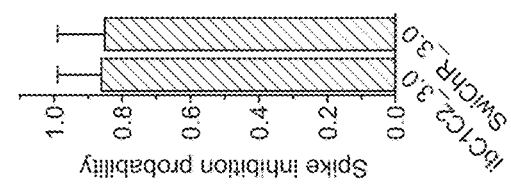
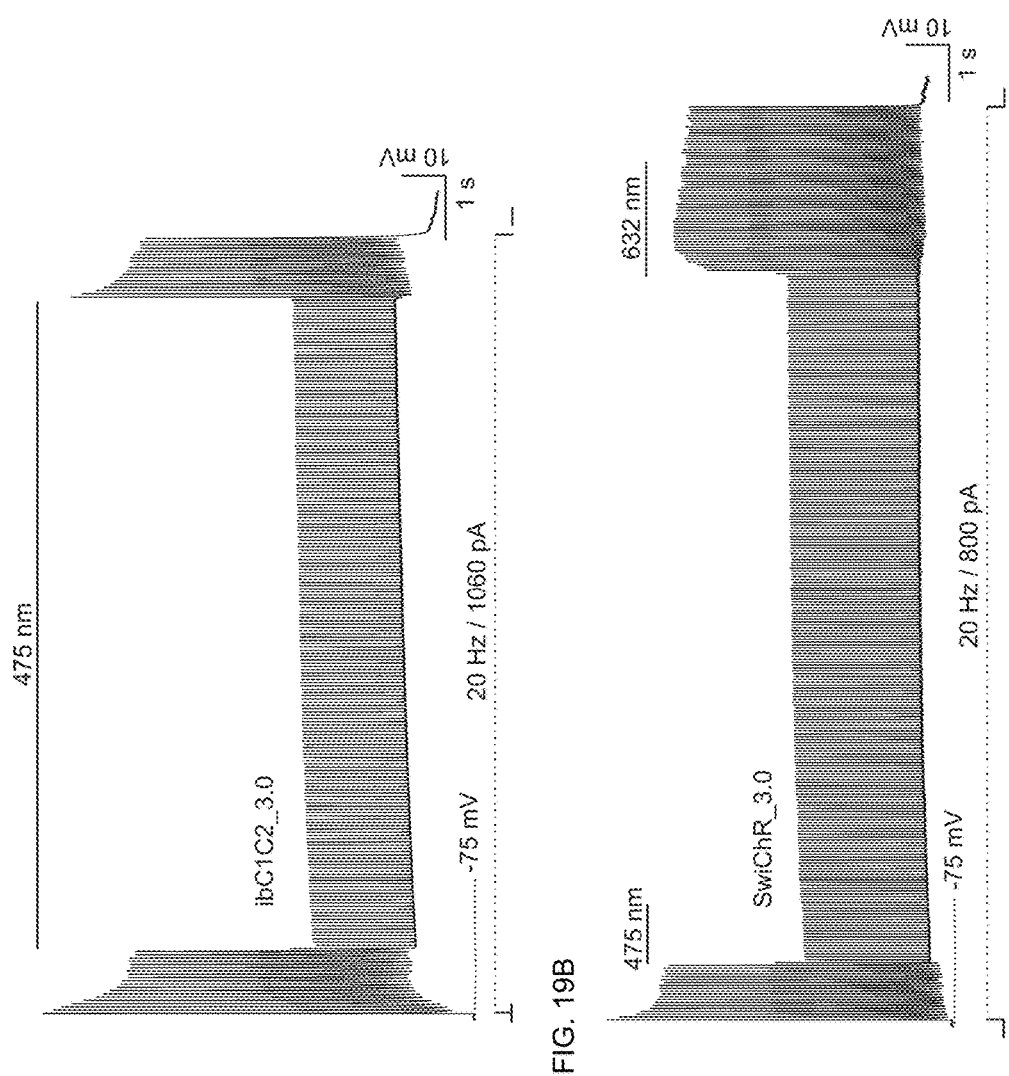
FIG. 19A
FIG. 19B
FIG. 19C

FIG. 21A iC1C2_3.0 (SEQ ID NO: 94)

MSRRPWLLALALAVALAAGSAGASTGSDATVPVATQDGPDYVFHRAHERMLFQTSYTLENNGSV
ICIPNNGQCFCLAWLKSNNTNAEKLAANILQWISFALSALCLMFYGYQTWKSTCGWENIYVATI
QMIKFIIEYFHSFDEPAVIYSSNGNKTRWLRYASWLLTCPVILIHLSNLTGLANDYNKRTMGLL
VSDIGTIVWGTTAALSKGYVRVIFFLMGLCYGIYTFFNAAKVYIEAYHTVPKGRCRQVVTGMAW
LFFVSWGMFPILFILGPEGFGVLSRYGSNVGHTIIDLMSKQCWGLLGHYLRVLIHSHILIHGDI
RKTTKLNIGGTEIEVETLVEDEAEAGAV iC1C2_3.0-D195N (SEQ ID NO: 95)

MSRRPWLLALALAVALAAGSAGASTGSDATVPVATQDGPDYVFHRAHERMLFQTSYTLENNGSV
ICIPNNGQCFCLAWLKSNNTNAEKLAANILQWISFALSALCLMFYGYQTWKSTCGWENIYVATI
QMIKFIIEYFHSFDEPAVIYSSNGNKTRWLRYASWLLTCPVILIHLSNLTGLANDYNKRTMGLL
VSNIGTIVWGTTAALSKGYVRVIFFLMGLCYGIYTFFNAAKVYIEAYHTVPKGRCRQVVTGMAW
LFFVSWGMFPILFILGPEGFGVLSRYGSNVGHTIIDLMSKQCWGLLGHYLRVLIHSHILIHGDI
RKTTKLNIGGTEIEVETLVEDEAEAGAV ibC1C2_3.0 (SEQ ID NO: 96)

MDYGGALSAVGLFQTSYTLENNGSVICIPNNGQCFCLAWLKSNNTNAEKLAANILQWISFALSA
LCLMFYGYQTWKSTCGWENIYVATIQMIKFIIEYFHSFDEPAVIYSSNGNKTRWLRYASWLLTC
PVILIHLSNLTGLANDYNKRTMGLLVSDIGTIVWGTTAALSKGYVRVIFFLMGLCYGIYTFFNA
AKVYIEAYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAV ibC1C2_3.0-D156N (SEQ ID NO: 97)

MDYGGALSAVGLFQTSYTLENNGSVICIPNNGQCFCLAWLKSNNTNAEKLAANILQWISFALSA
LCLMFYGYQTWKSTCGWENIYVATIQMIKFIIEYFHSFDEPAVIYSSNGNKTRWLRYASWLLTC
PVILIHLSNLTGLANDYNKRTMGLLVSNIGTIVWGTTAALSKGYVRVIFFLMGLCYGIYTFFNA
AKVYIEAYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAV

FIG. 21B iC1C2_3.0-C167T (SEQ ID NO: 98)

MSRRPWLLALALAVALAAGSAGASTGSDATVPVATQDGPDYVFHRAHERMLFQTSYTLENNGSV
ICIPNNGQCFCLAWLKSNNTNAEKLAANILQWISFALSALCLMFYGYQTWKSTCGWENIYVATI
QMIKFIIEYFHSFDEPAVIYSSNGNKTRWLRYASWLLTTPVILIHLSNLTGLANDYNKRTMGLL
VSDIGTIVWGTTAALSKGYVRVIFFLMGLCYGIYTFFNAAKVYIEAYHTVPKGRCRQVVTGMAW
LFFVSWGMFPILFILGPEGFGVLSRYGSNVGHTIIDLMSKQCWGLLGHYLRVLIHSHILIHGDI
RKTTKLNIGGTEIEVETLVEDEAEAGAV iC1C2_3.0-C167A (SEQ ID NO: 99)

MSRRPWLLALALAVALAAGSAGASTGSDATVPVATQDGPDYVFHRAHERMLFQTSYTLENNGSV
ICIPNNGQCFCLAWLKSNNTNAEKLAANILQWISFALSALCLMFYGYQTWKSTCGWENIYVATI
QMIKFIIEYFHSFDEPAVIYSSNGNKTRWLRYASWLLTAPVILIHLSNLTGLANDYNKRTMGLL
VSDIGTIVWGTTAALSKGYVRVIFFLMGLCYGIYTFFNAAKVYIEAYHTVPKGRCRQVVTGMAW
LFFVSWGMFPILFILGPEGFGVLSRYGSNVGHTIIDLMSKQCWGLLGHYLRVLIHSHILIHGDI
RKTTKLNIGGTEIEVETLVEDEAEAGAV iC1C2_3.0-C167S (SEQ ID NO: 100)

MSRRPWLLALALAVALAAGSAGASTGSDATVPVATQDGPDYVFHRAHERMLFQTSYTLENNGSV
ICIPNNGQCFCLAWLKSNNTNAEKLAANILQWISFALSALCLMFYGYQTWKSTCGWENIYVATI
QMIKFIIEYFHSFDEPAVIYSSNGNKTRWLRYASWLLTSPVILIHLSNLTGLANDYNKRTMGLL
VSDIGTIVWGTTAALSKGYVRVIFFLMGLCYGIYTFFNAAKVYIEAYHTVPKGRCRQVVTGMAW
LFFVSWGMFPILFILGPEGFGVLSRYGSNVGHTIIDLMSKQCWGLLGHYLRVLIHSHILIHGDI
RKTTKLNIGGTEIEVETLVEDEAEAGAV iC1C2_3.0-C167T-D195C (SEQ ID NO: 101)

MSRRPWLLALALAVALAAGSAGASTGSDATVPVATQDGPDYVFHRAHERMLFQTSYTLENNGSV
ICIPNNGQCFCLAWLKSNNTNAEKLAANILQWISFALSALCLMFYGYQTWKSTCGWENIYVATI
QMIKFIIEYFHSFDEPAVIYSSNGNKTRWLRYASWLLTTPVILIHLSNLTGLANDYNKRTMGLL
VSCIGTIVWGTTAALSKGYVRVIFFLMGLCYGIYTFFNAAKVYIEAYHTVPKGRCRQVVTGMAW
LFFVSWGMFPILFILGPEGFGVLSRYGSNVGHTIIDLMSKQCWGLLGHYLRVLIHSHILIHGDI
RKTTKLNIGGTEIEVETLVEDEAEAGAV

FIG. 21C iC1C2_3.0-C167T-D195N (SEQ ID NO: 102)

MSRRPWLLALALAVALAAGSAGASTGSDATVPVATQDGPDYVFHRAHERMLFQTSYTLENNGSV
ICIPNNGQCFCLAWLKSNNTNAEKLAANILQWISFALSALCLMFYGYQTWKSTCGWENIYVATI
QMIKFIIEYFHSFDEPAVIYSSNGNKTRWLRYASWLLTTPVILIHLSNLTGLANDYNKRTMGLL
VSNIGTIVWGTTAALSKGYVRVIFFLMGLCYGIYTFFNAAKVYIEAYHTVPKGRCRQVVTGMAW
LFFVSWGMFPILFILGPEGFGVLSRYGSNVGHTIIDLMSKQCWGLLGHYLRVLIHSHILIHGDI
RKTTKLNIGGTEIEVETLVEDEAEAGAV iC1C2_3.0-C167A-D195C (SEQ ID NO: 103)

MSRRPWLLALALAVALAAGSAGASTGSDATVPVATQDGPDYVFHRAHERMLFQTSYTLENNGSV
ICIPNNGQCFCLAWLKSNNTNAEKLAANILQWISFALSALCLMFYGYQTWKSTCGWENIYVATI
QMIKFIIEYFHSFDEPAVIYSSNGNKTRWLRYASWLLTAPVILIHLSNLTGLANDYNKRTMGLL
VSCIGTIVWGTTAALSKGYVRVIFFLMGLCYGIYTFFNAAKVYIEAYHTVPKGRCRQVVTGMAW
LFFVSWGMFPILFILGPEGFGVLSRYGSNVGHTIIDLMSKQCWGLLGHYLRVLIHSHILIHGDI
RKTTKLNIGGTEIEVETLVEDEAEAGAV iC1C2_3.0-C167A-D195N (SEQ ID NO: 104)

MSRRPWLLALALAVALAAGSAGASTGSDATVPVATQDGPDYVFHRAHERMLFQTSYTLENNGSV
ICIPNNGQCFCLAWLKSNNTNAEKLAANILQWISFALSALCLMFYGYQTWKSTCGWENIYVATI
QMIKFIIEYFHSFDEPAVIYSSNGNKTRWLRYASWLLTAPVILIHLSNLTGLANDYNKRTMGLL
VSNIGTIVWGTTAALSKGYVRVIFFLMGLCYGIYTFFNAAKVYIEAYHTVPKGRCRQVVTGMAW
LFFVSWGMFPILFILGPEGFGVLSRYGSNVGHTIIDLMSKQCWGLLGHYLRVLIHSHILIHGDI
RKTTKLNIGGTEIEVETLVEDEAEAGAV iC1C2_3.0-C167S-D195C (SEQ ID NO: 105)

MSRRPWLLALALAVALAAGSAGASTGSDATVPVATQDGPDYVFHRAHERMLFQTSYTLENNGSV
ICIPNNGQCFCLAWLKSNNTNAEKLAANILQWISFALSALCLMFYGYQTWKSTCGWENIYVATI
QMIKFIIEYFHSFDEPAVIYSSNGNKTRWLRYASWLLTSPVILIHLSNLTGLANDYNKRTMGLL
VSCIGTIVWGTTAALSKGYVRVIFFLMGLCYGIYTFFNAAKVYIEAYHTVPKGRCRQVVTGMAW
LFFVSWGMFPILFILGPEGFGVLSRYGSNVGHTIIDLMSKQCWGLLGHYLRVLIHSHILIHGDI
RKTTKLNIGGTEIEVETLVEDEAEAGAV

FIG. 21D iC1C2_3.0-C167S-D195N (SEQ ID NO: 106)

MSRRPWLLALALAVALAAGSAGASTGSDATVPVATQDGPDYVFHRAHERMLFQTSYTLENNGSV
ICIPNNGQCFCLAWLKSNNTNAEKLAANILQWISFALSALCLMFYGYQTWKSTCGWENIYVATI
QMIKFIIEYFHSFDEPAVIYSSNGNKTRWLRYASWLLTSPVILIHLSNLTGLANDYNKRTMGLL
VSNIGTIVWGTTAALSKGYVRVIFFLMGLCYGIYTFFNAAKVYIEAYHTVPKGRCRQVVTGMAW
LFFVSWGMFPILFILGPEGFGVLSRYGSNVGHTIIDLMSKQCWGLLGHYLRVLIHSHILIHGDI
RKTTKLNIGGTEIEVETLVEDEAEAGAV ibC1C2_3.0-C128T (SEQ ID NO: 107)

MDYGGALSAVGLFQTSYTLENNGSVICIPNNGQCFCLAWLKSNNTNAEKLAANILQWISFALSA
LCLMFYGYQTWKSTCGWENIYVATIQMIKFIIEYFHSFDEPAVIYSSNGNKTRWLRYASWLLTT
PVILIHLSNLTGLANDYNKRTMGLLVSDIGTIVWGTTAALSKGYVRVIFFLMGLCYGIYTFFNA
AKVYIEAYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAV ibC1C2_3.0-C128A (SwiChR_3.0) (SEQ ID NO: 108)

MDYGGALSAVGLFQTSYTLENNGSVICIPNNGQCFCLAWLKSNNTNAEKLAANILQWISFALSA
LCLMFYGYQTWKSTCGWENIYVATIQMIKFIIEYFHSFDEPAVIYSSNGNKTRWLRYASWLLTA
PVILIHLSNLTGLANDYNKRTMGLLVSDIGTIVWGTTAALSKGYVRVIFFLMGLCYGIYTFFNA
AKVYIEAYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAV ibC1C2_3.0-C128S (SEQ ID NO: 109)

MDYGGALSAVGLFQTSYTLENNGSVICIPNNGQCFCLAWLKSNNTNAEKLAANILQWISFALSA
LCLMFYGYQTWKSTCGWENIYVATIQMIKFIIEYFHSFDEPAVIYSSNGNKTRWLRYASWLLTS
PVILIHLSNLTGLANDYNKRTMGLLVSDIGTIVWGTTAALSKGYVRVIFFLMGLCYGIYTFFNA
AKVYIEAYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAV

FIG. 21E ibC1C2_3.0-C128T-D156C (SEQ ID NO: 110)

MDYGGALSAVGLFQTSYTLENNGSVICIPNNGQCFCLAWLKSNNTNAEKLAANILQWISFALSA
LCLMFYGYQTWKSTCGWENIYVATIQMIKFIIEYFHSFDEPAVIYSSNGNKTRWLRYASWLLTT
PVILIHLSNLTGLANDYNKRTMGLLVSCIGTIVWGTTAALSKGYVRVIFFLMGLCYGIYTFFNA
AKVYIEAYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAV ibC1C2_3.0-C128T-D156N (SEQ ID NO: 111)

MDYGGALSAVGLFQTSYTLENNGSVICIPNNGQCFCLAWLKSNNTNAEKLAANILQWISFALSA
LCLMFYGYQTWKSTCGWENIYVATIQMIKFIIEYFHSFDEPAVIYSSNGNKTRWLRYASWLLTT
PVILIHLSNLTGLANDYNKRTMGLLVSNIGTIVWGTTAALSKGYVRVIFFLMGLCYGIYTFFNA
AKVYIEAYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAV ibC1C2_3.0-C128A-D156C (SEQ ID NO: 112)

MDYGGALSAVGLFQTSYTLENNGSVICIPNNGQCFCLAWLKSNNTNAEKLAANILQWISFALSA
LCLMFYGYQTWKSTCGWENIYVATIQMIKFIIEYFHSFDEPAVIYSSNGNKTRWLRYASWLLTA
PVILIHLSNLTGLANDYNKRTMGLLVSCIGTIVWGTTAALSKGYVRVIFFLMGLCYGIYTFFNA
AKVYIEAYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAV ibC1C2_3.0-C128A-D156N (SEQ ID NO: 113)

MDYGGALSAVGLFQTSYTLENNGSVICIPNNGQCFCLAWLKSNNTNAEKLAANILQWISFALSA
LCLMFYGYQTWKSTCGWENIYVATIQMIKFIIEYFHSFDEPAVIYSSNGNKTRWLRYASWLLTA
PVILIHLSNLTGLANDYNKRTMGLLVSNIGTIVWGTTAALSKGYVRVIFFLMGLCYGIYTFFNA
AKVYIEAYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAV

FIG. 21F ibC1C2_3.0-C128S-D156C (SEQ ID NO: 114)

MDYGGALSAVGLFQTSYTLENNGSVICIPNNGQCFCLAWLKSNNTNAEKLAANILQWISFALSA
LCLMFYGYQTWKSTCGWENIYVATIQMIKFIIEYFHSFDEPAVIYSSNGNKTRWLRYASWLLTS
PVILIHLSNLTGLANDYNKRTMGLLVSCIGTIVWGTTAALSKGYVRVIFFLMGLCYGIYTFFNA
AKVYIEAYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAV ibC1C2_3.0-C128S-D156N (SEQ ID NO: 115)

MDYGGALSAVGLFQTSYTLENNGSVICIPNNGQCFCLAWLKSNNTNAEKLAANILQWISFALSA
LCLMFYGYQTWKSTCGWENIYVATIQMIKFIIEYFHSFDEPAVIYSSNGNKTRWLRYASWLLTS
PVILIHLSNLTGLANDYNKRTMGLLVSNIGTIVWGTTAALSKGYVRVIFFLMGLCYGIYTFFNA
AKVYIEAYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAV

FIG. 22A iChR2_3.0 (SEQ ID NO: 116)

MDYGGALSAVGRELLFVTNPVVVNGSVLVPEDQCYCAGWIESRGTNGAQTASNVLQWLSAGFSI
LLLMFYAYQTWKSTCGWENIYVCAIQMVKVILEFFFSFKNPSMLYLATGHRVRWLRYASWLLTC
PVILIHLSNLTGLSNDYSRRTMGLLVSDIGTIWGATSAMATGYVKVIFFCLGLCYGANTFFHA
AKAYIEGYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAVP iChR2_3.0-D156N (SEQ ID NO: 117)

MDYGGALSAVGRELLFVTNPVVVNGSVLVPEDQCYCAGWIESRGTNGAQTASNVLQWLSAGFSI
LLLMFYAYQTWKSTCGWENIYVCAIQMVKVILEFFFSFKNPSMLYLATGHRVRWLRYASWLLTC
PVILIHLSNLTGLSNDYSRRTMGLLVSNIGTIWGATSAMATGYVKVIFFCLGLCYGANTFFHA
AKAYIEGYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAVP iChR2_3.0-C128T (SEQ ID NO: 118)

MDYGGALSAVGRELLFVTNPVVVNGSVLVPEDQCYCAGWIESRGTNGAQTASNVLQWLSAGFSI
LLLMFYAYQTWKSTCGWENIYVCAIQMVKVILEFFFSFKNPSMLYLATGHRVRWLRYASWLLTT
PVILIHLSNLTGLSNDYSRRTMGLLVSDIGTIWGATSAMATGYVKVIFFCLGLCYGANTFFHA
AKAYIEGYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAVP iChR2_3.0-C128A (SEQ ID NO: 119)

MDYGGALSAVGRELLFVTNPVVVNGSVLVPEDQCYCAGWIESRGTNGAQTASNVLQWLSAGFSI
LLLMFYAYQTWKSTCGWENIYVCAIQMVKVILEFFFSFKNPSMLYLATGHRVRWLRYASWLLTA
PVILIHLSNLTGLSNDYSRRTMGLLVSDIGTIWGATSAMATGYVKVIFFCLGLCYGANTFFHA
AKAYIEGYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAVP

FIG. 22B iChR2_3.0-C128S (SEQ ID NO: 120)

MDYGGALSAVGRELLFVTNPVVNGSVLVPEDQCYCAGWIESRGTNGAQTASNVLQWLSAGFSI
LLLMFYAYQTWKSTCGWENIYVCAIQMVKVILEFFFSFKNPSMLYLATGHRVRWLRYASWLLTS
PVILIHLSNLTGLSNDYSRRTMGLLVSDIGTIVWGATSAMATGYVKVIFFCLGLCYGANTFFHA
AKAYIEGYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAVP iChR2_3.0-C128T-D156C (SEQ ID NO: 121)

MDYGGALSAVGRELLFVTNPVVNGSVLVPEDQCYCAGWIESRGTNGAQTASNVLQWLSAGFSI
LLLMFYAYQTWKSTCGWENIYVCAIQMVKVILEFFFSFKNPSMLYLATGHRVRWLRYASWLLTT
PVILIHLSNLTGLSNDYSRRTMGLLVSCIGTIVWGATSAMATGYVKVIFFCLGLCYGANTFFHA
AKAYIEGYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAVP iChR2-C128T_3.0-D156N (SEQ ID NO: 122)

MDYGGALSAVGRELLFVTNPVVNGSVLVPEDQCYCAGWIESRGTNGAQTASNVLQWLSAGFSI
LLLMFYAYQTWKSTCGWENIYVCAIQMVKVILEFFFSFKNPSMLYLATGHRVRWLRYASWLLTT
PVILIHLSNLTGLSNDYSRRTMGLLVSNIGTIVWGATSAMATGYVKVIFFCLGLCYGANTFFHA
AKAYIEGYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAVP iChR2_3.0-C128A-D156C (SEQ ID NO: 123)

MDYGGALSAVGRELLFVTNPVVNGSVLVPEDQCYCAGWIESRGTNGAQTASNVLQWLSAGFSI
LLLMFYAYQTWKSTCGWENIYVCAIQMVKVILEFFFSFKNPSMLYLATGHRVRWLRYASWLLTA
PVILIHLSNLTGLSNDYSRRTMGLLVSCIGTIVWGATSAMATGYVKVIFFCLGLCYGANTFFHA
AKAYIEGYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAVP

FIG. 22C iChR2_3.0-C128A-D156N (SEQ ID NO: 124)

MDYGGALSAVGRELLFVTNPVVVNGSVLVPEDQCYCAGWIESRGTNGAQTASNVLQWLSAGFSI
LLLMFYAYQTWKSTCGWENIYVCAIQMVKVILEFFFSFKNPSMLYLATGHRVRWLRYASWLLTA
PVILIHLSNLTGLSNDYSRRTMGLLVSNIGTIVWGATSAMATGYVKVIFFCLGLCYGANTFFHA
AKAYIEGYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAVP iChR2_3.0-C128S-D156C (SEQ ID NO: 125)

MDYGGALSAVGRELLFVTNPVVVNGSVLVPEDQCYCAGWIESRGTNGAQTASNVLQWLSAGFSI
LLLMFYAYQTWKSTCGWENIYVCAIQMVKVILEFFFSFKNPSMLYLATGHRVRWLRYASWLLTS
PVILIHLSNLTGLSNDYSRRTMGLLVSCIGTIVWGATSAMATGYVKVIFFCLGLCYGANTFFHA
AKAYIEGYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAVP iChR2-C128S-D156N (SEQ ID NO: 126)

MDYGGALSAVGRELLFVTNPVVVNGSVLVPEDQCYCAGWIESRGTNGAQTASNVLQWLSAGFSI
LLLMFYAYQTWKSTCGWENIYVCAIQMVKVILEFFFSFKNPSMLYLATGHRVRWLRYASWLLTS
PVILIHLSNLTGLSNDYSRRTMGLLVSNIGTIVWGATSAMATGYVKVIFFCLGLCYGANTFFHA
AKAYIEGYHTVPKGRCRQVVTGMAWLFFVSWGMFPILFILGPEGFGVLSRYGSNVGHTIIDLMS
KQCWGLLGHYLRVLIHSHILIHGDIRKTTKLNIGGTEIEVETLVEDEAEAGAVP

FIG. 23A iC1V1_3.0 (SEQ ID NO: 127)

MSRRPWLLALALAVALAAGSAGASTGSDATVPVATQDGPDYVFHRAHERMLFQTSYTLENNGSV
ICIPNNGQCFCLAWLKSNGTNAEKLAANILQWISFALSALCLMFYGYQTWKSTCGWENIYVATI
QMIKFIIEYFHSFDEPAVIYSSNGNKTRWLRYASWLLTCPVLLIHLSNLTGLKDDYSKRTMGLL
VSDVGCIVWGATSAMCTGWTKILFFLISLSYGMYTYFHAAKVYIEAFHTVPKGICRELVRVMAW
TFFVAWGMFPVLFLLGTEGFGHISRYGSNIGHSILDLIAKQMWGVLGNYLRVKIHSHILLYGDI
RKKQKITIAGQEMEVETLVAEEED iC1V1_3.0-D195N (SEQ ID NO: 128)

MSRRPWLLALALAVALAAGSAGASTGSDATVPVATQDGPDYVFHRAHERMLFQTSYTLENNGSV
ICIPNNGQCFCLAWLKSNGTNAEKLAANILQWISFALSALCLMFYGYQTWKSTCGWENIYVATI
QMIKFIIEYFHSFDEPAVIYSSNGNKTRWLRYASWLLTCPVLLIHLSNLTGLKDDYSKRTMGLL
VSNVGCIVWGATSAMCTGWTKILFFLISLSYGMYTYFHAAKVYIEAFHTVPKGICRELVRVMAW
TFFVAWGMFPVLFLLGTEGFGHISRYGSNIGHSILDLIAKQMWGVLGNYLRVKIHSHILLYGDI
RKKQKITIAGQEMEVETLVAEEED ibC1V1_3.0 (SEQ ID NO: 129)

MDYGGALSAVGLFQTSYTLENNGSVICIPNNGQCFCLAWLKSNGTNAEKLAANILQWISFALSA
LCLMFYGYQTWKSTCGWENIYVATIQMIKFIIEYFHSFDEPAVIYSSNGNKTRWLRYASWLLTC
PVLLIHLSNLTGLKDDYSKRTMGLLVSDVGCIVWGATSAMCTGWTKILFFLISLSYGMYTYFHA
AKVYIEAFHTVPKGICRELVRVMAWTFFVAWGMFPVLFLLGTEGFGHISRYGSNIGHSILDLIA
KQMWGVLGNYLRVKIHSHILLYGDIRKKQKITIAGQEMEVETLVAEEED ibC1V1_3.0-D156N (SEQ ID NO: 130)

MDYGGALSAVGLFQTSYTLENNGSVICIPNNGQCFCLAWLKSNGTNAEKLAANILQWISFALSA
LCLMFYGYQTWKSTCGWENIYVATIQMIKFIIEYFHSFDEPAVIYSSNGNKTRWLRYASWLLTC
PVLLIHLSNLTGLKDDYSKRTMGLLVSNVGCIVWGATSAMCTGWTKILFFLISLSYGMYTYFHA
AKVYIEAFHTVPKGICRELVRVMAWTFFVAWGMFPVLFLLGTEGFGHISRYGSNIGHSILDLIA
KQMWGVLGNYLRVKIHSHILLYGDIRKKQKITIAGQEMEVETLVAEEED

FIG. 23B iC1V1_3.0-C167T (SEQ ID NO: 131)

MSRRPWLLALALAVALAAGSAGASTGSDATVPVATQDGPDYVFHRAHERMLFQTSYTLENNGSV
ICIPNNGQCFCLAWLKSNGTNAEKLAANILQWISFALSALCLMFYGYQTWKSTCGWENIYVATI
QMIKFIIEYFHSFDEPAVIYSSNGNKTRWLRYASWLLTTPVLLIHLSNLTGLKDDYSKRTMGLL
VSDVGCIVWGATSAMCTGWTKILFFLISLSYGMYTYFHAAKVYIEAFHTVPKGICRELVRVMAW
TFFVAWGMFPVLFLLGTEGFGHISRYGSNIGHSILDLIAKQMWGVLGNYLRVKIHSHILLYGDI
RKKQKITIAGQEMEVETLVAEEED iC1V1_3.0-C167A (SEQ ID NO: 132)

MSRRPWLLALALAVALAAGSAGASTGSDATVPVATQDGPDYVFHRAHERMLFQTSYTLENNGSV
ICIPNNGQCFCLAWLKSNGTNAEKLAANILQWISFALSALCLMFYGYQTWKSTCGWENIYVATI
QMIKFIIEYFHSFDEPAVIYSSNGNKTRWLRYASWLLTAPVLLIHLSNLTGLKDDYSKRTMGLL
VSDVGCIVWGATSAMCTGWTKILFFLISLSYGMYTYFHAAKVYIEAFHTVPKGICRELVRVMAW
TFFVAWGMFPVLFLLGTEGFGHISRYGSNIGHSILDLIAKQMWGVLGNYLRVKIHSHILLYGDI
RKKQKITIAGQEMEVETLVAEEED iC1V1_3.0-C167S (SEQ ID NO: 133)

MSRRPWLLALALAVALAAGSAGASTGSDATVPVATQDGPDYVFHRAHERMLFQTSYTLENNGSV
ICIPNNGQCFCLAWLKSNGTNAEKLAANILQWISFALSALCLMFYGYQTWKSTCGWENIYVATI
QMIKFIIEYFHSFDEPAVIYSSNGNKTRWLRYASWLLTSPVLLIHLSNLTGLKDDYSKRTMGLL
VSDVGCIVWGATSAMCTGWTKILFFLISLSYGMYTYFHAAKVYIEAFHTVPKGICRELVRVMAW
TFFVAWGMFPVLFLLGTEGFGHISRYGSNIGHSILDLIAKQMWGVLGNYLRVKIHSHILLYGDI
RKKQKITIAGQEMEVETLVAEEED iC1V1_3.0-C167T-D195C (SEQ ID NO: 134)

MSRRPWLLALALAVALAAGSAGASTGSDATVPVATQDGPDYVFHRAHERMLFQTSYTLENNGSV
ICIPNNGQCFCLAWLKSNGTNAEKLAANILQWISFALSALCLMFYGYQTWKSTCGWENIYVATI
QMIKFIIEYFHSFDEPAVIYSSNGNKTRWLRYASWLLTTPVLLIHLSNLTGLKDDYSKRTMGLL
VSCVGCIVWGATSAMCTGWTKILFFLISLSYGMYTYFHAAKVYIEAFHTVPKGICRELVRVMAW
TFFVAWGMFPVLFLLGTEGFGHISRYGSNIGHSILDLIAKQMWGVLGNYLRVKIHSHILLYGDI
RKKQKITIAGQEMEVETLVAEEED

FIG. 23C iC1V1_3.0-C167T-D195N (SEQ ID NO: 135)

MSRRPWLLALALAVALAAGSAGASTGSDATVPVATQDGPDYVFHRAHERMLFQTSYTLENNGSV
ICIPNNGQCFCLAWLKSNGTNAEKLAANILQWISFALSALCLMFYGYQTWKSTCGWENIYVATI
QMIKFIIEYFHSFDEPAVIYSSNGNKTRWLRYASWLLTTPVLLIHLSNLTGLKDDYSKRTMGLL
VSNVGCIVWGATSAMCTGWTKILFFLISLSYGMYTYFHAAKVYIEAFHTVPKGICRELVRVMAW
TFFVAWGMFPVLFLLGTEGFGHISRYGSNIGHSILDLIAKQMWGVLGNYLRVKIHSHILLYGDI
RKKQKITIAGQEMEVETLVAEEED iC1V1_3.0-C167A-D195C (SEQ ID NO: 136)

MSRRPWLLALALAVALAAGSAGASTGSDATVPVATQDGPDYVFHRAHERMLFQTSYTLENNGSV
ICIPNNGQCFCLAWLKSNGTNAEKLAANILQWISFALSALCLMFYGYQTWKSTCGWENIYVATI
QMIKFIIEYFHSFDEPAVIYSSNGNKTRWLRYASWLLTAPVLLIHLSNLTGLKDDYSKRTMGLL
VSCVGCIVWGATSAMCTGWTKILFFLISLSYGMYTYFHAAKVYIEAFHTVPKGICRELVRVMAW
TFFVAWGMFPVLFLLGTEGFGHISRYGSNIGHSILDLIAKQMWGVLGNYLRVKIHSHILLYGDI
RKKQKITIAGQEMEVETLVAEEED iC1V1_3.0-C167A-D195N (SEQ ID NO: 137)

MSRRPWLLALALAVALAAGSAGASTGSDATVPVATQDGPDYVFHRAHERMLFQTSYTLENNGSV
ICIPNNGQCFCLAWLKSNGTNAEKLAANILQWISFALSALCLMFYGYQTWKSTCGWENIYVATI
QMIKFIIEYFHSFDEPAVIYSSNGNKTRWLRYASWLLTAPVLLIHLSNLTGLKDDYSKRTMGLL
VSNVGCIVWGATSAMCTGWTKILFFLISLSYGMYTYFHAAKVYIEAFHTVPKGICRELVRVMAW
TFFVAWGMFPVLFLLGTEGFGHISRYGSNIGHSILDLIAKQMWGVLGNYLRVKIHSHILLYGDI
RKKQKITIAGQEMEVETLVAEEED iC1V1_3.0-C167S-D195C (SEQ ID NO: 138)

MSRRPWLLALALAVALAAGSAGASTGSDATVPVATQDGPDYVFHRAHERMLFQTSYTLENNGSV
ICIPNNGQCFCLAWLKSNGTNAEKLAANILQWISFALSALCLMFYGYQTWKSTCGWENIYVATI
QMIKFIIEYFHSFDEPAVIYSSNGNKTRWLRYASWLLTSPVLLIHLSNLTGLKDDYSKRTMGLL
VSCVGCIVWGATSAMCTGWTKILFFLISLSYGMYTYFHAAKVYIEAFHTVPKGICRELVRVMAW
TFFVAWGMFPVLFLLGTEGFGHISRYGSNIGHSILDLIAKQMWGVLGNYLRVKIHSHILLYGDI
RKKQKITIAGQEMEVETLVAEEED

FIG. 23D iC1V1_3.0-C167S-D195N (SEQ ID NO: 139)

MGRRPWLLALALAVALAAGSAGASTGSDATVPVATQDGPDYVFHRAHERMLFQTSYTLENNGSV
ICIPNNGQCFCLAWLKSNGTNAEKLAANILQWISFALSALCLMFYGYQTWKSTCGWENIYVATI
QMIKFIIEYFHSFDEPAVIYSSNGNKTRWLRYASWLLTSPVLLIHLSNLTGLKDDYSKRTMGLL
VSNVGCIVWGATSAMCTGWTKILFFLISLSYGMYTYFHAAKVYIEAFHTVPKGICRELVRVMAW
TFFVAWGMFPVLFLLGTEGFGHISRYGSNIGHSILDLIAKQMWGVLGNYLRVKIHSHILLYGDI
RKKQKITIAGQEMEVETLVAEEED ibC1V1_3.0-C128T (SEQ ID NO: 140)

MDYGGALSAVGLFQTSYTLENNGSVICIPNNGQCFCLAWLKSNGTNAEKLAANILQWISFALSA
LCLMFYGYQTWKSTCGWENIYVATIQMIKFIIEYFHSFDEPAVIYSSNGNKTRWLRYASWLLTT
PVLLIHLSNLTGLKDDYSKRTMGLLVSDVGCIVWGATSAMCTGWTKILFFLISLSYGMYTYFHA
AKVYIEAFHTVPKGICRELVRVMAWTFFVAWGMFPVLFLLGTEGFGHISRYGSNIGHSILDLIA
KQMWGVLGNYLRVKIHSHILLYGDIRKKQKITIAGQEMEVETLVAEEED ibC1V1_3.0-C128A (SEQ ID NO: 141)

MDYGGALSAVGLFQTSYTLENNGSVICIPNNGQCFCLAWLKSNGTNAEKLAANILQWISFALSA
LCLMFYGYQTWKSTCGWENIYVATIQMIKFIIEYFHSFDEPAVIYSSNGNKTRWLRYASWLLTA
PVLLIHLSNLTGLKDDYSKRTMGLLVSDVGCIVWGATSAMCTGWTKILFFLISLSYGMYTYFHA
AKVYIEAFHTVPKGICRELVRVMAWTFFVAWGMFPVLFLLGTEGFGHISRYGSNIGHSILDLIA
KQMWGVLGNYLRVKIHSHILLYGDIRKKQKITIAGQEMEVETLVAEEED ibC1V1_3.0-C128S (SEQ ID NO: 142)

MDYGGALSAVGLFQTSYTLENNGSVICIPNNGQCFCLAWLKSNGTNAEKLAANILQWISFALSA
LCLMFYGYQTWKSTCGWENIYVATIQMIKFIIEYFHSFDEPAVIYSSNGNKTRWLRYASWLLTS
PVLLIHLSNLTGLKDDYSKRTMGLLVSDVGCIVWGATSAMCTGWTKILFFLISLSYGMYTYFHA
AKVYIEAFHTVPKGICRELVRVMAWTFFVAWGMFPVLFLLGTEGFGHISRYGSNIGHSILDLIA
KQMWGVLGNYLRVKIHSHILLYGDIRKKQKITIAGQEMEVETLVAEEED

FIG. 23E ibC1V1_3.0-C128T-D156C (SEQ ID NO: 143)

MDYGGALSAVGLFQTSYTLENNGSVICIPNNGQCFCLAWLKSNGTNAEKLAANILQWISFALSA
LCLMFYGYQTWKSTCGWENIYVATIQMIKFIIEYFHSFDEPAVIYSSNGNKTRWLRYASWLLTT
PVLLIHLSNLTGLKDDYSKRTMGLLVSCVGCIVWGATSAMCTGWTKILFFLISLSYGMYTYFHA
AKVYIEAFHTVPKGICRELVRVMAWTFFVAWGMFPVLFLLGTEGFGHISRYGSNIGHSILDLIA
KQMWGVLGNYLRVKIHSHILLYGDIRKKQKITIAGQEMEVETLVAEEED ibC1V1_3.0-C128T-D156N (SEQ ID NO: 144)

MDYGGALSAVGLFQTSYTLENNGSVICIPNNGQCFCLAWLKSNGTNAEKLAANILQWISFALSA
LCLMFYGYQTWKSTCGWENIYVATIQMIKFIIEYFHSFDEPAVIYSSNGNKTRWLRYASWLLTT
PVLLIHLSNLTGLKDDYSKRTMGLLVSNVGCIVWGATSAMCTGWTKILFFLISLSYGMYTYFHA
AKVYIEAFHTVPKGICRELVRVMAWTFFVAWGMFPVLFLLGTEGFGHISRYGSNIGHSILDLIA
KQMWGVLGNYLRVKIHSHILLYGDIRKKQKITIAGQEMEVETLVAEEED ibC1V1_3.0-C128A-D156C (SEQ ID NO: 145)

MDYGGALSAVGLFQTSYTLENNGSVICIPNNGQCFCLAWLKSNGTNAEKLAANILQWISFALSA
LCLMFYGYQTWKSTCGWENIYVATIQMIKFIIEYFHSFDEPAVIYSSNGNKTRWLRYASWLLTA
PVLLIHLSNLTGLKDDYSKRTMGLLVSCVGCIVWGATSAMCTGWTKILFFLISLSYGMYTYFHA
AKVYIEAFHTVPKGICRELVRVMAWTFFVAWGMFPVLFLLGTEGFGHISRYGSNIGHSILDLIA
KQMWGVLGNYLRVKIHSHILLYGDIRKKQKITIAGQEMEVETLVAEEED ibC1V1_3.0-C128A-D156N (SEQ ID NO: 146)

MDYGGALSAVGLFQTSYTLENNGSVICIPNNGQCFCLAWLKSNGTNAEKLAANILQWISFALSA
LCLMFYGYQTWKSTCGWENIYVATIQMIKFIIEYFHSFDEPAVIYSSNGNKTRWLRYASWLLTA
PVLLIHLSNLTGLKDDYSKRTMGLLVSNVGCIVWGATSAMCTGWTKILFFLISLSYGMYTYFHA
AKVYIEAFHTVPKGICRELVRVMAWTFFVAWGMFPVLFLLGTEGFGHISRYGSNIGHSILDLIA
KQMWGVLGNYLRVKIHSHILLYGDIRKKQKITIAGQEMEVETLVAEEED

FIG. 23F ibC1V1_3.0-C128S-D156C (SEQ ID NO: 147)

MDYGGALSAVGLFQTSYTLENNGSVICIPNNGQCFCLAWLKSNGTNAEKLAANILQWISFALSA
LCLMFYGYQTWKSTCGWENIYVATIQMIKFIIEYFHSFDEPAVIYSSNGNKTRWLRYASWLLTS
PVLLIHLSNLTGLKDDYSKRTMGLLVSCVGCIVWGATSAMCTGWTKILFFLISLSYGMYTYFHA
AKVYIEAFHTVPKGICRELVRVMAWTFFVAWGMFPVLFLLGTEGFGHISRYGSNIGHSILDLIA
KQMWGVLGNYLRVKIHSHILLYGDIRKKQKITIAGQEMEVETLVAEEED ibC1V1_3.0-C128S-D156N (SEQ ID NO: 148)

MDYGGALSAVGLFQTSYTLENNGSVICIPNNGQCFCLAWLKSNGTNAEKLAANILQWISFALSA
LCLMFYGYQTWKSTCGWENIYVATIQMIKFIIEYFHSFDEPAVIYSSNGNKTRWLRYASWLLTS
PVLLIHLSNLTGLKDDYSKRTMGLLVSNVGCIVWGATSAMCTGWTKILFFLISLSYGMYTYFHA
AKVYIEAFHTVPKGICRELVRVMAWTFFVAWGMFPVLFLLGTEGFGHISRYGSNIGHSILDLIA
KQMWGVLGNYLRVKIHSHILLYGDIRKKQKITIAGQEMEVETLVAEEED

FIG. 24A iReaChR_3.0 (SEQ ID NO: 149)

MVSRRPWLLALALAVALAAGSAGASTGSDATVPVATQDGPDYVFHRAHERMLFQTSYTLENNGS
VICIPNNGQCFCLAWLKSNGTNAEKLAANILQWVSFALSVACLGWYAYQAWRATCGWENVYVAL
IQMMKSIIEAFHSFDSPATLWLSSGNGVRWMRYGSWLLTCPVILIHLSNLTGLKDDYSKRTMGL
LVSDVGCIVWGATSAMCTGWTKILFFLISLSYGMYTYFHAAKVYIEAFHTVPKGLCRQLVRAMA
WLFFVSWGMFPVLFLLGPEGFGHISRYGSNIGHSILDLIAKQMWGVLGNYLRVKIHSHILLYGD
IRKKQKITIAGQEMEVETLVAEEEDKYESS iReaChR_3.0-D196N (SEQ ID NO: 150)

MVSRRPWLLALALAVALAAGSAGASTGSDATVPVATQDGPDYVFHRAHERMLFQTSYTLENNGS
VICIPNNGQCFCLAWLKSNGTNAEKLAANILQWVSFALSVACLGWYAYQAWRATCGWENVYVAL
IQMMKSIIEAFHSFDSPATLWLSSGNGVRWMRYGSWLLTCPVILIHLSNLTGLKDDYSKRTMGL
LVSNVGCIVWGATSAMCTGWTKILFFLISLSYGMYTYFHAAKVYIEAFHTVPKGLCRQLVRAMA
WLFFVSWGMFPVLFLLGPEGFGHISRYGSNIGHSILDLIAKQMWGVLGNYLRVKIHSHILLYGD
IRKKQKITIAGQEMEVETLVAEEEDKYESS ibReaChR_3.0 (SEQ ID NO: 151)

MDYGGALSAVGLFQTSYTLENNGSVICIPNNGQCFCLAWLKSNGTNAEKLAANILQWVSFALSV
ACLGWYAYQAWRATCGWENVYVALIQMMKSIIEAFHSFDSPATLWLSSGNGVRWMRYGSWLLTC
PVILIHLSNLTGLKDDYSKRTMGLLVSDVGCIVWGATSAMCTGWTKILFFLISLSYGMYTYFHA
AKVYIEAFHTVPKGLCRQLVRAMAWLFFVSWGMFPVLFLLGPEGFGHISRYGSNIGHSILDLIA
KQMWGVLGNYLRVKIHSHILLYGDIRKKQKITIAGQEMEVETLVAEEEDKYESS ibReaChR_3.0-D156N (SEQ ID NO: 152)

MDYGGALSAVGLFQTSYTLENNGSVICIPNNGQCFCLAWLKSNGTNAEKLAANILQWVSFALSV
ACLGWYAYQAWRATCGWENVYVALIQMMKSIIEAFHSFDSPATLWLSSGNGVRWMRYGSWLLTC
PVILIHLSNLTGLKDDYSKRTMGLLVSNVGCIVWGATSAMCTGWTKILFFLISLSYGMYTYFHA
AKVYIEAFHTVPKGLCRQLVRAMAWLFFVSWGMFPVLFLLGPEGFGHISRYGSNIGHSILDLIA
KQMWGVLGNYLRVKIHSHILLYGDIRKKQKITIAGQEMEVETLVAEEEDKYESS

FIG. 24B iReaChR_3.0-C168T (SEQ ID NO: 153)

MVSRRPWLLALALAVALAAGSAGASTGSDATVPVATQDGPDYVFHRAHERMLFQTSYTLENNGS
VICIPNNGQCFCLAWLKSNGTNAEKLAANILQWVSFALSVACLGWYAYQAWRATCGWENVYVAL
IQMMKSIIEAFHSFDSPATLWLSSGNGVRWMRYGSWLLTTPVILIHLSNLTGLKDDYSKRTMGL
LVSDVGCIVWGATSAMCTGWTKILFFLISLSYGMYTYFHAAKVYIEAFHTVPKGLCRQLVRAMA
WLFFVSWGMFPVLFLLGPEGFGHISRYGSNIGHSILDLIAKQMWGVLGNYLRVKIHSHILLYGD
IRKKQKITIAGQEMEVETLVAEEEDKYESS iReaChR_3.0-C168A (SEQ ID NO: 154)

MVSRRPWLLALALAVALAAGSAGASTGSDATVPVATQDGPDYVFHRAHERMLFQTSYTLENNGS
VICIPNNGQCFCLAWLKSNGTNAEKLAANILQWVSFALSVACLGWYAYQAWRATCGWENVYVAL
IQMMKSIIEAFHSFDSPATLWLSSGNGVRWMRYGSWLLTAPVILIHLSNLTGLKDDYSKRTMGL
LVSDVGCIVWGATSAMCTGWTKILFFLISLSYGMYTYFHAAKVYIEAFHTVPKGLCRQLVRAMA
WLFFVSWGMFPVLFLLGPEGFGHISRYGSNIGHSILDLIAKQMWGVLGNYLRVKIHSHILLYGD
IRKKQKITIAGQEMEVETLVAEEEDKYESS iReaChR_3.0-C168S (SEQ ID NO: 155)

MVSRRPWLLALALAVALAAGSAGASTGSDATVPVATQDGPDYVFHRAHERMLFQTSYTLENNGS
VICIPNNGQCFCLAWLKSNGTNAEKLAANILQWVSFALSVACLGWYAYQAWRATCGWENVYVAL
IQMMKSIIEAFHSFDSPATLWLSSGNGVRWMRYGSWLLTSPVILIHLSNLTGLKDDYSKRTMGL
LVSDVGCIVWGATSAMCTGWTKILFFLISLSYGMYTYFHAAKVYIEAFHTVPKGLCRQLVRAMA
WLFFVSWGMFPVLFLLGPEGFGHISRYGSNIGHSILDLIAKQMWGVLGNYLRVKIHSHILLYGD
IRKKQKITIAGQEMEVETLVAEEEDKYESS iReaChR_3.0-C168T-D196C (SEQ ID NO: 156)

MVSRRPWLLALALAVALAAGSAGASTGSDATVPVATQDGPDYVFHRAHERMLFQTSYTLENNGS
VICIPNNGQCFCLAWLKSNGTNAEKLAANILQWVSFALSVACLGWYAYQAWRATCGWENVYVAL
IQMMKSIIEAFHSFDSPATLWLSSGNGVRWMRYGSWLLTTPVILIHLSNLTGLKDDYSKRTMGL
LVSCVGCIVWGATSAMCTGWTKILFFLISLSYGMYTYFHAAKVYIEAFHTVPKGLCRQLVRAMA
WLFFVSWGMFPVLFLLGPEGFGHISRYGSNIGHSILDLIAKQMWGVLGNYLRVKIHSHILLYGD
IRKKQKITIAGQEMEVETLVAEEEDKYESS

FIG. 24C iReaChR_3.0-C168T-D196N (SEQ ID NO: 157)

MVSRRPWLLALALAVALAAGSAGASTGSDATVPVATQDGPDYVFHRAHERMLFQTSYTLENNGS
VICIPNNGQCFCLAWLKSNGTNAEKLAANILQWVSFALSVACLGWYAYQAWRATCGWENVYVAL
IQMMKSIIEAFHSFDSPATLWLSSGNGVRWMRYGSWLLTTPVILIHLSNLTGLKDDYSKRTMGL
LVSNVGCIVWGATSAMCTGWTKILFFLISLSYGMYTYFHAAKVYIEAFHTVPKGLCRQLVRAMA
WLFFVSWGMFPVLFLLGPEGFGHISRYGSNIGHSILDLIAKQMWGVLGNYLRVKIHSHILLYGD
IRKKQKITIAGQEMEVETLVAEEEDKYESS iReaChR_3.0-C168A-D196C (SEQ ID NO: 158)

MVSRRPWLLALALAVALAAGSAGASTGSDATVPVATQDGPDYVFHRAHERMLFQTSYTLENNGS
VICIPNNGQCFCLAWLKSNGTNAEKLAANILQWVSFALSVACLGWYAYQAWRATCGWENVYVAL
IQMMKSIIEAFHSFDSPATLWLSSGNGVRWMRYGSWLLTAPVILIHLSNLTGLKDDYSKRTMGL
LVSCVGCIVWGATSAMCTGWTKILFFLISLSYGMYTYFHAAKVYIEAFHTVPKGLCRQLVRAMA
WLFFVSWGMFPVLFLLGPEGFGHISRYGSNIGHSILDLIAKQMWGVLGNYLRVKIHSHILLYGD
IRKKQKITIAGQEMEVETLVAEEEDKYESS iReaChR_3.0-C168A-D196N (SEQ ID NO: 159)

MVSRRPWLLALALAVALAAGSAGASTGSDATVPVATQDGPDYVFHRAHERMLFQTSYTLENNGS
VICIPNNGQCFCLAWLKSNGTNAEKLAANILQWVSFALSVACLGWYAYQAWRATCGWENVYVAL
IQMMKSIIEAFHSFDSPATLWLSSGNGVRWMRYGSWLLTAPVILIHLSNLTGLKDDYSKRTMGL
LVSNVGCIVWGATSAMCTGWTKILFFLISLSYGMYTYFHAAKVYIEAFHTVPKGLCRQLVRAMA
WLFFVSWGMFPVLFLLGPEGFGHISRYGSNIGHSILDLIAKQMWGVLGNYLRVKIHSHILLYGD
IRKKQKITIAGQEMEVETLVAEEEDKYESS iReaChR_3.0-C168S-D196C (SEQ ID NO: 160)

MVSRRPWLLALALAVALAAGSAGASTGSDATVPVATQDGPDYVFHRAHERMLFQTSYTLENNGS
VICIPNNGQCFCLAWLKSNGTNAEKLAANILQWVSFALSVACLGWYAYQAWRATCGWENVYVAL
IQMMKSIIEAFHSFDSPATLWLSSGNGVRWMRYGSWLLTSPVILIHLSNLTGLKDDYSKRTMGL
LVSCVGCIVWGATSAMCTGWTKILFFLISLSYGMYTYFHAAKVYIEAFHTVPKGLCRQLVRAMA
WLFFVSWGMFPVLFLLGPEGFGHISRYGSNIGHSILDLIAKQMWGVLGNYLRVKIHSHILLYGD
IRKKQKITIAGQEMEVETLVAEEEDKYESS

FIG. 24D iReaChR_3.0-C168S-D196N (SEQ ID NO: 161)

MVSRRPWLLALALAVALAAGSAGASTGSDATVPVATQDGPDYVFHRAHERMLFQTSYTLENNGS
VICIPNNGQCFCLAWLKSNGTNAEKLAANILQWVSFALSVACLGWYAYQAWRATCGWENVYVAL
IQMMKSIIEAFHSFDSPATLWLSSGNGVRWMRYGSWLLTSPVILIHLSNLTGLKDDYSKRTMGL
LVSNVGCIVWGATSAMCTGWTKILFFLISLSYGMYTYFHAAKVYIEAFHTVPKGLCRQLVRAMA
WLFFVSWGMFPVLFLLGPEGFGHISRYGSNIGHSILDLIAKQMWGVLGNYLRVKIHSHILLYGD
IRKKQKITIAGQEMEVETLVAEEEDKYESS ibReaChR_3.0-C128T (SEQ ID NO: 162)

MDYGGALSAVGLFQTSYTLENNGSVICIPNNGQCFCLAWLKSNGTNAEKLAANILQWVSFALSV
ACLGWYAYQAWRATCGWENVYVALIQMMKSIIEAFHSFDSPATLWLSSGNGVRWMRYGSWLLTT
PVILIHLSNLTGLKDDYSKRTMGLLVSDVGCIVWGATSAMCTGWTKILFFLISLSYGMYTYFHA
AKVYIEAFHTVPKGLCRQLVRAMAWLFFVSWGMFPVLFLLGPEGFGHISRYGSNIGHSILDLIA
KQMWGVLGNYLRVKIHSHILLYGDIRKKQKITIAGQEMEVETLVAEEEDKYESS ibReaChR_3.0-C128A (SEQ ID NO: 163)

MDYGGALSAVGLFQTSYTLENNGSVICIPNNGQCFCLAWLKSNGTNAEKLAANILQWVSFALSV
ACLGWYAYQAWRATCGWENVYVALIQMMKSIIEAFHSFDSPATLWLSSGNGVRWMRYGSWLLTA
PVILIHLSNLTGLKDDYSKRTMGLLVSDVGCIVWGATSAMCTGWTKILFFLISLSYGMYTYFHA
AKVYIEAFHTVPKGLCRQLVRAMAWLFFVSWGMFPVLFLLGPEGFGHISRYGSNIGHSILDLIA
KQMWGVLGNYLRVKIHSHILLYGDIRKKQKITIAGQEMEVETLVAEEEDKYESS ibReaChR_3.0-C128S (SEQ ID NO: 164)

MDYGGALSAVGLFQTSYTLENNGSVICIPNNGQCFCLAWLKSNGTNAEKLAANILQWVSFALSV
ACLGWYAYQAWRATCGWENVYVALIQMMKSIIEAFHSFDSPATLWLSSGNGVRWMRYGSWLLTS
PVILIHLSNLTGLKDDYSKRTMGLLVSDVGCIVWGATSAMCTGWTKILFFLISLSYGMYTYFHA
AKVYIEAFHTVPKGLCRQLVRAMAWLFFVSWGMFPVLFLLGPEGFGHISRYGSNIGHSILDLIA
KQMWGVLGNYLRVKIHSHILLYGDIRKKQKITIAGQEMEVETLVAEEEDKYESS

FIG. 24E ibReaChR_3.0-C128T-D156C (SEQ ID NO: 165)

MDYGGALSAVGLFQTSYTLENNGSVICIPNNGQCFCLAWLKSNGTNAEKLAANILQWVSFALSV
ACLGWYAYQAWRATCGWENVYVALIQMMKSIIEAFHSFDSPATLWLSSGNGVRWMRYGSWLLTT
PVILIHLSNLTGLKDDYSKRTMGLLVSCVGCIVWGATSAMCTGWTKILFFLISLSYGMYTYFHA
AKVYIEAFHTVPKGLCRQLVRAMAWLFFVSWGMFPVLFLLGPEGFGHISRYGSNIGHSILDLIA
KQMWGVLGNYLRVKIHSHILLYGDIRKKQKITIAGQEMEVETLVAEEEDKYESS ibReaChR_3.0-C128T-D156N (SEQ ID NO: 166)

MDYGGALSAVGLFQTSYTLENNGSVICIPNNGQCFCLAWLKSNGTNAEKLAANILQWVSFALSV
ACLGWYAYQAWRATCGWENVYVALIQMMKSIIEAFHSFDSPATLWLSSGNGVRWMRYGSWLLTT
PVILIHLSNLTGLKDDYSKRTMGLLVSNVGCIVWGATSAMCTGWTKILFFLISLSYGMYTYFHA
AKVYIEAFHTVPKGLCRQLVRAMAWLFFVSWGMFPVLFLLGPEGFGHISRYGSNIGHSILDLIA
KQMWGVLGNYLRVKIHSHILLYGDIRKKQKITIAGQEMEVETLVAEEEDKYESS ibReaChR_3.0-C128A-D156C (SEQ ID NO: 167)

MDYGGALSAVGLFQTSYTLENNGSVICIPNNGQCFCLAWLKSNGTNAEKLAANILQWVSFALSV
ACLGWYAYQAWRATCGWENVYVALIQMMKSIIEAFHSFDSPATLWLSSGNGVRWMRYGSWLLTA
PVILIHLSNLTGLKDDYSKRTMGLLVSCVGCIVWGATSAMCTGWTKILFFLISLSYGMYTYFHA
AKVYIEAFHTVPKGLCRQLVRAMAWLFFVSWGMFPVLFLLGPEGFGHISRYGSNIGHSILDLIA
KQMWGVLGNYLRVKIHSHILLYGDIRKKQKITIAGQEMEVETLVAEEEDKYESS ibReaChR_3.0-C128A-D156N (SEQ ID NO: 168)

MDYGGALSAVGLFQTSYTLENNGSVICIPNNGQCFCLAWLKSNGTNAEKLAANILQWVSFALSV
ACLGWYAYQAWRATCGWENVYVALIQMMKSIIEAFHSFDSPATLWLSSGNGVRWMRYGSWLLTA
PVILIHLSNLTGLKDDYSKRTMGLLVSNVGCIVWGATSAMCTGWTKILFFLISLSYGMYTYFHA
AKVYIEAFHTVPKGLCRQLVRAMAWLFFVSWGMFPVLFLLGPEGFGHISRYGSNIGHSILDLIA
KQMWGVLGNYLRVKIHSHILLYGDIRKKQKITIAGQEMEVETLVAEEEDKYESS

FIG. 24F ibReaChR_3.0-C128S-D156C (SEQ ID NO: 169)

MDYGGALSAVGLFQTSYTLENNGSVICIPNNGQCFCLAWLKSNGTNAEKLAANILQWVSFALSV
ACLGWYAYQAWRATCGWENVYVALIQMMKSIIEAFHSFDSPATLWLSSGNGVRWMRYGSWLLTS
PVILIHLSNLTGLKDDYSKRTMGLLVSCVGCIVWGATSAMCTGWTKILFFLISLSYGMYTYFHA
AKVYIEAFHTVPKGLCRQLVRAMAWLFFVSWGMFPVLFLLGPEGFGHISRYGSNIGHSILDLIA
KQMWGVLGNYLRVKIHSHILLYGDIRKKQKITIAGQEMEVETLVAEEEDKYESS ibReaChR_3.0-C128S-D156N (SEQ ID NO: 170)

MDYGGALSAVGLFQTSYTLENNGSVICIPNNGQCFCLAWLKSNGTNAEKLAANILQWVSFALSV
ACLGWYAYQAWRATCGWENVYVALIQMMKSIIEAFHSFDSPATLWLSSGNGVRWMRYGSWLLTS
PVILIHLSNLTGLKDDYSKRTMGLLVSNVGCIVWGATSAMCTGWTKILFFLISLSYGMYTYFHA
AKVYIEAFHTVPKGLCRQLVRAMAWLFFVSWGMFPVLFLLGPEGFGHISRYGSNIGHSILDLIA
KQMWGVLGNYLRVKIHSHILLYGDIRKKQKITIAGQEMEVETLVAEEEDKYESS

SEQUENCE LISTING

<160> NUMBER OF SEQ ID NOS: 170

<210> SEQ ID NO 1
<211> LENGTH: 348
<212> TYPE: PRT
<213> ORGANISM: Artificial Sequence
<220> FEATURE:
<223> OTHER INFORMATION: Synthetic polypeptide

<400> SEQUENCE: 1

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Asn Ile Leu Gln Trp
            85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
            115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Cys Pro Val Ile Leu Ile Arg Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Lys Tyr Gly Ser Asn Val Gly His
        275                 280                 285

Thr Ile Ile Asp Leu Met Ser Lys Gln Cys Trp Gly Leu Leu Gly His
    290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

```
<210> SEQ ID NO 2
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 2

Met Ser Arg Arg Pro Trp Leu Leu Ala Leu Ala Leu Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Cys Pro Val Ile Leu Ile Arg Leu Ser Asn
                165                 170                 175

Leu Thr Gly Leu Ala Asn Asp Tyr Asn Lys Arg Thr Met Gly Leu Leu
            180                 185                 190

Val Ser Asn Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Lys Tyr Gly Ser Asn Val Gly His
        275                 280                 285

Thr Ile Ile Asp Leu Met Ser Lys Gln Cys Trp Gly Leu Leu Gly His
    290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 3
<211> LENGTH: 309
<212> TYPE: PRT
```

<213> ORGANISM: Artificial sequence
<220> FEATURE:
<223> OTHER INFORMATION: Synthetic polypeptide

<400> SEQUENCE: 3

```
Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Cys
            115                 120                 125

Pro Val Ile Leu Ile Arg Leu Ser Asn Leu Thr Gly Leu Ala Asn Asp
130                 135                 140

Tyr Asn Lys Arg Thr Met Gly Leu Leu Val Ser Asp Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
            195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val
305
```

<210> SEQ ID NO 4
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 4

```
Met Asp Tyr Gly Gly Ala Leu Ser Ala Val Gly Leu Phe Gln Thr Ser
1               5                   10                  15
```

```
Tyr Thr Leu Glu Asn Asn Gly Ser Val Ile Cys Ile Pro Asn Asn Gly
             20                  25                  30

Gln Cys Phe Cys Leu Ala Trp Leu Lys Ser Asn Gly Thr Asn Ala Glu
         35                  40                  45

Lys Leu Ala Ala Asn Ile Leu Gln Trp Ile Ser Phe Ala Leu Ser Ala
 50                  55                  60

Leu Cys Leu Met Phe Tyr Gly Tyr Gln Thr Trp Lys Ser Thr Cys Gly
 65                  70                  75                  80

Trp Glu Glu Ile Tyr Val Ala Thr Ile Ser Met Ile Lys Phe Ile Ile
                 85                  90                  95

Glu Tyr Phe His Ser Phe Asp Glu Pro Ala Val Ile Tyr Ser Ser Asn
                100                 105                 110

Gly Asn Lys Thr Lys Trp Leu Arg Tyr Ala Ser Trp Leu Leu Thr Cys
            115                 120                 125

Pro Val Ile Leu Ile Arg Leu Ser Asn Leu Thr Gly Leu Ala Asn Asp
        130                 135                 140

Tyr Asn Lys Arg Thr Met Gly Leu Leu Val Ser Asn Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
                180                 185                 190

Ala Lys Val Tyr Ile Glu Ala Tyr His Thr Val Pro Lys Gly Arg Cys
            195                 200                 205

Arg Gln Val Val Thr Gly Met Ala Trp Leu Phe Phe Val Ser Trp Gly
        210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val
305

<210> SEQ ID NO 5
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 5

Met Ser Arg Arg Pro Trp Leu Leu Ala Leu Ala Leu Ala Val Ala Leu
 1               5                  10                  15

Ala Ala Gly Ser Ala Gly Ala Ser Thr Gly Ser Asp Ala Thr Val Pro
             20                  25                  30

Val Ala Thr Gln Asp Gly Pro Asp Tyr Val Phe His Arg Ala His Glu
         35                  40                  45

Arg Met Leu Phe Gln Thr Ser Tyr Thr Leu Glu Asn Asn Gly Ser Val
 50                  55                  60
```

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Asn Ile Leu Gln Trp
            85                  90                  95

Ile Ser Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
                115                 120                 125

Ser Met Ile Lys Phe Ile Ile Glu Tyr Phe His Ser Phe Asp Glu Pro
            130                 135                 140

Ala Val Ile Tyr Ser Ser Asn Gly Asn Lys Thr Lys Trp Leu Arg Tyr
145                 150                 155                 160

Ala Ser Trp Leu Leu Thr Thr Pro Val Ile Leu Ile Arg Leu Ser Asn
                165                 170                 175

Leu Thr Gly Leu Ala Asn Asp Tyr Asn Lys Arg Thr Met Gly Leu Leu
                180                 185                 190

Val Ser Asp Ile Gly Thr Ile Val Trp Gly Thr Thr Ala Ala Leu Ser
            195                 200                 205

Lys Gly Tyr Val Arg Val Ile Phe Phe Leu Met Gly Leu Cys Tyr Gly
210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
                260                 265                 270

Pro Glu Gly Phe Gly Val Leu Ser Lys Tyr Gly Ser Asn Val Gly His
                275                 280                 285

Thr Ile Ile Asp Leu Met Ser Lys Gln Cys Trp Gly Leu Leu Gly His
            290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 6
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 6

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

```
Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Ala Pro Val Ile Leu Ile Arg Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Lys Tyr Gly Ser Asn Val Gly His
        275                 280                 285

Thr Ile Ile Asp Leu Met Ser Lys Gln Cys Trp Gly Leu Leu Gly His
    290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 7
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 7

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95
```

```
Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Ser Pro Val Ile Leu Ile Arg Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Lys Tyr Gly Ser Asn Val Gly His
        275                 280                 285

Thr Ile Ile Asp Leu Met Ser Lys Gln Cys Trp Gly Leu Leu Gly His
    290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 8
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 8

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110
```

Thr Trp Lys Ser Thr Cys Gly Trp Glu Glu Ile Tyr Val Ala Thr Ile
            115                 120                 125

Ser Met Ile Lys Phe Ile Ile Glu Tyr Phe His Ser Phe Asp Glu Pro
        130                 135                 140

Ala Val Ile Tyr Ser Ser Asn Gly Asn Lys Thr Lys Trp Leu Arg Tyr
145                 150                 155                 160

Ala Ser Trp Leu Leu Thr Thr Pro Val Ile Leu Ile Arg Leu Ser Asn
                165                 170                 175

Leu Thr Gly Leu Ala Asn Asp Tyr Asn Lys Arg Thr Met Gly Leu Leu
            180                 185                 190

Val Ser Ala Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Lys Tyr Gly Ser Asn Val Gly His
        275                 280                 285

Thr Ile Ile Asp Leu Met Ser Lys Gln Cys Trp Gly Leu Leu Gly His
            290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 9
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 9

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

```
Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Thr Pro Val Ile Leu Ile Arg Leu Ser Asn
                165                 170                 175

Leu Thr Gly Leu Ala Asn Asp Tyr Asn Lys Arg Thr Met Gly Leu Leu
                180                 185                 190

Val Ser Asn Ile Gly Thr Ile Val Trp Gly Thr Thr Ala Ala Leu Ser
                195                 200                 205

Lys Gly Tyr Val Arg Val Ile Phe Phe Leu Met Gly Leu Cys Tyr Gly
210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
                260                 265                 270

Pro Glu Gly Phe Gly Val Leu Ser Lys Tyr Gly Ser Asn Val Gly His
                275                 280                 285

Thr Ile Ile Asp Leu Met Ser Lys Gln Cys Trp Gly Leu Leu Gly His
    290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
                340                 345

<210> SEQ ID NO 10
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 10

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
    130                 135                 140
```

```
Ala Val Ile Tyr Ser Ser Asn Gly Asn Lys Thr Lys Trp Leu Arg Tyr
145                 150                 155                 160

Ala Ser Trp Leu Leu Thr Ala Pro Val Ile Leu Ile Arg Leu Ser Asn
                165                 170                 175

Leu Thr Gly Leu Ala Asn Asp Tyr Asn Lys Arg Thr Met Gly Leu Leu
            180                 185                 190

Val Ser Ala Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Lys Tyr Gly Ser Asn Val Gly His
        275                 280                 285

Thr Ile Ile Asp Leu Met Ser Lys Gln Cys Trp Gly Leu Leu Gly His
    290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 11
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 11

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160
```

```
Ala Ser Trp Leu Leu Thr Ala Pro Val Ile Leu Ile Arg Leu Ser Asn
            165                 170                 175

Leu Thr Gly Leu Ala Asn Asp Tyr Asn Lys Arg Thr Met Gly Leu Leu
        180                 185                 190

Val Ser Asn Ile Gly Thr Ile Val Trp Gly Thr Thr Ala Ala Leu Ser
            195                 200                 205

Lys Gly Tyr Val Arg Val Ile Phe Phe Leu Met Gly Leu Cys Tyr Gly
        210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
            245                 250                 255

Leu Phe Phe Val Ser Trp Gly Met Phe Pro Ile Leu Phe Ile Leu Gly
        260                 265                 270

Pro Glu Gly Phe Gly Val Leu Ser Lys Tyr Gly Ser Asn Val Gly His
            275                 280                 285

Thr Ile Ile Asp Leu Met Ser Lys Gln Cys Trp Gly Leu Leu Gly His
        290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
            325                 330                 335

Thr Leu Val Glu Asp Glu Ala Glu Ala Gly Ala Val
        340                 345

<210> SEQ ID NO 12
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 12

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
            85                  90                  95

Ile Ser Phe Ala Leu Ser Ala Leu Cys Leu Met Phe Tyr Gly Tyr Gln
        100                 105                 110

Thr Trp Lys Ser Thr Cys Gly Trp Glu Glu Ile Tyr Val Ala Thr Ile
    115                 120                 125

Ser Met Ile Lys Phe Ile Ile Glu Tyr Phe His Ser Phe Asp Glu Pro
130                 135                 140

Ala Val Ile Tyr Ser Ser Asn Gly Asn Lys Thr Lys Trp Leu Arg Tyr
145                 150                 155                 160

Ala Ser Trp Leu Leu Thr Ser Pro Val Ile Leu Ile Arg Leu Ser Asn
            165                 170                 175
```

```
Leu Thr Gly Leu Ala Asn Asp Tyr Asn Lys Arg Thr Met Gly Leu Leu
                180                 185                 190

Val Ser Ala Ile Gly Thr Ile Val Trp Gly Thr Thr Ala Ala Leu Ser
            195                 200                 205

Lys Gly Tyr Val Arg Val Ile Phe Phe Leu Met Gly Leu Cys Tyr Gly
        210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Lys Tyr Gly Ser Asn Val Gly His
        275                 280                 285

Thr Ile Ile Asp Leu Met Ser Lys Gln Cys Trp Gly Leu Leu Gly His
        290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 13
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 13

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
130                 135                 140

Ala Val Ile Tyr Ser Ser Asn Gly Asn Lys Thr Lys Trp Leu Arg Tyr
145                 150                 155                 160

Ala Ser Trp Leu Leu Thr Ser Pro Val Ile Leu Ile Arg Leu Ser Asn
                165                 170                 175

Leu Thr Gly Leu Ala Asn Asp Tyr Asn Lys Arg Thr Met Gly Leu Leu
            180                 185                 190
```

```
Val Ser Asn Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Lys Tyr Gly Ser Asn Val Gly His
        275                 280                 285

Thr Ile Ile Asp Leu Met Ser Lys Gln Cys Trp Gly Leu Leu Gly His
290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 14
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 14

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Thr
        115                 120                 125

Pro Val Ile Leu Ile Arg Leu Ser Asn Leu Thr Gly Leu Ala Asn Asp
130                 135                 140

Tyr Asn Lys Arg Thr Met Gly Leu Leu Val Ser Asp Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
        195                 200                 205
```

```
Arg Gln Val Val Thr Gly Met Ala Trp Leu Phe Phe Val Ser Trp Gly
    210                 215                 220
Met Phe Pro Ile Leu Phe Ile Leu Gly Pro Glu Gly Phe Gly Val Leu
225                 230                 235                 240
Ser Lys Tyr Gly Ser Asn Val Gly His Thr Ile Ile Asp Leu Met Ser
                245                 250                 255
Lys Gln Cys Trp Gly Leu Leu Gly His Tyr Leu Arg Val Leu Ile His
            260                 265                 270
Glu His Ile Leu Ile His Gly Asp Ile Arg Lys Thr Thr Lys Leu Asn
                275                 280                 285
Ile Gly Gly Thr Glu Ile Glu Val Glu Thr Leu Val Glu Asp Glu Ala
290                 295                 300
Glu Ala Gly Ala Val
305
```

<210> SEQ ID NO 15
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 15

```
Met Asp Tyr Gly Gly Ala Leu Ser Ala Val Gly Leu Phe Gln Thr Ser
1               5                   10                  15
Tyr Thr Leu Glu Asn Asn Gly Ser Val Ile Cys Ile Pro Asn Asn Gly
                20                  25                  30
Gln Cys Phe Cys Leu Ala Trp Leu Lys Ser Asn Gly Thr Asn Ala Glu
            35                  40                  45
Lys Leu Ala Ala Asn Ile Leu Gln Trp Ile Ser Phe Ala Leu Ser Ala
        50                  55                  60
Leu Cys Leu Met Phe Tyr Gly Tyr Gln Thr Trp Lys Ser Thr Cys Gly
65                  70                  75                  80
Trp Glu Glu Ile Tyr Val Ala Thr Ile Ser Met Ile Lys Phe Ile Ile
                85                  90                  95
Glu Tyr Phe His Ser Phe Asp Glu Pro Ala Val Ile Tyr Ser Ser Asn
            100                 105                 110
Gly Asn Lys Thr Lys Trp Leu Arg Tyr Ala Ser Trp Leu Leu Thr Ala
        115                 120                 125
Pro Val Ile Leu Ile Arg Leu Ser Asn Leu Thr Gly Leu Ala Asn Asp
    130                 135                 140
Tyr Asn Lys Arg Thr Met Gly Leu Leu Val Ser Asp Ile Gly Thr Ile
145                 150                 155                 160
Val Trp Gly Thr Thr Ala Ala Leu Ser Lys Gly Tyr Val Arg Val Ile
                165                 170                 175
Phe Phe Leu Met Gly Leu Cys Tyr Gly Ile Tyr Thr Phe Phe Asn Ala
            180                 185                 190
Ala Lys Val Tyr Ile Glu Ala Tyr His Thr Val Pro Lys Gly Arg Cys
        195                 200                 205
Arg Gln Val Val Thr Gly Met Ala Trp Leu Phe Phe Val Ser Trp Gly
    210                 215                 220
Met Phe Pro Ile Leu Phe Ile Leu Gly Pro Glu Gly Phe Gly Val Leu
225                 230                 235                 240
Ser Lys Tyr Gly Ser Asn Val Gly His Thr Ile Ile Asp Leu Met Ser
                245                 250                 255
```

```
Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val
305

<210> SEQ ID NO 16
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 16

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Ser
        115                 120                 125

Pro Val Ile Leu Ile Arg Leu Ser Asn Leu Thr Gly Leu Ala Asn Asp
130                 135                 140

Tyr Asn Lys Arg Thr Met Gly Leu Leu Val Ser Asp Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300
```

Glu Ala Gly Ala Val
305

<210> SEQ ID NO 17
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 17

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
    50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Thr
        115                 120                 125

Pro Val Ile Leu Ile Arg Leu Ser Asn Leu Thr Gly Leu Ala Asn Asp
    130                 135                 140

Tyr Asn Lys Arg Thr Met Gly Leu Leu Val Ser Ala Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val
305

<210> SEQ ID NO 18
<211> LENGTH: 309
<212> TYPE: PRT
<213> ORGANISM: Artificial sequence
<220> FEATURE:

<223> OTHER INFORMATION: Synthetic polypeptide

<400> SEQUENCE: 18

```
Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
    50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Thr
        115                 120                 125

Pro Val Ile Leu Ile Arg Leu Ser Asn Leu Thr Gly Leu Ala Asn Asp
    130                 135                 140

Tyr Asn Lys Arg Thr Met Gly Leu Leu Val Ser Asn Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val
305
```

<210> SEQ ID NO 19
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 19

```
Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30
```

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
 50                  55                  60

Leu Cys Leu Met Phe Tyr Gly Tyr Gln Thr Trp Lys Ser Thr Cys Gly
 65                  70                  75                  80

Trp Glu Glu Ile Tyr Val Ala Thr Ile Ser Met Ile Lys Phe Ile Ile
                 85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Ala
            115                 120                 125

Pro Val Ile Leu Ile Arg Leu Ser Asn Leu Thr Gly Leu Ala Asn Asp
130                 135                 140

Tyr Asn Lys Arg Thr Met Gly Leu Leu Val Ser Ala Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
            195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val
305

<210> SEQ ID NO 20
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 20

Met Asp Tyr Gly Gly Ala Leu Ser Ala Val Gly Leu Phe Gln Thr Ser
 1               5                  10                  15

Tyr Thr Leu Glu Asn Asn Gly Ser Val Ile Cys Ile Pro Asn Asn Gly
             20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
 50                  55                  60

Leu Cys Leu Met Phe Tyr Gly Tyr Gln Thr Trp Lys Ser Thr Cys Gly
 65                  70                  75                  80

```
Trp Glu Glu Ile Tyr Val Ala Thr Ile Ser Met Ile Lys Phe Ile Ile
                 85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Ala
        115                 120                 125

Pro Val Ile Leu Ile Arg Leu Ser Asn Leu Thr Gly Leu Ala Asn Asp
    130                 135                 140

Tyr Asn Lys Arg Thr Met Gly Leu Leu Val Ser Asn Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val
305

<210> SEQ ID NO 21
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 21

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
    50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Ser
        115                 120                 125
```

```
Pro Val Ile Leu Ile Arg Leu Ser Asn Leu Thr Gly Leu Ala Asn Asp
            130                 135                 140

Tyr Asn Lys Arg Thr Met Gly Leu Leu Val Ser Ala Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
                180                 185                 190

Ala Lys Val Tyr Ile Glu Ala Tyr His Thr Val Pro Lys Gly Arg Cys
            195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Gly Thr Leu Val Glu Asp Glu Ala
290                 295                 300

Glu Ala Gly Ala Val
305

<210> SEQ ID NO 22
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 22

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Ser
        115                 120                 125

Pro Val Ile Leu Ile Arg Leu Ser Asn Leu Thr Gly Leu Ala Asn Asp
            130                 135                 140

Tyr Asn Lys Arg Thr Met Gly Leu Leu Val Ser Asn Ile Gly Thr Ile
145                 150                 155                 160

Val Trp Gly Thr Thr Ala Ala Leu Ser Lys Gly Tyr Val Arg Val Ile
                165                 170                 175
```

```
Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val
305

<210> SEQ ID NO 23
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 23

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ser Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Ser Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Lys Trp Leu Arg Tyr Ala Ser Trp Leu Leu Thr Cys
        115                 120                 125

Pro Val Ile Leu Ile Arg Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220
```

```
Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
            245                 250                 255

Lys Gln Cys Trp Gly Leu Leu Gly His Tyr Leu Arg Val Leu Ile His
        260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
        290                 295                 300

Glu Ala Gly Ala Val Pro
305                 310

<210> SEQ ID NO 24
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 24

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ser Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Ser Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Lys Trp Leu Arg Tyr Ala Ser Trp Leu Leu Thr Cys
        115                 120                 125

Pro Val Ile Leu Ile Arg Leu Ser Asn Leu Thr Gly Leu Ser Asn Asp
    130                 135                 140

Tyr Ser Arg Arg Thr Met Gly Leu Leu Val Ser Asn Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
            245                 250                 255

Lys Gln Cys Trp Gly Leu Leu Gly His Tyr Leu Arg Val Leu Ile His
        260                 265                 270
```

```
Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 25
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 25

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ser Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Ser Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Lys Trp Leu Arg Tyr Ala Ser Trp Leu Leu Thr Thr
            115                 120                 125

Pro Val Ile Leu Ile Arg Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
    290                 295                 300

Glu Ala Gly Ala Val Pro
305                 310
```

<210> SEQ ID NO 26
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 26

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ser Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Ser Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Lys Trp Leu Arg Tyr Ala Ser Trp Leu Leu Thr Ala
        115                 120                 125

Pro Val Ile Leu Ile Arg Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310
```

<210> SEQ ID NO 27
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 27

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
                35                  40                  45

Gln Thr Ala Ser Asn Val Leu Gln Trp Leu Ser Ala Gly Phe Ser Ile
            50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Ser Met Val Lys Val Ile Leu
                85                  90                  95

Glu Phe Phe Phe Ser Phe Lys Asn Pro Ser Met Leu Tyr Leu Ala Thr
                100                 105                 110

Gly His Arg Val Lys Trp Leu Arg Tyr Ala Ser Trp Leu Leu Thr Ser
            115                 120                 125

Pro Val Ile Leu Ile Arg Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
290                 295                 300

Glu Ala Gly Ala Val Pro
305                 310

<210> SEQ ID NO 28
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 28

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala

```
                    35                   40                    45
Gln Thr Ala Ser Asn Val Leu Gln Trp Leu Ser Ala Gly Phe Ser Ile
             50                   55                   60

Leu Leu Leu Met Phe Tyr Ala Tyr Gln Thr Trp Lys Ser Thr Cys Gly
 65                  70                   75                   80

Trp Glu Glu Ile Tyr Val Cys Ala Ile Ser Met Val Lys Val Ile Leu
                     85                   90                   95

Glu Phe Phe Ser Phe Lys Asn Pro Ser Met Leu Tyr Leu Ala Thr
            100                  105                  110

Gly His Arg Val Lys Trp Leu Arg Tyr Ala Ser Trp Leu Leu Thr Thr
            115                  120                  125

Pro Val Ile Leu Ile Arg Leu Ser Asn Leu Thr Gly Leu Ser Asn Asp
            130                  135                  140

Tyr Ser Arg Arg Thr Met Gly Leu Leu Val Ser Ala Ile Gly Thr Ile
145                  150                  155                  160

Val Trp Gly Ala Thr Ser Ala Met Ala Thr Gly Tyr Val Lys Val Ile
                     165                  170                  175

Phe Phe Cys Leu Gly Leu Cys Tyr Gly Ala Asn Thr Phe Phe His Ala
                180                  185                  190

Ala Lys Ala Tyr Ile Glu Gly Tyr His Thr Val Pro Lys Gly Arg Cys
            195                  200                  205

Arg Gln Val Val Thr Gly Met Ala Trp Leu Phe Phe Val Ser Trp Gly
210                  215                  220

Met Phe Pro Ile Leu Phe Ile Leu Gly Pro Glu Gly Phe Gly Val Leu
225                  230                  235                  240

Ser Lys Tyr Gly Ser Asn Val Gly His Thr Ile Ile Asp Leu Met Ser
                245                  250                  255

Lys Gln Cys Trp Gly Leu Leu Gly His Tyr Leu Arg Val Leu Ile His
                260                  265                  270

Glu His Ile Leu Ile His Gly Asp Ile Arg Lys Thr Thr Lys Leu Asn
            275                  280                  285

Ile Gly Gly Thr Glu Ile Glu Val Glu Thr Leu Val Glu Asp Glu Ala
            290                  295                  300

Glu Ala Gly Ala Val Pro
305              310

<210> SEQ ID NO 29
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 29

Met Asp Tyr Gly Gly Ala Leu Ser Ala Val Gly Arg Glu Leu Leu Phe
 1                5                  10                   15

Val Thr Asn Pro Val Val Asn Gly Ser Val Leu Val Pro Glu Asp
             20                   25                   30

Gln Cys Tyr Cys Ala Gly Trp Ile Glu Ser Arg Gly Thr Asn Gly Ala
             35                   40                   45

Gln Thr Ala Ser Asn Val Leu Gln Trp Leu Ser Ala Gly Phe Ser Ile
             50                   55                   60

Leu Leu Leu Met Phe Tyr Ala Tyr Gln Thr Trp Lys Ser Thr Cys Gly
 65                  70                   75                   80

Trp Glu Glu Ile Tyr Val Cys Ala Ile Ser Met Val Lys Val Ile Leu
```

```
                85                  90                  95
Glu Phe Phe Ser Phe Lys Asn Pro Ser Met Leu Tyr Leu Ala Thr
            100                 105                 110
Gly His Arg Val Lys Trp Leu Arg Tyr Ala Ser Trp Leu Leu Thr Thr
            115                 120                 125
Pro Val Ile Leu Ile Arg Leu Ser Asn Leu Thr Gly Leu Ser Asn Asp
130                 135                 140
Tyr Ser Arg Arg Thr Met Gly Leu Leu Val Ser Asn Ile Gly Thr Ile
145                 150                 155                 160
Val Trp Gly Ala Thr Ser Ala Met Ala Thr Gly Tyr Val Lys Val Ile
                165                 170                 175
Phe Phe Cys Leu Gly Leu Cys Tyr Gly Ala Asn Thr Phe Phe His Ala
                180                 185                 190
Ala Lys Ala Tyr Ile Glu Gly Tyr His Thr Val Pro Lys Gly Arg Cys
                195                 200                 205
Arg Gln Val Val Thr Gly Met Ala Trp Leu Phe Phe Val Ser Trp Gly
            210                 215                 220
Met Phe Pro Ile Leu Phe Ile Leu Gly Pro Glu Gly Phe Gly Val Leu
225                 230                 235                 240
Ser Lys Tyr Gly Ser Asn Val Gly His Thr Ile Ile Asp Leu Met Ser
                245                 250                 255
Lys Gln Cys Trp Gly Leu Leu Gly His Tyr Leu Arg Val Leu Ile His
                260                 265                 270
Glu His Ile Leu Ile His Gly Asp Ile Arg Lys Thr Thr Lys Leu Asn
            275                 280                 285
Ile Gly Gly Thr Glu Ile Glu Val Glu Thr Leu Val Glu Asp Glu Ala
            290                 295                 300
Glu Ala Gly Ala Val Pro
305                 310

<210> SEQ ID NO 30
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 30

Met Asp Tyr Gly Gly Ala Leu Ser Ala Val Gly Arg Glu Leu Leu Phe
1               5                   10                  15
Val Thr Asn Pro Val Val Asn Gly Ser Val Leu Val Pro Glu Asp
            20                  25                  30
Gln Cys Tyr Cys Ala Gly Trp Ile Glu Ser Arg Gly Thr Asn Gly Ala
            35                  40                  45
Gln Thr Ala Ser Asn Val Leu Gln Trp Leu Ala Gly Phe Ser Ile
50                  55                  60
Leu Leu Leu Met Phe Tyr Ala Tyr Gln Thr Trp Lys Ser Thr Cys Gly
65                  70                  75                  80
Trp Glu Glu Ile Tyr Val Cys Ala Ile Ser Met Val Lys Val Ile Leu
                85                  90                  95
Glu Phe Phe Ser Phe Lys Asn Pro Ser Met Leu Tyr Leu Ala Thr
            100                 105                 110
Gly His Arg Val Lys Trp Leu Arg Tyr Ala Ser Trp Leu Leu Thr Ala
            115                 120                 125
Pro Val Ile Leu Ile Arg Leu Ser Asn Leu Thr Gly Leu Ser Asn Asp
```

```
                130                 135                 140
Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
                195                 200                 205

Arg Gln Val Val Thr Gly Met Ala Trp Leu Phe Phe Val Ser Trp Gly
                210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ala
                290                 295                 300

Glu Ala Gly Ala Val Pro
305                 310

<210> SEQ ID NO 31
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 31

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
                20                  25                  30

Gln Cys Tyr Cys Ala Gly Trp Ile Glu Ser Arg Gly Thr Asn Gly Ala
                35                  40                  45

Gln Thr Ala Ser Asn Val Leu Gln Trp Leu Ser Ala Gly Phe Ser Ile
                50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Ser Met Val Lys Val Ile Leu
                85                  90                  95

Glu Phe Phe Phe Ser Phe Lys Asn Pro Ser Met Leu Tyr Leu Ala Thr
                100                 105                 110

Gly His Arg Val Lys Trp Leu Arg Tyr Ala Ser Trp Leu Leu Thr Ala
                115                 120                 125

Pro Val Ile Leu Ile Arg Leu Ser Asn Leu Thr Gly Leu Ser Asn Asp
                130                 135                 140

Tyr Ser Arg Arg Thr Met Gly Leu Leu Val Ser Asn Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
```

```
            180             185              190
Ala Lys Ala Tyr Ile Glu Gly Tyr His Thr Val Pro Lys Gly Arg Cys
            195             200              205

Arg Gln Val Val Thr Gly Met Ala Trp Leu Phe Phe Val Ser Trp Gly
            210             215              220

Met Phe Pro Ile Leu Phe Ile Leu Gly Pro Glu Gly Phe Gly Val Leu
225             230             235              240

Ser Lys Tyr Gly Ser Asn Val Gly His Thr Ile Ile Asp Leu Met Ser
            245             250              255

Lys Gln Cys Trp Gly Leu Leu Gly His Tyr Leu Arg Val Leu Ile His
            260             265              270

Glu His Ile Leu Ile His Gly Asp Ile Arg Lys Thr Thr Lys Leu Asn
            275             280              285

Ile Gly Gly Thr Glu Ile Glu Val Glu Thr Leu Val Glu Asp Glu Ala
            290             295              300

Glu Ala Gly Ala Val Pro
305             310

<210> SEQ ID NO 32
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 32

Met Asp Tyr Gly Gly Ala Leu Ser Ala Val Gly Arg Glu Leu Leu Phe
1               5               10               15

Val Thr Asn Pro Val Val Asn Gly Ser Val Leu Val Pro Glu Asp
            20              25              30

Gln Cys Tyr Cys Ala Gly Trp Ile Glu Ser Arg Gly Thr Asn Gly Ala
            35              40              45

Gln Thr Ala Ser Asn Val Leu Gln Trp Leu Ser Ala Gly Phe Ser Ile
            50              55              60

Leu Leu Leu Met Phe Tyr Ala Tyr Gln Thr Trp Lys Ser Thr Cys Gly
65              70              75               80

Trp Glu Glu Ile Tyr Val Cys Ala Ile Ser Met Val Lys Val Ile Leu
                85              90               95

Glu Phe Phe Phe Ser Phe Lys Asn Pro Ser Met Leu Tyr Leu Ala Thr
            100             105              110

Gly His Arg Val Lys Trp Leu Arg Tyr Ala Ser Trp Leu Leu Thr Ser
            115             120              125

Pro Val Ile Leu Ile Arg Leu Ser Asn Leu Thr Gly Leu Ser Asn Asp
            130             135              140

Tyr Ser Arg Arg Thr Met Gly Leu Leu Val Ser Ala Ile Gly Thr Ile
145             150             155              160

Val Trp Gly Ala Thr Ser Ala Met Ala Thr Gly Tyr Val Lys Val Ile
            165             170              175

Phe Phe Cys Leu Gly Leu Cys Tyr Gly Ala Asn Thr Phe Phe His Ala
            180             185              190

Ala Lys Ala Tyr Ile Glu Gly Tyr His Thr Val Pro Lys Gly Arg Cys
            195             200              205

Arg Gln Val Val Thr Gly Met Ala Trp Leu Phe Phe Val Ser Trp Gly
            210             215              220

Met Phe Pro Ile Leu Phe Ile Leu Gly Pro Glu Gly Phe Gly Val Leu
```

```
                225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ala
                290                 295                 300

Glu Ala Gly Ala Val Pro
305                 310

<210> SEQ ID NO 33
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 33

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
                20                  25                  30

Gln Cys Tyr Cys Ala Gly Trp Ile Glu Ser Arg Gly Thr Asn Gly Ala
                35                  40                  45

Gln Thr Ala Ser Asn Val Leu Gln Trp Leu Ser Ala Gly Phe Ser Ile
50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Ser Met Val Lys Val Ile Leu
                85                  90                  95

Glu Phe Phe Phe Ser Phe Lys Asn Pro Ser Met Leu Tyr Leu Ala Thr
                100                 105                 110

Gly His Arg Val Lys Trp Leu Arg Tyr Ala Ser Trp Leu Leu Thr Ser
                115                 120                 125

Pro Val Ile Leu Ile Arg Leu Ser Asn Leu Thr Gly Leu Ser Asn Asp
                130                 135                 140

Tyr Ser Arg Arg Thr Met Gly Leu Leu Val Ser Asn Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
                195                 200                 205

Arg Gln Val Val Thr Gly Met Ala Trp Leu Phe Phe Val Ser Trp Gly
                210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
```

```
                275                 280                 285

Ile Gly Gly Thr Glu Ile Glu Val Glu Thr Leu Val Glu Asp Glu Ala
            290                 295                 300

Glu Ala Gly Ala Val Pro
305             310

<210> SEQ ID NO 34
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 34

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
130                 135                 140

Ala Val Ile Tyr Ser Ser Asn Gly Asn Lys Thr Lys Trp Leu Arg Tyr
145                 150                 155                 160

Ala Ser Trp Leu Leu Thr Cys Pro Val Leu Leu Ile Arg Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Lys Tyr Gly Ser Asn Ile Gly His
        275                 280                 285

Ser Ile Leu Asp Leu Ile Ala Lys Gln Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
```

Thr Leu Val Ala Glu Glu Glu Asp
            340

<210> SEQ ID NO 35
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 35

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Cys Pro Val Leu Leu Ile Arg Leu Ser Asn
                165                 170                 175

Leu Thr Gly Leu Lys Asp Asp Tyr Ser Lys Arg Thr Met Gly Leu Leu
            180                 185                 190

Val Ser Asn Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Lys Tyr Gly Ser Asn Ile Gly His
        275                 280                 285

Ser Ile Leu Asp Leu Ile Ala Lys Gln Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp

<210> SEQ ID NO 36
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 36

```
Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
    50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Cys
        115                 120                 125

Pro Val Leu Leu Ile Arg Leu Ser Asn Leu Thr Gly Leu Lys Asp Asp
    130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
    210                 215                 220

Met Phe Pro Val Leu Phe Leu Gly Thr Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Glu His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu
    290                 295                 300

Asp
305
```

<210> SEQ ID NO 37
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 37

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
    50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Cys
        115                 120                 125

Pro Val Leu Leu Ile Arg Leu Ser Asn Leu Thr Gly Leu Lys Asp Asp
130                 135                 140

Tyr Ser Lys Arg Thr Met Gly Leu Leu Val Ser Asn Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
210                 215                 220

Met Phe Pro Val Leu Phe Leu Leu Gly Thr Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Glu His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu
    290                 295                 300

Asp
305

<210> SEQ ID NO 38
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 38

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

```
Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
 50                  55                  60

Ile Cys Ile Pro Asn Asn Gly Gln Cys Phe Cys Leu Ala Trp Leu Lys
 65                  70                  75                  80

Ser Asn Gly Thr Asn Ala Glu Lys Leu Ala Ala Asn Ile Leu Gln Trp
                 85                  90                  95

Ile Ser Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
            115                 120                 125

Ser Met Ile Lys Phe Ile Ile Glu Tyr Phe His Ser Phe Asp Glu Pro
130                 135                 140

Ala Val Ile Tyr Ser Ser Asn Gly Asn Lys Thr Lys Trp Leu Arg Tyr
145                 150                 155                 160

Ala Ser Trp Leu Leu Thr Thr Pro Val Leu Leu Ile Arg Leu Ser Asn
                165                 170                 175

Leu Thr Gly Leu Lys Asp Asp Tyr Ser Lys Arg Thr Met Gly Leu Leu
                180                 185                 190

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
            210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
                260                 265                 270

Thr Glu Gly Phe Gly His Ile Ser Lys Tyr Gly Ser Asn Ile Gly His
            275                 280                 285

Ser Ile Leu Asp Leu Ile Ala Lys Gln Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 39
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 39

Met Ser Arg Arg Pro Trp Leu Leu Ala Leu Ala Leu Ala Val Ala Leu
 1               5                  10                  15

Ala Ala Gly Ser Ala Gly Ala Ser Thr Gly Ser Asp Ala Thr Val Pro
                 20                  25                  30

Val Ala Thr Gln Asp Gly Pro Asp Tyr Val Phe His Arg Ala His Glu
            35                  40                  45
```

Arg Met Leu Phe Gln Thr Ser Tyr Thr Leu Glu Asn Asn Gly Ser Val
50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Ile Tyr Val Ala Thr Ile
            115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Ala Pro Val Leu Leu Ile Arg Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
    195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Lys Tyr Gly Ser Asn Ile Gly His
    275                 280                 285

Ser Ile Leu Asp Leu Ile Ala Lys Gln Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 40
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 40

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
            85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
            115                 120                 125

Ser Met Ile Lys Phe Ile Glu Tyr Phe His Ser Phe Asp Glu Pro
            130                 135                 140

Ala Val Ile Tyr Ser Ser Asn Gly Asn Lys Thr Lys Trp Leu Arg Tyr
145                 150                 155                 160

Ala Ser Trp Leu Leu Thr Ser Pro Val Leu Leu Ile Arg Leu Ser Asn
            165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
            260                 265                 270

Thr Glu Gly Phe Gly His Ile Ser Lys Tyr Gly Ser Asn Ile Gly His
            275                 280                 285

Ser Ile Leu Asp Leu Ile Ala Lys Gln Met Trp Gly Val Leu Gly Asn
            290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
            325                 330                 335

Thr Leu Val Ala Glu Glu Glu Asp
            340

<210> SEQ ID NO 41
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 41

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
            50                  55                  60

Ile Cys Ile Pro Asn Asn Gly Gln Cys Phe Cys Leu Ala Trp Leu Lys
65                  70                  75                  80

```
Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Thr Pro Val Leu Leu Ile Arg Leu Ser Asn
                165                 170                 175

Leu Thr Gly Leu Lys Asp Asp Tyr Ser Lys Arg Thr Met Gly Leu Leu
            180                 185                 190

Val Ser Ala Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Lys Tyr Gly Ser Asn Ile Gly His
        275                 280                 285

Ser Ile Leu Asp Leu Ile Ala Lys Gln Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Glu Met Glu Val Glu
                325                 330                 335

Thr Leu Val Ala Glu Glu Glu Asp
            340

<210> SEQ ID NO 42
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 42

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95
```

Ile Ser Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Thr Pro Val Leu Leu Ile Arg Leu Ser Asn
                165                 170                 175

Leu Thr Gly Leu Lys Asp Asp Tyr Ser Lys Arg Thr Met Gly Leu Leu
            180                 185                 190

Val Ser Asn Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Lys Tyr Gly Ser Asn Ile Gly His
        275                 280                 285

Ser Ile Leu Asp Leu Ile Ala Lys Gln Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp
            340

<210> SEQ ID NO 43
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 43

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
            115                 120                 125

Ser Met Ile Lys Phe Ile Ile Glu Tyr Phe His Ser Phe Asp Glu Pro
        130                 135                 140

Ala Val Ile Tyr Ser Ser Asn Gly Asn Lys Thr Lys Trp Leu Arg Tyr
145                 150                 155                 160

Ala Ser Trp Leu Leu Thr Ala Pro Val Leu Ile Arg Leu Ser Asn
                165                 170                 175

Leu Thr Gly Leu Lys Asp Asp Tyr Ser Lys Arg Thr Met Gly Leu Leu
                180                 185                 190

Val Ser Ala Val Gly Cys Ile Val Trp Gly Ala Thr Ser Ala Met Cys
                195                 200                 205

Thr Gly Trp Thr Lys Ile Leu Phe Phe Leu Ile Ser Leu Ser Tyr Gly
        210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
                260                 265                 270

Thr Glu Gly Phe Gly His Ile Ser Lys Tyr Gly Ser Asn Ile Gly His
                275                 280                 285

Ser Ile Leu Asp Leu Ile Ala Lys Gln Met Trp Gly Val Leu Gly Asn
        290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
                340

<210> SEQ ID NO 44
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 44

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
            115                 120                 125

Ser Met Ile Lys Phe Ile Ile Glu Tyr Phe His Ser Phe Asp Glu Pro
130                 135                 140

Ala Val Ile Tyr Ser Ser Asn Gly Asn Lys Thr Lys Trp Leu Arg Tyr
145                 150                 155                 160

Ala Ser Trp Leu Leu Thr Ala Pro Val Leu Leu Ile Arg Leu Ser Asn
            165                 170                 175

Leu Thr Gly Leu Lys Asp Asp Tyr Ser Lys Arg Thr Met Gly Leu Leu
            180                 185                 190

Val Ser Asn Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
                260                 265                 270

Thr Glu Gly Phe Gly His Ile Ser Lys Tyr Gly Ser Asn Ile Gly His
                275                 280                 285

Ser Ile Leu Asp Leu Ile Ala Lys Gln Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 45
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 45

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
            115                 120                 125

Ser Met Ile Lys Phe Ile Ile Glu Tyr Phe His Ser Phe Asp Glu Pro
130                 135                 140

Ala Val Ile Tyr Ser Ser Asn Gly Asn Lys Thr Lys Trp Leu Arg Tyr
145                 150                 155                 160

Ala Ser Trp Leu Leu Thr Ser Pro Val Leu Ile Arg Leu Ser Asn
            165                 170                 175

Leu Thr Gly Leu Lys Asp Asp Tyr Ser Lys Arg Thr Met Gly Leu Leu
            180                 185                 190

Val Ser Ala Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
            260                 265                 270

Thr Glu Gly Phe Gly His Ile Ser Lys Tyr Gly Ser Asn Ile Gly His
            275                 280                 285

Ser Ile Leu Asp Leu Ile Ala Lys Gln Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
            325                 330                 335

Thr Leu Val Ala Glu Glu Asp
            340

<210> SEQ ID NO 46
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 46

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
            85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
130                 135                 140

Ala Val Ile Tyr Ser Ser Asn Gly Asn Lys Thr Lys Trp Leu Arg Tyr
145                 150                 155                 160

```
Ala Ser Trp Leu Leu Thr Ser Pro Val Leu Ile Arg Leu Ser Asn
            165                 170                 175

Leu Thr Gly Leu Lys Asp Asp Tyr Ser Lys Arg Thr Met Gly Leu Leu
        180                 185                 190

Val Ser Asn Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Lys Tyr Gly Ser Asn Ile Gly His
        275                 280                 285

Ser Ile Leu Asp Leu Ile Ala Lys Gln Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp
            340

<210> SEQ ID NO 47
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 47

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
    50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Thr
        115                 120                 125

Pro Val Leu Leu Ile Arg Leu Ser Asn Leu Thr Gly Leu Lys Asp Asp
    130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175
```

```
Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
    210                 215                 220

Met Phe Pro Val Leu Phe Leu Gly Thr Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Glu His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
    290                 295                 300

Asp
305

<210> SEQ ID NO 48
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 48

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Ala
        115                 120                 125

Pro Val Leu Leu Ile Arg Leu Ser Asn Leu Thr Gly Leu Lys Asp Asp
130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
    210                 215                 220
```

```
Met Phe Pro Val Leu Phe Leu Gly Thr Glu Gly Phe Gly His Ile
225                 230                 235                 240

Ser Lys Tyr Gly Ser Asn Ile Gly His Ser Ile Leu Asp Leu Ile Ala
            245                 250                 255

Lys Gln Met Trp Gly Val Leu Gly Asn Tyr Leu Arg Val Lys Ile His
            260                 265                 270

Glu His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
        290                 295                 300

Asp
305
```

<210> SEQ ID NO 49
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 49

```
Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
    50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Ser
        115                 120                 125

Pro Val Leu Leu Ile Arg Leu Ser Asn Leu Thr Gly Leu Lys Asp Asp
    130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
    210                 215                 220

Met Phe Pro Val Leu Phe Leu Gly Thr Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270
```

```
Glu His Ile Leu Leu Tyr Gly Asp Ile Arg Lys Lys Gln Lys Ile Thr
            275                 280                 285

Ile Ala Gly Gln Glu Met Glu Val Glu Thr Leu Val Ala Glu Glu Glu
    290                 295                 300

Asp
305

<210> SEQ ID NO 50
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 50

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
    50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Thr
        115                 120                 125

Pro Val Leu Leu Ile Arg Leu Ser Asn Leu Thr Gly Leu Lys Asp Asp
    130                 135                 140

Tyr Ser Lys Arg Thr Met Gly Leu Leu Val Ser Ala Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
    210                 215                 220

Met Phe Pro Val Leu Phe Leu Gly Thr Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Glu His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
    290                 295                 300

Asp
305
```

```
<210> SEQ ID NO 51
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 51

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Thr
        115                 120                 125

Pro Val Leu Leu Ile Arg Leu Ser Asn Leu Thr Gly Leu Lys Asp Asp
130                 135                 140

Tyr Ser Lys Arg Thr Met Gly Leu Leu Val Ser Asn Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
210                 215                 220

Met Phe Pro Val Leu Phe Leu Leu Gly Thr Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Glu His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
290                 295                 300

Asp
305

<210> SEQ ID NO 52
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 52
```

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Ala
        115                 120                 125

Pro Val Leu Leu Ile Arg Leu Ser Asn Leu Thr Gly Leu Lys Asp Asp
130                 135                 140

Tyr Ser Lys Arg Thr Met Gly Leu Leu Val Ser Ala Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
210                 215                 220

Met Phe Pro Val Leu Phe Leu Gly Thr Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Glu His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
290                 295                 300

Asp
305

<210> SEQ ID NO 53
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 53

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

```
Lys Leu Ala Ala Asn Ile Leu Gln Trp Ile Ser Phe Ala Leu Ser Ala
 50                  55                  60

Leu Cys Leu Met Phe Tyr Gly Tyr Gln Thr Trp Lys Ser Thr Cys Gly
 65                  70                  75                  80

Trp Glu Glu Ile Tyr Val Ala Thr Ile Ser Met Ile Lys Phe Ile Ile
                 85                  90                  95

Glu Tyr Phe His Ser Phe Asp Glu Pro Ala Val Ile Tyr Ser Ser Asn
                100                 105                 110

Gly Asn Lys Thr Lys Trp Leu Arg Tyr Ala Ser Trp Leu Leu Thr Ala
            115                 120                 125

Pro Val Leu Leu Ile Arg Leu Ser Asn Leu Thr Gly Leu Lys Asp Asp
130                 135                 140

Tyr Ser Lys Arg Thr Met Gly Leu Leu Val Ser Asn Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
                180                 185                 190

Ala Lys Val Tyr Ile Glu Ala Phe His Thr Val Pro Lys Gly Ile Cys
            195                 200                 205

Arg Glu Leu Val Arg Val Met Ala Trp Thr Phe Phe Val Ala Trp Gly
210                 215                 220

Met Phe Pro Val Leu Phe Leu Leu Gly Thr Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
                260                 265                 270

Glu His Ile Leu Leu Tyr Gly Asp Ile Arg Lys Lys Gln Lys Ile Thr
            275                 280                 285

Ile Ala Gly Gln Glu Met Glu Val Glu Thr Leu Val Ala Glu Glu Glu
290                 295                 300

Asp
305

<210> SEQ ID NO 54
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 54

Met Asp Tyr Gly Gly Ala Leu Ser Ala Val Gly Leu Phe Gln Thr Ser
 1               5                  10                  15

Tyr Thr Leu Glu Asn Asn Gly Ser Val Ile Cys Ile Pro Asn Asn Gly
                 20                  25                  30

Gln Cys Phe Cys Leu Ala Trp Leu Lys Ser Asn Gly Thr Asn Ala Glu
             35                  40                  45

Lys Leu Ala Ala Asn Ile Leu Gln Trp Ile Ser Phe Ala Leu Ser Ala
 50                  55                  60

Leu Cys Leu Met Phe Tyr Gly Tyr Gln Thr Trp Lys Ser Thr Cys Gly
 65                  70                  75                  80

Trp Glu Glu Ile Tyr Val Ala Thr Ile Ser Met Ile Lys Phe Ile Ile
                 85                  90                  95
```

Glu Tyr Phe His Ser Phe Asp Glu Pro Ala Val Ile Tyr Ser Ser Asn
                100                 105                 110

Gly Asn Lys Thr Lys Trp Leu Arg Tyr Ala Ser Trp Leu Leu Thr Ser
            115                 120                 125

Pro Val Leu Leu Ile Arg Leu Ser Asn Leu Thr Gly Leu Lys Asp Asp
130                 135                 140

Tyr Ser Lys Arg Thr Met Gly Leu Leu Val Ser Ala Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
            195                 200                 205

Arg Glu Leu Val Arg Val Met Ala Trp Thr Phe Phe Val Ala Trp Gly
        210                 215                 220

Met Phe Pro Val Leu Phe Leu Leu Gly Thr Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Glu His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
    290                 295                 300

Asp
305

<210> SEQ ID NO 55
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 55

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
    50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
                100                 105                 110

Gly Asn Lys Thr Lys Trp Leu Arg Tyr Ala Ser Trp Leu Leu Thr Ser
            115                 120                 125

Pro Val Leu Leu Ile Arg Leu Ser Asn Leu Thr Gly Leu Lys Asp Asp
130                 135                 140

```
Tyr Ser Lys Arg Thr Met Gly Leu Leu Val Ser Asn Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
    210                 215                 220

Met Phe Pro Val Leu Phe Leu Leu Gly Thr Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Glu His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu
    290                 295                 300

Asp
305

<210> SEQ ID NO 56
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 56

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
        115                 120                 125

Ile Ser Met Met Lys Ser Ile Ile Glu Ala Phe His Ser Phe Asp Ser
    130                 135                 140

Pro Ala Thr Leu Trp Leu Ser Ser Gly Asn Gly Val Leu Trp Met Arg
145                 150                 155                 160

Tyr Gly Ser Trp Leu Leu Thr Cys Pro Val Ile Leu Ile Arg Leu Ser
                165                 170                 175

Asn Leu Thr Gly Leu Lys Asp Asp Tyr Ser Lys Arg Thr Met Gly Leu
            180                 185                 190
```

```
Leu Val Ser Asp Val Gly Cys Ile Val Trp Gly Ala Thr Ser Ala Met
            195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
            245                 250                 255

Trp Leu Phe Phe Val Ser Trp Gly Met Phe Pro Val Leu Phe Leu Leu
            260                 265                 270

Gly Pro Glu Gly Phe Gly His Ile Ser Lys Tyr Gly Ser Asn Ile Gly
            275                 280                 285

His Ser Ile Leu Asp Leu Ile Ala Lys Gln Met Trp Gly Val Leu Gly
290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
            325                 330                 335

Glu Thr Leu Val Ala Glu Glu Asp Lys Tyr Glu Ser Ser
            340                 345                 350
```

<210> SEQ ID NO 57
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 57

```
Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
            85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
            115                 120                 125

Ile Ser Met Met Lys Ser Ile Ile Glu Ala Phe His Ser Phe Asp Ser
            130                 135                 140

Pro Ala Thr Leu Trp Leu Ser Ser Gly Asn Gly Val Lys Trp Met Arg
145                 150                 155                 160

Tyr Gly Ser Trp Leu Leu Thr Cys Pro Val Ile Leu Ile Arg Leu Ser
            165                 170                 175

Asn Leu Thr Gly Leu Lys Asp Asp Tyr Ser Lys Arg Thr Met Gly Leu
            180                 185                 190

Leu Val Ser Asn Val Gly Cys Ile Val Trp Gly Ala Thr Ser Ala Met
            195                 200                 205
```

```
Cys Thr Gly Trp Thr Lys Ile Leu Phe Phe Leu Ile Ser Leu Ser Tyr
        210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
            245                 250                 255

Trp Leu Phe Phe Val Ser Trp Gly Met Phe Pro Val Leu Phe Leu Leu
        260                 265                 270

Gly Pro Glu Gly Phe Gly His Ile Ser Lys Tyr Gly Ser Asn Ile Gly
    275                 280                 285

His Ser Ile Leu Asp Leu Ile Ala Lys Gln Met Trp Gly Val Leu Gly
        290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
            340                 345                 350

<210> SEQ ID NO 58
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 58

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Val Ser Phe Ala Leu Ser Val
50                  55                  60

Ala Cys Leu Gly Trp Tyr Ala Tyr Gln Ala Trp Arg Ala Thr Cys Gly
65                  70                  75                  80

Trp Glu Glu Val Tyr Val Ala Leu Ile Ser Met Met Lys Ser Ile Ile
                85                  90                  95

Glu Ala Phe His Ser Phe Asp Ser Pro Ala Thr Leu Trp Leu Ser Ser
            100                 105                 110

Gly Asn Gly Val Lys Trp Met Arg Tyr Gly Ser Trp Leu Leu Thr Cys
        115                 120                 125

Pro Val Ile Leu Ile Arg Leu Ser Asn Leu Thr Gly Leu Lys Asp Asp
    130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
    210                 215                 220
```

```
Met Phe Pro Val Leu Phe Leu Gly Pro Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Glu His Ile Leu Leu Tyr Gly Asp Ile Arg Lys Gln Lys Ile Thr
            275                 280                 285

Ile Ala Gly Gln Glu Met Glu Val Glu Thr Leu Val Ala Glu Glu Glu
    290                 295                 300

Asp Lys Tyr Glu Ser Ser
305                 310
```

<210> SEQ ID NO 59
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 59

```
Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Val Ser Phe Ala Leu Ser Val
50                  55                  60

Ala Cys Leu Gly Trp Tyr Ala Tyr Gln Ala Trp Arg Ala Thr Cys Gly
65                  70                  75                  80

Trp Glu Glu Val Tyr Val Ala Leu Ile Ser Met Met Lys Ser Ile Ile
                85                  90                  95

Glu Ala Phe His Ser Phe Asp Ser Pro Ala Thr Leu Trp Leu Ser Ser
            100                 105                 110

Gly Asn Gly Val Lys Trp Met Arg Tyr Gly Ser Trp Leu Leu Thr Cys
        115                 120                 125

Pro Val Ile Leu Ile Arg Leu Ser Asn Leu Thr Gly Leu Lys Asp Asp
    130                 135                 140

Tyr Ser Lys Arg Thr Met Gly Leu Leu Val Ser Asn Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
    210                 215                 220

Met Phe Pro Val Leu Phe Leu Gly Pro Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270
```

```
Glu His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
290                 295                 300

Asp Lys Tyr Glu Ser Ser
305                 310

<210> SEQ ID NO 60
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 60

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
        115                 120                 125

Ile Ser Met Met Lys Ser Ile Ile Glu Ala Phe His Ser Phe Asp Ser
130                 135                 140

Pro Ala Thr Leu Trp Leu Ser Ser Gly Asn Gly Val Lys Trp Met Arg
145                 150                 155                 160

Tyr Gly Ser Trp Leu Leu Thr Thr Pro Val Ile Leu Ile Arg Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Lys Tyr Gly Ser Asn Ile Gly
        275                 280                 285

His Ser Ile Leu Asp Leu Ile Ala Lys Gln Met Trp Gly Val Leu Gly
290                 295                 300

Asn Tyr Leu Arg Val Lys Ile His Glu His Ile Leu Leu Tyr Gly Asp
305                 310                 315                 320
```

Ile Arg Lys Lys Gln Lys Ile Thr Ile Ala Gly Gln Glu Met Glu Val
        325                 330                 335

Glu Thr Leu Val Ala Glu Glu Asp Lys Tyr Glu Ser Ser
        340                 345                 350

<210> SEQ ID NO 61
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 61

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
        115                 120                 125

Ile Ser Met Met Lys Ser Ile Ile Glu Ala Phe His Ser Phe Asp Ser
    130                 135                 140

Pro Ala Thr Leu Trp Leu Ser Ser Gly Asn Gly Val Lys Trp Met Arg
145                 150                 155                 160

Tyr Gly Ser Trp Leu Leu Thr Ala Pro Val Ile Leu Ile Arg Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
    210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Lys Tyr Gly Ser Asn Ile Gly
        275                 280                 285

His Ser Ile Leu Asp Leu Ile Ala Lys Gln Met Trp Gly Val Leu Gly
    290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

```
Glu Thr Leu Val Ala Glu Glu Asp Lys Tyr Glu Ser Ser
            340                 345                 350

<210> SEQ ID NO 62
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 62

Met Val Ser Arg Arg Pro Trp Leu Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
            115                 120                 125

Ile Ser Met Met Lys Ser Ile Ile Glu Ala Phe His Ser Phe Asp Ser
130                 135                 140

Pro Ala Thr Leu Trp Leu Ser Ser Gly Asn Gly Val Lys Trp Met Arg
145                 150                 155                 160

Tyr Gly Ser Trp Leu Leu Thr Ser Pro Val Ile Leu Ile Arg Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
            195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Lys Tyr Gly Ser Asn Ile Gly
            275                 280                 285

His Ser Ile Leu Asp Leu Ile Ala Lys Gln Met Trp Gly Val Leu Gly
290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
            340                 345                 350
```

<210> SEQ ID NO 63
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 63

```
Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
        115                 120                 125

Ile Ser Met Met Lys Ser Ile Ile Glu Ala Phe His Ser Phe Asp Ser
130                 135                 140

Pro Ala Thr Leu Trp Leu Ser Ser Gly Asn Gly Val Lys Trp Met Arg
145                 150                 155                 160

Tyr Gly Ser Trp Leu Leu Thr Thr Pro Val Ile Leu Ile Arg Leu Ser
                165                 170                 175

Asn Leu Thr Gly Leu Lys Asp Asp Tyr Ser Lys Arg Thr Met Gly Leu
            180                 185                 190

Leu Val Ser Ala Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Lys Tyr Gly Ser Asn Ile Gly
        275                 280                 285

His Ser Ile Leu Asp Leu Ile Ala Lys Gln Met Trp Gly Val Leu Gly
290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Glu Asp Lys Tyr Glu Ser Ser
            340                 345                 350
```

<210> SEQ ID NO 64

<211> LENGTH: 350
<212> TYPE: PRT
<213> ORGANISM: Artificial sequence
<220> FEATURE:
<223> OTHER INFORMATION: Synthetic polypeptide

<400> SEQUENCE: 64

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Val Tyr Val Ala Leu
        115                 120                 125

Ile Ser Met Met Lys Ser Ile Ile Glu Ala Phe His Ser Phe Asp Ser
130                 135                 140

Pro Ala Thr Leu Trp Leu Ser Ser Gly Asn Gly Val Lys Trp Met Arg
145                 150                 155                 160

Tyr Gly Ser Trp Leu Leu Thr Thr Pro Val Ile Leu Ile Arg Leu Ser
                165                 170                 175

Asn Leu Thr Gly Leu Lys Asp Asp Tyr Ser Lys Arg Thr Met Gly Leu
            180                 185                 190

Leu Val Ser Asn Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Lys Tyr Gly Ser Asn Ile Gly
        275                 280                 285

His Ser Ile Leu Asp Leu Ile Ala Lys Gln Met Trp Gly Val Leu Gly
290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
            340                 345                 350

<210> SEQ ID NO 65
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 65

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
                20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
        50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
        115                 120                 125

Ile Ser Met Met Lys Ser Ile Ile Glu Ala Phe His Ser Phe Asp Ser
    130                 135                 140

Pro Ala Thr Leu Trp Leu Ser Ser Gly Asn Gly Val Lys Trp Met Arg
145                 150                 155                 160

Tyr Gly Ser Trp Leu Leu Thr Ala Pro Val Ile Leu Ile Arg Leu Ser
                165                 170                 175

Asn Leu Thr Gly Leu Lys Asp Asp Tyr Ser Lys Arg Thr Met Gly Leu
            180                 185                 190

Leu Val Ser Ala Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
    210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Lys Tyr Gly Ser Asn Ile Gly
        275                 280                 285

His Ser Ile Leu Asp Leu Ile Ala Lys Gln Met Trp Gly Val Leu Gly
    290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Glu Asp Lys Tyr Glu Ser Ser
            340                 345                 350

<210> SEQ ID NO 66
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 66

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
        115                 120                 125

Ile Ser Met Met Lys Ser Ile Ile Glu Ala Phe His Ser Phe Asp Ser
130                 135                 140

Pro Ala Thr Leu Trp Leu Ser Ser Gly Asn Gly Val Lys Trp Met Arg
145                 150                 155                 160

Tyr Gly Ser Trp Leu Leu Thr Ala Pro Val Ile Leu Ile Arg Leu Ser
                165                 170                 175

Asn Leu Thr Gly Leu Lys Asp Asp Tyr Ser Lys Arg Thr Met Gly Leu
            180                 185                 190

Leu Val Ser Asn Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Lys Tyr Gly Ser Asn Ile Gly
        275                 280                 285

His Ser Ile Leu Asp Leu Ile Ala Lys Gln Met Trp Gly Val Leu Gly
290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Glu Asp Lys Tyr Glu Ser Ser
            340                 345                 350

<210> SEQ ID NO 67
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 67

Met Val Ser Arg Arg Pro Trp Leu Leu Ala Leu Ala Leu Ala Val Ala

```
  1               5                  10                 15
Leu Ala Ala Gly Ser Ala Gly Ala Ser Thr Gly Ser Asp Ala Thr Val
            20                  25                 30
Pro Val Ala Thr Gln Asp Gly Pro Asp Tyr Val Phe His Arg Ala His
            35                  40                 45
Glu Arg Met Leu Phe Gln Thr Ser Tyr Thr Leu Glu Asn Asn Gly Ser
 50                      55                 60
Val Ile Cys Ile Pro Asn Asn Gly Gln Cys Phe Cys Leu Ala Trp Leu
 65                      70                 75                 80
Lys Ser Asn Gly Thr Asn Ala Glu Lys Leu Ala Ala Asn Ile Leu Gln
                85                  90                 95
Trp Val Ser Phe Ala Leu Ser Val Ala Cys Leu Gly Trp Tyr Ala Tyr
                100                 105                110
Gln Ala Trp Arg Ala Thr Cys Gly Trp Glu Glu Val Tyr Val Ala Leu
                115                 120                125
Ile Ser Met Met Lys Ser Ile Ile Glu Ala Phe His Ser Phe Asp Ser
130                     135                 140
Pro Ala Thr Leu Trp Leu Ser Ser Gly Asn Gly Val Lys Trp Met Arg
145                     150                 155                160
Tyr Gly Ser Trp Leu Leu Thr Ser Pro Val Ile Leu Ile Arg Leu Ser
                165                 170                175
Asn Leu Thr Gly Leu Lys Asp Asp Tyr Ser Lys Arg Thr Met Gly Leu
                180                 185                190
Leu Val Ser Ala Val Gly Cys Ile Val Trp Gly Ala Thr Ser Ala Met
                195                 200                205
Cys Thr Gly Trp Thr Lys Ile Leu Phe Phe Leu Ile Ser Leu Ser Tyr
210                     215                 220
Gly Met Tyr Thr Tyr Phe His Ala Ala Lys Val Tyr Ile Glu Ala Phe
225                     230                 235                240
His Thr Val Pro Lys Gly Leu Cys Arg Gln Leu Val Arg Ala Met Ala
                245                 250                255
Trp Leu Phe Phe Val Ser Trp Gly Met Phe Pro Val Leu Phe Leu Leu
                260                 265                270
Gly Pro Glu Gly Phe Gly His Ile Ser Lys Tyr Gly Ser Asn Ile Gly
                275                 280                285
His Ser Ile Leu Asp Leu Ile Ala Lys Gln Met Trp Gly Val Leu Gly
                290                 295                300
Asn Tyr Leu Arg Val Lys Ile His Glu His Ile Leu Leu Tyr Gly Asp
305                     310                 315                320
Ile Arg Lys Lys Gln Lys Ile Thr Ile Ala Gly Gln Glu Met Glu Val
                325                 330                335
Glu Thr Leu Val Ala Glu Glu Asp Lys Tyr Glu Ser Ser
                340                 345                350

<210> SEQ ID NO 68
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 68

Met Val Ser Arg Arg Pro Trp Leu Leu Ala Leu Ala Leu Ala Val Ala
 1               5                  10                 15

Leu Ala Ala Gly Ser Ala Gly Ala Ser Thr Gly Ser Asp Ala Thr Val
```

```
            20                  25                  30
Pro Val Ala Thr Gln Asp Gly Pro Asp Tyr Val Phe His Arg Ala His
            35                  40                  45
Glu Arg Met Leu Phe Gln Thr Ser Tyr Thr Leu Glu Asn Asn Gly Ser
 50                  55                  60
Val Ile Cys Ile Pro Asn Asn Gly Gln Cys Phe Cys Leu Ala Trp Leu
 65                  70                  75                  80
Lys Ser Asn Gly Thr Asn Ala Glu Lys Leu Ala Ala Asn Ile Leu Gln
                 85                  90                  95
Trp Val Ser Phe Ala Leu Ser Val Ala Cys Leu Gly Trp Tyr Ala Tyr
                100                 105                 110
Gln Ala Trp Arg Ala Thr Cys Gly Trp Glu Val Tyr Val Ala Leu
            115                 120                 125
Ile Ser Met Met Lys Ser Ile Ile Glu Ala Phe His Ser Phe Asp Ser
            130                 135                 140
Pro Ala Thr Leu Trp Leu Ser Ser Gly Asn Gly Val Lys Trp Met Arg
145                 150                 155                 160
Tyr Gly Ser Trp Leu Leu Thr Ser Pro Val Ile Leu Ile Arg Leu Ser
                165                 170                 175
Asn Leu Thr Gly Leu Lys Asp Asp Tyr Ser Lys Arg Thr Met Gly Leu
            180                 185                 190
Leu Val Ser Asn Val Gly Cys Ile Val Trp Gly Ala Thr Ser Ala Met
        195                 200                 205
Cys Thr Gly Trp Thr Lys Ile Leu Phe Phe Leu Ile Ser Leu Ser Tyr
    210                 215                 220
Gly Met Tyr Thr Tyr Phe His Ala Ala Lys Val Tyr Ile Glu Ala Phe
225                 230                 235                 240
His Thr Val Pro Lys Gly Leu Cys Arg Gln Leu Val Arg Ala Met Ala
                245                 250                 255
Trp Leu Phe Phe Val Ser Trp Gly Met Phe Pro Val Leu Phe Leu Leu
            260                 265                 270
Gly Pro Glu Gly Phe Gly His Ile Ser Lys Tyr Gly Ser Asn Ile Gly
        275                 280                 285
His Ser Ile Leu Asp Leu Ile Ala Lys Gln Met Trp Gly Val Leu Gly
    290                 295                 300
Asn Tyr Leu Arg Val Lys Ile His Glu His Ile Leu Leu Tyr Gly Asp
305                 310                 315                 320
Ile Arg Lys Lys Gln Lys Ile Thr Ile Ala Gly Gln Glu Met Glu Val
                325                 330                 335
Glu Thr Leu Val Ala Glu Glu Asp Lys Tyr Glu Ser Ser
            340                 345                 350

<210> SEQ ID NO 69
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 69

Met Asp Tyr Gly Gly Ala Leu Ser Ala Val Gly Leu Phe Gln Thr Ser
 1               5                  10                  15
Tyr Thr Leu Glu Asn Asn Gly Ser Val Ile Cys Ile Pro Asn Asn Gly
            20                  25                  30
Gln Cys Phe Cys Leu Ala Trp Leu Lys Ser Asn Gly Thr Asn Ala Glu
```

```
            35                  40                  45
Lys Leu Ala Ala Asn Ile Leu Gln Trp Val Ser Phe Ala Leu Ser Val
 50                  55                  60
Ala Cys Leu Gly Trp Tyr Ala Tyr Gln Ala Trp Arg Ala Thr Cys Gly
 65                  70                  75                  80
Trp Glu Glu Val Tyr Val Ala Leu Ile Ser Met Met Lys Ser Ile Ile
                     85                  90                  95
Glu Ala Phe His Ser Phe Asp Ser Pro Ala Thr Leu Trp Leu Ser Ser
                100                 105                 110
Gly Asn Gly Val Lys Trp Met Arg Tyr Gly Ser Trp Leu Leu Thr Thr
            115                 120                 125
Pro Val Ile Leu Ile Arg Leu Ser Asn Leu Thr Gly Leu Lys Asp Asp
130                 135                 140
Tyr Ser Lys Arg Thr Met Gly Leu Leu Val Ser Asp Val Gly Cys Ile
145                 150                 155                 160
Val Trp Gly Ala Thr Ser Ala Met Cys Thr Gly Trp Thr Lys Ile Leu
                165                 170                 175
Phe Phe Leu Ile Ser Leu Ser Tyr Gly Met Tyr Thr Tyr Phe His Ala
                180                 185                 190
Ala Lys Val Tyr Ile Glu Ala Phe His Thr Val Pro Lys Gly Leu Cys
            195                 200                 205
Arg Gln Leu Val Arg Ala Met Ala Trp Leu Phe Phe Val Ser Trp Gly
210                 215                 220
Met Phe Pro Val Leu Phe Leu Leu Gly Pro Glu Gly Phe Gly His Ile
225                 230                 235                 240
Ser Lys Tyr Gly Ser Asn Ile Gly His Ser Ile Leu Asp Leu Ile Ala
                245                 250                 255
Lys Gln Met Trp Gly Val Leu Gly Asn Tyr Leu Arg Val Lys Ile His
                260                 265                 270
Glu His Ile Leu Leu Tyr Gly Asp Ile Arg Lys Gln Lys Ile Thr
            275                 280                 285
Ile Ala Gly Gln Glu Met Glu Val Glu Thr Leu Val Ala Glu Glu Glu
290                 295                 300
Asp Lys Tyr Glu Ser Ser
305                 310

<210> SEQ ID NO 70
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 70

Met Asp Tyr Gly Gly Ala Leu Ser Ala Val Gly Leu Phe Gln Thr Ser
 1                   5                  10                  15
Tyr Thr Leu Glu Asn Asn Gly Ser Val Ile Cys Ile Pro Asn Asn Gly
                 20                  25                  30
Gln Cys Phe Cys Leu Ala Trp Leu Lys Ser Asn Gly Thr Asn Ala Glu
             35                  40                  45
Lys Leu Ala Ala Asn Ile Leu Gln Trp Val Ser Phe Ala Leu Ser Val
 50                  55                  60
Ala Cys Leu Gly Trp Tyr Ala Tyr Gln Ala Trp Arg Ala Thr Cys Gly
 65                  70                  75                  80
Trp Glu Glu Val Tyr Val Ala Leu Ile Ser Met Met Lys Ser Ile Ile
```

```
            85                  90                  95
Glu Ala Phe His Ser Phe Asp Ser Pro Ala Thr Leu Trp Leu Ser Ser
                100                 105                 110
Gly Asn Gly Val Lys Trp Met Arg Tyr Gly Ser Trp Leu Leu Thr Ala
                115                 120                 125
Pro Val Ile Leu Ile Arg Leu Ser Asn Leu Thr Gly Leu Lys Asp Asp
            130                 135                 140
Tyr Ser Lys Arg Thr Met Gly Leu Leu Val Ser Asp Val Gly Cys Ile
145                 150                 155                 160
Val Trp Gly Ala Thr Ser Ala Met Cys Thr Gly Trp Thr Lys Ile Leu
                165                 170                 175
Phe Phe Leu Ile Ser Leu Ser Tyr Gly Met Tyr Thr Tyr Phe His Ala
                180                 185                 190
Ala Lys Val Tyr Ile Glu Ala Phe His Thr Val Pro Lys Gly Leu Cys
                195                 200                 205
Arg Gln Leu Val Arg Ala Met Ala Trp Leu Phe Phe Val Ser Trp Gly
            210                 215                 220
Met Phe Pro Val Leu Phe Leu Leu Gly Pro Glu Gly Phe Gly His Ile
225                 230                 235                 240
Ser Lys Tyr Gly Ser Asn Ile Gly His Ser Ile Leu Asp Leu Ile Ala
                245                 250                 255
Lys Gln Met Trp Gly Val Leu Gly Asn Tyr Leu Arg Val Lys Ile His
                260                 265                 270
Glu His Ile Leu Leu Tyr Gly Asp Ile Arg Lys Lys Gln Lys Ile Thr
            275                 280                 285
Ile Ala Gly Gln Glu Met Glu Val Glu Thr Leu Val Ala Glu Glu Glu
            290                 295                 300
Asp Lys Tyr Glu Ser Ser
305                 310

<210> SEQ ID NO 71
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 71

Met Asp Tyr Gly Gly Ala Leu Ser Ala Val Gly Leu Phe Gln Thr Ser
1               5                   10                  15
Tyr Thr Leu Glu Asn Asn Gly Ser Val Ile Cys Ile Pro Asn Asn Gly
            20                  25                  30
Gln Cys Phe Cys Leu Ala Trp Leu Lys Ser Asn Gly Thr Asn Ala Glu
            35                  40                  45
Lys Leu Ala Ala Asn Ile Leu Gln Trp Val Ser Phe Ala Leu Ser Val
50                  55                  60
Ala Cys Leu Gly Trp Tyr Ala Tyr Gln Ala Trp Arg Ala Thr Cys Gly
65                  70                  75                  80
Trp Glu Glu Val Tyr Val Ala Leu Ile Ser Met Met Lys Ser Ile Ile
                85                  90                  95
Glu Ala Phe His Ser Phe Asp Ser Pro Ala Thr Leu Trp Leu Ser Ser
                100                 105                 110
Gly Asn Gly Val Lys Trp Met Arg Tyr Gly Ser Trp Leu Leu Thr Ser
                115                 120                 125
Pro Val Ile Leu Ile Arg Leu Ser Asn Leu Thr Gly Leu Lys Asp Asp
```

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
    210                 215                 220

Met Phe Pro Val Leu Phe Leu Leu Gly Pro Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
                260                 265                 270

Glu His Ile Leu Leu Tyr Gly Asp Ile Arg Lys Lys Gln Lys Ile Thr
            275                 280                 285

Ile Ala Gly Gln Glu Met Glu Val Glu Thr Leu Val Ala Glu Glu Glu
        290                 295                 300

Asp Lys Tyr Glu Ser Ser
305                 310

<210> SEQ ID NO 72
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 72

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Val Ser Phe Ala Leu Ser Val
    50                  55                  60

Ala Cys Leu Gly Trp Tyr Ala Tyr Gln Ala Trp Arg Ala Thr Cys Gly
65                  70                  75                  80

Trp Glu Glu Val Tyr Val Ala Leu Ile Ser Met Met Lys Ser Ile Ile
                85                  90                  95

Glu Ala Phe His Ser Phe Asp Ser Pro Ala Thr Leu Trp Leu Ser Ser
            100                 105                 110

Gly Asn Gly Val Lys Trp Met Arg Tyr Gly Ser Trp Leu Leu Thr Thr
        115                 120                 125

Pro Val Ile Leu Ile Arg Leu Ser Asn Leu Thr Gly Leu Lys Asp Asp
    130                 135                 140

Tyr Ser Lys Arg Thr Met Gly Leu Leu Val Ser Ala Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala

```
                        180                 185                 190
Ala Lys Val Tyr Ile Glu Ala Phe His Thr Val Pro Lys Gly Leu Cys
                195                 200                 205

Arg Gln Leu Val Arg Ala Met Ala Trp Leu Phe Phe Val Ser Trp Gly
        210                 215                 220

Met Phe Pro Val Leu Phe Leu Leu Gly Pro Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
                260                 265                 270

Glu His Ile Leu Leu Tyr Gly Asp Ile Arg Lys Lys Gln Lys Ile Thr
            275                 280                 285

Ile Ala Gly Gln Glu Met Glu Val Glu Thr Leu Val Ala Glu Glu Glu
            290                 295                 300

Asp Lys Tyr Glu Ser Ser
305                 310

<210> SEQ ID NO 73
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 73

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Val Ser Phe Ala Leu Ser Val
        50                  55                  60

Ala Cys Leu Gly Trp Tyr Ala Tyr Gln Ala Trp Arg Ala Thr Cys Gly
65                  70                  75                  80

Trp Glu Glu Val Tyr Val Ala Leu Ile Ser Met Met Lys Ser Ile Ile
                85                  90                  95

Glu Ala Phe His Ser Phe Asp Ser Pro Ala Thr Leu Trp Leu Ser Ser
            100                 105                 110

Gly Asn Gly Val Lys Trp Met Arg Tyr Gly Ser Trp Leu Leu Thr Thr
        115                 120                 125

Pro Val Ile Leu Ile Arg Leu Ser Asn Leu Thr Gly Leu Lys Asp Asp
130                 135                 140

Tyr Ser Lys Arg Thr Met Gly Leu Leu Val Ser Asn Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
    210                 215                 220

Met Phe Pro Val Leu Phe Leu Leu Gly Pro Glu Gly Phe Gly His Ile
```

```
              225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
                260                 265                 270

Glu His Ile Leu Leu Tyr Gly Asp Ile Arg Lys Lys Gln Lys Ile Thr
                275                 280                 285

Ile Ala Gly Gln Glu Met Glu Val Thr Leu Val Ala Glu Glu
                290                 295                 300

Asp Lys Tyr Glu Ser Ser
305                 310

<210> SEQ ID NO 74
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 74

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
                35                  40                  45

Lys Leu Ala Ala Asn Ile Leu Gln Trp Val Ser Phe Ala Leu Ser Val
        50                  55                  60

Ala Cys Leu Gly Trp Tyr Ala Tyr Gln Ala Trp Arg Ala Thr Cys Gly
65              70                  75                  80

Trp Glu Glu Val Tyr Val Ala Leu Ile Ser Met Met Lys Ser Ile Ile
                85                  90                  95

Glu Ala Phe His Ser Phe Asp Ser Pro Ala Thr Leu Trp Leu Ser Ser
                100                 105                 110

Gly Asn Gly Val Lys Trp Met Arg Tyr Gly Ser Trp Leu Leu Thr Ala
                115                 120                 125

Pro Val Ile Leu Ile Arg Leu Ser Asn Leu Thr Gly Leu Lys Asp Asp
                130                 135                 140

Tyr Ser Lys Arg Thr Met Gly Leu Leu Val Ser Ala Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
                180                 185                 190

Ala Lys Val Tyr Ile Glu Ala Phe His Thr Val Pro Lys Gly Leu Cys
                195                 200                 205

Arg Gln Leu Val Arg Ala Met Ala Trp Leu Phe Phe Val Ser Trp Gly
                210                 215                 220

Met Phe Pro Val Leu Phe Leu Leu Gly Pro Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
                260                 265                 270

Glu His Ile Leu Leu Tyr Gly Asp Ile Arg Lys Lys Gln Lys Ile Thr
```

```
            275                 280                 285
Ile Ala Gly Gln Glu Met Glu Val Glu Thr Leu Val Ala Glu Glu Glu
            290                 295                 300

Asp Lys Tyr Glu Ser Ser
305                 310

<210> SEQ ID NO 75
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 75

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Val Ser Phe Ala Leu Ser Val
50                  55                  60

Ala Cys Leu Gly Trp Tyr Ala Tyr Gln Ala Trp Arg Ala Thr Cys Gly
65                  70                  75                  80

Trp Glu Glu Val Tyr Val Ala Leu Ile Ser Met Met Lys Ser Ile Ile
                85                  90                  95

Glu Ala Phe His Ser Phe Asp Ser Pro Ala Thr Leu Trp Leu Ser Ser
            100                 105                 110

Gly Asn Gly Val Lys Trp Met Arg Tyr Gly Ser Trp Leu Leu Thr Ala
        115                 120                 125

Pro Val Ile Leu Ile Arg Leu Ser Asn Leu Thr Gly Leu Lys Asp Asp
130                 135                 140

Tyr Ser Lys Arg Thr Met Gly Leu Leu Val Ser Asn Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
210                 215                 220

Met Phe Pro Val Leu Phe Leu Gly Pro Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Glu His Ile Leu Leu Tyr Gly Asp Ile Arg Lys Gln Lys Ile Thr
        275                 280                 285

Ile Ala Gly Gln Glu Met Glu Val Glu Thr Leu Val Ala Glu Glu Glu
            290                 295                 300

Asp Lys Tyr Glu Ser Ser
305                 310
```

<210> SEQ ID NO 76
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 76

```
Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Val Ser Phe Ala Leu Ser Val
50                  55                  60

Ala Cys Leu Gly Trp Tyr Ala Tyr Gln Ala Trp Arg Ala Thr Cys Gly
65                  70                  75                  80

Trp Glu Glu Val Tyr Val Ala Leu Ile Ser Met Met Lys Ser Ile Ile
                85                  90                  95

Glu Ala Phe His Ser Phe Asp Ser Pro Ala Thr Leu Trp Leu Ser Ser
            100                 105                 110

Gly Asn Gly Val Lys Trp Met Arg Tyr Gly Ser Trp Leu Leu Thr Ser
        115                 120                 125

Pro Val Ile Leu Ile Arg Leu Ser Asn Leu Thr Gly Leu Lys Asp Asp
130                 135                 140

Tyr Ser Lys Arg Thr Met Gly Leu Leu Val Ser Ala Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
210                 215                 220

Met Phe Pro Val Leu Phe Leu Gly Pro Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Glu His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
290                 295                 300

Asp Lys Tyr Glu Ser Ser
305                 310
```

<210> SEQ ID NO 77
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 77

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Val Ser Phe Ala Leu Ser Val
    50                  55                  60

Ala Cys Leu Gly Trp Tyr Ala Tyr Gln Ala Trp Arg Ala Thr Cys Gly
65                  70                  75                  80

Trp Glu Glu Val Tyr Val Ala Leu Ile Ser Met Met Lys Ser Ile Ile
                85                  90                  95

Glu Ala Phe His Ser Phe Asp Ser Pro Ala Thr Leu Trp Leu Ser Ser
            100                 105                 110

Gly Asn Gly Val Lys Trp Met Arg Tyr Gly Ser Trp Leu Leu Thr Ser
        115                 120                 125

Pro Val Ile Leu Ile Arg Leu Ser Asn Leu Thr Gly Leu Lys Asp Asp
    130                 135                 140

Tyr Ser Lys Arg Thr Met Gly Leu Leu Val Ser Asn Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
    210                 215                 220

Met Phe Pro Val Leu Phe Leu Leu Gly Pro Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Glu His Ile Leu Leu Tyr Gly Asp Ile Arg Lys Gln Lys Ile Thr
        275                 280                 285

Ile Ala Gly Gln Glu Met Glu Val Glu Thr Leu Val Ala Glu Glu Glu
    290                 295                 300

Asp Lys Tyr Glu Ser Ser
305                 310

<210> SEQ ID NO 78
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 78

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

```
Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
 65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
               100                 105                 110

Thr Trp Lys Ser Thr Cys Gly Trp Glu Ile Tyr Val Ala Thr Ile
               115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
                180                 185                 190

Val Ser Asp Ile Gly Thr Ile Val Trp Gly Thr Thr Ala Ala Leu Ser
    195                 200                 205

Lys Gly Tyr Val Arg Val Ile Phe Phe Leu Met Gly Leu Cys Tyr Gly
210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
                260                 265                 270

Pro Glu Gly Phe Gly Val Leu Ser Val Tyr Gly Ser Thr Val Gly His
                275                 280                 285

Thr Ile Ile Asp Leu Met Ser Lys Asn Cys Trp Gly Leu Leu Gly His
    290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
                340                 345

<210> SEQ ID NO 79
<211> LENGTH: 310
<212> TYPE: PRT
<213> ORGANISM: Chlamydomonas rheinhardtii

<400> SEQUENCE: 79

Met Asp Tyr Gly Gly Ala Leu Ser Ala Val Gly Arg Glu Leu Leu Phe
  1               5                  10                  15

Val Thr Asn Pro Val Val Val Asn Gly Ser Val Leu Val Pro Glu Asp
                 20                  25                  30

Gln Cys Tyr Cys Ala Gly Trp Ile Glu Ser Arg Gly Thr Asn Gly Ala
             35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
 65                  70                  75                  80
```

```
Trp Glu Glu Ile Tyr Val Cys Ala Ile Glu Met Val Lys Val Ile Leu
             85                  90                  95

Glu Phe Phe Phe Glu Phe Lys Asn Pro Ser Met Leu Tyr Leu Ala Thr
        100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
                195                 200                 205

Arg Gln Val Val Thr Gly Met Ala Trp Leu Phe Phe Val Ser Trp Gly
                210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ala
                290                 295                 300

Glu Ala Gly Ala Val Pro
305                 310

<210> SEQ ID NO 80
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 80

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
                35                  40                  45

Arg Met Leu Phe Gln Thr Ser Tyr Thr Leu Glu Asn Asn Gly Ser Val
            50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
                115                 120                 125
```

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Ile His Leu Ser Asn
                165                 170                 175

Leu Thr Gly Leu Lys Asp Asp Tyr Ser Lys Arg Thr Met Gly Leu Leu
                180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
                260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 81
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 81

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
                20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Thr Phe Ala Leu Ser Val Ala Cys Leu Gly Tyr Ala Tyr
                100                 105                 110

Gln Ala Trp Arg Ala Thr Cys Gly Trp Glu Glu Val Tyr Val Ala Leu
            115                 120                 125

Ile Glu Met Met Lys Ser Ile Ile Glu Ala Phe His Glu Phe Asp Ser
    130                 135                 140

Pro Ala Thr Leu Trp Leu Ser Ser Gly Asn Gly Val Trp Met Arg
145                 150                 155                 160

Tyr Gly Glu Trp Leu Leu Thr Cys Pro Val Ile Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
    210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
                260                 265                 270

Gly Pro Glu Gly Phe Gly His Ile Ser Pro Tyr Gly Ser Ala Ile Gly
            275                 280                 285

His Ser Ile Leu Asp Leu Ile Ala Lys Asn Met Trp Gly Val Leu Gly
290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
            340                 345                 350

<210> SEQ ID NO 82
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 82

Met Asp Tyr Gly Gly Ala Leu Ser Ala Val Gly
1               5                   10

<210> SEQ ID NO 83
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 83

Lys Ser Arg Ile Thr Ser Glu Gly Glu Tyr Ile Pro Leu Asp Gln Ile
1               5                   10                  15

Asp Ile Asn Val
            20

<210> SEQ ID NO 84
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 84

```
Phe Cys Tyr Glu Asn Glu Val
1               5
```

<210> SEQ ID NO 85
<211> LENGTH: 26
<212> TYPE: PRT
<213> ORGANISM: Artificial sequence
<220> FEATURE:
<223> OTHER INFORMATION: Synthetic polypeptide

<400> SEQUENCE: 85

```
Met Asp Tyr Gly Gly Ala Leu Ser Ala Val Gly Arg Glu Leu Leu Phe
1               5                   10                  15

Val Thr Asn Pro Val Val Val Asn Gly Ser
            20                  25
```

<210> SEQ ID NO 86
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 86

```
Met Ala Gly His Ser Asn Ser Met Ala Leu Phe Ser Phe Ser Leu Leu
1               5                   10                  15

Trp Leu Cys Ser Gly Val Leu Gly Thr Glu Phe
            20                  25
```

<210> SEQ ID NO 87
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 87

```
Met Gly Leu Arg Ala Leu Met Leu Trp Leu Leu Ala Ala Ala Gly Leu
1               5                   10                  15

Val Arg Glu Ser Leu Gln Gly
            20
```

<210> SEQ ID NO 88
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 88

```
Met Arg Gly Thr Pro Leu Leu Leu Val Val Ser Leu Phe Ser Leu Leu
1               5                   10                  15

Gln Asp
```

<210> SEQ ID NO 89
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 89

```
Val Lys Glu Ser Leu
1               5
```

<210> SEQ ID NO 90
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 90

```
Val Leu Gly Ser Leu
1               5
```

<210> SEQ ID NO 91
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 91

```
Asn Ala Asn Ser Phe Cys Tyr Glu Asn Glu Val Ala Leu Thr Ser Lys
1               5                   10                  15
```

<210> SEQ ID NO 92
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 92

```
Phe Xaa Tyr Glu Asn Glu
1               5
```

<210> SEQ ID NO 93
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 93

```
Phe Cys Tyr Glu Asn Glu Val
1               5
```

<210> SEQ ID NO 94
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 94

```
Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
```

65                  70                  75                  80
Ser Asn Asn Thr Asn Ala Glu Lys Leu Ala Ala Asn Ile Leu Gln Trp
                        85                  90                  95
Ile Ser Phe Ala Leu Ser Ala Leu Cys Leu Met Phe Tyr Gly Tyr Gln
                100                 105                 110
Thr Trp Lys Ser Thr Cys Gly Trp Glu Asn Ile Tyr Val Ala Thr Ile
            115                 120                 125
Gln Met Ile Lys Phe Ile Ile Glu Tyr Phe His Ser Phe Asp Glu Pro
        130                 135                 140
Ala Val Ile Tyr Ser Ser Asn Gly Asn Lys Thr Arg Trp Leu Arg Tyr
145                 150                 155                 160
Ala Ser Trp Leu Leu Thr Cys Pro Val Ile Leu Ile His Leu Ser Asn
                165                 170                 175
Leu Thr Gly Leu Ala Asn Asp Tyr Asn Lys Arg Thr Met Gly Leu Leu
            180                 185                 190
Val Ser Asp Ile Gly Thr Ile Val Trp Gly Thr Thr Ala Ala Leu Ser
        195                 200                 205
Lys Gly Tyr Val Arg Val Ile Phe Phe Leu Met Gly Leu Cys Tyr Gly
    210                 215                 220
Ile Tyr Thr Phe Phe Asn Ala Ala Lys Val Tyr Ile Glu Ala Tyr His
225                 230                 235                 240
Thr Val Pro Lys Gly Arg Cys Arg Gln Val Val Thr Gly Met Ala Trp
                245                 250                 255
Leu Phe Phe Val Ser Trp Gly Met Phe Pro Ile Leu Phe Ile Leu Gly
            260                 265                 270
Pro Glu Gly Phe Gly Val Leu Ser Arg Tyr Gly Ser Asn Val Gly His
        275                 280                 285
Thr Ile Ile Asp Leu Met Ser Lys Gln Cys Trp Gly Leu Leu Gly His
    290                 295                 300
Tyr Leu Arg Val Leu Ile His Ser His Ile Leu Ile His Gly Asp Ile
305                 310                 315                 320
Arg Lys Thr Thr Lys Leu Asn Ile Gly Gly Thr Glu Ile Glu Val Glu
                325                 330                 335
Thr Leu Val Glu Asp Glu Ala Glu Ala Gly Ala Val
                340                 345

<210> SEQ ID NO 95
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 95

Met Ser Arg Arg Pro Trp Leu Leu Ala Leu Ala Leu Ala Val Ala Leu
1               5                   10                  15
Ala Ala Gly Ser Ala Gly Ala Ser Thr Gly Ser Asp Ala Thr Val Pro
                20                  25                  30
Val Ala Thr Gln Asp Gly Pro Asp Tyr Val Phe His Arg Ala His Glu
            35                  40                  45
Arg Met Leu Phe Gln Thr Ser Tyr Thr Leu Glu Asn Asn Gly Ser Val
        50                  55                  60
Ile Cys Ile Pro Asn Asn Gly Gln Cys Phe Cys Leu Ala Trp Leu Lys
65                  70                  75                  80
Ser Asn Asn Thr Asn Ala Glu Lys Leu Ala Ala Asn Ile Leu Gln Trp

```
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Asn Ile Tyr Val Ala Thr Ile
        115                 120                 125

Gln Met Ile Lys Phe Ile Ile Glu Tyr Phe His Ser Phe Asp Glu Pro
    130                 135                 140

Ala Val Ile Tyr Ser Ser Asn Gly Asn Lys Thr Arg Trp Leu Arg Tyr
145                 150                 155                 160

Ala Ser Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asn Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Pro Val Ser Trp Gly Met Phe Pro Ile Leu Phe Ile Leu Gly
            260                 265                 270

Pro Glu Gly Phe Gly Val Leu Ser Arg Tyr Gly Ser Asn Val Gly His
        275                 280                 285

Thr Ile Ile Asp Leu Met Ser Lys Gln Cys Trp Gly Leu Leu Gly His
    290                 295                 300

Tyr Leu Arg Val Leu Ile His Ser His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 96
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 96

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Asn Thr Asn Ala Glu
        35                  40                  45

Lys Leu Ala Ala Asn Ile Leu Gln Trp Ile Ser Phe Ala Leu Ser Ala
    50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
                85                  90                  95

Glu Tyr Phe His Ser Phe Asp Glu Pro Ala Val Ile Tyr Ser Ser Asn
```

```
                   100                 105                 110
Gly Asn Lys Thr Arg Trp Leu Arg Tyr Ala Ser Trp Leu Leu Thr Cys
            115                 120                 125

Pro Val Ile Leu Ile His Leu Ser Asn Leu Thr Gly Leu Ala Asn Asp
130                 135                 140

Tyr Asn Lys Arg Thr Met Gly Leu Leu Val Ser Asp Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
            195                 200                 205

Arg Gln Val Val Thr Gly Met Ala Trp Leu Phe Phe Val Ser Trp Gly
            210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val
305

<210> SEQ ID NO 97
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 97

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Asn Thr Asn Ala Glu
            35                  40                  45

Lys Leu Ala Ala Asn Ile Leu Gln Trp Ile Ser Phe Ala Leu Ser Ala
        50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
                85                  90                  95

Glu Tyr Phe His Ser Phe Asp Glu Pro Ala Val Ile Tyr Ser Ser Asn
                100                 105                 110

Gly Asn Lys Thr Arg Trp Leu Arg Tyr Ala Ser Trp Leu Leu Thr Cys
            115                 120                 125

Pro Val Ile Leu Ile His Leu Ser Asn Leu Thr Gly Leu Ala Asn Asp
130                 135                 140

Tyr Asn Lys Arg Thr Met Gly Leu Leu Val Ser Asn Ile Gly Thr Ile
```

```
145                 150                 155                 160
Val Trp Gly Thr Thr Ala Ala Leu Ser Lys Gly Tyr Val Arg Val Ile
                165                 170                 175
Phe Phe Leu Met Gly Leu Cys Tyr Gly Ile Tyr Thr Phe Phe Asn Ala
                180                 185                 190
Ala Lys Val Tyr Ile Glu Ala Tyr His Thr Val Pro Lys Gly Arg Cys
                195                 200                 205
Arg Gln Val Val Thr Gly Met Ala Trp Leu Phe Phe Val Ser Trp Gly
            210                 215                 220
Met Phe Pro Ile Leu Phe Ile Leu Gly Pro Glu Gly Phe Gly Val Leu
225                 230                 235                 240
Ser Arg Tyr Gly Ser Asn Val Gly His Thr Ile Ile Asp Leu Met Ser
                245                 250                 255
Lys Gln Cys Trp Gly Leu Leu Gly His Tyr Leu Arg Val Leu Ile His
                260                 265                 270
Ser His Ile Leu Ile His Gly Asp Ile Arg Lys Thr Thr Lys Leu Asn
            275                 280                 285
Ile Gly Gly Thr Glu Ile Glu Val Glu Thr Leu Val Glu Asp Glu Ala
        290                 295                 300
Glu Ala Gly Ala Val
305

<210> SEQ ID NO 98
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 98

Met Ser Arg Arg Pro Trp Leu Leu Ala Leu Ala Leu Ala Val Ala Leu
1               5                   10                  15
Ala Ala Gly Ser Ala Gly Ala Ser Thr Gly Ser Asp Ala Thr Val Pro
                20                  25                  30
Val Ala Thr Gln Asp Gly Pro Asp Tyr Val Phe His Arg Ala His Glu
            35                  40                  45
Arg Met Leu Phe Gln Thr Ser Tyr Thr Leu Glu Asn Asn Gly Ser Val
        50                  55                  60
Ile Cys Ile Pro Asn Asn Gly Gln Cys Phe Cys Leu Ala Trp Leu Lys
65                  70                  75                  80
Ser Asn Asn Thr Asn Ala Glu Lys Leu Ala Ala Asn Ile Leu Gln Trp
                85                  90                  95
Ile Ser Phe Ala Leu Ser Ala Leu Cys Leu Met Phe Tyr Gly Tyr Gln
                100                 105                 110
Thr Trp Lys Ser Thr Cys Gly Trp Glu Asn Ile Tyr Val Ala Thr Ile
            115                 120                 125
Gln Met Ile Lys Phe Ile Ile Glu Tyr Phe His Ser Phe Asp Glu Pro
        130                 135                 140
Ala Val Ile Tyr Ser Ser Asn Gly Asn Lys Thr Arg Trp Leu Arg Tyr
145                 150                 155                 160
Ala Ser Trp Leu Leu Thr Thr Pro Val Ile Leu Ile His Leu Ser Asn
                165                 170                 175
Leu Thr Gly Leu Ala Asn Asp Tyr Asn Lys Arg Thr Met Gly Leu Leu
                180                 185                 190
Val Ser Asp Ile Gly Thr Ile Val Trp Gly Thr Thr Ala Ala Leu Ser
```

```
              195                 200                 205
Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
                260                 265                 270

Pro Glu Gly Phe Gly Val Leu Ser Arg Tyr Gly Ser Asn Val Gly His
                275                 280                 285

Thr Ile Ile Asp Leu Met Ser Lys Gln Cys Trp Gly Leu Leu Gly His
            290                 295                 300

Tyr Leu Arg Val Leu Ile His Ser His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
                340                 345

<210> SEQ ID NO 99
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 99

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
50                  55                  60

Ile Cys Ile Pro Asn Asn Gly Gln Cys Phe Cys Leu Ala Trp Leu Lys
65                  70                  75                  80

Ser Asn Asn Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
                100                 105                 110

Thr Trp Lys Ser Thr Cys Gly Trp Glu Asn Ile Tyr Val Ala Thr Ile
            115                 120                 125

Gln Met Ile Lys Phe Ile Ile Glu Tyr Phe His Ser Phe Asp Glu Pro
130                 135                 140

Ala Val Ile Tyr Ser Ser Asn Gly Asn Lys Thr Arg Trp Leu Arg Tyr
145                 150                 155                 160

Ala Ser Trp Leu Leu Thr Ala Pro Val Ile Leu Ile His Leu Ser Asn
                165                 170                 175

Leu Thr Gly Leu Ala Asn Asp Tyr Asn Lys Arg Thr Met Gly Leu Leu
                180                 185                 190

Val Ser Asp Ile Gly Thr Ile Val Trp Gly Thr Thr Ala Ala Leu Ser
            195                 200                 205

Lys Gly Tyr Val Arg Val Ile Phe Phe Leu Met Gly Leu Cys Tyr Gly
```

```
              210                 215                 220
Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
                260                 265                 270

Pro Glu Gly Phe Gly Val Leu Ser Arg Tyr Gly Ser Asn Val Gly His
                275                 280                 285

Thr Ile Ile Asp Leu Met Ser Lys Gln Cys Trp Gly Leu Leu Gly His
                290                 295                 300

Tyr Leu Arg Val Leu Ile His Ser His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
                340                 345

<210> SEQ ID NO 100
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 100

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
                35                  40                  45

Arg Met Leu Phe Gln Thr Ser Tyr Thr Leu Glu Asn Asn Gly Ser Val
            50                  55                  60

Ile Cys Ile Pro Asn Asn Gly Gln Cys Phe Cys Leu Ala Trp Leu Lys
65                  70                  75                  80

Ser Asn Asn Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
                100                 105                 110

Thr Trp Lys Ser Thr Cys Gly Trp Glu Asn Ile Tyr Val Ala Thr Ile
            115                 120                 125

Gln Met Ile Lys Phe Ile Ile Glu Tyr Phe His Ser Phe Asp Glu Pro
            130                 135                 140

Ala Val Ile Tyr Ser Ser Asn Gly Asn Lys Thr Arg Trp Leu Arg Tyr
145                 150                 155                 160

Ala Ser Trp Leu Leu Thr Ser Pro Val Ile Leu Ile His Leu Ser Asn
                165                 170                 175

Leu Thr Gly Leu Ala Asn Asp Tyr Asn Lys Arg Thr Met Gly Leu Leu
                180                 185                 190

Val Ser Asp Ile Gly Thr Ile Val Trp Gly Thr Thr Ala Ala Leu Ser
            195                 200                 205

Lys Gly Tyr Val Arg Val Ile Phe Phe Leu Met Gly Leu Cys Tyr Gly
            210                 215                 220

Ile Tyr Thr Phe Phe Asn Ala Ala Lys Val Tyr Ile Glu Ala Tyr His
```

```
            225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
                260                 265                 270

Pro Glu Gly Phe Gly Val Leu Ser Arg Tyr Gly Ser Asn Val Gly His
                275                 280                 285

Thr Ile Ile Asp Leu Met Ser Lys Gln Cys Trp Gly Leu Leu Gly His
                290                 295                 300

Tyr Leu Arg Val Leu Ile His Ser His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
                340                 345

<210> SEQ ID NO 101
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 101

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

Ser Asn Asn Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
                100                 105                 110

Thr Trp Lys Ser Thr Cys Gly Trp Glu Asn Ile Tyr Val Ala Thr Ile
            115                 120                 125

Gln Met Ile Lys Phe Ile Ile Glu Tyr Phe His Ser Phe Asp Glu Pro
        130                 135                 140

Ala Val Ile Tyr Ser Ser Asn Gly Asn Lys Thr Arg Trp Leu Arg Tyr
145                 150                 155                 160

Ala Ser Trp Leu Leu Thr Thr Pro Val Ile Leu Ile His Leu Ser Asn
                165                 170                 175

Leu Thr Gly Leu Ala Asn Asp Tyr Asn Lys Arg Thr Met Gly Leu Leu
                180                 185                 190

Val Ser Cys Ile Gly Thr Ile Val Trp Gly Thr Thr Ala Ala Leu Ser
            195                 200                 205

Lys Gly Tyr Val Arg Val Ile Phe Phe Leu Met Gly Leu Cys Tyr Gly
        210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
```

```
                       245                 250                 255
Leu Phe Val Ser Trp Gly Met Phe Pro Ile Leu Phe Ile Leu Gly
            260                 265                 270

Pro Glu Gly Phe Gly Val Leu Ser Arg Tyr Gly Ser Asn Val Gly His
            275                 280                 285

Thr Ile Ile Asp Leu Met Ser Lys Gln Cys Trp Gly Leu Leu Gly His
290                 295                 300

Tyr Leu Arg Val Leu Ile His Ser His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 102
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 102

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Asn Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Asn Ile Tyr Val Ala Thr Ile
        115                 120                 125

Gln Met Ile Lys Phe Ile Ile Glu Tyr Phe His Ser Phe Asp Glu Pro
    130                 135                 140

Ala Val Ile Tyr Ser Ser Asn Gly Asn Lys Thr Arg Trp Leu Arg Tyr
145                 150                 155                 160

Ala Ser Trp Leu Leu Thr Thr Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asn Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
```

```
                    260                 265                 270
Pro Glu Gly Phe Gly Val Leu Ser Arg Tyr Gly Ser Asn Val Gly His
                275                 280                 285

Thr Ile Ile Asp Leu Met Ser Lys Gln Cys Trp Gly Leu Leu Gly His
                290                 295                 300

Tyr Leu Arg Val Leu Ile His Ser His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
                340                 345

<210> SEQ ID NO 103
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 103

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
                35                  40                  45

Arg Met Leu Phe Gln Thr Ser Tyr Thr Leu Glu Asn Asn Gly Ser Val
                50                  55                  60

Ile Cys Ile Pro Asn Asn Gly Gln Cys Phe Cys Leu Ala Trp Leu Lys
65                  70                  75                  80

Ser Asn Asn Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
                100                 105                 110

Thr Trp Lys Ser Thr Cys Gly Trp Glu Asn Ile Tyr Val Ala Thr Ile
                115                 120                 125

Gln Met Ile Lys Phe Ile Ile Glu Tyr Phe His Ser Phe Asp Glu Pro
                130                 135                 140

Ala Val Ile Tyr Ser Ser Asn Gly Asn Lys Thr Arg Trp Leu Arg Tyr
145                 150                 155                 160

Ala Ser Trp Leu Leu Thr Ala Pro Val Ile Leu Ile His Leu Ser Asn
                165                 170                 175

Leu Thr Gly Leu Ala Asn Asp Tyr Asn Lys Arg Thr Met Gly Leu Leu
                180                 185                 190

Val Ser Cys Ile Gly Thr Ile Val Trp Gly Thr Thr Ala Ala Leu Ser
                195                 200                 205

Lys Gly Tyr Val Arg Val Ile Phe Phe Leu Met Gly Leu Cys Tyr Gly
                210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
                260                 265                 270

Pro Glu Gly Phe Gly Val Leu Ser Arg Tyr Gly Ser Asn Val Gly His
```

```
            275                 280                 285
Thr Ile Ile Asp Leu Met Ser Lys Gln Cys Trp Gly Leu Leu Gly His
        290                 295                 300

Tyr Leu Arg Val Leu Ile His Ser His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
        340                 345
```

<210> SEQ ID NO 104
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 104

```
Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Asn Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Asn Ile Tyr Val Ala Thr Ile
        115                 120                 125

Gln Met Ile Lys Phe Ile Ile Glu Tyr Phe His Ser Phe Asp Glu Pro
    130                 135                 140

Ala Val Ile Tyr Ser Ser Asn Gly Asn Lys Thr Arg Trp Leu Arg Tyr
145                 150                 155                 160

Ala Ser Trp Leu Leu Thr Ala Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asn Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Arg Tyr Gly Ser Asn Val Gly His
        275                 280                 285

Thr Ile Ile Asp Leu Met Ser Lys Gln Cys Trp Gly Leu Leu Gly His
```

290                 295                 300
Tyr Leu Arg Val Leu Ile His Ser His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 105
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 105

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
50                  55                  60

Ile Cys Ile Pro Asn Asn Gly Gln Cys Phe Cys Leu Ala Trp Leu Lys
65                  70                  75                  80

Ser Asn Asn Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Asn Ile Tyr Val Ala Thr Ile
        115                 120                 125

Gln Met Ile Lys Phe Ile Ile Glu Tyr Phe His Ser Phe Asp Glu Pro
130                 135                 140

Ala Val Ile Tyr Ser Ser Asn Gly Asn Lys Thr Arg Trp Leu Arg Tyr
145                 150                 155                 160

Ala Ser Trp Leu Leu Thr Ser Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Cys Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Arg Tyr Gly Ser Asn Val Gly His
        275                 280                 285

Thr Ile Ile Asp Leu Met Ser Lys Gln Cys Trp Gly Leu Leu Gly His
290                 295                 300

Tyr Leu Arg Val Leu Ile His Ser His Ile Leu Ile His Gly Asp Ile

```
                305                 310                 315                 320
Arg Lys Thr Thr Lys Leu Asn Ile Gly Gly Thr Glu Ile Glu Val Glu
                    325                 330                 335

Thr Leu Val Glu Asp Glu Ala Glu Ala Gly Ala Val
                340                 345

<210> SEQ ID NO 106
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 106

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

Ser Asn Asn Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Asn Ile Tyr Val Ala Thr Ile
        115                 120                 125

Gln Met Ile Lys Phe Ile Ile Glu Tyr Phe His Ser Phe Asp Glu Pro
130                 135                 140

Ala Val Ile Tyr Ser Ser Asn Gly Asn Lys Thr Arg Trp Leu Arg Tyr
145                 150                 155                 160

Ala Ser Trp Leu Leu Thr Ser Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asn Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Arg Tyr Gly Ser Asn Val Gly His
        275                 280                 285

Thr Ile Ile Asp Leu Met Ser Lys Gln Cys Trp Gly Leu Leu Gly His
290                 295                 300

Tyr Leu Arg Val Leu Ile His Ser His Ile Leu Ile His Gly Asp Ile
305                 310                 315                 320

Arg Lys Thr Thr Lys Leu Asn Ile Gly Gly Thr Glu Ile Glu Val Glu
```

325                 330                 335
Thr Leu Val Glu Asp Glu Ala Glu Ala Gly Ala Val
                340                 345

<210> SEQ ID NO 107
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 107

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Asn Thr Asn Ala Glu
            35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Arg Trp Leu Arg Tyr Ala Ser Trp Leu Leu Thr Thr
        115                 120                 125

Pro Val Ile Leu Ile His Leu Ser Asn Leu Thr Gly Leu Ala Asn Asp
130                 135                 140

Tyr Asn Lys Arg Thr Met Gly Leu Leu Val Ser Asp Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val
305

<210> SEQ ID NO 108
<211> LENGTH: 309
<212> TYPE: PRT

<213> ORGANISM: Artificial sequence
<220> FEATURE:
<223> OTHER INFORMATION: Synthetic polypeptide

<400> SEQUENCE: 108

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Asn Thr Asn Ala Glu
        35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Arg Trp Leu Arg Tyr Ala Ser Trp Leu Leu Thr Ala
        115                 120                 125

Pro Val Ile Leu Ile His Leu Ser Asn Leu Thr Gly Leu Ala Asn Asp
130                 135                 140

Tyr Asn Lys Arg Thr Met Gly Leu Leu Val Ser Asp Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
        290                 295                 300

Glu Ala Gly Ala Val
305

<210> SEQ ID NO 109
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 109

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Asn Thr Asn Ala Glu
        35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Arg Trp Leu Arg Tyr Ala Ser Trp Leu Leu Thr Ser
        115                 120                 125

Pro Val Ile Leu Ile His Leu Ser Asn Leu Thr Gly Leu Ala Asn Asp
130                 135                 140

Tyr Asn Lys Arg Thr Met Gly Leu Leu Val Ser Asp Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val
305

<210> SEQ ID NO 110
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 110

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Asn Thr Asn Ala Glu
        35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
                85                  90                  95

Glu Tyr Phe His Ser Phe Asp Glu Pro Ala Val Ile Tyr Ser Ser Asn
                100                 105                 110

Gly Asn Lys Thr Arg Trp Leu Arg Tyr Ala Ser Trp Leu Leu Thr Thr
                115                 120                 125

Pro Val Ile Leu Ile His Leu Ser Asn Leu Thr Gly Leu Ala Asn Asp
130                 135                 140

Tyr Asn Lys Arg Thr Met Gly Leu Leu Val Ser Cys Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
                180                 185                 190

Ala Lys Val Tyr Ile Glu Ala Tyr His Thr Val Pro Lys Gly Arg Cys
                195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
                260                 265                 270

Ser His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ala
                290                 295                 300

Glu Ala Gly Ala Val
305

<210> SEQ ID NO 111
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 111

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Asn Thr Asn Ala Glu
                35                  40                  45

Lys Leu Ala Ala Asn Ile Leu Gln Trp Ile Ser Phe Ala Leu Ser Ala
                50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
                85                  90                  95

Glu Tyr Phe His Ser Phe Asp Glu Pro Ala Val Ile Tyr Ser Ser Asn
                100                 105                 110

Gly Asn Lys Thr Arg Trp Leu Arg Tyr Ala Ser Trp Leu Leu Thr Thr
            115                 120                 125

Pro Val Ile Leu Ile His Leu Ser Asn Leu Thr Gly Leu Ala Asn Asp
130                 135                 140

Tyr Asn Lys Arg Thr Met Gly Leu Leu Val Ser Asn Ile Gly Thr Ile
145                 150                 155                 160

Val Trp Gly Thr Thr Ala Ala Leu Ser Lys Gly Tyr Val Arg Val Ile
            165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
            195                 200                 205

Arg Gln Val Val Thr Gly Met Ala Trp Leu Phe Phe Val Ser Trp Gly
            210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
            245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val
305

<210> SEQ ID NO 112
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 112

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Asn Thr Asn Ala Glu
            35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
            85                  90                  95

Glu Tyr Phe His Ser Phe Asp Glu Pro Ala Val Ile Tyr Ser Ser Asn
            100                 105                 110

Gly Asn Lys Thr Arg Trp Leu Arg Tyr Ala Ser Trp Leu Leu Thr Ala
            115                 120                 125

Pro Val Ile Leu Ile His Leu Ser Asn Leu Thr Gly Leu Ala Asn Asp
            130                 135                 140

Tyr Asn Lys Arg Thr Met Gly Leu Leu Val Ser Cys Ile Gly Thr Ile
145                 150                 155                 160

```
Val Trp Gly Thr Thr Ala Ala Leu Ser Lys Gly Tyr Val Arg Val Ile
            165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
            195                 200                 205

Arg Gln Val Val Thr Gly Met Ala Trp Leu Phe Phe Val Ser Trp Gly
            210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
            245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val
305

<210> SEQ ID NO 113
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 113

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Asn Thr Asn Ala Glu
            35                  40                  45

Lys Leu Ala Ala Asn Ile Leu Gln Trp Ile Ser Phe Ala Leu Ser Ala
        50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
            85                  90                  95

Glu Tyr Phe His Ser Phe Asp Glu Pro Ala Val Ile Tyr Ser Ser Asn
            100                 105                 110

Gly Asn Lys Thr Arg Trp Leu Arg Tyr Ala Ser Trp Leu Leu Thr Ala
            115                 120                 125

Pro Val Ile Leu Ile His Leu Ser Asn Leu Thr Gly Leu Ala Asn Asp
130                 135                 140

Tyr Asn Lys Arg Thr Met Gly Leu Leu Val Ser Asn Ile Gly Thr Ile
145                 150                 155                 160

Val Trp Gly Thr Thr Ala Ala Leu Ser Lys Gly Tyr Val Arg Val Ile
            165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
            195                 200                 205
```

```
Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
            245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
290                 295                 300

Glu Ala Gly Ala Val
305

<210> SEQ ID NO 114
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 114

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Asn Thr Asn Ala Glu
        35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Arg Trp Leu Arg Tyr Ala Ser Trp Leu Leu Thr Ser
        115                 120                 125

Pro Val Ile Leu Ile His Leu Ser Asn Leu Thr Gly Leu Ala Asn Asp
130                 135                 140

Tyr Asn Lys Arg Thr Met Gly Leu Leu Val Ser Cys Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
            245                 250                 255
```

```
Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val
305

<210> SEQ ID NO 115
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 115

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Asn Thr Asn Ala Glu
            35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
            85                  90                  95

Glu Tyr Phe His Ser Phe Asp Glu Pro Ala Val Ile Tyr Ser Ser Asn
            100                 105                 110

Gly Asn Lys Thr Arg Trp Leu Arg Tyr Ala Ser Trp Leu Leu Thr Ser
            115                 120                 125

Pro Val Ile Leu Ile His Leu Ser Asn Leu Thr Gly Leu Ala Asn Asp
130                 135                 140

Tyr Asn Lys Arg Thr Met Gly Leu Leu Val Ser Asn Ile Gly Thr Ile
145                 150                 155                 160

Val Trp Gly Thr Thr Ala Ala Leu Ser Lys Gly Tyr Val Arg Val Ile
            165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
            195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
            245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300
```

Glu Ala Gly Ala Val
305

<210> SEQ ID NO 116
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 116

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ser Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Asn Ile Tyr Val Cys Ala Ile Gln Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Arg Trp Leu Arg Tyr Ala Ser Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 117
<211> LENGTH: 310
<212> TYPE: PRT
<213> ORGANISM: Artificial sequence
<220> FEATURE:

<223> OTHER INFORMATION: Synthetic polypeptide

<400> SEQUENCE: 117

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ser Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Asn Ile Tyr Val Cys Ala Ile Gln Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Arg Trp Leu Arg Tyr Ala Ser Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asn Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 118
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 118

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

-continued

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ser Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Asn Ile Tyr Val Cys Ala Ile Gln Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Arg Trp Leu Arg Tyr Ala Ser Trp Leu Leu Thr Thr
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 119
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 119

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
                20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ser Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Asn Ile Tyr Val Cys Ala Ile Gln Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Arg Trp Leu Arg Tyr Ala Ser Trp Leu Leu Thr Ala
        115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val Pro
305                 310

<210> SEQ ID NO 120
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 120

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ser Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Asn Ile Tyr Val Cys Ala Ile Gln Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Arg Trp Leu Arg Tyr Ala Ser Trp Leu Leu Thr Ser
        115                 120                 125

```
Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
        275                 280                 285

Ile Gly Gly Thr Glu Ile Glu Val Gly Thr Leu Val Glu Asp Glu Ala
    290                 295                 300

Glu Ala Gly Ala Val Pro
305                 310

<210> SEQ ID NO 121
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 121

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
                20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ser Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Asn Ile Tyr Val Cys Ala Ile Gln Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Arg Trp Leu Arg Tyr Ala Ser Trp Leu Leu Thr Thr
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Cys Ile Gly Thr Ile
145                 150                 155                 160

Val Trp Gly Ala Thr Ser Ala Met Ala Thr Gly Tyr Val Lys Val Ile
                165                 170                 175
```

```
Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 122
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 122

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ser Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Asn Ile Tyr Val Cys Ala Ile Gln Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Arg Trp Leu Arg Tyr Ala Ser Trp Leu Leu Thr Thr
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asn Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220
```

```
Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
            245                 250                 255

Lys Gln Cys Trp Gly Leu Leu Gly His Tyr Leu Arg Val Leu Ile His
        260                 265                 270

Ser His Ile Leu Ile His Gly Asp Ile Arg Lys Thr Thr Lys Leu Asn
    275                 280                 285

Ile Gly Gly Thr Glu Ile Glu Val Glu Thr Leu Val Glu Asp Glu Ala
290                 295                 300

Glu Ala Gly Ala Val Pro
305                 310

<210> SEQ ID NO 123
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 123

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ser Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Asn Ile Tyr Val Cys Ala Ile Gln Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Arg Trp Leu Arg Tyr Ala Ser Trp Leu Leu Thr Ala
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Cys Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270
```

```
Ser His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 124
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 124

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ser Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Asn Ile Tyr Val Cys Ala Ile Gln Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Arg Trp Leu Arg Tyr Ala Ser Trp Leu Leu Thr Ala
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asn Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310
```

<210> SEQ ID NO 125
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 125

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ser Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Asn Ile Tyr Val Cys Ala Ile Gln Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Arg Trp Leu Arg Tyr Ala Ser Trp Leu Leu Thr Ser
        115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Cys Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 126
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 126

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ser Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Asn Ile Tyr Val Cys Ala Ile Gln Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Arg Trp Leu Arg Tyr Ala Ser Trp Leu Leu Thr Ser
        115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asn Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Arg Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Ser His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val Pro
305                 310

<210> SEQ ID NO 127
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 127

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu

```
                35                  40                  45
Arg Met Leu Phe Gln Thr Ser Tyr Thr Leu Glu Asn Asn Gly Ser Val
 50                  55                  60

Ile Cys Ile Pro Asn Asn Gly Gln Cys Phe Cys Leu Ala Trp Leu Lys
 65                  70                  75                  80

Ser Asn Gly Thr Asn Ala Glu Lys Leu Ala Asn Ile Leu Gln Trp
                 85                  90                  95

Ile Ser Phe Ala Leu Ser Ala Leu Cys Leu Met Phe Tyr Gly Tyr Gln
                100                 105                 110

Thr Trp Lys Ser Thr Cys Gly Trp Glu Asn Ile Tyr Val Ala Thr Ile
                115                 120                 125

Gln Met Ile Lys Phe Ile Ile Glu Tyr Phe His Ser Phe Asp Glu Pro
                130                 135                 140

Ala Val Ile Tyr Ser Ser Asn Gly Asn Lys Thr Arg Trp Leu Arg Tyr
145                 150                 155                 160

Ala Ser Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
                180                 185                 190

Val Ser Asp Val Gly Cys Ile Val Trp Gly Ala Thr Ser Ala Met Cys
                195                 200                 205

Thr Gly Trp Thr Lys Ile Leu Phe Phe Leu Ile Ser Leu Ser Tyr Gly
                210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
                260                 265                 270

Thr Glu Gly Phe Gly His Ile Ser Arg Tyr Gly Ser Asn Ile Gly His
                275                 280                 285

Ser Ile Leu Asp Leu Ile Ala Lys Gln Met Trp Gly Val Leu Gly Asn
                290                 295                 300

Tyr Leu Arg Val Lys Ile His Ser His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
                340

<210> SEQ ID NO 128
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 128

Met Ser Arg Arg Pro Trp Leu Leu Ala Leu Ala Leu Ala Val Ala Leu
 1               5                  10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
                35                  40                  45

Arg Met Leu Phe Gln Thr Ser Tyr Thr Leu Glu Asn Asn Gly Ser Val
```

```
                 50                  55                  60

Ile Cys Ile Pro Asn Asn Gly Gln Cys Phe Cys Leu Ala Trp Leu Lys
 65                  70                  75                  80

Ser Asn Gly Thr Asn Ala Glu Lys Leu Ala Ala Asn Ile Leu Gln Trp
                 85                  90                  95

Ile Ser Phe Ala Leu Ser Ala Leu Cys Leu Met Phe Tyr Gly Tyr Gln
                100                 105                 110

Thr Trp Lys Ser Thr Cys Gly Trp Glu Asn Ile Tyr Val Ala Thr Ile
                115                 120                 125

Gln Met Ile Lys Phe Ile Ile Glu Tyr Phe His Ser Phe Asp Glu Pro
130                 135                 140

Ala Val Ile Tyr Ser Ser Asn Gly Asn Lys Thr Arg Trp Leu Arg Tyr
145                 150                 155                 160

Ala Ser Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
                180                 185                 190

Val Ser Asn Val Gly Cys Ile Val Trp Gly Ala Thr Ser Ala Met Cys
                195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
                260                 265                 270

Thr Glu Gly Phe Gly His Ile Ser Arg Tyr Gly Ser Asn Ile Gly His
                275                 280                 285

Ser Ile Leu Asp Leu Ile Ala Lys Gln Met Trp Gly Val Leu Gly Asn
290                 295                 300

Tyr Leu Arg Val Lys Ile His Ser His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp
                340

<210> SEQ ID NO 129
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 129

Met Asp Tyr Gly Gly Ala Leu Ser Ala Val Gly Leu Phe Gln Thr Ser
 1               5                  10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Ile Ser Phe Ala Leu Ser Ala
 50                  55                  60

Leu Cys Leu Met Phe Tyr Gly Tyr Gln Thr Trp Lys Ser Thr Cys Gly
```

```
            65                  70                  75                  80
Trp Glu Asn Ile Tyr Val Ala Thr Ile Gln Met Ile Lys Phe Ile Ile
                    85                  90                  95

Glu Tyr Phe His Ser Phe Asp Glu Pro Ala Val Ile Tyr Ser Ser Asn
                100                 105                 110

Gly Asn Lys Thr Arg Trp Leu Arg Tyr Ala Ser Trp Leu Leu Thr Cys
                115                 120                 125

Pro Val Leu Leu Ile His Leu Ser Asn Leu Thr Gly Leu Lys Asp Asp
        130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                    165                 170                 175

Phe Phe Leu Ile Ser Leu Ser Tyr Gly Met Tyr Thr Tyr Phe His Ala
                180                 185                 190

Ala Lys Val Tyr Ile Glu Ala Phe His Thr Val Pro Lys Gly Ile Cys
                195                 200                 205

Arg Glu Leu Val Arg Val Met Ala Trp Thr Phe Phe Val Ala Trp Gly
        210                 215                 220

Met Phe Pro Val Leu Phe Leu Leu Gly Thr Glu Gly Phe Gly His Ile
225                 230                 235                 240

Ser Arg Tyr Gly Ser Asn Ile Gly His Ser Ile Leu Asp Leu Ile Ala
                    245                 250                 255

Lys Gln Met Trp Gly Val Leu Gly Asn Tyr Leu Arg Val Lys Ile His
                260                 265                 270

Ser His Ile Leu Leu Tyr Gly Asp Ile Arg Lys Lys Gln Lys Ile Thr
                275                 280                 285

Ile Ala Gly Gln Glu Met Glu Val Glu Thr Leu Val Ala Glu Glu
        290                 295                 300

Asp
305

<210> SEQ ID NO 130
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 130

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Ile Ser Phe Ala Leu Ser Ala
        50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
                    85                  90                  95

Glu Tyr Phe His Ser Phe Asp Glu Pro Ala Val Ile Tyr Ser Ser Asn
                100                 105                 110

Gly Asn Lys Thr Arg Trp Leu Arg Tyr Ala Ser Trp Leu Leu Thr Cys
```

115                 120                 125
Pro Val Leu Leu Ile His Leu Ser Asn Leu Thr Gly Leu Lys Asp Asp
130                 135                 140

Tyr Ser Lys Arg Thr Met Gly Leu Leu Val Ser Asn Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
                180                 185                 190

Ala Lys Val Tyr Ile Glu Ala Phe His Thr Val Pro Lys Gly Ile Cys
                195                 200                 205

Arg Glu Leu Val Arg Val Met Ala Trp Thr Phe Phe Val Ala Trp Gly
210                 215                 220

Met Phe Pro Val Leu Phe Leu Gly Thr Gly Phe Gly His Ile
225                 230                 235                 240

Ser Arg Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
                260                 265                 270

Ser His Ile Leu Leu Tyr Gly Asp Ile Arg Lys Lys Gln Lys Ile Thr
                275                 280                 285

Ile Ala Gly Gln Glu Met Glu Val Glu Thr Leu Val Ala Glu Glu
290                 295                 300

Asp
305

<210> SEQ ID NO 131
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 131

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Asn Ile Tyr Val Ala Thr Ile
        115                 120                 125

Gln Met Ile Lys Phe Ile Ile Glu Tyr Phe His Ser Phe Asp Glu Pro
    130                 135                 140

Ala Val Ile Tyr Ser Ser Asn Gly Asn Lys Thr Arg Trp Leu Arg Tyr
145                 150                 155                 160

Ala Ser Trp Leu Leu Thr Thr Pro Val Leu Leu Ile His Leu Ser Asn

```
                    165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
            210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
            260                 265                 270

Thr Glu Gly Phe Gly His Ile Ser Arg Tyr Gly Ser Asn Ile Gly His
            275                 280                 285

Ser Ile Leu Asp Leu Ile Ala Lys Gln Met Trp Gly Val Leu Gly Asn
            290                 295                 300

Tyr Leu Arg Val Lys Ile His Ser His Ile Leu Leu Tyr Gly Asp Ile
305                 310                 315                 320

Arg Lys Lys Gln Lys Ile Thr Ile Ala Gly Gln Glu Met Glu Val Glu
            325                 330                 335

Thr Leu Val Ala Glu Glu Asp
            340
```

<210> SEQ ID NO 132
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 132

```
Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
            50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
            85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Asn Ile Tyr Val Ala Thr Ile
            115                 120                 125

Gln Met Ile Lys Phe Ile Ile Glu Tyr Phe His Ser Phe Asp Glu Pro
            130                 135                 140

Ala Val Ile Tyr Ser Ser Asn Gly Asn Lys Thr Arg Trp Leu Arg Tyr
145                 150                 155                 160

Ala Ser Trp Leu Leu Thr Ala Pro Val Leu Ile His Leu Ser Asn
            165                 170                 175

Leu Thr Gly Leu Lys Asp Asp Tyr Ser Lys Arg Thr Met Gly Leu Leu
```

```
                    180                 185                 190
Val Ser Asp Val Gly Cys Ile Val Trp Gly Ala Thr Ser Ala Met Cys
            195                 200                 205

Thr Gly Trp Thr Lys Ile Leu Phe Leu Ile Ser Leu Ser Tyr Gly
        210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Arg Tyr Gly Ser Asn Ile Gly His
        275                 280                 285

Ser Ile Leu Asp Leu Ile Ala Lys Gln Met Trp Gly Val Leu Gly Asn
    290                 295                 300

Tyr Leu Arg Val Lys Ile His Ser His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp
            340

<210> SEQ ID NO 133
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 133

Met Ser Arg Arg Pro Trp Leu Leu Ala Leu Ala Leu Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Asn Ile Tyr Val Ala Thr Ile
        115                 120                 125

Gln Met Ile Lys Phe Ile Ile Glu Tyr Phe His Ser Phe Asp Glu Pro
    130                 135                 140

Ala Val Ile Tyr Ser Ser Asn Gly Asn Lys Thr Arg Trp Leu Arg Tyr
145                 150                 155                 160

Ala Ser Trp Leu Leu Thr Ser Pro Val Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
```

```
            195                 200                 205
Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Arg Tyr Gly Ser Asn Ile Gly His
        275                 280                 285

Ser Ile Leu Asp Leu Ile Ala Lys Gln Met Trp Gly Val Leu Gly Asn
    290                 295                 300

Tyr Leu Arg Val Lys Ile His Ser His Ile Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp
            340

<210> SEQ ID NO 134
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 134

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Asn Ile Tyr Val Ala Thr Ile
        115                 120                 125

Gln Met Ile Lys Phe Ile Ile Glu Tyr Phe His Ser Phe Asp Glu Pro
130                 135                 140

Ala Val Ile Tyr Ser Ser Asn Gly Asn Lys Thr Arg Trp Leu Arg Tyr
145                 150                 155                 160

Ala Ser Trp Leu Leu Thr Thr Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Cys Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
```

```
            210                 215                 220
Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Arg Tyr Gly Ser Asn Ile Gly His
        275                 280                 285

Ser Ile Leu Asp Leu Ile Ala Lys Gln Met Trp Gly Val Leu Gly Asn
    290                 295                 300

Tyr Leu Arg Val Lys Ile His Ser His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 135
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 135

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Asn Ile Tyr Val Ala Thr Ile
        115                 120                 125

Gln Met Ile Lys Phe Ile Ile Glu Tyr Phe His Ser Phe Asp Glu Pro
    130                 135                 140

Ala Val Ile Tyr Ser Ser Asn Gly Asn Lys Thr Arg Trp Leu Arg Tyr
145                 150                 155                 160

Ala Ser Trp Leu Leu Thr Thr Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asn Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
```

```
225                 230                 235                 240
Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Arg Tyr Gly Ser Asn Ile Gly His
        275                 280                 285

Ser Ile Leu Asp Leu Ile Ala Lys Gln Met Trp Gly Val Leu Gly Asn
    290                 295                 300

Tyr Leu Arg Val Lys Ile His Ser His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
                340

<210> SEQ ID NO 136
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 136

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Asn Ile Tyr Val Ala Thr Ile
        115                 120                 125

Gln Met Ile Lys Phe Ile Ile Glu Tyr Phe His Ser Phe Asp Glu Pro
    130                 135                 140

Ala Val Ile Tyr Ser Ser Asn Gly Asn Lys Thr Arg Trp Leu Arg Tyr
145                 150                 155                 160

Ala Ser Trp Leu Leu Thr Ala Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Cys Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
```

```
                245                 250                 255

Thr Phe Phe Val Ala Trp Gly Met Phe Pro Val Leu Phe Leu Leu Gly
            260                 265                 270

Thr Glu Gly Phe Gly His Ile Ser Arg Tyr Gly Ser Asn Ile Gly His
        275                 280                 285

Ser Ile Leu Asp Leu Ile Ala Lys Gln Met Trp Gly Val Leu Gly Asn
    290                 295                 300

Tyr Leu Arg Val Lys Ile His Ser His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 137
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 137

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Asn Ile Tyr Val Ala Thr Ile
        115                 120                 125

Gln Met Ile Lys Phe Ile Ile Glu Tyr Phe His Ser Phe Asp Glu Pro
    130                 135                 140

Ala Val Ile Tyr Ser Ser Asn Gly Asn Lys Thr Arg Trp Leu Arg Tyr
145                 150                 155                 160

Ala Ser Trp Leu Leu Thr Ala Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asn Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
```

```
                      260                 265                 270
Thr Glu Gly Phe Gly His Ile Ser Arg Tyr Gly Ser Asn Ile Gly His
            275                 280                 285

Ser Ile Leu Asp Leu Ile Ala Lys Gln Met Trp Gly Val Leu Gly Asn
        290                 295                 300

Tyr Leu Arg Val Lys Ile His Ser His Ile Leu Leu Tyr Gly Asp Ile
305                 310                 315                 320

Arg Lys Lys Gln Lys Ile Thr Ile Ala Gly Gln Glu Met Glu Val Glu
            325                 330                 335

Thr Leu Val Ala Glu Glu Glu Asp
            340

<210> SEQ ID NO 138
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 138

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Asn Ile Tyr Val Ala Thr Ile
        115                 120                 125

Gln Met Ile Lys Phe Ile Ile Glu Tyr Phe His Ser Phe Asp Glu Pro
    130                 135                 140

Ala Val Ile Tyr Ser Ser Asn Gly Asn Lys Thr Arg Trp Leu Arg Tyr
145                 150                 155                 160

Ala Ser Trp Leu Leu Thr Ser Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Cys Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Arg Tyr Gly Ser Asn Ile Gly His
```

```
            275                 280                 285
Ser Ile Leu Asp Leu Ile Ala Lys Gln Met Trp Gly Val Leu Gly Asn
    290                 295                 300

Tyr Leu Arg Val Lys Ile His Ser His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 139
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 139

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Asn Ile Tyr Val Ala Thr Ile
        115                 120                 125

Gln Met Ile Lys Phe Ile Ile Glu Tyr Phe His Ser Phe Asp Glu Pro
    130                 135                 140

Ala Val Ile Tyr Ser Ser Asn Gly Asn Lys Thr Arg Trp Leu Arg Tyr
145                 150                 155                 160

Ala Ser Trp Leu Leu Thr Ser Pro Val Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asn Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Arg Tyr Gly Ser Asn Ile Gly His
        275                 280                 285

Ser Ile Leu Asp Leu Ile Ala Lys Gln Met Trp Gly Val Leu Gly Asn
```

```
                290                 295                 300
Tyr Leu Arg Val Lys Ile His Ser His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp
            340

<210> SEQ ID NO 140
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 140

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Arg Trp Leu Arg Tyr Ala Ser Trp Leu Leu Thr Thr
        115                 120                 125

Pro Val Leu Leu Ile His Leu Ser Asn Leu Thr Gly Leu Lys Asp Asp
    130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
    210                 215                 220

Met Phe Pro Val Leu Phe Leu Gly Thr Glu Gly Phe His Gly His Ile
225                 230                 235                 240

Ser Arg Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Ser His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Asp
    290                 295                 300

Asp
```

<210> SEQ ID NO 141
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 141

```
Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Arg Trp Leu Arg Tyr Ala Ser Trp Leu Leu Thr Ala
        115                 120                 125

Pro Val Leu Leu Ile His Leu Ser Asn Leu Thr Gly Leu Lys Asp Asp
130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
210                 215                 220

Met Phe Pro Val Leu Phe Leu Leu Gly Thr Glu Gly Phe Gly His Ile
225                 230                 235                 240

Ser Arg Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Ser His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Asp
290                 295                 300

Asp
305
```

<210> SEQ ID NO 142
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 142

```
Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
    50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Arg Trp Leu Arg Tyr Ala Ser Trp Leu Leu Thr Ser
        115                 120                 125

Pro Val Leu Leu Ile His Leu Ser Asn Leu Thr Gly Leu Lys Asp Asp
    130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
    210                 215                 220

Met Phe Pro Val Leu Phe Leu Leu Gly Thr Glu Gly Phe Gly His Ile
225                 230                 235                 240

Ser Arg Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Ser His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
    290                 295                 300

Asp
305
```

<210> SEQ ID NO 143
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 143

```
Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30
```

```
Gln Cys Phe Cys Leu Ala Trp Leu Lys Ser Asn Gly Thr Asn Ala Glu
         35                  40                  45

Lys Leu Ala Ala Asn Ile Leu Gln Trp Ile Ser Phe Ala Leu Ser Ala
 50                  55                  60

Leu Cys Leu Met Phe Tyr Gly Tyr Gln Thr Trp Lys Ser Thr Cys Gly
 65                  70                  75                  80

Trp Glu Asn Ile Tyr Val Ala Thr Ile Gln Met Ile Lys Phe Ile Ile
                 85                  90                  95

Glu Tyr Phe His Ser Phe Asp Glu Pro Ala Val Ile Tyr Ser Ser Asn
            100                 105                 110

Gly Asn Lys Thr Arg Trp Leu Arg Tyr Ala Ser Trp Leu Leu Thr Thr
            115                 120                 125

Pro Val Leu Leu Ile His Leu Ser Asn Leu Thr Gly Leu Lys Asp Asp
130                 135                 140

Tyr Ser Lys Arg Thr Met Gly Leu Leu Val Ser Cys Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
            195                 200                 205

Arg Glu Leu Val Arg Val Met Ala Trp Thr Phe Phe Val Ala Trp Gly
            210                 215                 220

Met Phe Pro Val Leu Phe Leu Leu Gly Thr Glu Gly Phe Gly His Ile
225                 230                 235                 240

Ser Arg Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Ser His Ile Leu Leu Tyr Gly Asp Ile Arg Lys Lys Gln Lys Ile Thr
            275                 280                 285

Ile Ala Gly Gln Glu Met Glu Val Glu Thr Leu Val Ala Glu Glu Glu
290                 295                 300

Asp
305

<210> SEQ ID NO 144
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 144

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
         35                  40                  45

Lys Leu Ala Ala Asn Ile Leu Gln Trp Ile Ser Phe Ala Leu Ser Ala
 50                  55                  60

Leu Cys Leu Met Phe Tyr Gly Tyr Gln Thr Trp Lys Ser Thr Cys Gly
 65                  70                  75                  80
```

Trp Glu Asn Ile Tyr Val Ala Thr Ile Gln Met Ile Lys Phe Ile Ile
            85                  90                  95

Glu Tyr Phe His Ser Phe Asp Glu Pro Ala Val Ile Tyr Ser Ser Asn
        100                 105                 110

Gly Asn Lys Thr Arg Trp Leu Arg Tyr Ala Ser Trp Leu Leu Thr Thr
        115                 120                 125

Pro Val Leu Leu Ile His Leu Ser Asn Leu Thr Gly Leu Lys Asp Asp
    130                 135                 140

Tyr Ser Lys Arg Thr Met Gly Leu Leu Val Ser Asn Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
    210                 215                 220

Met Phe Pro Val Leu Phe Leu Leu Gly Thr Glu Gly Phe Gly His Ile
225                 230                 235                 240

Ser Arg Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Ser His Ile Leu Leu Tyr Gly Asp Ile Arg Lys Gln Lys Ile Thr
        275                 280                 285

Ile Ala Gly Gln Glu Met Glu Val Glu Thr Leu Val Ala Glu Glu Glu
    290                 295                 300

Asp
305

<210> SEQ ID NO 145
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 145

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
    50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
            85                  90                  95

Glu Tyr Phe His Ser Phe Asp Glu Pro Ala Val Ile Tyr Ser Ser Asn
        100                 105                 110

Gly Asn Lys Thr Arg Trp Leu Arg Tyr Ala Ser Trp Leu Leu Thr Ala
    115                 120                 125

Pro Val Leu Leu Ile His Leu Ser Asn Leu Thr Gly Leu Lys Asp Asp
130                 135                 140

Tyr Ser Lys Arg Thr Met Gly Leu Leu Val Ser Cys Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
                180                 185                 190

Ala Lys Val Tyr Ile Glu Ala Phe His Thr Val Pro Lys Gly Ile Cys
            195                 200                 205

Arg Glu Leu Val Arg Val Met Ala Trp Thr Phe Phe Val Ala Trp Gly
210                 215                 220

Met Phe Pro Val Leu Phe Leu Leu Gly Thr Glu Gly Phe Gly His Ile
225                 230                 235                 240

Ser Arg Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
                260                 265                 270

Ser His Ile Leu Leu Tyr Gly Asp Ile Arg Lys Lys Gln Lys Ile Thr
            275                 280                 285

Ile Ala Gly Gln Glu Met Glu Val Glu Thr Leu Val Ala Glu Glu Glu
290                 295                 300

Asp
305

<210> SEQ ID NO 146
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 146

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Arg Trp Leu Arg Tyr Ala Ser Trp Leu Leu Thr Ala
            115                 120                 125

Pro Val Leu Leu Ile His Leu Ser Asn Leu Thr Gly Leu Lys Asp Asp
130                 135                 140

Tyr Ser Lys Arg Thr Met Gly Leu Leu Val Ser Asn Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
                180                 185                 190

Ala Lys Val Tyr Ile Glu Ala Phe His Thr Val Pro Lys Gly Ile Cys
            195                 200                 205

Arg Glu Leu Val Arg Val Met Ala Trp Thr Phe Phe Val Ala Trp Gly
        210                 215                 220

Met Phe Pro Val Leu Phe Leu Gly Thr Glu Gly Phe Gly His Ile
225                 230                 235                 240

Ser Arg Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Ser His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
    290                 295                 300

Asp
305

<210> SEQ ID NO 147
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 147

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Arg Trp Leu Arg Tyr Ala Ser Trp Leu Leu Thr Ser
        115                 120                 125

Pro Val Leu Leu Ile His Leu Ser Asn Leu Thr Gly Leu Lys Asp Asp
    130                 135                 140

Tyr Ser Lys Arg Thr Met Gly Leu Leu Val Ser Cys Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
    210                 215                 220

```
Met Phe Pro Val Leu Phe Leu Gly Thr Glu Gly Phe Gly His Ile
225                 230                 235                 240

Ser Arg Tyr Gly Ser Asn Ile Gly His Ser Ile Leu Asp Leu Ile Ala
            245                 250                 255

Lys Gln Met Trp Gly Val Leu Gly Asn Tyr Leu Arg Val Lys Ile His
        260                 265                 270

Ser His Ile Leu Leu Tyr Gly Asp Ile Arg Lys Gln Lys Ile Thr
        275                 280                 285

Ile Ala Gly Gln Glu Met Glu Val Glu Thr Leu Val Ala Glu Glu Glu
    290                 295                 300

Asp
305

<210> SEQ ID NO 148
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 148

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
    50                  55                  60

Leu Cys Leu Met Phe Tyr Gly Tyr Gln Thr Trp Lys Ser Thr Cys Gly
65                  70                  75                  80

Trp Glu Asn Ile Tyr Val Ala Thr Ile Gln Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Arg Trp Leu Arg Tyr Ala Ser Trp Leu Leu Thr Ser
        115                 120                 125

Pro Val Leu Leu Ile His Leu Ser Asn Leu Thr Gly Leu Lys Asp Asp
    130                 135                 140

Tyr Ser Lys Arg Thr Met Gly Leu Leu Val Ser Asn Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
    210                 215                 220

Met Phe Pro Val Leu Phe Leu Gly Thr Glu Gly Phe Gly His Ile
225                 230                 235                 240

Ser Arg Tyr Gly Ser Asn Ile Gly His Ser Ile Leu Asp Leu Ile Ala
            245                 250                 255

Lys Gln Met Trp Gly Val Leu Gly Asn Tyr Leu Arg Val Lys Ile His
        260                 265                 270
```

Ser His Ile Leu Leu Tyr Gly Asp Ile Arg Lys Lys Gln Lys Ile Thr
275 280 285

Ile Ala Gly Gln Glu Met Glu Val Glu Thr Leu Val Ala Glu Glu Glu
290 295 300

Asp
305

<210> SEQ ID NO 149
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 149

Met Val Ser Arg Arg Pro Trp Leu Leu Ala Leu Ala Leu Ala Val Ala
1 5 10 15

Leu Ala Ala Gly Ser Ala Gly Ala Ser Thr Gly Ser Asp Ala Thr Val
20 25 30

Pro Val Ala Thr Gln Asp Gly Pro Asp Tyr Val Phe His Arg Ala His
35 40 45

Glu Arg Met Leu Phe Gln Thr Ser Tyr Thr Leu Glu Asn Asn Gly Ser
50 55 60

Val Ile Cys Ile Pro Asn Asn Gly Gln Cys Phe Cys Leu Ala Trp Leu
65 70 75 80

Lys Ser Asn Gly Thr Asn Ala Glu Lys Leu Ala Ala Asn Ile Leu Gln
85 90 95

Trp Val Ser Phe Ala Leu Ser Val Ala Cys Leu Gly Trp Tyr Ala Tyr
100 105 110

Gln Ala Trp Arg Ala Thr Cys Gly Trp Glu Asn Val Tyr Val Ala Leu
115 120 125

Ile Gln Met Met Lys Ser Ile Ile Glu Ala Phe His Ser Phe Asp Ser
130 135 140

Pro Ala Thr Leu Trp Leu Ser Ser Gly Asn Gly Val Arg Trp Met Arg
145 150 155 160

Tyr Gly Ser Trp Leu Leu Thr Cys Pro Val Ile Leu Ile His Leu Ser
165 170 175

Asn Leu Thr Gly Leu Lys Asp Asp Tyr Ser Lys Arg Thr Met Gly Leu
180 185 190

Leu Val Ser Asp Val Gly Cys Ile Val Trp Gly Ala Thr Ser Ala Met
195 200 205

Cys Thr Gly Trp Thr Lys Ile Leu Phe Phe Leu Ile Ser Leu Ser Tyr
210 215 220

Gly Met Tyr Thr Tyr Phe His Ala Ala Lys Val Tyr Ile Glu Ala Phe
225 230 235 240

His Thr Val Pro Lys Gly Leu Cys Arg Gln Leu Val Arg Ala Met Ala
245 250 255

Trp Leu Phe Phe Val Ser Trp Gly Met Phe Pro Val Leu Phe Leu Leu
260 265 270

Gly Pro Glu Gly Phe Gly His Ile Ser Arg Tyr Gly Ser Asn Ile Gly
275 280 285

His Ser Ile Leu Asp Leu Ile Ala Lys Gln Met Trp Gly Val Leu Gly
290 295 300

Asn Tyr Leu Arg Val Lys Ile His Ser His Ile Leu Leu Tyr Gly Asp
305 310 315 320

```
Ile Arg Lys Lys Gln Lys Ile Thr Ile Ala Gly Gln Glu Met Glu Val
            325                 330                 335

Glu Thr Leu Val Ala Glu Glu Asp Lys Tyr Glu Ser Ser
        340                 345                 350

<210> SEQ ID NO 150
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 150

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
        50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Asn Val Tyr Val Ala Leu
        115                 120                 125

Ile Gln Met Met Lys Ser Ile Ile Glu Ala Phe His Ser Phe Asp Ser
130                 135                 140

Pro Ala Thr Leu Trp Leu Ser Ser Gly Asn Gly Val Arg Trp Met Arg
145                 150                 155                 160

Tyr Gly Ser Trp Leu Leu Thr Cys Pro Val Ile Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Asn Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Arg Tyr Gly Ser Asn Ile Gly
        275                 280                 285

His Ser Ile Leu Asp Leu Ile Ala Lys Gln Met Trp Gly Val Leu Gly
290                 295                 300

Asn Tyr Leu Arg Val Lys Ile His Ser His Ile Leu Leu Tyr Gly Asp
305                 310                 315                 320

Ile Arg Lys Lys Gln Lys Ile Thr Ile Ala Gly Gln Glu Met Glu Val
                325                 330                 335
```

```
Glu Thr Leu Val Ala Glu Glu Asp Lys Tyr Glu Ser Ser
            340             345             350
```

<210> SEQ ID NO 151
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 151

```
Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Val Ser Phe Ala Leu Ser Val
50                  55                  60

Ala Cys Leu Gly Trp Tyr Ala Tyr Gln Ala Trp Arg Ala Thr Cys Gly
65                  70                  75                  80

Trp Glu Asn Val Tyr Val Ala Leu Ile Gln Met Met Lys Ser Ile Ile
                85                  90                  95

Glu Ala Phe His Ser Phe Asp Ser Pro Ala Thr Leu Trp Leu Ser Ser
            100                 105                 110

Gly Asn Gly Val Arg Trp Met Arg Tyr Gly Ser Trp Leu Leu Thr Cys
        115                 120                 125

Pro Val Ile Leu Ile His Leu Ser Asn Leu Thr Gly Leu Lys Asp Asp
130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
210                 215                 220

Met Phe Pro Val Leu Phe Leu Gly Pro Glu Gly Phe Gly His Ile
225                 230                 235                 240

Ser Arg Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Ser His Ile Leu Leu Tyr Gly Asp Ile Arg Lys Gln Lys Ile Thr
        275                 280                 285

Ile Ala Gly Gln Glu Met Glu Val Glu Thr Leu Val Ala Glu Glu Glu
290                 295                 300

Asp Lys Tyr Glu Ser Ser
305                 310
```

<210> SEQ ID NO 152
<211> LENGTH: 310
<212> TYPE: PRT
<213> ORGANISM: Artificial sequence
<220> FEATURE:

<223> OTHER INFORMATION: Synthetic polypeptide

<400> SEQUENCE: 152

Met Asp Tyr Gly Gly Ala Leu Ser Ala Val Gly Leu Phe Gln Thr Ser
1               5                   10                  15
Tyr Thr Leu Glu Asn Asn Gly Ser Val Ile Cys Ile Pro Asn Asn Gly
            20                  25                  30
Gln Cys Phe Cys Leu Ala Trp Leu Lys Ser Asn Gly Thr Asn Ala Glu
        35                  40                  45
Lys Leu Ala Ala Asn Ile Leu Gln Trp Val Ser Phe Ala Leu Ser Val
    50                  55                  60
Ala Cys Leu Gly Trp Tyr Ala Tyr Gln Ala Trp Arg Ala Thr Cys Gly
65                  70                  75                  80
Trp Glu Asn Val Tyr Val Ala Leu Ile Gln Met Met Lys Ser Ile Ile
                85                  90                  95
Glu Ala Phe His Ser Phe Asp Ser Pro Ala Thr Leu Trp Leu Ser Ser
            100                 105                 110
Gly Asn Gly Val Arg Trp Met Arg Tyr Gly Ser Trp Leu Leu Thr Cys
        115                 120                 125
Pro Val Ile Leu Ile His Leu Ser Asn Leu Thr Gly Leu Lys Asp Asp
    130                 135                 140
Tyr Ser Lys Arg Thr Met Gly Leu Leu Val Ser Asn Val Gly Cys Ile
145                 150                 155                 160
Val Trp Gly Ala Thr Ser Ala Met Cys Thr Gly Trp Thr Lys Ile Leu
                165                 170                 175
Phe Phe Leu Ile Ser Leu Ser Tyr Gly Met Tyr Thr Tyr Phe His Ala
            180                 185                 190
Ala Lys Val Tyr Ile Glu Ala Phe His Thr Val Pro Lys Gly Leu Cys
        195                 200                 205
Arg Gln Leu Val Arg Ala Met Ala Trp Leu Phe Phe Val Ser Trp Gly
    210                 215                 220
Met Phe Pro Val Leu Phe Leu Leu Gly Pro Glu Gly Phe Gly His Ile
225                 230                 235                 240
Ser Arg Tyr Gly Ser Asn Ile Gly His Ser Ile Leu Asp Leu Ile Ala
                245                 250                 255
Lys Gln Met Trp Gly Val Leu Gly Asn Tyr Leu Arg Val Lys Ile His
            260                 265                 270
Ser His Ile Leu Leu Tyr Gly Asp Ile Arg Lys Lys Gln Lys Ile Thr
        275                 280                 285
Ile Ala Gly Gln Glu Met Glu Val Glu Thr Leu Val Ala Glu Glu Glu
    290                 295                 300
Asp Lys Tyr Glu Ser Ser
305                 310

<210> SEQ ID NO 153
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 153

Met Val Ser Arg Arg Pro Trp Leu Leu Ala Leu Ala Leu Ala Val Ala
1               5                   10                  15
Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
 50                  55                  60

Val Ile Cys Ile Pro Asn Asn Gly Gln Cys Phe Cys Leu Ala Trp Leu
 65                  70                  75                  80

Lys Ser Asn Gly Thr Asn Ala Glu Lys Leu Ala Ala Asn Ile Leu Gln
                 85                  90                  95

Trp Val Ser Phe Ala Leu Ser Val Ala Cys Leu Gly Trp Tyr Ala Tyr
                100                 105                 110

Gln Ala Trp Arg Ala Thr Cys Gly Trp Glu Asn Val Tyr Val Ala Leu
                115                 120                 125

Ile Gln Met Met Lys Ser Ile Ile Glu Ala Phe His Ser Phe Asp Ser
130                 135                 140

Pro Ala Thr Leu Trp Leu Ser Ser Gly Asn Gly Val Arg Trp Met Arg
145                 150                 155                 160

Tyr Gly Ser Trp Leu Leu Thr Thr Pro Val Ile Leu Ile His Leu Ser
                165                 170                 175

Asn Leu Thr Gly Leu Lys Asp Asp Tyr Ser Lys Arg Thr Met Gly Leu
                180                 185                 190

Leu Val Ser Asp Val Gly Cys Ile Val Trp Gly Ala Thr Ser Ala Met
                195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
                260                 265                 270

Gly Pro Glu Gly Phe Gly His Ile Ser Arg Tyr Gly Ser Asn Ile Gly
                275                 280                 285

His Ser Ile Leu Asp Leu Ile Ala Lys Gln Met Trp Gly Val Leu Gly
                290                 295                 300

Asn Tyr Leu Arg Val Lys Ile His Ser His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
                340                 345                 350

<210> SEQ ID NO 154
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 154

Met Val Ser Arg Arg Pro Trp Leu Leu Ala Leu Ala Leu Ala Val Ala
1                5                  10                  15

Leu Ala Ala Gly Ser Ala Gly Ala Ser Thr Gly Ser Asp Ala Thr Val
                20                  25                  30

Pro Val Ala Thr Gln Asp Gly Pro Asp Tyr Val Phe His Arg Ala His
            35                  40                  45

```
Glu Arg Met Leu Phe Gln Thr Ser Tyr Thr Leu Glu Asn Asn Gly Ser
         50                  55                  60

Val Ile Cys Ile Pro Asn Asn Gly Gln Cys Phe Cys Leu Ala Trp Leu
 65                  70                  75                  80

Lys Ser Asn Gly Thr Asn Ala Glu Lys Leu Ala Ala Asn Ile Leu Gln
                 85                  90                  95

Trp Val Ser Phe Ala Leu Ser Val Ala Cys Leu Gly Trp Tyr Ala Tyr
                100                 105                 110

Gln Ala Trp Arg Ala Thr Cys Gly Trp Glu Asn Val Tyr Val Ala Leu
            115                 120                 125

Ile Gln Met Met Lys Ser Ile Ile Glu Ala Phe His Ser Phe Asp Ser
        130                 135                 140

Pro Ala Thr Leu Trp Leu Ser Ser Gly Asn Gly Val Arg Trp Met Arg
145                 150                 155                 160

Tyr Gly Ser Trp Leu Leu Thr Ala Pro Val Ile Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Arg Tyr Gly Ser Asn Ile Gly
        275                 280                 285

His Ser Ile Leu Asp Leu Ile Ala Lys Gln Met Trp Gly Val Leu Gly
    290                 295                 300

Asn Tyr Leu Arg Val Lys Ile His Ser His Ile Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
            340                 345                 350

<210> SEQ ID NO 155
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 155

Met Val Ser Arg Arg Pro Trp Leu Leu Ala Leu Ala Leu Ala Val Ala
1               5                  10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60
```

```
Val Ile Cys Ile Pro Asn Asn Gly Gln Cys Phe Cys Leu Ala Trp Leu
 65                  70                  75                  80

Lys Ser Asn Gly Thr Asn Ala Glu Lys Leu Ala Ala Asn Ile Leu Gln
                 85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Asn Val Tyr Val Ala Leu
        115                 120                 125

Ile Gln Met Met Lys Ser Ile Ile Glu Ala Phe His Ser Phe Asp Ser
    130                 135                 140

Pro Ala Thr Leu Trp Leu Ser Ser Gly Asn Gly Val Arg Trp Met Arg
145                 150                 155                 160

Tyr Gly Ser Trp Leu Leu Thr Ser Pro Val Ile Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
    210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Arg Tyr Gly Ser Asn Ile Gly
        275                 280                 285

His Ser Ile Leu Asp Leu Ile Ala Lys Gln Met Trp Gly Val Leu Gly
    290                 295                 300

Asn Tyr Leu Arg Val Lys Ile His Ser His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Glu Asp Lys Tyr Glu Ser Ser
            340                 345                 350

<210> SEQ ID NO 156
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 156

Met Val Ser Arg Arg Pro Trp Leu Leu Ala Leu Ala Leu Ala Val Ala
 1               5                  10                  15

Leu Ala Ala Gly Ser Ala Gly Ala Ser Thr Gly Ser Asp Ala Thr Val
                 20                  25                  30

Pro Val Ala Thr Gln Asp Gly Pro Asp Tyr Val Phe His Arg Ala His
             35                  40                  45

Glu Arg Met Leu Phe Gln Thr Ser Tyr Thr Leu Glu Asn Asn Gly Ser
         50                  55                  60

Val Ile Cys Ile Pro Asn Asn Gly Gln Cys Phe Cys Leu Ala Trp Leu
 65                  70                  75                  80
```

```
Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Asn Val Tyr Val Ala Leu
        115                 120                 125

Ile Gln Met Met Lys Ser Ile Ile Glu Ala Phe His Ser Phe Asp Ser
    130                 135                 140

Pro Ala Thr Leu Trp Leu Ser Ser Gly Asn Gly Val Arg Trp Met Arg
145                 150                 155                 160

Tyr Gly Ser Trp Leu Leu Thr Thr Pro Val Ile Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Cys Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
    210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Arg Tyr Gly Ser Asn Ile Gly
        275                 280                 285

His Ser Ile Leu Asp Leu Ile Ala Lys Gln Met Trp Gly Val Leu Gly
    290                 295                 300

Asn Tyr Leu Arg Val Lys Ile His Ser His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
            340                 345                 350

<210> SEQ ID NO 157
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 157

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95
```

```
Trp Val Ser Phe Ala Leu Ser Val Ala Cys Leu Gly Trp Tyr Ala Tyr
            100                 105                 110

Gln Ala Trp Arg Ala Thr Cys Gly Trp Glu Asn Val Tyr Val Ala Leu
            115                 120                 125

Ile Gln Met Met Lys Ser Ile Ile Glu Ala Phe His Ser Phe Asp Ser
130                 135                 140

Pro Ala Thr Leu Trp Leu Ser Ser Gly Asn Gly Val Arg Trp Met Arg
145                 150                 155                 160

Tyr Gly Ser Trp Leu Leu Thr Thr Pro Val Ile Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Asn Val Gly Cys Ile Val Trp Gly Ala Thr Ser Ala Met
            195                 200                 205

Cys Thr Gly Trp Thr Lys Ile Leu Phe Phe Leu Ile Ser Leu Ser Tyr
            210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Arg Tyr Gly Ser Asn Ile Gly
            275                 280                 285

His Ser Ile Leu Asp Leu Ile Ala Lys Gln Met Trp Gly Val Leu Gly
            290                 295                 300

Asn Tyr Leu Arg Val Lys Ile His Ser His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
            340                 345                 350

<210> SEQ ID NO 158
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 158

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Trp Tyr Ala Tyr
            100                 105                 110
```

```
Gln Ala Trp Arg Ala Thr Cys Gly Trp Glu Asn Val Tyr Val Ala Leu
            115                 120                 125

Ile Gln Met Met Lys Ser Ile Ile Glu Ala Phe His Ser Phe Asp Ser
130                 135                 140

Pro Ala Thr Leu Trp Leu Ser Ser Gly Asn Gly Val Arg Trp Met Arg
145                 150                 155                 160

Tyr Gly Ser Trp Leu Leu Thr Ala Pro Val Ile Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Cys Val Gly Cys Ile Val Trp Gly Ala Thr Ser Ala Met
            195                 200                 205

Cys Thr Gly Trp Thr Lys Ile Leu Phe Phe Leu Ile Ser Leu Ser Tyr
            210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Arg Tyr Gly Ser Asn Ile Gly
            275                 280                 285

His Ser Ile Leu Asp Leu Ile Ala Lys Gln Met Trp Gly Val Leu Gly
            290                 295                 300

Asn Tyr Leu Arg Val Lys Ile His Ser His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
            340                 345                 350

<210> SEQ ID NO 159
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 159

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
            50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Asn Val Tyr Val Ala Leu
            115                 120                 125
```

```
Ile Gln Met Met Lys Ser Ile Ile Glu Ala Phe His Ser Phe Asp Ser
    130                 135                 140

Pro Ala Thr Leu Trp Leu Ser Ser Gly Asn Gly Val Arg Trp Met Arg
145                 150                 155                 160

Tyr Gly Ser Trp Leu Leu Thr Ala Pro Val Ile Leu Ile His Leu Ser
                165                 170                 175

Asn Leu Thr Gly Leu Lys Asp Asp Tyr Ser Lys Arg Thr Met Gly Leu
                180                 185                 190

Leu Val Ser Asn Val Gly Cys Ile Val Trp Gly Ala Thr Ser Ala Met
                195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
                260                 265                 270

Gly Pro Glu Gly Phe Gly His Ile Ser Arg Tyr Gly Ser Asn Ile Gly
                275                 280                 285

His Ser Ile Leu Asp Leu Ile Ala Lys Gln Met Trp Gly Val Leu Gly
290                 295                 300

Asn Tyr Leu Arg Val Lys Ile His Ser His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
                340                 345                 350

<210> SEQ ID NO 160
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 160

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
                20                  25                  30

Pro Val Ala Thr Gln Asp Gly Pro Asp Tyr Val Phe His Arg Ala His
                35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Tyr Ala Tyr
                100                 105                 110

Gln Ala Trp Arg Ala Thr Cys Gly Trp Glu Asn Val Tyr Val Ala Leu
            115                 120                 125

Ile Gln Met Met Lys Ser Ile Ile Glu Ala Phe His Ser Phe Asp Ser
    130                 135                 140
```

Pro Ala Thr Leu Trp Leu Ser Ser Gly Asn Gly Val Arg Trp Met Arg
145                 150                 155                 160

Tyr Gly Ser Trp Leu Leu Thr Ser Pro Val Ile Leu Ile His Leu Ser
            165                 170                 175

Asn Leu Thr Gly Leu Lys Asp Asp Tyr Ser Lys Arg Thr Met Gly Leu
        180                 185                 190

Leu Val Ser Cys Val Gly Cys Ile Val Trp Gly Ala Thr Ser Ala Met
    195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Arg Tyr Gly Ser Asn Ile Gly
        275                 280                 285

His Ser Ile Leu Asp Leu Ile Ala Lys Gln Met Trp Gly Val Leu Gly
    290                 295                 300

Asn Tyr Leu Arg Val Lys Ile His Ser His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
            340                 345                 350

<210> SEQ ID NO 161
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 161

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
            85                  90                  95

Trp Val Ser Phe Ala Leu Ser Val Ala Cys Leu Gly Trp Tyr Ala Tyr
        100                 105                 110

Gln Ala Trp Arg Ala Thr Cys Gly Trp Glu Asn Val Tyr Val Ala Leu
    115                 120                 125

Ile Gln Met Met Lys Ser Ile Ile Glu Ala Phe His Ser Phe Asp Ser
130                 135                 140

Pro Ala Thr Leu Trp Leu Ser Ser Gly Asn Gly Val Arg Trp Met Arg
145                 150                 155                 160

Tyr Gly Ser Trp Leu Leu Thr Ser Pro Val Ile Leu Ile His Leu Ser
            165                 170                 175

Asn Leu Thr Gly Leu Lys Asp Asp Tyr Ser Lys Arg Thr Met Gly Leu
            180                 185                 190

Leu Val Ser Asn Val Gly Cys Ile Val Trp Gly Ala Thr Ser Ala Met
            195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
            245                 250                 255

Trp Leu Phe Phe Val Ser Trp Gly Met Phe Pro Val Leu Phe Leu Leu
            260                 265                 270

Gly Pro Glu Gly Phe Gly His Ile Ser Arg Tyr Gly Ser Asn Ile Gly
            275                 280                 285

His Ser Ile Leu Asp Leu Ile Ala Lys Gln Met Trp Gly Val Leu Gly
            290                 295                 300

Asn Tyr Leu Arg Val Lys Ile His Ser His Ile Leu Leu Tyr Gly Asp
305                 310                 315                 320

Ile Arg Lys Lys Gln Lys Ile Thr Ile Ala Gly Gln Glu Met Glu Val
            325                 330                 335

Glu Thr Leu Val Ala Glu Glu Asp Lys Tyr Glu Ser Ser
            340                 345                 350

<210> SEQ ID NO 162
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 162

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Val Ser Phe Ala Leu Ser Val
50                  55                  60

Ala Cys Leu Gly Trp Tyr Ala Tyr Gln Ala Trp Arg Ala Thr Cys Gly
65                  70                  75                  80

Trp Glu Asn Val Tyr Val Ala Leu Ile Gln Met Met Lys Ser Ile Ile
            85                  90                  95

Glu Ala Phe His Ser Phe Asp Ser Pro Ala Thr Leu Trp Leu Ser Ser
            100                 105                 110

Gly Asn Gly Val Arg Trp Met Arg Tyr Gly Ser Trp Leu Leu Thr Thr
            115                 120                 125

Pro Val Ile Leu Ile His Leu Ser Asn Leu Thr Gly Leu Lys Asp Asp
            130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
            165                 170                 175

```
Phe Phe Leu Ile Ser Leu Ser Tyr Gly Met Tyr Thr Tyr Phe His Ala
                180                 185                 190

Ala Lys Val Tyr Ile Glu Ala Phe His Thr Val Pro Lys Gly Leu Cys
            195                 200                 205

Arg Gln Leu Val Arg Ala Met Ala Trp Leu Phe Phe Val Ser Trp Gly
        210                 215                 220

Met Phe Pro Val Leu Phe Leu Gly Pro Glu Gly Phe Gly His Ile
225                 230                 235                 240

Ser Arg Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Ser His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
290                 295                 300

Asp Lys Tyr Glu Ser Ser
305                 310

<210> SEQ ID NO 163
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 163

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Val Ser Phe Ala Leu Ser Val
    50                  55                  60

Ala Cys Leu Gly Trp Tyr Ala Tyr Gln Ala Trp Arg Ala Thr Cys Gly
65                  70                  75                  80

Trp Glu Asn Val Tyr Val Ala Leu Ile Gln Met Met Lys Ser Ile Ile
                85                  90                  95

Glu Ala Phe His Ser Phe Asp Ser Pro Ala Thr Leu Trp Leu Ser Ser
            100                 105                 110

Gly Asn Gly Val Arg Trp Met Arg Tyr Gly Ser Trp Leu Leu Thr Ala
        115                 120                 125

Pro Val Ile Leu Ile His Leu Ser Asn Leu Thr Gly Leu Lys Asp Asp
    130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
    210                 215                 220
```

```
Met Phe Pro Val Leu Phe Leu Gly Pro Glu Gly Phe Gly His Ile
225                 230                 235                 240

Ser Arg Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Ser His Ile Leu Leu Tyr Gly Asp Ile Arg Lys Gln Lys Ile Thr
        275                 280                 285

Ile Ala Gly Gln Glu Met Glu Val Glu Thr Leu Val Ala Glu Glu Glu
290                 295                 300

Asp Lys Tyr Glu Ser Ser
305                 310
```

<210> SEQ ID NO 164
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 164

```
Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Val Ser Phe Ala Leu Ser Val
50                  55                  60

Ala Cys Leu Gly Trp Tyr Ala Tyr Gln Ala Trp Arg Ala Thr Cys Gly
65                  70                  75                  80

Trp Glu Asn Val Tyr Val Ala Leu Ile Gln Met Met Lys Ser Ile Ile
                85                  90                  95

Glu Ala Phe His Ser Phe Asp Ser Pro Ala Thr Leu Trp Leu Ser Ser
            100                 105                 110

Gly Asn Gly Val Arg Trp Met Arg Tyr Gly Ser Trp Leu Leu Thr Ser
            115                 120                 125

Pro Val Ile Leu Ile His Leu Ser Asn Leu Thr Gly Leu Lys Asp Asp
            130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
            195                 200                 205

Arg Gln Leu Val Arg Ala Met Ala Trp Leu Phe Phe Val Ser Trp Gly
            210                 215                 220

Met Phe Pro Val Leu Phe Leu Gly Pro Glu Gly Phe Gly His Ile
225                 230                 235                 240

Ser Arg Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270
```

Ser His Ile Leu Leu Tyr Gly Asp Ile Arg Lys Lys Gln Lys Ile Thr
275 280 285

Ile Ala Gly Gln Glu Met Glu Val Glu Thr Leu Val Ala Glu Glu Glu
290 295 300

Asp Lys Tyr Glu Ser Ser
305 310

<210> SEQ ID NO 165
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 165

Met Asp Tyr Gly Gly Ala Leu Ser Ala Val Gly Leu Phe Gln Thr Ser
1 5 10 15

Tyr Thr Leu Glu Asn Asn Gly Ser Val Ile Cys Ile Pro Asn Asn Gly
20 25 30

Gln Cys Phe Cys Leu Ala Trp Leu Lys Ser Asn Gly Thr Asn Ala Glu
35 40 45

Lys Leu Ala Ala Asn Ile Leu Gln Trp Val Ser Phe Ala Leu Ser Val
50 55 60

Ala Cys Leu Gly Trp Tyr Ala Tyr Gln Ala Trp Arg Ala Thr Cys Gly
65 70 75 80

Trp Glu Asn Val Tyr Val Ala Leu Ile Gln Met Met Lys Ser Ile Ile
85 90 95

Glu Ala Phe His Ser Phe Asp Ser Pro Ala Thr Leu Trp Leu Ser Ser
100 105 110

Gly Asn Gly Val Arg Trp Met Arg Tyr Gly Ser Trp Leu Leu Thr Thr
115 120 125

Pro Val Ile Leu Ile His Leu Ser Asn Leu Thr Gly Leu Lys Asp Asp
130 135 140

Tyr Ser Lys Arg Thr Met Gly Leu Leu Val Ser Cys Val Gly Cys Ile
145 150 155 160

Val Trp Gly Ala Thr Ser Ala Met Cys Thr Gly Trp Thr Lys Ile Leu
165 170 175

Phe Phe Leu Ile Ser Leu Ser Tyr Gly Met Tyr Thr Tyr Phe His Ala
180 185 190

Ala Lys Val Tyr Ile Glu Ala Phe His Thr Val Pro Lys Gly Leu Cys
195 200 205

Arg Gln Leu Val Arg Ala Met Ala Trp Leu Phe Phe Val Ser Trp Gly
210 215 220

Met Phe Pro Val Leu Phe Leu Leu Gly Pro Glu Gly Phe Gly His Ile
225 230 235 240

Ser Arg Tyr Gly Ser Asn Ile Gly His Ser Ile Leu Asp Leu Ile Ala
245 250 255

Lys Gln Met Trp Gly Val Leu Gly Asn Tyr Leu Arg Val Lys Ile His
260 265 270

Ser His Ile Leu Leu Tyr Gly Asp Ile Arg Lys Lys Gln Lys Ile Thr
275 280 285

Ile Ala Gly Gln Glu Met Glu Val Glu Thr Leu Val Ala Glu Glu Glu
290 295 300

Asp Lys Tyr Glu Ser Ser
305 310

<210> SEQ ID NO 166
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 166

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Val Ser Phe Ala Leu Ser Val
        50                  55                  60

Ala Cys Leu Gly Trp Tyr Ala Tyr Gln Ala Trp Arg Ala Thr Cys Gly
65                  70                  75                  80

Trp Glu Asn Val Tyr Val Ala Leu Ile Gln Met Met Lys Ser Ile Ile
                85                  90                  95

Glu Ala Phe His Ser Phe Asp Ser Pro Ala Thr Leu Trp Leu Ser Ser
            100                 105                 110

Gly Asn Gly Val Arg Trp Met Arg Tyr Gly Ser Trp Leu Leu Thr Thr
        115                 120                 125

Pro Val Ile Leu Ile His Leu Ser Asn Leu Thr Gly Leu Lys Asp Asp
    130                 135                 140

Tyr Ser Lys Arg Thr Met Gly Leu Leu Val Ser Asn Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
    210                 215                 220

Met Phe Pro Val Leu Phe Leu Leu Gly Pro Glu Gly Phe Gly His Ile
225                 230                 235                 240

Ser Arg Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Ser His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
    290                 295                 300

Asp Lys Tyr Glu Ser Ser
305                 310

<210> SEQ ID NO 167
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 167

```
Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Val Ser Phe Ala Leu Ser Val
    50                  55                  60

Ala Cys Leu Gly Trp Tyr Ala Tyr Gln Ala Trp Arg Ala Thr Cys Gly
65                  70                  75                  80

Trp Glu Asn Val Tyr Val Ala Leu Ile Gln Met Met Lys Ser Ile Ile
                85                  90                  95

Glu Ala Phe His Ser Phe Asp Ser Pro Ala Thr Leu Trp Leu Ser Ser
            100                 105                 110

Gly Asn Gly Val Arg Trp Met Arg Tyr Gly Ser Trp Leu Leu Thr Ala
        115                 120                 125

Pro Val Ile Leu Ile His Leu Ser Asn Leu Thr Gly Leu Lys Asp Asp
    130                 135                 140

Tyr Ser Lys Arg Thr Met Gly Leu Leu Val Ser Cys Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
    210                 215                 220

Met Phe Pro Val Leu Phe Leu Gly Pro Glu Gly Phe Gly His Ile
225                 230                 235                 240

Ser Arg Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Ser His Ile Leu Leu Tyr Gly Asp Ile Arg Lys Gln Lys Ile Thr
        275                 280                 285

Ile Ala Gly Gln Glu Met Glu Val Glu Thr Leu Val Ala Glu Glu Glu
    290                 295                 300

Asp Lys Tyr Glu Ser Ser
305                 310
```

<210> SEQ ID NO 168
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 168

```
Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
```

```
            35                  40                  45
Lys Leu Ala Ala Asn Ile Leu Gln Trp Val Ser Phe Ala Leu Ser Val
 50                  55                  60

Ala Cys Leu Gly Trp Tyr Ala Tyr Gln Ala Trp Arg Ala Thr Cys Gly
 65                  70                  75                  80

Trp Glu Asn Val Tyr Val Ala Leu Ile Gln Met Met Lys Ser Ile Ile
                     85                  90                  95

Glu Ala Phe His Ser Phe Asp Ser Pro Ala Thr Leu Trp Leu Ser Ser
                100                 105                 110

Gly Asn Gly Val Arg Trp Met Arg Tyr Gly Ser Trp Leu Leu Thr Ala
            115                 120                 125

Pro Val Ile Leu Ile His Leu Ser Asn Leu Thr Gly Leu Lys Asp Asp
        130                 135                 140

Tyr Ser Lys Arg Thr Met Gly Leu Leu Val Ser Asn Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
                180                 185                 190

Ala Lys Val Tyr Ile Glu Ala Phe His Thr Val Pro Lys Gly Leu Cys
            195                 200                 205

Arg Gln Leu Val Arg Ala Met Ala Trp Leu Phe Phe Val Ser Trp Gly
        210                 215                 220

Met Phe Pro Val Leu Phe Leu Gly Pro Glu Gly Phe Gly His Ile
225                 230                 235                 240

Ser Arg Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Ser His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
        290                 295                 300

Asp Lys Tyr Glu Ser Ser
305                 310

<210> SEQ ID NO 169
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 169

Met Asp Tyr Gly Gly Ala Leu Ser Ala Val Gly Leu Phe Gln Thr Ser
 1               5                  10                  15

Tyr Thr Leu Glu Asn Asn Gly Ser Val Ile Cys Ile Pro Asn Asn Gly
                 20                  25                  30

Gln Cys Phe Cys Leu Ala Trp Leu Lys Ser Asn Gly Thr Asn Ala Glu
             35                  40                  45

Lys Leu Ala Ala Asn Ile Leu Gln Trp Val Ser Phe Ala Leu Ser Val
 50                  55                  60

Ala Cys Leu Gly Trp Tyr Ala Tyr Gln Ala Trp Arg Ala Thr Cys Gly
 65                  70                  75                  80

Trp Glu Asn Val Tyr Val Ala Leu Ile Gln Met Met Lys Ser Ile Ile
```

```
                     85                  90                  95
Glu Ala Phe His Ser Phe Asp Ser Pro Ala Thr Leu Trp Leu Ser Ser
                100                 105                 110
Gly Asn Gly Val Arg Trp Met Arg Tyr Gly Ser Trp Leu Leu Thr Ser
            115                 120                 125
Pro Val Ile Leu Ile His Leu Ser Asn Leu Thr Gly Leu Lys Asp Asp
        130                 135                 140
Tyr Ser Lys Arg Thr Met Gly Leu Leu Ser Cys Val Gly Cys Ile
145                 150                 155                 160
Val Trp Gly Ala Thr Ser Ala Met Cys Thr Gly Trp Thr Lys Ile Leu
                165                 170                 175
Phe Phe Leu Ile Ser Leu Ser Tyr Gly Met Tyr Thr Tyr Phe His Ala
                180                 185                 190
Ala Lys Val Tyr Ile Glu Ala Phe His Thr Val Pro Lys Gly Leu Cys
            195                 200                 205
Arg Gln Leu Val Arg Ala Met Ala Trp Leu Phe Phe Val Ser Trp Gly
        210                 215                 220
Met Phe Pro Val Leu Phe Leu Leu Gly Pro Glu Gly Phe Gly His Ile
225                 230                 235                 240
Ser Arg Tyr Gly Ser Asn Ile Gly His Ser Ile Leu Asp Leu Ile Ala
                245                 250                 255
Lys Gln Met Trp Gly Val Leu Gly Asn Tyr Leu Arg Val Lys Ile His
                260                 265                 270
Ser His Ile Leu Leu Tyr Gly Asp Ile Arg Lys Lys Gln Lys Ile Thr
            275                 280                 285
Ile Ala Gly Gln Glu Met Glu Val Glu Thr Leu Val Ala Glu Glu Glu
        290                 295                 300
Asp Lys Tyr Glu Ser Ser
305                 310

<210> SEQ ID NO 170
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 170

Met Asp Tyr Gly Gly Ala Leu Ser Ala Val Gly Leu Phe Gln Thr Ser
1               5                   10                  15
Tyr Thr Leu Glu Asn Asn Gly Ser Val Ile Cys Ile Pro Asn Asn Gly
                20                  25                  30
Gln Cys Phe Cys Leu Ala Trp Leu Lys Ser Asn Gly Thr Asn Ala Glu
            35                  40                  45
Lys Leu Ala Ala Asn Ile Leu Gln Trp Val Ser Phe Ala Leu Ser Val
        50                  55                  60
Ala Cys Leu Gly Trp Tyr Ala Tyr Gln Ala Trp Arg Ala Thr Cys Gly
65                  70                  75                  80
Trp Glu Asn Val Tyr Val Ala Leu Ile Gln Met Met Lys Ser Ile Ile
                85                  90                  95
Glu Ala Phe His Ser Phe Asp Ser Pro Ala Thr Leu Trp Leu Ser Ser
                100                 105                 110
Gly Asn Gly Val Arg Trp Met Arg Tyr Gly Ser Trp Leu Leu Thr Ser
            115                 120                 125
Pro Val Ile Leu Ile His Leu Ser Asn Leu Thr Gly Leu Lys Asp Asp
```

-continued

```
            130                 135                 140
Tyr Ser Lys Arg Thr Met Gly Leu Leu Val Ser Asn Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
    210                 215                 220

Met Phe Pro Val Leu Phe Leu Leu Gly Pro Glu Gly Phe Gly His Ile
225                 230                 235                 240

Ser Arg Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Ser His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
    290                 295                 300

Asp Lys Tyr Glu Ser Ser
305                 310
```

ENGINEERED LIGHT-ACTIVATED ANION CHANNEL PROTEINS AND METHODS OF USE THEREOF

CROSS REFERENCE TO RELATED APPLICATION

This application is a national phase application under 35 U.S.C. § 371 of PCT/US2015/023087, filed Mar. 27, 2015, which claims priority benefit of the filing date of U.S. Provisional Patent Application Ser. No. 61/972,182, filed on Mar. 28, 2014, the disclosures of which applications are herein incorporated by reference in their entirety.

INCORPORATION BY REFERENCE OF SEQUENCE LISTING PROVIDED AS A TEXT FILE

A Sequence Listing is provided herewith as a text file, "STAN-1115WO SeqList_ST25.txt" created on Mar. 27, 2015 and having a size of 449 KB. The contents of the text file are incorporated by reference herein in their entirety.

INTRODUCTION

Optogenetics refers to the combination of genetic and optical methods used to control specific events in target cells with the temporal precision (millisecond-timescale) needed to keep pace with functioning intact biological systems. Optogenetics involves the introduction of fast light-responsive ion channel or pump proteins into the plasma membranes of target cells to allow temporally precise manipulation of membrane potentials while maintaining cell-type resolution through the use of specific targeting mechanisms, such as tissue-specific promoters.

Using light to silence electrical activity in target cells is a major goal of optogenetics. Available optogenetic proteins that directly move ions to achieve silencing are often inefficient, pumping only a single ion per photon across the cell membrane, rather than allowing many ions per photon to flow through an ion channel pore.

There is a need in the art for improved light-responsive ion channels.

SUMMARY

Aspects of the disclosure include compositions, devices, systems and methods for optogenetic modulation of action potentials in target cells. The subject devices include light-generating devices, control devices, and delivery devices for delivering light-responsive polypeptides, or nucleic acids encoding same, to target cells. The subject compositions and systems include light-activated polypeptides, nucleic acids comprising nucleotide sequences encoding these polypeptides, as well as expression systems that facilitate expression of these polypeptides in target cells. Also provided are methods of using the subject devices and systems to optogenetically manipulate action potentials in target cells, e.g., to treat a neurological or psychiatric condition in a human or animal subject.

The present disclosure provides a light-activated polypeptide comprising an amino acid sequence that is at least 58% identical to SEQ ID NOS: 1, 23, 34 or 56, wherein the polypeptide functions as a light-activated anion channel. The present disclosure provides a nucleic acid comprising a nucleotide sequence encoding a light-activated polypeptide comprising an amino acid sequence that is at least 58% identical to SEQ ID NOS: 1, 23, 34 or 56, wherein the polypeptide functions as a light-activated anion channel. The present disclosure provides a recombinant expression vector comprising a nucleic acid comprising a nucleotide sequence encoding a light-activated polypeptide comprising an amino acid sequence that is at least 58% identical to SEQ ID NOS: 1, 23, 34 or 56, wherein the polypeptide functions as a light-activated anion channel. In some cases, the polypeptide functions as a light-activated chloride anion channel. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:1 and comprises 1, 2, 3, 4, 5, 6, 7, 8, or 9 amino acid substitutions selected from T98S, E129S, E140S, E162S, V156K, H173R, T285N, V281K and/or N297Q, relative to the amino acid sequence of C1C2 (SEQ ID NO:78). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue or an asparagine residue. In some cases, the polypeptide comprises an amino acid sequence as provided in any one of SEQ ID NOs: 1-22. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:34 and comprises 1, 2, 3, 4, 5, 6, 7, 8, or 9 amino acid substitutions selected from T98S, E129S, E140S, E162S, V156K, H173R, A285N, P281K and/or N297Q, relative to the amino acid sequence of C1V1 (SEQ ID NO:80); in some cases, the first 50 N-terminal amino acid residues are replaced by the following amino acids residues: MDYGGALSAVG (SEQ ID NO:82); in some cases, the cysteine residue at position 167 is changed to a threonine, alanine or serine residue; in some cases, the aspartic acid residue at position 195 is changed to an alanine residue or an asparagine residue. In some cases, the polypeptide comprises an amino acid sequence as provided in any one of SEQ ID NOs: 34-55. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:56 and comprises 1, 2, 3, 4, 5, 6, 7, 8, or 9 amino acid substitutions selected from T99S, E130S, E141S, E163S, V157K, H174R, A286N, P282K and/or N298Q, relative to the amino acid sequence of ReaChR (SEQ ID NO:81); in some cases, the first 51 N-terminal amino acid residues are replaced by the following amino acids residues: MDYGGALSAVG (SEQ ID NO:82); in some cases, the cysteine residue at position 168 is changed to a threonine, alanine or serine residue; in some cases, the aspartic acid residue at position 196 is changed to an alanine residue or an asparagine residue. In some cases, the polypeptide comprises an amino acid sequence as provided in any one of SEQ ID NOs: 56-77. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:23 and comprises 1, 2, 3, 4, 5, 6, 7, 8, or 9 amino acid substitutions selected from A59S, E90S, E101S, E123S, Q117K, H134R, V242K, T246N and/or N258Q, relative to the amino acid sequence of ChR2 (SEQ ID NO:79); in some cases, the cysteine residue at position 128 is changed to a threonine, alanine or serine residue; in some cases, the aspartic acid residue at position 156 is changed to an alanine residue or an asparagine residue. In some cases, the polypeptide comprises an amino acid sequence as provided in any one of SEQ ID NOs: 23-33.

The present disclosure provides a pharmaceutical composition comprising; a) a nucleic acid comprising a nucleotide sequence encoding a light-activated polypeptide as described above, and elsewhere herein; and b) a pharmaceutically acceptable carrier. The present disclosure provides a pharmaceutical composition comprising; a) a light-activated polypeptide as described above, and elsewhere herein; and b) a pharmaceutically acceptable carrier.

The present disclosure provides a cell comprising a nucleic acid comprising a nucleotide sequence encoding a light-activated polypeptide as described above, and elsewhere herein. The present disclosure provides a cell comprising a recombinant expression vector comprising a nucleic acid comprising a nucleotide sequence encoding a light-activated polypeptide as described above, and elsewhere herein.

The present disclosure provides a system for modulating the membrane potential of a cell, the system comprising: a nucleic acid encoding a polypeptide that comprises an amino acid sequence that is at least 58% identical to SEQ ID NOs: 1, 23, 34 or 56, wherein the polypeptide functions as a light-activated anion channel; and a device configured to illuminate a target location with light. In some cases, the polypeptide functions as a light-activated chloride ion channel. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:1 and comprises 1, 2, 3, 4, 5, 6, 7, 8, or 9 amino acid substitutions selected from T98S, E129S, E140S, E162S, V156K, H173R, T285N, V281K and/or N297Q, relative to the amino acid sequence of C1C2 (SEQ ID NO:78). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue or an asparagine residue. In some cases, the polypeptide comprises an amino acid sequence as provided in any one of SEQ ID NOs: 1-22. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:34 and comprises 1, 2, 3, 4, 5, 6, 7, 8, or 9 amino acid substitutions selected from T98S, E129S, E140S, E162S, V156K, H173R, A285N, P281K and/or N297Q, relative to the amino acid sequence of C1V1 (SEQ ID NO:80). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue or an asparagine residue. In some cases, the polypeptide has an amino acid sequence as provided in any one of SEQ ID NOs: 34-55. In some cases, the polypeptide comprises an amino acid sequence that is at least 75%, at least 80%, at least 85%, at least 90%, at least 95%, at least 98%, or at least 99% identical, or is 100% identical, identical to the amino acid sequence provided in SEQ ID NO:56 and comprises 1, 2, 3, 4, 5, 6, 7, 8, or 9 amino acid substitutions selected from T99S, E130S, E141S, E163S, V157K, H174R, A286N, P282K and/or N298Q, relative to the amino acid sequence of ReaChR (SEQ ID NO:81). In some cases, the first 51 N-terminal amino acid residues are replaced by the following amino acids residues: MDYGGALSAVG (SEQ ID NO:82). In some cases, the cysteine residue at position 168 is changed to a threonine, alanine or serine residue. In some cases, the aspartic acid residue at position 196 is changed to an alanine residue or an asparagine residue. In some cases, the polypeptide has an amino acid sequence as provided in any one of SEQ ID NOs: 56-77. In some cases, the polypeptide comprises an amino acid sequence that is at least 75%, at least 80%, at least 85%, at least 90%, at least 95%, at least 98%, or at least 99% identical, or is 100% identical, identical to the amino acid sequence provided in SEQ ID NO:23 and comprises 1, 2, 3, 4, 5, 6, 7, 8, or 9 amino acid substitutions selected from A59S, E90S, E101S, E123S, Q117K, H134R, V242K, T246N and/or N258Q, relative to the amino acid sequence of ChR2 (SEQ ID NO:79). In some cases, the cysteine residue at position 128 is changed to a threonine, alanine or serine residue. In some cases, the aspartic acid residue at position 156 is changed to an alanine residue or an asparagine residue. In some cases, the polypeptide comprises an amino acid sequence as provided in any one of SEQ ID NOs: 23-33. In some cases, the device is configured to illuminate the target location with light having a wavelength ranging from about 350 to about 750 nm. In some cases, the device is configured to illuminate the target location with light having a wavelength ranging from about 450 up to about 500 nm. In some cases, the device is configured to constantly illuminate the target location with light. In some cases, the device is configured to illuminate the target location with pulses of light. In some cases, the device is configured to modulate the wavelength and/or the intensity of the light. In some cases, the device is configured to modulate the frequency and/or the duration of the pulses of light. In some cases, the device is configured to illuminate the target location in response to a user input. In some cases, the user input comprises: the wavelength of light, the intensity of light, the duration of a light pulse, the frequency of a light pulse, and/or the target location. In some cases, the device is adapted to be implanted in a subject. In some cases, the target location is: a cell, a portion of a cell, a plurality of cells, a bundle of nerve fibers, a neuromuscular junction, a central nervous system (CNS) tissue, a peripheral nervous system (PNS) tissue, or an anatomical region.

The present disclosure provides a method for modulating the membrane potential of a cell in response to light, the method comprising: exposing a cell to light of an activating wavelength, wherein the cell is genetically modified with a nucleic acid encoding a polypeptide that comprises an amino acid sequence that is at least 58% identical to SEQ ID NOs: 1, 23, 34 or 56, wherein the polypeptide functions as a light-activated anion channel. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:1 and comprises 1, 2, 3, 4, 5, 6, 7, 8, or 9 amino acid substitutions selected from T98S, E129S, E140S, E162S, V156K, H173R, T285N, V281K and/or N297Q, relative to the amino acid sequence of C1C2 (SEQ ID NO:78). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue or an asparagine residue. In some cases, the polypeptide has an amino acid sequence as provided in any one of SEQ ID NOs: 1-22. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:34 and comprises 1, 2, 3, 4, 5, 6, 7, 8, or 9 amino acid substitutions selected from T98S, E129S, E140S, E162S, V156K, H173R, A285N, P281K and/or N297Q, relative to the amino acid sequence of C1V1 (SEQ ID NO:80). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue or an asparagine residue. In some cases, the polypeptide has an amino acid sequence as provided in any one of SEQ ID NOs: 34-55. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:56 and comprises 1, 2, 3, 4, 5, 6, 7, 8, or 9 amino acid substitutions selected from T99S, E130S, E141S, E163S, V157K, H174R, A286N, P282K and/or N298Q, relative to the amino acid sequence of ReaChR (SEQ ID NO:81). In some cases, the first 51 N-terminal amino acid residues are replaced by the following amino acids residues: MDYGGALSAVG (SEQ ID NO:82). In some cases, the cysteine residue at position 168 is changed to a threonine, alanine or serine residue. In some cases, the aspartic acid residue at position 196 is changed to an alanine residue or an asparagine residue. In some cases, the polypeptide comprises an amino acid sequence as provided in any one of SEQ ID NOs: 56-77. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:23 and comprises 1, 2, 3, 4, 5, 6, 7, 8, or 9 amino acid substitutions selected from A59S, E90S, E101S, E123S, Q117K, H134R, V242K, T246N and/or N258Q, relative to the amino acid sequence of ChR2 (SEQ ID NO:79). In some cases, the cysteine residue at position 128 is changed to a threonine, alanine or serine residue. In some cases, the aspartic acid residue at position 156 is changed to an alanine residue or an asparagine residue. In some cases, the polypeptide comprises an amino acid sequence as provided in any one of SEQ ID NOs: 23-33.

The present disclosure provides a method of treating a condition in a subject, the method comprising genetically modifying a target cell of the subject with a nucleic acid comprising a nucleotide sequence encoding a polypeptide that comprises an amino acid sequence that is at least 58% identical to SEQ ID NOs: 1, 23, 34 or 56, wherein the polypeptide functions as a light-activated anion channel; and exposing the target cell to light of an activating wavelength to treat the subject for the condition. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:1 and comprises 1, 2, 3, 4, 5, 6, 7, 8, or 9 amino acid substitutions selected from T98S, E129S, E140S, E162S, V156K, H173R, T285N, V281K and/or N297Q, relative to the amino acid sequence of C1C2 (SEQ ID NO:78). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue or an asparagine residue. In some cases, the polypeptide comprises an amino acid sequence as provided in any one of SEQ ID NOs: 1-22. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:34 and comprises 1, 2, 3, 4, 5, 6, 7, 8, or 9 amino acid substitutions selected from T98S, E129S, E140S, E162S, V156K, H173R, A285N, P281K and/or N297Q, relative to the amino acid sequence of C1V1 (SEQ ID NO:80). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue or an asparagine residue. In some cases, the polypeptide comprises an amino acid sequence as provided in any one of SEQ ID NOs: 34-55. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:56 and comprises 1, 2, 3, 4, 5, 6, 7, 8, or 9 amino acid substitutions selected from T99S, E130S, E141S, E163S, V157K, H174R, A286N, P282K and/or N298Q, relative to the amino acid sequence of ReaChR (SEQ ID NO:81). In some cases, the first 51 N-terminal amino acid residues are replaced by the following amino acids residues: MDYGGALSAVG (SEQ ID NO:82). In some cases, the cysteine residue at position 168 is changed to a threonine, alanine or serine residue. In some cases, the aspartic acid residue at position 196 is changed to an alanine residue or an asparagine residue. In some cases, the polypeptide comprises an amino acid sequence as provided in any one of SEQ ID NOs: 56-77. In some cases, the polypeptide has an amino acid sequence that is at least 75%, at least 80%, at least 85%, at least 90%, at least 95%, at least 98%, or at least 99% identical, or is 100% identical, to the amino acid sequence provided in SEQ ID NO:23 and comprises 1, 2, 3, 4, 5, 6, 7, 8, or 9 amino acid substitutions selected from A59S, E90S, E101S, E123S, Q117K, H134R, V242K, T246N and/or N258Q, relative to the amino acid sequence of ChR2 (SEQ ID NO:79). In some cases, the cysteine residue at position 128 is changed to a threonine, alanine or serine residue. In some cases, the aspartic acid residue at position 156 is changed to an alanine residue or an asparagine residue. In some cases, the polypeptide has an amino acid sequence as provided in any one of SEQ ID NOs: 23-33. In some cases, the target cell is a nerve cell.

The present disclosure provides a method of inhibiting the formation of an action potential in a nerve cell or a portion thereof, the method comprising: genetically modifying the nerve cell with a nucleic acid comprising a nucleotide sequence encoding a polypeptide that comprises an amino acid sequence that is at least 58% identical to SEQ ID NOs: 1, 23, 34 or 56, wherein the polypeptide functions as a light-activated anion channel; and exposing at least a portion of the nerve cell to light of an activating wavelength to inhibit the formation of an action potential in the nerve cell or in a portion thereof. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:1 and comprises 1, 2, 3, 4, 5, 6, 7, 8, or 9 amino acid substitutions selected from T98S, E129S, E140S, E162S, V156K, H173R, T285N, V281K and/or N297Q, relative to the amino acid sequence of C1C2 (SEQ ID NO:78). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue or an asparagine residue. In some cases, the polypeptide comprises an amino acid sequence as provided in any one of SEQ ID NOs: 1-22. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:34 and comprises 1, 2, 3, 4, 5, 6, 7, 8, or 9 amino acid substitutions selected from T98S, E129S, E140S, E162S, V156K, H173R, A285N, P281K and/or N297Q, relative to the amino acid sequence of C1V1 (SEQ ID NO:80). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue or an asparagine residue. In some cases, the polypeptide comprises an amino acid sequence as provided in any one of SEQ ID NOs: 34-55. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:56 and comprises 1, 2, 3, 4, 5, 6, 7, 8, or 9 amino acid substitutions selected from T99S, E130S, E141S, E163S, V157K, H174R, A286N, P282K and/or N298Q, relative to the amino acid sequence of ReaChR (SEQ ID NO:81). In some cases, the first 51 N-terminal amino acid residues are replaced by the following amino acids residues: MDYGGALSAVG (SEQ ID NO:82). In some cases, the cysteine residue at position 168 is changed to a threonine, alanine or serine residue. In some cases, the aspartic acid residue at position 196 is changed to an alanine residue or an asparagine residue. In some cases, the polypeptide has an amino acid sequence as provided in any one of SEQ ID NOs: 56-77. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:23 and comprises 1, 2, 3, 4, 5, 6, 7, 8, or 9 amino acid substitutions selected from A59S, E90S, E101S, E123S, Q117K, H134R, V242K, T246N and/or N258Q, relative to the amino acid sequence of ChR2 (SEQ ID NO:79). In some cases, the cysteine residue at position 128 is changed to a threonine, alanine or serine residue. In some cases, the aspartic acid residue at position 156 is changed to an alanine residue or an asparagine residue. In some cases, the polypeptide comprises an amino acid sequence as provided in any of SEQ ID NOs: 23-33.

The present disclosure provides a kit comprising: a nucleic acid encoding a polypeptide that is at least 58% identical to SEQ ID NOs: 1, 23, 34 or 56, wherein the polypeptide functions as a light-activated anion channel. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:1 and comprises 1, 2, 3, 4, 5, 6, 7, 8, or 9 amino acid substitutions selected from T98S, E129S, E140S, E162S, V156K, H173R, T285N, V281K and/or N297Q, relative to the amino acid sequence of C1C2 (SEQ ID NO:78). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue or an asparagine residue. In some cases, the polypeptide comprises an amino acid sequence as provided in any one of SEQ ID NOs: 1-22. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:34 and comprises 1, 2, 3, 4, 5, 6, 7, 8, or 9 amino acid substitutions selected from T98S, E129S, E140S, E162S, V156K, H173R, A285N, P281K and/or N297Q, relative to the amino acid sequence of C1V1 (SEQ ID NO:80). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue or an asparagine residue. In some cases, the polypeptide has an amino acid sequence as provided in any one of SEQ ID NOs: 34-55. In some cases, the polypeptide comprises an amino acid sequence that is at least 75%, at least 80%, at least 85%, at least 90%, at least 95%, at least 98%, at least 99% identical, or is 100% identical, to the amino acid sequence provided in SEQ ID NO:56 and comprises 1, 2, 3, 4, 5, 6, 7, 8, or 9 amino acid substitutions selected from T99S, E130S, E141S, E163S, V157K, H174R, A286N, P282K and/or N298Q, relative to the amino acid sequence of ReaChR (SEQ ID NO:81). In some cases, the first 51 N-terminal amino acid residues are replaced by the following amino acids residues: MDYGGALSAVG (SEQ ID NO:82). In some cases, the cysteine residue at position 168 is changed to a threonine, alanine or serine residue. In some cases, the aspartic acid residue at position 196 is changed to an alanine residue or an asparagine residue. In some cases, the polypeptide comprises an amino acid sequence as provided in any one of SEQ ID NOs: 56-77. In some cases, the polypeptide comprises an amino acid sequence that is at least 75%, at least 80%, at least 85%, at least 90%, at least 95%, at least 98%, at least 99% identical, or is 100% identical, to the amino acid sequence provided in SEQ ID NO:23 and comprises 1, 2, 3, 4, 5, 6, 7, 8, or 9 amino acid substitutions selected from A59S, E90S, E101S, E123S, Q117K, H134R, V242K, T246N and/or N258Q, relative to the amino acid sequence of ChR2 (SEQ ID NO:79). In some cases, the cysteine residue at position 128 is changed to a threonine, alanine or serine residue. In some cases, the aspartic acid residue at position 156 is changed to an alanine residue or an asparagine residue. In some cases, the polypeptide has an amino acid sequence as provided in any one of SEQ ID NOs: 23-33. In some cases, kit further comprises a device configured to illuminate a target location with a light. In some cases, the device is configured to illuminate the target location with light having a wavelength ranging from about 350 to about 750 nm. In some cases, the device is configured to illuminate the target location with light having a wavelength ranging from about 450 up to about 500 nm. In some cases, the device is configured to constantly illuminate the target location with a light. In some cases, the device is configured to illuminate the target location with pulses of light. In some cases, the device is configured to modulate the wavelength and/or the intensity of the light. In some cases, the device is configured to modulate the frequency and/or duration of the pulses of light. In some cases, the device is configured to illuminate the target location in response to a user input. In some cases, the user input comprises: the wavelength of light, the intensity of light, the duration of a light pulse, the frequency of a light pulse, and/or the target location to be illuminated by the light. In some cases, the device is adapted to be implanted in a subject. In some cases, the target location is: a cell, a portion of a cell, a plurality of cells, a bundle of nerve fibers, a neuromuscular junction, a CNS tissue, a PNS tissue, or an anatomical region.

The present disclosure provides a light-activated polypeptide comprising an amino acid sequence that is at least 60% identical to SEQ ID NOS: 94, 116, 127 or 149, wherein the polypeptide functions as a light-activated anion channel. The present disclosure provides a nucleic acid comprising a nucleotide sequence encoding a light-activated polypeptide comprising an amino acid sequence that is at least 60% identical to SEQ ID NOS: 94, 116, 127 or 149, wherein the polypeptide functions as a light-activated anion channel. The present disclosure provides a recombinant expression vector comprising a nucleic acid comprising a nucleotide sequence encoding a light-activated polypeptide comprising an amino acid sequence that is at least 60% identical to SEQ ID NOS: 94, 116, 127 or 149, wherein the polypeptide functions as a light-activated anion channel. In some cases, the polypeptide functions as a light-activated chloride anion channel. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:94 and comprises 1, 2, 3, 4, 5, 6, 7, 8, 9 or 10 amino acid substitutions selected from T98S, E122N, E129Q, E140S, V156R, E162S, V281R, T285N, N297Q and/or E312S, relative to the amino acid sequence of C1C2 (SEQ ID NO:78). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue, an asparagine residue, or a cysteine residue. In some cases, the aspartic acid residue at position 156 is changed to an alanine residue, an asparagine residue, or a cysteine residue. In some cases, the polypeptide has an amino acid sequence as provided in any one of SEQ ID NOs: 94-115. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:127 and comprises 1, 2, 3, 4, 5, 6, 7, 8, 9 or 10 amino acid substitutions selected from T98S, E122N, E129Q, E140S, V156R, E162S, P281R, A285N, N297Q and/or E312S, relative to the amino acid sequence of C1V1 (SEQ ID NO:80). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue, an asparagine residue, or a cysteine residue. In some cases, the aspartic acid residue at position 156 is changed to an alanine residue, an asparagine residue, or a cysteine residue. In some cases, the polypeptide has an amino acid sequence as provided in any one of SEQ ID NOs: 127-148. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:149 and comprises 1, 2, 3, 4, 5, 6, 7, 8, 9 or 10 amino acid substitutions selected from T99S, E123N, E130Q, E141S, V157R, E163S, P282R, A286N, N298Q and/or E313S, relative to the amino acid sequence of ReaChR (SEQ ID NO:81). In some cases, the first 51 N-terminal amino acid residues are replaced by the following amino acids residues: MDYGGALSAVG (SEQ ID NO:82). In some cases, the cysteine residue at position 168 is changed to a threonine, alanine or serine residue. In some cases, the aspartic acid residue at position 196 is changed to an alanine residue, an asparagine residue, or a cysteine residue. In some cases, the aspartic acid residue at position 156 is changed to an alanine residue, an asparagine residue, or a cysteine residue. In some cases, the polypeptide has an amino acid sequence as provided in any one of SEQ ID NOs: 149-170. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:116 and comprises 1, 2, 3, 4, 5, 6, 7, 8, 9 or 10 amino acid substitutions selected from A59S, E83N, E90Q, E101S, Q117R, E123S, V242R, T246N, N258Q and/or E273S, relative to the amino acid sequence of ChR2 (SEQ ID NO:79). In some cases, the cysteine residue at position 128 is changed to a threonine, alanine or serine residue. In some cases, the aspartic acid residue at position 156 is changed to an alanine residue, an asparagine residue, or a cysteine residue. In some cases, the polypeptide comprises an amino acid sequence as provided in any one of SEQ ID NOs: 116-126.

The present disclosure provides a pharmaceutical composition comprising: a) a nucleic acid comprising a nucleotide sequence encoding a light-activated polypeptide comprising an amino acid sequence that is at least 60% identical to SEQ ID NOS: 94, 116, 127 or 149, wherein the polypeptide functions as a light-activated anion channel; and b) a pharmaceutically acceptable carrier.

The present disclosure provides a cell comprising a nucleic acid comprising a nucleotide sequence encoding a light-activated polypeptide comprising an amino acid sequence that is at least 60% identical to SEQ ID NOS: 94, 116, 127 or 149, wherein the polypeptide functions as a light-activated anion channel. The present disclosure provides a cell comprising a recombinant expression vector comprising a nucleotide sequence encoding a light-activated polypeptide comprising an amino acid sequence that is at least 60% identical to SEQ ID NOS: 94, 116, 127 or 149, wherein the polypeptide functions as a light-activated anion channel.

The present disclosure provides a system for modulating the membrane potential of a cell, the system comprising: a) a nucleic acid comprising a nucleotide sequence encoding a polypeptide that comprises an amino acid sequence that is at least 60% identical to SEQ ID NOS: 94, 116, 127 or 149, wherein the polypeptide functions as a light-activated anion channel; and b) a device configured to illuminate a target location with light. In some cases, the polypeptide functions as a light-activated chloride ion channel. In some cases, the polypeptide comprises an amino acid sequence that is at least 75%, at least 80%, at least 85%, at least 90%, at least 95%, at least 98%, at least 99%, identical, or is 100% identical, to the amino acid sequence provided in SEQ ID NO:94 and comprises 1, 2, 3, 4, 5, 6, 7, 8, 9 or 10 amino acid substitutions selected from T98S, E122N, E129Q, E140S, V156R, E162S, V281R, T285N, N297Q and/or E312S, relative to the amino acid sequence of C1C2 (SEQ ID NO:78). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue, an asparagine residue, or a cysteine residue. In some cases, the aspartic acid residue at position 156 is changed to an alanine residue, an asparagine residue, or a cysteine residue. In some cases, the polypeptide has an amino acid sequence as provided in any one of SEQ ID NOs: 94-115. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:127 and comprises 1, 2, 3, 4, 5, 6, 7, 8, 9 or 10 amino acid substitutions selected from T98S, E122N, E129Q, E140S, V156R, E162S, P281R, A285N, N297Q and/or E312S, relative to the amino acid sequence of C1V1 (SEQ ID NO:80). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue, an asparagine residue, or a cysteine residue. In some cases, the aspartic acid residue at position 156 is changed to an alanine residue, an asparagine residue, or a cysteine residue. In some cases, the polypeptide has an amino acid sequence as provided in any one of SEQ ID NOs: 127-148. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:149 and comprises 1, 2, 3, 4, 5, 6, 7, 8, 9 or 10 amino acid substitutions selected from T99S, E123N, E130Q, E141S, V157R, E163S, P282R, A286N, N298Q and/or E313S, relative to the amino acid sequence of ReaChR (SEQ ID NO:81). In some cases, the first 51 N-terminal amino acid residues are replaced by the following amino acids residues: MDYGGALSAVG (SEQ ID NO:82). In some cases, the cysteine residue at position 168 is changed to a threonine, alanine or serine residue. In some cases, the aspartic acid residue at position 196 is changed to an alanine residue, an asparagine residue, or a cysteine residue. In some cases, the aspartic acid residue at position 156 is changed to an alanine residue, an asparagine residue, or a cysteine residue. In some cases, the polypeptide comprises an amino acid sequence as provided in any one of SEQ ID NOs: 149-170. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:116 and comprises 1, 2, 3, 4, 5, 6, 7, 8, 9 or 10 amino acid substitutions selected from A59S, E83N, E90Q, E101S, Q117R, E123S, V242R, T246N, N258Q and/or E273S, relative to the amino acid sequence of ChR2 (SEQ ID NO:79). In some cases, the cysteine residue at position 128 is changed to a threonine, alanine or serine residue. In some cases, the aspartic acid residue at position 156 is changed to an alanine residue, an asparagine residue, or a cysteine residue. In some cases, the polypeptide comprises an amino acid sequence as provided in any one of SEQ ID NOs: 116-126. In some cases, the device is configured to illuminate the target location with light having a wavelength ranging from about 350 to about 750 nm. In some cases, the device is configured to illuminate the target location with light having a wavelength ranging from about 450 up to about 500 nm. In some cases, the device is configured to constantly illuminate the target location with light. In some cases, the device is configured to illuminate the target location with pulses of light. In some cases, the device is configured to modulate the wavelength and/or the intensity of the light. In some cases, the device is configured to modulate the frequency and/or the duration of the pulses of light. In some cases, the device is configured to illuminate the target location in response to a user input. In some cases, the user input comprises: the wavelength of light, the intensity of light, the duration of a light pulse, the frequency of a light pulse, and/or the target location. In some cases, the device is adapted to be implanted in a subject. In some cases, the target location is: a cell, a portion of a cell, a plurality of cells, a bundle of nerve fibers, a neuromuscular junction, a CNS tissue, a PNS tissue, or an anatomical region.

The present disclosure provides a method for modulating the membrane potential of a cell in response to light, the method comprising: exposing a cell to light of an activating wavelength, wherein the cell is genetically modified with a nucleic acid comprising a nucleotide sequence encoding a polypeptide that comprises an amino acid sequence that is at least 58% identical to SEQ ID NOs: 94, 116, 127 or 149, wherein the polypeptide functions as a light-activated anion channel. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:94 and comprises 1, 2, 3, 4, 5, 6, 7, 8, 9 or 10 amino acid substitutions selected from T98S, E122N, E129Q, E140S, V156R, E162S, V281R, T285N, N297Q and/or E312S, relative to the amino acid sequence of C1C2 (SEQ ID NO:78). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue, an asparagine residue, or a cysteine residue. In some cases, the aspartic acid residue at position 156 is changed to an alanine residue, an asparagine residue, or a cysteine residue. In some cases, the polypeptide has an amino acid sequence as provided in any one of SEQ ID NOs: 94-115. In some cases, the polypeptide comprises an amino acid sequence that is at least 75%, at least 80%, at least 85%, at least 90%, at least 95%, at least 98%, at least 99% identical, or is 100% identical, to the amino acid sequence provided in SEQ ID NO:127 and comprises 1, 2, 3, 4, 5, 6, 7, 8, 9 or 10 amino acid substitutions selected from T98S, E122N, E129Q, E140S, V156R, E162S, P281R, A285N, N297Q and/or E312S, relative to the amino acid sequence of C1V1 (SEQ ID NO:80). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue, an asparagine residue, or a cysteine residue. In some cases, the aspartic acid residue at position 156 is changed to an alanine residue, an asparagine residue, or a cysteine residue. In some cases, the polypeptide has an amino acid sequence as provided in any one of SEQ ID NOs: 127-148. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:149 and comprises 1, 2, 3, 4, 5, 6, 7, 8, 9 or 10 amino acid substitutions selected from T99S, E123N, E130Q, E141S, V157R, E163S, P282R, A286N, N298Q and/or E313S, relative to the amino acid sequence of ReaChR (SEQ ID NO:81). In some cases, the first 51 N-terminal amino acid residues are replaced by the following amino acids residues: MDYGGALSAVG (SEQ ID NO:82). In some cases, the cysteine residue at position 168 is changed to a threonine, alanine or serine residue. In some cases, the aspartic acid residue at position 196 is changed to an alanine residue, an asparagine residue, or a cysteine residue. In some cases, the aspartic acid residue at position 156 is changed to an alanine residue, an asparagine residue, or a cysteine residue. In some cases, the polypeptide has an amino acid sequence as provided in any one of SEQ ID NOs: 149-170. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:116 and comprises 1, 2, 3, 4, 5, 6, 7, 8, 9 or 10 amino acid substitutions selected from A59S, E83N, E90Q, E101S, Q117R, E123S, V242R, T246N, N258Q and/or E273S, relative to the amino acid sequence of ChR2 (SEQ ID NO:79). In some cases, the cysteine residue at position 128 is changed to a threonine, alanine or serine residue. In some cases, the aspartic acid residue at position 156 is changed to an alanine residue, an asparagine residue, or a cysteine residue. In some cases, the polypeptide comprises an amino acid sequence as provided in any one of SEQ ID NOs: 116-126.

The present disclosure provides a method of treating a condition in a subject, the method comprising: a) genetically modifying a target cell of the subject with a nucleic acid comprising a nucleotide sequence encoding a polypeptide that comprises an amino acid sequence that is at least 60% identical to SEQ ID NOs: 94, 116, 127 or 149, wherein the polypeptide functions as a light-activated anion channel; and b) exposing the target cell to light of an activating wavelength to treat the subject for the condition. In some cases, the polypeptide comprises an amino acid sequence that is at least 75%, at least 80%, at least 85%, at least 90%, at least 95%, at least 98%, or at least 99% identical, or is 100% identical to the amino acid sequence provided in SEQ ID NO:94 and comprises 1, 2, 3, 4, 5, 6, 7, 8, 9 or 10 amino acid substitutions selected from T98S, E122N, E129Q, E140S, V156R, E162S, V281R, T285N, N297Q and/or E312S, relative to the amino acid sequence of C1C2 (SEQ ID NO:78). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue, an asparagine residue, or a cysteine residue. In some cases, the aspartic acid residue at position 156 is changed to an alanine residue, an asparagine residue, or a cysteine residue. In some cases, the polypeptide has an amino acid sequence as provided in any one of SEQ ID NOs: 94-115. In some cases, the polypeptide comprises an amino acid sequence that is at least 75%, at least 80%, at least 85%, at least 90%, at least 95%, at least 98%, or at least 99% identical, or is 100% identical to the amino acid sequence provided in SEQ ID NO:127 and comprises 1, 2, 3, 4, 5, 6, 7, 8, 9 or 10 amino acid substitutions selected from T98S, E122N, E129Q, E140S, V156R, E162S, P281R, A285N, N297Q and/or E312S, relative to the amino acid sequence of C1V1 (SEQ ID NO:80). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue, an asparagine residue, or a cysteine residue. In some cases, the aspartic acid residue at position 156 is changed to an alanine residue, an asparagine residue, or a cysteine residue. In some cases, the polypeptide has an amino acid sequence as provided in any one of SEQ ID NOs: 127-148. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:149 and comprises 1, 2, 3, 4, 5, 6, 7, 8, 9 or 10 amino acid substitutions selected from T99S, E123N, E130Q, E141S, V157R, E163S, P282R, A286N, N298Q and/or E313S, relative to the amino acid sequence of ReaChR (SEQ ID NO:81). In some cases, the first 51 N-terminal amino acid residues are replaced by the following amino acids residues: MDYGGALSAVG (SEQ ID NO:82). In some cases, the cysteine residue at position 168 is changed to a threonine, alanine or serine residue. In some cases, the aspartic acid residue at position 196 is changed to an alanine residue, an asparagine residue, or a cysteine residue. In some cases, the aspartic acid residue at position 156 is changed to an alanine residue, an asparagine residue, or a cysteine residue. In some cases, the polypeptide has an amino acid sequence as provided in any one of SEQ ID NOs: 149-170. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:116 and comprises 1, 2, 3, 4, 5, 6, 7, 8, 9 or 10 amino acid substitutions selected from A59S, E83N, E90Q, E101S, Q117R, E123S, V242R, T246N, N258Q and/or E273S, relative to the amino acid sequence of ChR2 (SEQ ID NO:79). In some cases, the cysteine residue at position 128 is changed to a threonine, alanine or serine residue. In some cases, the aspartic acid residue at position 156 is changed to an alanine residue, an asparagine residue, or a cysteine residue. In some cases, the polypeptide has an amino acid sequence as provided in any one of SEQ ID NOs: 116-126. In some cases, the target cell is a nerve cell.

The present disclosure provides a method of inhibiting the formation of an action potential in a nerve cell or a portion thereof, the method comprising: a) genetically modifying the nerve cell with a nucleic acid comprising a nucleotide sequence encoding a polypeptide that comprises an amino acid sequence that is at least 60% identical to SEQ ID NOs: 94, 116, 127 or 149, wherein the polypeptide functions as a light-activated anion channel; and b) exposing at least a portion of the nerve cell to light of an activating wavelength to inhibit the formation of an action potential in the nerve cell or in a portion thereof. In some cases, the polypeptide comprises an amino acid sequence that is at least 75%, at least 80%, at least 85%, at least 90%, at least 95%, at least 98%, or at least 99% identical, or is 100% identical to the amino acid sequence provided in SEQ ID NO:94 and comprises 1, 2, 3, 4, 5, 6, 7, 8, 9 or 10 amino acid substitutions selected from T98S, E122N, E129Q, E140S, V156R, E162S, V281R, T285N, N297Q and/or E312S, relative to the amino acid sequence of C1C2 (SEQ ID NO:78). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue, an asparagine residue, or a cysteine residue. In some cases, the aspartic acid residue at position 156 is changed to an alanine residue, an asparagine residue, or a cysteine residue. In some cases, the polypeptide comprises an amino acid sequence as provided in any one of SEQ ID NOs: 94-115. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:127 and comprises 1, 2, 3, 4, 5, 6, 7, 8, 9 or 10 amino acid substitutions selected from T98S, E122N, E129Q, E140S, V156R, E162S, P281R, A285N, N297Q and/or E312S, relative to the amino acid sequence of C1V1 (SEQ ID NO:80). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue, an asparagine residue, or a cysteine residue. In some cases, the aspartic acid residue at position 156 is changed to an alanine residue, an asparagine residue, or a cysteine residue. In some cases, the polypeptide comprises an amino acid sequence as provided in any one of SEQ ID NOs: 127-148. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:149 and comprises 1, 2, 3, 4, 5, 6, 7, 8, 9 or 10 amino acid substitutions selected from T99S, E123N, E130Q, E141S, V157R, E163S, P282R, A286N, N298Q and/or E313S, relative to the amino acid sequence of ReaChR (SEQ ID NO:81). In some cases, the first 51 N-terminal amino acid residues are replaced by the following amino acids residues: MDYGGALSAVG (SEQ ID NO:82). In some cases, the cysteine residue at position 168 is changed to a threonine, alanine or serine residue. In some cases, the aspartic acid residue at position 196 is changed to an alanine residue, an asparagine residue, or a cysteine residue. In some cases, the aspartic acid residue at position 156 is changed to an alanine residue, an asparagine residue, or a cysteine residue. In some cases, the polypeptide comprises an amino acid sequence as provided in any one of SEQ ID NOs: 149-170. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:116 and comprises 1, 2, 3, 4, 5, 6, 7, 8, 9 or 10 amino acid substitutions selected from A59S, E83N, E90Q, E101S, Q117R, E123S, V242R, T246N, N258Q and/or E273S, relative to the amino acid sequence of ChR2 (SEQ ID NO:79). In some cases, the cysteine residue at position 128 is changed to a threonine, alanine or serine residue. In some cases, the aspartic acid residue at position 156 is changed to an alanine residue, an asparagine residue, or a cysteine residue. In some cases, the polypeptide has an amino acid sequence as provided in any of SEQ ID NOs: 116-126.

The present disclosure provides a kit comprising: a nucleic acid encoding a polypeptide that is at least 60% identical to SEQ ID NOs: 94, 116, 127 or 149, wherein the polypeptide functions as a light-activated anion channel. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:94 and comprises 1, 2, 3, 4, 5, 6, 7, 8, 9 or 10 amino acid substitutions selected from T98S, E122N, E129Q, E140S, V156R, E162S, V281R, T285N, N297Q and/or E312S, relative to the amino acid sequence of C1C2 (SEQ ID NO:78). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue, an asparagine residue, or a cysteine residue. In some cases, the aspartic acid residue at position 156 is changed to an alanine residue, an asparagine residue, or a cysteine residue. In some cases, the polypeptide has an amino acid sequence as provided in any one of SEQ ID NOs: 94-115. In some cases, the polypeptide comprises an amino acid sequence that is at least 75%, at least 80%, at least 85%, at least 90%, at least 95%, at least 98%, or at least 99% identical, or is 100% identical to the amino acid sequence provided in SEQ ID NO:127 and comprises 1, 2, 3, 4, 5, 6, 7, 8, 9 or 10 amino acid substitutions selected from T98S, E122N, E129Q, E140S, V156R, E162S, P281R, A285N, N297Q and/or E312S, relative to the amino acid sequence of C1V1 (SEQ ID NO:80). In some cases, the first 50 N-terminal amino acid residues are replaced by the following amino acids residues: MDYGGALSAVG (SEQ ID NO:82). In some cases, the cysteine residue at position 167 is changed to a threonine, alanine or serine residue. In some cases, the aspartic acid residue at position 195 is changed to an alanine residue, an asparagine residue, or a cysteine residue. In some cases, the aspartic acid residue at position 156 is changed to an alanine residue, an asparagine residue, or a cysteine residue. In some cases, the polypeptide comprises an amino acid sequence as provided in any one of SEQ ID NOs: 127-148. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:149 and comprises 1, 2, 3, 4, 5, 6, 7, 8, 9 or 10 amino acid substitutions selected from T99S, E123N, E130Q, E141S, V157R, E163S, P282R, A286N, N298Q and/or E313S, relative to the amino acid sequence of ReaChR (SEQ ID NO:81). In some cases, the first 51 N-terminal amino acid residues are replaced by the following amino acids residues: MDYGGALSAVG (SEQ ID NO:82). In some cases, the cysteine residue at position 168 is changed to a threonine, alanine or serine residue. In some cases, the aspartic acid residue at position 196 is changed to an alanine residue, an asparagine residue, or a cysteine residue. In some cases, the aspartic acid residue at position 156 is changed to an alanine residue, an asparagine residue, or a cysteine residue. In some cases, the polypeptide comprises an amino acid sequence as provided in any one of SEQ ID NOs: 149-170. In some cases, the polypeptide comprises an amino acid sequence that is at least 75%, at least 80%, at least 85%, at least 90%, at least 95%, at least 98%, or at least 99% identical, or is 100% identical, to the amino acid sequence provided in SEQ ID NO:116 and comprises 1, 2, 3, 4, 5, 6, 7, 8, 9 or 10 amino acid substitutions selected from A59S, E83N, E90Q, E101S, Q117R, E123S, V242R, T246N, N258Q and/or E273S, relative to the amino acid sequence of ChR2 (SEQ ID NO:79). In some cases, the cysteine residue at position 128 is changed to a threonine, alanine or serine residue. In some cases, the aspartic acid residue at position 156 is changed to an alanine residue, an asparagine residue, or a cysteine residue. In some cases, the polypeptide has an amino acid sequence as provided in any one of SEQ ID NOs: 116-126. In some cases, the kit further comprises a device configured to illuminate a target location with a light. In some cases, the device is configured to illuminate the target location with light having a wavelength ranging from about 350 to about 750 nm. In some cases, the device is configured to illuminate the target location with light having a wavelength ranging from about 450 up to about 500 nm. In some cases, the device is configured to constantly illuminate the target location with a light. In some cases, the device is configured to illuminate the target location with pulses of light. In some cases, the device is configured to modulate the wavelength and/or the intensity of the light. In some cases, the device is configured to modulate the frequency and/or duration of the pulses of light. In some cases, the device is configured to illuminate the target location in response to a user input. In some cases, the user input comprises: the wavelength of light, the intensity of light, the duration of a light pulse, the frequency of a light pulse, and/or the target location to be illuminated by the light. In some cases, the device is adapted to be implanted in a subject. In some cases, the target location is: a cell, a portion of a cell, a plurality of cells, a bundle of nerve fibers, a neuromuscular junction, a CNS tissue, a PNS tissue, or an anatomical region.

BRIEF DESCRIPTION OF THE DRAWINGS

(FIG. 1A) C1C2 crystal structure with residues used for screening. (FIG. 1B) C1C2 mutations screened in neurons for photocurrent size at −80 mV (n=6-8). Arrows: nine mutations selected for C1C2_5x (T98S/E129S/E140S/E162S/T285N) and C1C2_4x (V156K/H173R/V281K/N297Q) constructs. (FIG. 1C) $V_{rev}$ of C1C2 single-mutation constructs (n=6-8). (FIG. 1D) Comparison of photocurrent sizes for C1C2, C1C2_4x and C1C2_5x. (FIG. 1E) Comparison of $V_{rev}$ for C1C2, C1C2_4x and C1C2_5x (n=8-10). Error bars: s.e.m.

(FIG. 2A) C1C2 structure with the nine residues mutated in C1C2_4x and C1C2_5x. (FIG. 2B) Representative photocurrents and (FIG. 2C) corresponding current-voltage relationships recorded at membrane potentials from −75 mV to +55 mV upon 475 nm light activation (power density: 5 mW/mm²). (-FIG. 2D) $V_{rev}$ of C1C2, iC1C2, C1C2_4x, and C1C2_5x (neuronal recording solutions in Methods). (FIG. 2E) Activation spectra of NpHR, C1C2, and iC1C2 measured at power density 0.65 mW/mm² for each wavelength and normalized to the maximum amplitude (n=6). (FIG. 2F) $V_{rev}$ of C1C2, iC1C2, C1C2_4x, and C1C2_5x with internal (int) 120 mM KCl and external (ext) 120 mM NaCl, CsCl, or Na-Gluconate, pH 7.3, characterized in HEK cells. (FIG. 2G) As in (FIG. 2A), with ext 120 mM NaCl and int 120 mM KCl, CsCl, or K-Gluconate, pH 7.3 (n=6-17). (FIG. 2H) $V_{rev}$ of iC1C2 under equal (eq) external and internal pH, generating a Nernst potential for protons of 0 mV (upper dotted line) at pH 6 and 7.3. [Cl⁻]$_i$ concentration was 8 mM and [Cl⁻]$_o$ was 128 mM, generating a Nernst potential for Cl⁻ of −71 mV (lower dotted line) (n=6-9). (FIG. 2I) Current-voltage relationship recorded with equal external and internal pH values at pH 6 and 7.3; internal and external [Cl⁻] of 8 mM and 128 mM, respectively (n=3-8). (FIG. 2J) Photocurrent of iC1C2 at 0 mV from the current-voltage relationship in (FIG. 2I). Error bars: s.e.m.

FIG. 3A-3F show data relating to characterization of iC1C2 in mammalian neurons. (FIG. 3A) Representative photocurrents of C1C2 (left) and iC1C2 (right) recorded at membrane potentials ranging from −80 to 0 mV 475 nm light ("475 nm" bar) was applied at 5 mW/mm². (FIG. 3B) Corresponding current-voltage relationship for photocurrents. (FIG. 3C) $V_{rev}$ of C1C2 and iC1C2 relative to threshold for spike generation ($V_{AP}$) and to neuron resting potential ($V_{rest}$) (n=8-22). (FIG. 3D) Photocurrent amplitudes (left) and membrane polarization at $V_{AP}$ (right) (n=9-14). (FIG. 3E) Mean changes in input resistances were normalized to pre-light value (n=9-20). (F) Sample voltage traces of iC1C2-expressing neuron stimulated with varying current injections for 1.5 s, and additional 0.5 s, 475 nm, 5 mW/mm² pulses showing effective clamping toward $V_{rev}$: note hyperpolarizing responses below $V_{AP}$. Error bars: s.e.m.

FIG. 4A-4H show data relating to fast and bistable inhibition of neuronal spiking with iC1C2 and SwiChR. Representative voltage traces of iC1C2-expressing neurons stimulated with either (FIG. 4A) a continuous electrical pulse (3 s) or (FIG. 4B) pulsed current injections (10 Hz/3 s). Electrically evoked spikes were inhibited by 475 nm light ("475 nm" bar) at 5 mW/mm². (FIG. 4C) Distribution of spike-inhibition probability for iC1C2-expressing cells (n=18 neurons; fraction of spikes blocked shown). (FIG. 4D) Inward and outward photocurrents of SwiChR$_{CT}$ in HEK cell upon 475 nm light ("475 nm" bar). (FIG. 4E) Channel off-kinetics (τ) for iC1C2, SwiChR$_{CT}$, and SwiChR$_{CT}$ exposed to red light during channel closure. (FIG. 4F) Light sensitivity of SwiChR$_{CT}$ compared to iC1C2 and NpHR. iC1C2 and SwiChR$_{CT}$ were activated with 470 nm and NpHR with 560 nm. Photocurrents were measured at light intensities between 0.0036 and 5 mW/mm², holding potential was −80 mV. Amplitudes were normalized to the maximum value for each construct (n=6-8). (FIG. 4G) Reversal potential of iC1C2 and iC1C2-C167T relative to VAP and $V_{rest}$ (n=10-22) (left). Photocurrent amplitudes at VAP shown at right (n=9-15). (FIG. 4H) Bistable spiking modulation by SwiChR$_{CT}$. Spiking was induced by a continuous electrical pulse (3 s) and stably inhibited by 475 nm light ("475 nm" bar). Spiking resumed after 632 nm light application ("632 nm" bar). Light power density was 5 mW/mm². Error bars: s.e.m.

FIG. 5 shows a protein sequence alignment of the proteins C1C2 (SEQ ID NO:78) and iC1C2 (SEQ ID NO:1) to ChR2 (SEQ ID NO:79). The mutated residues are shown in boxes, and the transmembrane helices are indicated with the bars labeled TM 1-7. Positioning of the SwiChR mutations is indicated by dashed ellipse.

(FIG. 7A) Bistable spiking modulation with SwiChR$_{CT}$. Spiking was induced by a continuous electrical pulse (3 s), stably inhibited by 475 nm light ("475 nm" bar) delivered at 5 mW/mm², and resumed after 632 nm light application ("632 nm" bar) (left). Prolonged spiking modulation in the same cell after only 475 nm light delivery ("475 nm" bar) at 5 mW/mm² (right) with the same current injection as in left panel. (FIG. 7B) Current-voltage relationship of SwiChR$_{CA}$ recorded at membrane potentials from −80 mV to −30 mV upon 470 nm activation pulses ("475 nm" bar) followed by 632 nm ("632 nm" bar) light pulses. (FIG. 7C) Representative photocurrent of SwiChR$_{CA}$ upon 470 nm activation ("475 nm" bar) followed by a second light pulse at 632 nm ("632 nm" bar). Light power density was 5 mW/mm$^2$. (FIG. 7D) (left) Bistable spiking modulation by SwiChR$_{CA}$. Spiking was induced by a continuous electrical pulse (3 s) and stably inhibited by 475 nm light ("475 nm" bar) delivered at 5 mW/mm$^2$. Spiking resumed after 632 nm light application ("632 nm" bar). (FIG. 7E) Prolonged spiking modulation of SwiChR$_{CA}$ of the same cell as in (FIG. 7D) with 475 nm light ("475 nm" bar) only, delivered at 5 mW/mm$^2$; the same current injection was used to induce spiking as in (FIG. 7D).

FIG. 12A-12E provide amino acid sequences of examples of polypeptides that relate to the compositions of the disclosure.

FIG. 13A-13C provide amino acid sequences of examples of polypeptides that relate to the compositions of the disclosure.

FIG. 14A-14E provide amino acid sequences of examples of polypeptides that relate to the compositions of the disclosure.

FIG. 15A-15E provide amino acid sequences of examples of polypeptides that relate to the compositions of the disclosure.

FIG. 16A-16C provide amino acid sequences of examples of polypeptides that relate to the compositions of the disclosure.

FIG. 17A, left: The reversal potential of ibC1C2_3.0 (SEQ ID NO: 96) is −79 mV at 4 mM internal chloride concentration which is lower than the threshold for action potentials (VAP) and the resting potential of neurons (VRest). FIG. 17A, Right: Outward currents at VAP compared to regular ibC1C2 (SEQ ID NO: 3). FIG. 17B, Left: At 12 mM internal chloride, the reversal potentials of ibC1C2_3.0 (SEQ ID NO: 96) and SwiChR_3.0 (SEQ ID NO: 108) overlap with the equilibrium potential for chloride (VEq). FIG. 17B, Right: Photocurrents of ibC1C2_3.0 (SEQ ID NO: 96) are 7 times larger compared to ibC1C2 (SEQ ID NO: 3). (Error bars=standard error of the mean, number of recordings ≥6).

FIG. 18A: A 4 s light pulse (475 nm, 5 mW/mm$^2$) inhibits action potentials in an ibC1C2_3.0 (SEQ ID NO: 96)-expressing neuron during a 6 second period of electrical stimulations at 10 Hz. FIG. 18B: Spike inhibition probability at 4 mM and (FIG. 18C) 12 mM internal chloride. (Error bars=standard error of the mean, number of recordings ≥6).

FIG. 19A-19C show graphs that demonstrate inhibition of strong, extended stimulations in cultured neurons at 12 mM internal chloride. FIG. 19A: Inhibition of an ibC1C2_3.0 (SEQ ID NO: 96)-expressing neuron with a 10 s blue light pulse (475 nm, 5 mW/mm$^2$) during a 12 second period of electrical stimulation at 20 Hz. FIG. 19B: Bimodal inhibition of a SwiChR_3.0 (SEQ ID NO: 108)-expressing neuron: Electrical stimulations were applied for 16 seconds at 20 Hz. After 1 s, a brief blue light pulse (1 s, 475 nm, 5 mW/mm$^2$) inhibits action potentials for 13 seconds. Subsequently, a red light pulse (2 s, 632 nm, 10 mW/mm$^2$) recovers action potential generation. FIG. 19C: Spike inhibition probability for both constructs under these conditions. (Error bars=standard error of the mean, number of recordings ibC1C2_3.0 (SEQ ID NO: 96): n=15, SwiChR_3.0 (SEQ ID NO: 108): n=5).

FIG. 21A-21F provide amino acid sequences of examples of polypeptides that relate to the compositions of the disclosure.

FIG. 22A-22C provide amino acid sequences of examples of polypeptides that relate to the compositions of the disclosure.

FIG. 23A-23F provide amino acid sequences of examples of polypeptides that relate to the compositions of the disclosure.

FIG. 24A-24F provide amino acid sequences of examples of polypeptides that relate to the compositions of the disclosure.

DEFINITIONS

Figure 1A:
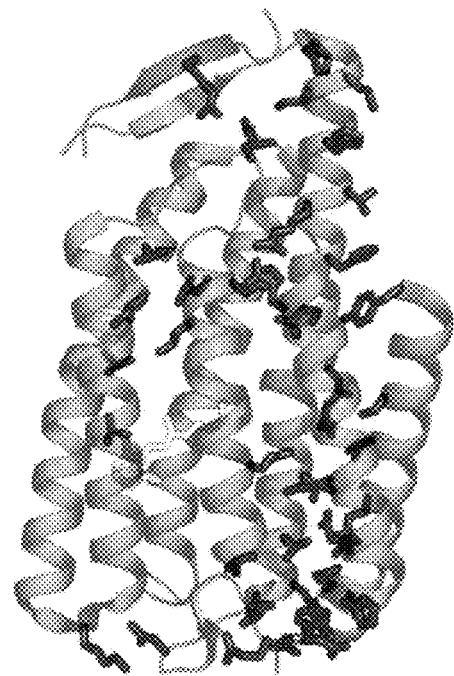
FIG. 1A-1E show details of the rational design and screen: $V_{rev}$-shifted ChRs.

As used herein, an "individual," "subject," or "patient" can be a mammal, including a human. Mammals include, but are not limited to, ungulates, canines, felines, bovines, ovines, non-human primates, lagomorphs, and rodents (e.g., mice and rats). In one aspect, an individual is a human. In another aspect, an individual is a non-human mammal.

The terms "polypeptide," "peptide," and "protein," used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. NH$_2$ refers to the free amino group present at the amino terminus of a polypeptide. COOH refers to the free carboxyl group present at the carboxyl terminus of a polypeptide. In keeping with standard polypeptide nomenclature, J. Biol. Chem., 243 (1969), 3552-59 is used.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The nucleic acid may be double stranded, single stranded, or contain portions of both double stranded or single stranded sequence. As will be appreciated by those in the art, the depiction of a single strand ("Watson") also defines the sequence of the other strand ("Crick"). By the term "recombinant nucleic acid" herein is meant nucleic acid, originally formed in vitro, in general, by the manipulation of nucleic acid by endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Nucleic acid sequence identity (as well as amino acid sequence identity) is calculated based on a reference sequence, which may be a subset of a larger sequence, such as a conserved motif, coding region, flanking region, etc. A reference sequence will usually be at least about 18 residues long, more usually at least about 30 residues long, and may extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17). As used herein, an amino acid sequence that is "at least x % identical" shares at least x % amino acid sequence identity with a reference sequence. For example, as used herein, an amino acid sequence that is "at least 99% identical" shares at least 99% amino acid sequence identity with a reference sequence.

The term "genetic modification" and refers to a permanent or transient genetic change induced in a cell following introduction into the cell of new nucleic acid (i.e., nucleic acid exogenous to the cell). Genetic change ("modification") can be accomplished by incorporation of the new nucleic acid into the genome of the host cell, or by transient or stable maintenance of the new nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells. An isolated polypeptide will in some embodiments be synthetic. "Synthetic polypeptides" are assembled from amino acids, and are chemically synthesized in vitro, e.g., cell-free chemical synthesis, using procedures known to those skilled in the art.

Amino acid substitutions in a native protein sequence may be "conservative" or "non-conservative" and such substituted amino acid residues may or may not be one encoded by the genetic code. A "conservative amino acid substitution" is one in which the amino acid residue is replaced with an amino acid residue having a chemically similar side chain (i.e., replacing an amino acid possessing a basic side chain with another amino acid with a basic side chain). A "non-conservative amino acid substitution" is one in which the amino acid residue is replaced with an amino acid residue having a chemically different side chain (i.e., replacing an amino acid having a basic side chain with an amino acid having an aromatic side chain). The standard twenty amino acid "alphabet" is divided into chemical families based on chemical properties of their side chains. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and side chains having aromatic groups (e.g., tyrosine, phenylalanine, tryptophan, histidine).

As used herein, the term "light-activated protein" means a protein that undergoes a conformational change when exposed to light of an activating wavelength.

As used herein, the term "anion channel protein" means a protein that includes an anion pore that can be opened to allow a stream of anions to pass from one side of a cell membrane to the other.

As used herein, an "effective dosage" or "effective amount" of a drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective dosage can be administered in one or more administrations. For purposes of this disclosure, an effective dosage of a drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "treatment" or "treating" is an approach for obtaining beneficial or desired results including clinical results. For purposes of this disclosure, beneficial or desired clinical results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of embodiments of the invention in greater detail, aspects of the systems and devices of various embodiments are reviewed first in greater detail, followed by a discussion of methods and kits according to certain embodiments of the invention.

DETAILED DESCRIPTION

Aspects of the disclosure include compositions, devices, systems and methods for optogenetic modulation of action potentials in target cells. The subject devices include light-generating devices, control devices, and delivery devices for delivering light-responsive polypeptides, or nucleic acids encoding same, to target cells. The subject compositions and systems include light-activated polypeptides, nucleic acids comprising nucleotide sequences encoding these polypeptides, as well as expression systems that facilitate expression of these polypeptides in target cells. Also provided are methods of using the subject devices and systems to optogenetically manipulate action potentials in target cells, e.g., to treat a neurological or psychiatric condition in a human or animal subject.

Compositions

Aspects of the disclosure include compositions for optogenetically modulating action potentials in target cells. The subject compositions generally include an engineered light-activated anion channel protein that is adapted to allow a plurality of anions to pass through a cell membrane in response to light. In some embodiments, the subject compositions include nucleic acids comprising nucleotide sequences encoding the subject proteins, as well as additional components, such as transcriptional control elements (e.g., promoter sequences, such as tissue-specific or cell type-specific promoter sequences, inducible promoter sequences, and the like), trafficking sequences, signal sequences, endoplasmic reticulum export sequences, and the like. Each of these components is now further described in greater detail.

Engineered Anion Channel Proteins

As summarized above, aspects of the present disclosure include engineered light-activated ion channel polypeptides that are adapted to allow one or more anions to pass through the plasma membrane of a target cell when the polypeptide is illuminated with light of an activating wavelength. The subject polypeptides are in some embodiments specific to a particular species of ion, meaning that the subject light-activated polypeptides only allow ions of a particular species to pass through the membrane of a cell. In some embodiments, the subject engineered light-activated anion channel polypeptides are specific to chloride ions ($Cl^-$). In some embodiments, the subject engineered light-activated anion channel polypeptides provide increased chloride conductivity and/or increased chloride selectivity. In certain embodiments, the subject engineered light-activated anion channel polypeptides provide stronger light-induced inhibition of neuronal activity over a wider range of conditions, such as high internal chloride concentrations.

In some embodiments, a subject light-activated polypeptide, when expressed on the membrane of a cell (e.g., a mammalian cell), and when exposed to light of an activating wavelength, hyperpolarizes the membrane. In some embodiments, a subject light-activated polypeptide exhibits prolonged stability of photocurrents. In some embodiments, a subject light-activated polypeptide exhibits enhanced expression in cell membranes and larger photocurrents in cultured neurons. In some embodiments, a subject light-activated polypeptide exhibits decelerated channel kinetics/decelerated channel closure. In some embodiments, a subject light-activated polypeptide conduct anions and inhibits the formation of action potentials in neurons for an extended period of time (e.g., from about 0.5 hours, up to about 0.75 hours, up to about 1 hour, up to about 1.25 hours, up to about 1.5 hours, up to about 1.75 hours, up to about 2 hours, up to about 2.25 hours, up to about 2.5 hours, up to about 2.75 hours, up to about 3 hours or more) after brief light stimulations at lower light intensities.

In some embodiments, the subject engineered light-activated anion channel polypeptides are activated by blue light. In some embodiments, the subject engineered light-activated anion channel polypeptides are activated by green light. In some embodiments, the subject engineered light-activated anion channel polypeptides are activated by yellow light. In some embodiments, the subject engineered light-activated anion channel polypeptides are activated by orange light. In some embodiments, the subject engineered light-activated anion channel polypeptides are activated by red light.

In some embodiments, the subject engineered light-activated anion channel polypeptides are derived from a cation channel polypeptide that comprises an ion pore and a vestibule. In some embodiments, the amino acid sequence of a cation channel polypeptide has been engineered to introduce amino acid substitutions and/or sequence modifications that change the electrostatic potential of the polypeptide in the region surrounding the ion pore and the vestibule. In certain embodiments, the amino acid substitutions and/or sequence modifications are selected so that the polarity of the cation channel polypeptide is reversed, thereby allowing the passage of anions through the pore instead of allowing cations through the pore. In some embodiments, the amino acid substitutions and/or sequence modifications are selected so that the subject engineered anion channel polypeptides allow anions to pass through the ion pore, while still maintaining appropriate protein folding, membrane expression, optical activation, and pore gating. In certain embodiments, a subject polypeptide comprises an amino acid sequence that is at least 58% (e.g., at least 58%, at least 60%, at least 65%, at least 70%, at least 75%, at least 80%, at least 85%, at least 90%, at least 95%, at least 98%, at least 99%, or 100%) identical to SEQ ID NOS: 1, 23, 34 or 56 and functions as an anion channel protein. In certain embodiments, a subject polypeptide comprises an amino acid sequence that is at least 60% (e.g., at least 60%, at least 65%, at least 70%, at least 75%, at least 80%, at least 85%, at least 90%, at least 95%, at least 98%, at least 99%, or 100%) identical to SEQ ID NOS: 94, 116, 127 or 149, and functions as an anion channel protein.

Representative embodiments of the subject engineered light-activated anion channel proteins are further described below.

Anion Channel Polypeptides Based on C1C2

In some embodiments, a subject engineered light-activated anion channel polypeptide is based on the amino acid sequence of the protein C1C2. The amino acid sequence of C1C2 is set forth in SEQ ID NO:78. In some embodiments, the amino acid sequence of the C1C2 protein has been modified by introducing one or more of the following mutations into the amino acid sequence: T98S, E129S, E140S, E162S, V156K, H173R, T285N, V281K and/or N297Q. In some embodiments, a subject engineered light-activated anion channel polypeptide comprises the amino acid sequence of the protein C1C2 with all 9 of the above-listed amino acid substitutions, such that the amino acid sequence of the polypeptide is provided in SEQ ID NO:1.

In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:1; and comprises 1, 2, 3, 4, 5, 6, 7, 8, or 9 amino acid substitutions selected from T98S, E129S, E140S, E162S, V156K, H173R, T285N, V281K and/or N297Q, relative to the amino acid sequence of C1C2 (SEQ ID NO:78). In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:1; and comprises T98S, E129S, E140S, E162S, and T285N substitutions relative to the amino acid sequence of C1C2 (SEQ ID NO: 78). This polypeptide is referred to herein as C1C2_5×. In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:1; and comprises V156K, H173R, V281K, and N297Q substitutions relative to the amino acid sequence of C1C2 (SEQ ID NO: 78). This polypeptide is referred to herein as C1C2_4×.

In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:1; and comprises 1, 2, 3, 4, 5, 6, 7, 8, or 9 of: S98, S129, S140, S162, K156, R173, N285, K281, and Q297, where the amino acid numbering is as set forth in SEQ ID NO:1. In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:1; and comprises S98, S129, S140, S162, K156, R173, N285, K281, and Q297, where the amino acid numbering is as set forth in SEQ ID NO:1. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:2; and comprises 1, 2, 3, 4, 5, 6, 7, 8, or 9 of: S98, S129, S140, S162, K156, R173, N285, K281, and Q297, and comprises N195, where the amino acid numbering is as set forth in SEQ ID NO:2. In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:2; and comprises S98, S129, S140, S162, K156, R173, N285, K281, and Q297, and comprises N195, where the amino acid numbering is as set forth in SEQ ID NO:2. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1C2 (SEQ ID NO:78), wherein the amino acid sequence has been modified by replacing the first 50 N-terminal amino acids of C1C2 with amino acids 1-11 from the protein ChR2 (MDYGGALSAVG) (SEQ ID NO:82). In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:3; and comprises 1, 2, 3, 4, 5, 6, 7, 8, or 9 of: S59, S90, 5101, S123, K117, R134, N246, K242, and Q258, where the amino acid numbering is as set forth in SEQ ID NO:3. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:3; and comprises S59, S90, S101, S123, K117, R134, N246, K242, and Q258, where the amino acid numbering is as set forth in SEQ ID NO:3. In some embodiments, a subject light-activated anion channel polypeptide comprises the amino acid sequence set forth in SEQ ID NO:3. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1C2 (SEQ ID NO:78), wherein the amino acid sequence has been modified by replacing the first 50 N-terminal amino acids of C1C2 with amino acids 1-11 from the protein ChR2 (MDYGGALSAVG) (SEQ ID NO:82). In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:4; and comprises 1, 2, 3, 4, 5, 6, 7, 8, or 9 of: S59, S90, 5101, S123, K117, R134, N246, K242, and Q258, and comprises N156, where the amino acid numbering is as set forth in SEQ ID NO:4. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:4; and comprises S59, S90, S101, S123, K117, R134, N246, K242, and Q258, and comprises N156, where the amino acid numbering is as set forth in SEQ ID NO:4. In some embodiments, a subject light-activated anion channel polypeptide comprises the amino acid sequence set forth in SEQ ID NO:4. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1C2 (SEQ ID NO:78), wherein the cysteine amino acid residue at position 167 has been replaced by a threonine residue. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:5; and comprises 1, 2, 3, 4, 5, 6, 7, 8, or 9 of: S98, S129, S140, S162, K156, R173, N285, K281, and Q297; and comprises T167. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:5; and comprises S98, S129, S140, S162, K156, R173, N285, K281, and Q297; and comprises T167, where the amino acid numbering is as set forth in SEQ ID NO:5. In some embodiments, the engineered light-activated anion channel polypeptide comprises the amino acid sequence provided in SEQ ID NO:5. In some of these embodiments, the light-activated polypeptide exhibits prolonged stability of photocurrents. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1C2, wherein the cysteine amino acid residue at position 167 has been replaced by an alanine residue. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:6; and comprises 1, 2, 3, 4, 5, 6, 7, 8, or 9 of: S98, S129, S140, S162, K156, R173, N285, K281, and Q297; and comprises A167, where the amino acid numbering is as set forth in SEQ ID NO:6. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:6; and comprises S98, S129, S140, S162, K156, R173, N285, K281, and Q297; and comprises A167, where the amino acid numbering is as set forth in SEQ ID NO:6. In some embodiments, the engineered light-activated anion channel polypeptide comprises the amino sequence provided in SEQ ID NO:6. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1C2, wherein the cysteine amino acid residue at position 167 has been replaced by a serine residue. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:7; and comprises 1, 2, 3, 4, 5, 6, 7, 8, or 9 of: S98, S129, S140, S162, K156, R173, N285, K281, and Q297; and comprises S167, where the amino acid numbering is as set forth in SEQ ID NO:7. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:7; and comprises S98, S129, S140, S162, K156, R173, N285, K281, and Q297; and comprises S167, where the amino acid numbering is as set forth in SEQ ID NO:7. In some embodiments, a subject engineered light-activated anion channel polypeptide comprises the amino acid sequence provided in SEQ ID NO:7. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:8; and comprises 1, 2, 3, 4, 5, 6, 7, 8, or 9 of: S98, S129, S140, S162, K156, R173, N285, K281, and Q297; comprises A195; and comprises T167, where the amino acid numbering is as set forth in SEQ ID NO:8. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:8; and comprises S98, S129, S140, S162, K156, R173, N285, K281, and Q297; comprises T167; and comprises A195, where the amino acid numbering is as set forth in SEQ ID NO:8. In some embodiments, a subject engineered light-activated anion channel polypeptide comprises the amino acid sequence provided in SEQ ID NO:8. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:9; and comprises 1, 2, 3, 4, 5, 6, 7, 8, or 9 of: S98, S129, S140, S162, K156, R173, N285, K281, and Q297; comprises N195; and comprises T167, where the amino acid numbering is as set forth in SEQ ID NO:9. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:9; and comprises S98, S129, S140, S162, K156, R173, N285, K281, and Q297; comprises T167; and comprises N195, where the amino acid numbering is as set forth in SEQ ID NO:9. In some embodiments, a subject engineered light-activated anion channel polypeptide comprises the amino acid sequence provided in SEQ ID NO:9. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:10; and comprises 1, 2, 3, 4, 5, 6, 7, 8, or 9 of: S98, S129, S140, S162, K156, R173, N285, K281, and Q297; comprises A195; and comprises A167, where the amino acid numbering is as set forth in SEQ ID NO:10. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:10; and comprises S98, S129, S140, S162, K156, R173, N285, K281, and Q297; comprises A167; and comprises A195, where the amino acid numbering is as set forth in SEQ ID NO:10. In some embodiments, a subject engineered light-activated anion channel polypeptide comprises the amino acid sequence provided in SEQ ID NO:10. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:11; and comprises 1, 2, 3, 4, 5, 6, 7, 8, or 9 of: S98, S129, S140, S162, K156, R173, N285, K281, and Q297; comprises N195; and comprises A167, where the amino acid numbering is as set forth in SEQ ID NO:11. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:11; and comprises S98, S129, S140, S162, K156, R173, N285, K281, and Q297; comprises A167; and comprises N195, where the amino acid numbering is as set forth in SEQ ID NO:11. In some embodiments, a subject engineered light-activated anion channel polypeptide comprises the amino acid sequence provided in SEQ ID NO:11. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:12; and comprises 1, 2, 3, 4, 5, 6, 7, 8, or 9 of: S98, S129, S140, S162, K156, R173, N285, K281, and Q297; comprises A195; and comprises S167, where the amino acid numbering is as set forth in SEQ ID NO:12. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:12; and comprises S98, S129, S140, S162, K156, R173, N285, K281, and Q297; comprises S167; and comprises A195, where the amino acid numbering is as set forth in SEQ ID NO:12. In some embodiments, a subject engineered light-activated anion channel polypeptide comprises the amino acid sequence provided in SEQ ID NO:12. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:13; and comprises 1, 2, 3, 4, 5, 6, 7, 8, or 9 of: S98, S129, S140, S162, K156, R173, N285, K281, and Q297; comprises N195; and comprises S167, where the amino acid numbering is as set forth in SEQ ID NO:13. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:13; and comprises S98, S129, S140, S162, K156, R173, N285, K281, and Q297; comprises S167; and comprises N195, where the amino acid numbering is as set forth in SEQ ID NO:13. In some embodiments, a subject engineered light-activated anion channel polypeptide comprises the amino acid sequence provided in SEQ ID NO:13. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1C2 with one or more of the modifications described above, wherein the aspartate amino acid residue at original position 195 has been replaced by an alanine residue. In certain embodiments wherein the first 50 N-terminal amino acids of the protein are replaced by amino acids 1-11 from the protein ChR2, the aspartate amino acid residue at position 156 (which corresponds to original position 195 of the C1C2 amino acid sequence set forth in SEQ ID NO:78) is replaced by an alanine residue.

In some embodiments, a subject engineered light-activated anion channel polypeptide is based on the amino acid sequence of the protein C1C2 with one or more of the modifications described above, wherein the aspartate amino acid residue at original position 195 has been replaced by an asparagine residue. In certain embodiments wherein the first 50 N-terminal amino acids of the protein are replaced by amino acids 1-11 from the protein ChR2, the aspartate amino acid residue at position 156 (which corresponds to original position 195 of the C1C2 amino acid sequence set forth in SEQ ID NO:78) is replaced by an asparagine residue.

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:14; and comprises 1, 2, 3, 4, 5, 6, 7, 8, or 9 of: S59, S90, S101, S123, K117, R134, N246, K242, and Q258; and comprises T128, where the amino acid numbering is as set forth in SEQ ID NO:14. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:14; and comprises S59, S90, S101, S123, K117, R134, N246, K242, and Q258; and comprises T128, where the amino acid numbering is as set forth in SEQ ID NO:14. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:15; and comprises 1, 2, 3, 4, 5, 6, 7, 8, or 9 of: S59, S90, S101, S123, K117, R134, N246, K242, and Q258; and comprises A128, where the amino acid numbering is as set forth in SEQ ID NO:15. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:15; and comprises S59, S90, S101, S123, K117, R134, N246, K242, and Q258; and comprises A128, where the amino acid numbering is as set forth in SEQ ID NO:15. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:16; and comprises 1, 2, 3, 4, 5, 6, 7, 8, or 9 of: S59, S90, S101, S123, K117, R134, N246, K242, and Q258; and comprises S128, where the amino acid numbering is as set forth in SEQ ID NO:16. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:16; and comprises S59, S90, S101, S123, K117, R134, N246, K242, and Q258; and comprises S128, where the amino acid numbering is as set forth in SEQ ID NO:16. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:17; and comprises 1, 2, 3, 4, 5, 6, 7, 8, or 9 of: S59, S90, S101, S123, K117, R134, N246, K242, and Q258; and comprises T128 and A156, where the amino acid numbering is as set forth in SEQ ID NO:17. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:17; and comprises S59, S90, S101, S123, K117, R134, N246, K242, and Q258; and comprises T128 and A156, where the amino acid numbering is as set forth in SEQ ID NO:17. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:18; and comprises 1, 2, 3, 4, 5, 6, 7, 8, or 9 of: S59, S90, S101, S123, K117, R134, N246, K242, and Q258; and comprises T128 and N156, where the amino acid numbering is as set forth in SEQ ID NO:18. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:18; and comprises S59, S90, S101, S123, K117, R134, N246, K242, and Q258; and comprises T128 and N156, where the amino acid numbering is as set forth in SEQ ID NO:18. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQ-IDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:19; and comprises 1, 2, 3, 4, 5, 6, 7, 8, or 9 of: S59, S90, S101, S123, K117, R134, N246, K242, and Q258; and comprises A128 and A156, where the amino acid numbering is as set forth in SEQ ID NO:19. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:19; and comprises S59, S90, S101, S123, K117, R134, N246, K242, and Q258; and comprises A128 and A156, where the amino acid numbering is as set forth in SEQ ID NO:19. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQ-IDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:20; and comprises 1, 2, 3, 4, 5, 6, 7, 8, or 9 of: S59, S90, S101, S123, K117, R134, N246, K242, and Q258; and comprises A128 and N156, where the amino acid numbering is as set forth in SEQ ID NO:20. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:20; and comprises S59, S90, S101, S123, K117, R134, N246, K242, and Q258; and comprises A128 and N156, where the amino acid numbering is as set forth in SEQ ID NO:20. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQ-IDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:21; and comprises 1, 2, 3, 4, 5, 6, 7, 8, or 9 of: S59, S90, S101, S123, K117, R134, N246, K242, and Q258; and comprises S128 and A156, where the amino acid numbering is as set forth in SEQ ID NO:21. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:21; and comprises S59, S90, S101, S123, K117, R134, N246, K242, and Q258; and comprises S128 and A156, where the amino acid numbering is as set forth in SEQ ID NO:21. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQ-IDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:22; and comprises 1, 2, 3, 4, 5, 6, 7, 8, or 9 of: S59, S90, S101, S123, K117, R134, N246, K242, and Q258; and comprises S128 and N156, where the amino acid numbering is as set forth in SEQ ID NO:22. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:22; and comprises S59, S90, S101, S123, K117, R134, N246, K242, and Q258; and comprises S128 and N156, where the amino acid numbering is as set forth in SEQ ID NO:22. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQ-IDINV (SEQ ID NO:83)) and an ER export signal (e.g., FCYENEV (SEQ ID NO:84)).

In certain embodiments, a subject engineered light-activated anion channel polypeptide is based on the amino acid sequence of the protein C1C2, wherein the amino acid sequence is at least about 90%, 91%, 92%, 93%, 94%, 95%, 96%, 97%, 98%, 99%, or 100% identical to the sequence provided in one of SEQ ID NOS:1-22.

In some embodiments, the amino acid sequence of the C1C2 protein has been modified by introducing one or more of the following mutations into the amino acid sequence: T98S, E122N, E129Q, E140S, V156R, E162S, V281R, T285N, N297Q and E312S. In some embodiments, a subject engineered light-activated anion channel polypeptide comprises the amino acid sequence of the protein C1C2 with all 10 of the above-listed amino acid substitutions, such that the amino acid sequence of the polypeptide is provided in SEQ ID NO: 94.

In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:94; and comprises 1, 2, 3, 4, 5, 6, 7, 8, 9 or 10 amino acid substitutions selected from T98S, E122N, E129Q, E140S, V156R, E162S, V281R, T285N, N297Q and E312S, relative to the amino acid sequence of C1C2 (SEQ ID NO:78).

In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100% amino acid sequence identity to the amino acid sequence set forth in SEQ ID NO:94; and comprises 1, 2, 3, 4, 5, 6, 7, 8, 9 or 10 of: 98S, 122N, 129Q, 140S, 156R, 162S, 281R, 285N, 297Q and 312S, where the amino acid numbering is as set forth in SEQ ID NO:94. In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100% amino acid sequence identity to the amino acid sequence set forth in SEQ ID NO:94; and comprises 98S, 122N, 129Q, 140S, 156R, 162S, 281R, 285N, 297Q and 312S, where the amino acid numbering is as set forth in SEQ ID NO:94. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:95; and comprises 1, 2, 3, 4, 5, 6, 7, 8, 9 or 10 of: 98S, 122N, 129Q, 140S, 156R, 162S, 281R, 285N, 297Q and 312S, and comprises 195N, where the amino acid numbering is as set forth in SEQ ID NO:95. In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:95; and comprises 98S, 122N, 129Q, 140S, 156R, 162S, 281R, 285N, 297Q and 312S, and comprises 195N, where the amino acid numbering is as set forth in SEQ ID NO:95. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1C2 (SEQ ID NO:78), wherein the amino acid sequence has been modified by replacing the first 50 N-terminal amino acids of C1C2 with amino acids 1-11 from the protein ChR2 (MDYGGALSAVG) (SEQ ID NO:82). In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:96; and comprises 1, 2, 3, 4, 5, 6, 7, 8, 9 or 10 of: S59, 83N, 90Q, 101S, 117R, 123S, 242R, 246N, 258Q and 273S, where the amino acid numbering is as set forth in SEQ ID NO:96. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:96; and comprises S59, 83N, 90Q, 101S, 117R, 123S, 242R, 246N, 258Q and 273S, where the amino acid numbering is as set forth in SEQ ID NO:96. In some embodiments, a subject light-activated anion channel polypeptide comprises the amino acid sequence set forth in SEQ ID NO:96. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1C2 (SEQ ID NO:78), wherein the amino acid sequence has been modified by replacing the first 50 N-terminal amino acids of C1C2 with amino acids 1-11 from the protein ChR2 (MDYGGALSAVG) (SEQ ID NO:82). In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:97; and comprises 1, 2, 3, 4, 5, 6, 7, 8, 9 or 10 of: 59S, 83N, 90Q, 101S, 117R, 123S, 242R, 246N, 258Q and 273S, and comprises 156N, where the amino acid numbering is as set forth in SEQ ID NO:97. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:97; and comprises 59S, 83N, 90Q, 101S, 117R, 123S, 242R, 246N, 258Q and 273S, and comprises 156N, where the amino acid numbering is as set forth in SEQ ID NO:97. In some embodiments, a subject light-activated anion channel polypeptide comprises the amino acid sequence set forth in SEQ ID NO:97. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1C2 (SEQ ID NO:78), wherein the cysteine amino acid residue at position 167 has been replaced by a threonine residue. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:98; and comprises 1, 2, 3, 4, 5, 6, 7, 8, 9 or 10 of: 98S, 122N, 129Q, 140S, 156R, 162S, 281R, 285N, 297Q and 312S; and comprises 167T. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:98; and comprises 98S, 122N, 129Q, 140S, 156R, 162S, 281R, 285N, 297Q and 312S; and comprises 167T, where the amino acid numbering is as set forth in SEQ ID NO:98. In some embodiments, the engineered light-activated anion channel polypeptide comprises the amino acid sequence provided in SEQ ID NO:98. In some of these embodiments, the light-activated polypeptide exhibits prolonged stability of photocurrents. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1C2, wherein the cysteine amino acid residue at position 167 has been replaced by an alanine residue. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:99; and comprises 1, 2, 3, 4, 5, 6, 7, 8, 9 or 10 of: 98S, 122N, 129Q, 140S, 156R, 162S, 281R, 285N, 297Q and 312S; and comprises 167A, where the amino acid numbering is as set forth in SEQ ID NO:99. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:99; and comprises 98S, 122N, 129Q, 140S, 156R, 162S, 281R, 285N, 297Q and 312S; and comprises 167A, where the amino acid numbering is as set forth in SEQ ID NO:99. In some embodiments, the engineered light-activated anion channel polypeptide comprises the amino sequence provided in SEQ ID NO:99. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1C2, wherein the cysteine amino acid residue at position 167 has been replaced by a serine residue. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:100; and comprises 1, 2, 3, 4, 5, 6, 7, 8, 9 or 10 of: 98S, 122N, 129Q, 140S, 156R, 162S, 281R, 285N, 297Q and 312S; and comprises 167S, where the amino acid numbering is as set forth in SEQ ID NO:100. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100% amino acid sequence identity to the amino acid sequence set forth SEQ ID NO:100; and comprises 98S, 122N, 129Q, 140S, 156R, 162S, 281R, 285N, 297Q and 312S; and comprises 167S, where the amino acid numbering is as set forth in SEQ ID NO:100. In some embodiments, a subject engineered light-activated anion channel polypeptide comprises the amino acid sequence provided in SEQ ID NO:100. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:101; and comprises 1, 2, 3, 4, 5, 6, 7, 8, 9 or 10 of: 98S, 122N, 129Q, 140S, 156R, 162S, 281R, 285N, 297Q and 312S; comprises 195C; and comprises 167T, where the amino acid numbering is as set forth in SEQ ID NO:101. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:101; and comprises 98S, 122N, 129Q, 140S, 156R, 162S, 281R, 285N, 297Q and 312S; comprises 167T; and comprises 195C, where the amino acid numbering is as set forth in SEQ ID NO:101. In some embodiments, a subject engineered light-activated anion channel polypeptide comprises the amino acid sequence provided in SEQ ID NO:101. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:102; and comprises 1, 2, 3, 4, 5, 6, 7, 8, 9 or 10 of: 98S, 122N, 129Q, 140S, 156R, 162S, 281R, 285N, 297Q and 312S; comprises 195N; and comprises 167T, where the amino acid numbering is as set forth in SEQ ID NO:102. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:102; and comprises 98S, 122N, 129Q, 140S, 156R, 162S, 281R, 285N, 297Q and 312S; comprises 167T; and comprises 195N, where the amino acid numbering is as set forth in SEQ ID NO:102. In some embodiments, a subject engineered light-activated anion channel polypeptide comprises the amino acid sequence provided in SEQ ID NO:102. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:103; and comprises 1, 2, 3, 4, 5, 6, 7, 8, 9 or 10 of: 98S, 122N, 129Q, 140S, 156R, 162S, 281R, 285N, 297Q and 312S; comprises 195C; and comprises 167A, where the amino acid numbering is as set forth in SEQ ID NO:103. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:103; and comprises 98S, 122N, 129Q, 140S, 156R, 162S, 281R, 285N, 297Q and 312S; comprises 167A; and comprises 195C, where the amino acid numbering is as set forth in SEQ ID NO:103. In some embodiments, a subject engineered light-activated anion channel polypeptide comprises the amino acid sequence provided in SEQ ID NO:103. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:104; and comprises 1, 2, 3, 4, 5, 6, 7, 8, 9 or 10 of: 98S, 122N, 129Q, 140S, 156R, 162S, 281R, 285N, 297Q and 312S; comprises 195N; and comprises 167A, where the amino acid numbering is as set forth in SEQ ID NO:104. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:104; and comprises 98S, 122N, 129Q, 140S, 156R, 162S, 281R, 285N, 297Q and 312S; comprises 167A; and comprises 195N, where the amino acid numbering is as set forth in SEQ ID NO:104. In some embodiments, a subject engineered light-activated anion channel polypeptide comprises the amino acid sequence provided in SEQ ID NO:104. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:105; and comprises 1, 2, 3, 4, 5, 6, 7, 8, 9 or 10 of:

98S, 122N, 129Q, 140S, 156R, 162S, 281R, 285N, 297Q and 312S; comprises 195C; and comprises 167S, where the amino acid numbering is as set forth in SEQ ID NO:105. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:105; and comprises 98S, 122N, 129Q, 140S, 156R, 162S, 281R, 285N, 297Q and 312S; comprises 167S; and comprises 195C, where the amino acid numbering is as set forth in SEQ ID NO:105. In some embodiments, a subject engineered light-activated anion channel polypeptide comprises the amino acid sequence provided in SEQ ID NO:105. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:106; and comprises 1, 2, 3, 4, 5, 6, 7, 8, 9 or 10 of: 98S, 122N, 129Q, 140S, 156R, 162S, 281R, 285N, 297Q and 312S; comprises 195N; and comprises 167S, where the amino acid numbering is as set forth in SEQ ID NO:106. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:106; and comprises 98S, 122N, 129Q, 140S, 156R, 162S, 281R, 285N, 297Q and 312S; comprises 167S; and comprises 195N, where the amino acid numbering is as set forth in SEQ ID NO:106. In some embodiments, a subject engineered light-activated anion channel polypeptide comprises the amino acid sequence provided in SEQ ID NO:106. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1C2 with one or more of the modifications described above, wherein the aspartate amino acid residue at original position 195 has been replaced by an alanine residue. In certain embodiments wherein the first 50 N-terminal amino acids of the protein are replaced by amino acids 1-11 from the protein ChR2, the aspartate amino acid residue at position 156 (which corresponds to original position 195 of the C1C2 amino acid sequence set forth in SEQ ID NO:78) is replaced by an alanine residue.

In some embodiments, a subject engineered light-activated anion channel polypeptide is based on the amino acid sequence of the protein C1C2 with one or more of the modifications described above, wherein the aspartate amino acid residue at original position 195 has been replaced by an asparagine residue. In certain embodiments wherein the first 50 N-terminal amino acids of the protein are replaced by amino acids 1-11 from the protein ChR2, the aspartate amino acid residue at position 156 (which corresponds to original position 195 of the C1C2 amino acid sequence set forth in SEQ ID NO:78) is replaced by an asparagine residue.

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:107; and comprises 1, 2, 3, 4, 5, 6, 7, 8, 9 or 10 of: 59S, 83N, 90Q, 101S, 117R, 123S, 242R, 246N, 258Q and 273S; and comprises 128T, where the amino acid numbering is as set forth in SEQ ID NO:107. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:107; and comprises 59S, 83N, 90Q, 101S, 117R, 123S, 242R, 246N, 258Q and 273S; and comprises 128T, where the amino acid numbering is as set forth in SEQ ID NO:107. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:108; and comprises 1, 2, 3, 4, 5, 6, 7, 8, 9 or 10 of: 59S, 83N, 90Q, 101S, 117R, 123S, 242R, 246N, 258Q and 273S; and comprises 128A, where the amino acid numbering is as set forth in SEQ ID NO:108. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:108; and comprises 59S, 83N, 90Q, 101S, 117R, 123S, 242R, 246N, 258Q and 273S; and comprises 128A, where the amino acid numbering is as set forth in SEQ ID NO:108. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:109; and comprises 1, 2, 3, 4, 5, 6, 7, 8, 9 or 10 of: 59S, 83N, 90Q, 101S, 117R, 123S, 242R, 246N, 258Q and 273S; and comprises 128S, where the amino acid numbering is as set forth in SEQ ID NO:109. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:109; and comprises 59S, 83N, 90Q, 101S, 117R, 123S, 242R, 246N, 258Q and 273S; and comprises 128S, where the amino acid numbering is as set forth in SEQ ID NO:109. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:110; and comprises 1, 2, 3, 4, 5, 6, 7, 8, 9 or 10 of: 59S, 83N, 90Q, 101S, 117R, 123S, 242R, 246N, 258Q and 273S; and comprises 128T and 156C where the amino acid numbering is as set forth in SEQ ID NO:110. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:110; and comprises 59S, 83N, 90Q, 101S, 117R, 123S, 242R, 246N, 258Q and 273S; and comprises 128T and 156C, where the amino acid numbering is as set forth in SEQ ID NO:110. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:111; and comprises 1, 2, 3, 4, 5, 6, 7, 8, 9 or 10 of: 59S, 83N, 90Q, 101S, 117R, 123S, 242R, 246N, 258Q and 273S; and comprises 128T and 156N, where the amino acid numbering is as set forth in SEQ ID NO:111. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:111; and comprises 59S, 83N, 90Q, 101S, 117R, 123S, 242R, 246N, 258Q and 273S; and comprises 128T and 156N, where the amino acid numbering is as set forth in SEQ ID NO:111. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:112; and comprises 1, 2, 3, 4, 5, 6, 7, 8, 9 or 10 of: 59S, 83N, 90Q, 101S, 117R, 123S, 242R, 246N, 258Q and 273S; and comprises 128A and 156C, where the amino acid numbering is as set forth in SEQ ID NO:112. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:112; and comprises 59S, 83N, 90Q, 101S, 117R, 123S, 242R, 246N, 258Q and 273S; and comprises 128A and 156C, where the amino acid numbering is as set forth in SEQ ID NO:112. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:113; and comprises 1, 2, 3, 4, 5, 6, 7, 8, 9 or 10 of: 59S, 83N, 90Q, 101S, 117R, 123S, 242R, 246N, 258Q and 273S; and comprises 128A and 156N, where the amino acid numbering is as set forth in SEQ ID NO:113. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:113; and comprises 59S, 83N, 90Q, 101S, 117R, 123S, 242R, 246N, 258Q and 273S; and comprises 128A and 156N, where the amino acid numbering is as set forth in SEQ ID NO:113. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:114; and comprises 1, 2, 3, 4, 5, 6, 7, 8, 9 or 10 of: 59S, 83N, 90Q, 101S, 117R, 123S, 242R, 246N, 258Q and 273S; and comprises 128S and 156C, where the amino acid numbering is as set forth in SEQ ID NO:114. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:114; and comprises 59S, 83N, 90Q, 101S, 117R, 123S, 242R, 246N, 258Q and 273S; and comprises 128S and 156C, where the amino acid numbering is as set forth in SEQ ID NO:114. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:115; and comprises 1, 2, 3, 4, 5, 6, 7, 8, 9 or 10 of: 59S, 83N, 90Q, 101S, 117R, 123S, 242R, 246N, 258Q and 273S; and comprises 128S and 156N, where the amino acid numbering is as set forth in SEQ ID NO:115. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:115; and comprises 59S, 83N, 90Q, 101S, 117R, 123S, 242R, 246N, 258Q and 273S; and comprises 128S and 156N, where the amino acid numbering is as set forth in SEQ ID NO:115. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In certain embodiments, a subject engineered light-activated anion channel polypeptide is based on the amino acid sequence of the protein C1C2, wherein the amino acid sequence is at least about 90%, 91%, 92%, 93%, 94%, 95%, 96%, 97%, 98%, 99%, or 100% identical to the sequence provided in one of SEQ ID NOS:94-115.

Anion Channel Polypeptides Based on C1V1

In some embodiments, a subject engineered light-activated anion channel polypeptide is based on the amino acid sequence of the protein C1V1. The amino acid sequence of C1V1 is set forth in SEQ ID NO:80. In some embodiments, the amino acid sequence of the C1V1 protein has been modified by introducing one or more of the following mutations into the amino acid sequence: T98S, E129S, E140S, E162S, V156K, H173R, A285N, P281K and/or N297Q. In some embodiments, a subject engineered light-activated anion channel polypeptide comprises the amino acid sequence of the protein C1V1 with all 9 of the above-listed amino acid substitutions, such that the amino acid sequence of the polypeptide is provided in SEQ ID NO:34.

In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:34; and comprises 1, 2, 3, 4, 5, 6, 7, 8, or 9 amino acid substitutions selected from T98S, E129S, E140S, E162S, V156K, H173R, A285N, P281K and/or N297Q, relative to the amino acid sequence of C1V1 (SEQ ID NO:80).

In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:34; and comprises 1, 2, 3, 4, 5, 6, 7, 8, or 9 of: S98, S129, S140, S162, K156, R173, N285, K281, and Q297, where the amino acid numbering is as set forth in SEQ ID NO:34. In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:34; and comprises S98, S129, S140, S162, K156, R173, N285, K281, and Q297, where the amino acid numbering is as set forth in SEQ ID NO:34. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:35; and comprises 1, 2, 3, 4, 5, 6, 7, 8, or 9 of: S98, S129, S140, S162, K156, R173, N285, K281, and Q297, and comprises N195, where the amino acid numbering is as set forth in SEQ ID NO:35. In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:35; and comprises S98, S129, S140, S162, K156, R173, N285, K281, and Q297, and comprises N195, where the amino acid numbering is as set forth in SEQ ID NO:35. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1V1 (SEQ ID NO:80), wherein the amino acid sequence has been modified by replacing the first 50 N-terminal amino acids of C1V1 with amino acids 1-11 from the protein ChR2 (MDYGGALSAVG) (SEQ ID NO:82). In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:36; and comprises 1, 2, 3, 4, 5, 6, 7, 8, or 9 of: S59, S90, S101, S123, K117, R134, N246, K242, and Q258, where the amino acid numbering is as set forth in SEQ ID NO:36. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:36; and comprises S59, S90, S101, S123, K117, R134, N246, K242, and Q258, where the amino acid numbering is as set forth in SEQ ID NO:36. In some embodiments, a subject light-activated anion channel polypeptide comprises the amino acid sequence set forth in SEQ ID NO:36. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1V1 (SEQ ID NO:80), wherein the amino acid sequence has been modified by replacing the first 50 N-terminal amino acids of C1V1 with amino acids 1-11 from the protein ChR2 (MDYGGALSAVG) (SEQ ID NO:82). In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:37; and comprises 1, 2, 3, 4, 5, 6, 7, 8, or 9 of: S59, S90, S101, S123, K117, R134, N246, K242, and Q258, and comprises N156, where the amino acid numbering is as set forth in SEQ ID NO:37. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:37; and comprises S59, S90, S101, S123, K117, R134, N246, K242, and Q258, and comprises N156, where the amino acid numbering is as set forth in SEQ ID NO:37. In some embodiments, a subject light-activated anion channel polypeptide comprises the amino acid sequence set forth in SEQ ID NO:37. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1V1 (SEQ ID NO:80), wherein the cysteine amino acid residue at position 167 has been replaced by a threonine residue. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:38; and comprises 1, 2, 3, 4, 5, 6, 7, 8, or 9 of: S98, 5129, 5140, S162, K156, R173, N285, K281, and Q297; and comprises T167. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:38; and comprises S98, S129, S140, S162, K156, R173, N285, K281, and Q297; and comprises T167, where the amino acid numbering is as set forth in SEQ ID NO:38. In some embodiments, the engineered light-activated anion channel polypeptide comprises the amino acid sequence provided in SEQ ID NO:38. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1V1, wherein the cysteine amino acid residue at position 167 has been replaced by an alanine residue. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:39; and comprises 1, 2, 3, 4, 5, 6, 7, 8, or 9 of: S98, S129, S140, S162, K156, R173, N285, K281, and Q297; and comprises A167, where the amino acid numbering is as set forth in SEQ ID NO:39. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:39; and comprises S98, S129, S140, S162, K156, R173, N285, K281, and Q297; and comprises A167, where the amino acid numbering is as set forth in SEQ ID NO:39. In some embodiments, the engineered light-activated anion channel polypeptide comprises the amino sequence provided in SEQ ID NO:39. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1V1, wherein the cysteine amino acid residue at position 167 has been replaced by a serine residue. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:40; and comprises 1, 2, 3, 4, 5, 6, 7, 8, or 9 of: S98, S129, S140, S162, K156, R173, N285, K281, and Q297; and comprises S167, where the amino acid numbering is as set forth in SEQ ID NO:40. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:40; and comprises S98, S129, S140, S162, K156, R173, N285, K281, and Q297; and comprises S167, where the amino acid numbering is as set forth in SEQ ID NO:40. In some embodiments, a subject engineered light-activated anion channel polypeptide comprises the amino acid sequence provided in SEQ ID NO:40. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:41; and comprises 1, 2, 3, 4, 5, 6, 7, 8, or 9 of: S98, S129, S140, S162, K156, R173, N285, K281, and Q297; comprises A195; and comprises T167, where the amino acid numbering is as set forth in SEQ ID NO:41. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:41; and comprises S98, S129, S140, S162, K156, R173, N285, K281, and Q297; comprises T167; and comprises A195, where the amino acid numbering is as set forth in SEQ ID NO:41. In some embodiments, a subject engineered light-activated anion channel polypeptide comprises the amino acid sequence provided in SEQ ID NO:41. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:42; and comprises 1, 2, 3, 4, 5, 6, 7, 8, or 9 of: S98, S129, S140, S162, K156, R173, N285, K281, and Q297; comprises N195; and comprises T167, where the amino acid numbering is as set forth in SEQ ID NO:42. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:42; and comprises S98, S129, S140, S162, K156, R173, N285, K281, and Q297; comprises T167; and comprises N195, where the amino acid numbering is as set forth in SEQ ID NO:42. In some embodiments, a subject engineered light-activated anion channel polypeptide comprises the amino acid sequence provided in SEQ ID NO:42. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:43; and comprises 1, 2, 3, 4, 5, 6, 7, 8, or 9 of: S98, S129, S140, S162, K156, R173, N285, K281, and Q297; comprises A195; and comprises A167, where the amino acid numbering is as set forth in SEQ ID NO:43. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:43; and comprises S98, S129, S140, S162, K156, R173, N285, K281, and Q297; comprises A167; and comprises A195, where the amino acid numbering is as set forth in SEQ ID NO:43. In some embodiments, a subject engineered light-activated anion channel polypeptide comprises the amino acid sequence provided in SEQ ID NO:43. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:44; and comprises 1, 2, 3, 4, 5, 6, 7, 8, or 9 of: S98, S129, S140, S162, K156, R173, N285, K281, and Q297; comprises N195; and comprises A167, where the amino acid numbering is as set forth in SEQ ID NO:44. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:44; and comprises S98, S129, S140, S162, K156, R173, N285, K281, and Q297; comprises A167; and comprises N195, where the amino acid numbering is as set forth in SEQ ID NO:44. In some embodiments, a subject engineered light-activated anion channel polypeptide comprises the amino acid sequence provided in SEQ ID NO:44. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:45; and comprises 1, 2, 3, 4, 5, 6, 7, 8, or 9 of: S98, S129, S140, S162, K156, R173, N285, K281, and Q297; comprises A195; and comprises S167, where the amino acid numbering is as set forth in SEQ ID NO:45. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:45; and comprises S98, S129, S140, S162, K156, R173, N285, K281, and Q297; comprises S167; and comprises A195, where the amino acid numbering is as set forth in SEQ ID NO:45. In some embodiments, a subject engineered light-activated anion channel polypeptide comprises the amino acid sequence provided in SEQ ID NO:45. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:46; and comprises 1, 2, 3, 4, 5, 6, 7, 8, or 9 of: S98, S129, S140, S162, K156, R173, N285, K281, and Q297; comprises N195; and comprises S167, where the amino acid numbering is as set forth in SEQ ID NO:46. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:46; and comprises S98, S129, S140, S162, K156, R173, N285, K281, and Q297; comprises S167; and comprises N195, where the amino acid numbering is as set forth in SEQ ID NO:46. In some embodiments, a subject engineered light-activated anion channel polypeptide comprises the amino acid sequence provided in SEQ ID NO:46. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1V1 with one or more of the modifications described above, wherein the aspartate amino acid residue at original position 195 has been replaced by an alanine residue. In certain embodiments wherein the first 50 N-terminal amino acids of the protein are replaced by amino acids 1-11 from the protein ChR2, the aspartate amino acid residue at position 156 (which corresponds to original position 195 of the C1V1 amino acid sequence set forth in SEQ ID NO:80) is replaced by an alanine residue.

In some embodiments, a subject engineered light-activated anion channel polypeptide is based on the amino acid sequence of the protein C1V1 with one or more of the modifications described above, wherein the aspartate amino acid residue at original position 195 has been replaced by an asparagine residue. In certain embodiments wherein the first 50 N-terminal amino acids of the protein are replaced by amino acids 1-11 from the protein ChR2, the aspartate amino acid residue at position 156 (which corresponds to original position 195 of the C1V1 amino acid sequence set forth in SEQ ID NO:80) is replaced by an asparagine residue.

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:47; and comprises 1, 2, 3, 4, 5, 6, 7, 8, or 9 of: S59, S90, S101, S123, K117, R134, N246, K242, and Q258; and comprises T128, where the amino acid numbering is as set forth in SEQ ID NO:47. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:47; and comprises S59, S90, S101, S123, K117, R134, N246, K242, and Q258; and comprises T128, where the amino acid numbering is as set forth in SEQ ID NO:47. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:48; and comprises 1, 2, 3, 4, 5, 6, 7, 8, or 9 of: S59, S90, S101, S123, K117, R134, N246, K242, and Q258; and comprises A128, where the amino acid numbering is as set forth in SEQ ID NO:48. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:48; and comprises S59, S90, S101, S123, K117, R134, N246, K242, and Q258; and comprises A128, where the amino acid numbering is as set forth in SEQ ID NO:48. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:49; and comprises 1, 2, 3, 4, 5, 6, 7, 8, or 9 of: S59, S90, S101, S123, K117, R134, N246, K242, and Q258; and comprises S128, where the amino acid numbering is as set forth in SEQ ID NO:49. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:49; and comprises S59, S90, S101, S123, K117, R134, N246, K242, and Q258; and comprises S128, where the amino acid numbering is as set forth in SEQ ID NO:49. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:50; and comprises 1, 2, 3, 4, 5, 6, 7, 8, or 9 of: S59, S90, S101, S123, K117, R134, N246, K242, and Q258; and comprises T128 and A156, where the amino acid numbering is as set forth in SEQ ID NO:50. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:50; and comprises S59, S90, S101, S123, K117, R134, N246, K242, and Q258; and comprises T128 and A156, where the amino acid numbering is as set forth in SEQ ID NO:50. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQ-IDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:51; and comprises 1, 2, 3, 4, 5, 6, 7, 8, or 9 of: S59, S90, S101, S123, K117, R134, N246, K242, and Q258; and comprises T128 and N156, where the amino acid numbering is as set forth in SEQ ID NO:51. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:51; and comprises S59, S90, S101, S123, K117, R134, N246, K242, and Q258; and comprises T128 and N156, where the amino acid numbering is as set forth in SEQ ID NO:51. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQ-IDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:52; and comprises 1, 2, 3, 4, 5, 6, 7, 8, or 9 of: S59, S90, S101, S123, K117, R134, N246, K242, and Q258; and comprises A128 and A156, where the amino acid numbering is as set forth in SEQ ID NO:52. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:52; and comprises S59, S90, S101, S123, K117, R134, N246, K242, and Q258; and comprises A128 and A156, where the amino acid numbering is as set forth in SEQ ID NO:52. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQ-IDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:53; and comprises 1, 2, 3, 4, 5, 6, 7, 8, or 9 of: S59, S90, S101, S123, K117, R134, N246, K242, and Q258; and comprises A128 and N156, where the amino acid numbering is as set forth in SEQ ID NO:53. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:53; and comprises S59, S90, S101, S123, K117, R134, N246, K242, and Q258; and comprises A128 and N156, where the amino acid numbering is as set forth in SEQ ID NO:53. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQ-IDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:54; and comprises 1, 2, 3, 4, 5, 6, 7, 8, or 9 of: S59, S90, S101, S123, K117, R134, N246, K242, and Q258; and comprises S128 and A156, where the amino acid numbering is as set forth in SEQ ID NO:54. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:54; and comprises S59, S90, S101, S123, K117, R134, N246, K242, and Q258; and comprises S128 and A156, where the amino acid numbering is as set forth in SEQ ID NO:54. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQ-IDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:55; and comprises 1, 2, 3, 4, 5, 6, 7, 8, or 9 of: S59, S90, S101, S123, K117, R134, N246, K242, and Q258; and comprises S128 and N156, where the amino acid numbering is as set forth in SEQ ID NO:55. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:55; and comprises S59, S90, S101, S123, K117, R134, N246, K242, and Q258; and comprises S128 and N156, where the amino acid numbering is as set forth in SEQ ID NO:55. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In certain embodiments, a subject engineered light-activated anion channel polypeptide is based on the amino acid sequence of the protein C1V1, wherein the amino acid sequence is at least about 90%, 91%, 92%, 93%, 94%, 95%, 96%, 97%, 98%, 99%, or 100% identical to the sequence provided in one of SEQ ID NOS: 34-55.

In some embodiments, the amino acid sequence of the C1V1 protein has been modified by introducing one or more of the following mutations into the amino acid sequence: T98S, E122N, E129Q, E140S, V156R, E162S, P281R, A285N, N297Q and/or E312S. In some embodiments, a subject engineered light-activated anion channel polypeptide comprises the amino acid sequence of the protein C1V1 with all 10 of the above-listed amino acid substitutions, such that the amino acid sequence of the polypeptide is provided in SEQ ID NO:127.

In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:127; and comprises 1, 2, 3, 4, 5, 6, 7, 8, 9 or 10 amino acid substitutions selected from T98S, E122N, E129Q, E140S, V156R, E162S, P281R, A285N, N297Q and/or E312S, relative to the amino acid sequence of C1V1 (SEQ ID NO:80).

In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:127; and comprises 1, 2, 3, 4, 5, 6, 7, 8, 9 or 10 of: 98S, 122N, 129Q, 140S, 156R, 162S, 281R, 285N, 297Q and 312S, where the amino acid numbering is as set forth in SEQ ID NO:127. In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:127; and comprises 98S, 122N, 129Q, 140S, 156R, 162S, 281R, 285N, 297Q and 312S, where the amino acid numbering is as set forth in SEQ ID NO:127. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:128; and comprises 1, 2, 3, 4, 5, 6, 7, 8, 9 or 10 of: 98S, 122N, 129Q, 140S, 156R, 162S, 281R, 285N, 297Q and 312S, and comprises 195N, where the amino acid numbering is as set forth in SEQ ID NO:128. In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:128; and comprises 98S, 122N, 129Q, 140S, 156R, 162S, 281R, 285N, 297Q and 312S, and comprises 195N, where the amino acid numbering is as set forth in SEQ ID NO:128. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1V1 (SEQ ID NO:80), wherein the amino acid sequence has been modified by replacing the first 50 N-terminal amino acids of C1V1 with amino acids 1-11 from the protein ChR2 (MDYGGALSAVG) (SEQ ID NO:82). In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:129; and comprises 1, 2, 3, 4, 5, 6, 7, 8, 9 or 10 of: 59S, 83N, 90Q, 101S, 117R, 123S, 242R, 246N, 258Q and 273S, where the amino acid numbering is as set forth in SEQ ID NO:129. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:129; and comprises 59S, 83N, 90Q, 101S, 117R, 123S, 242R, 246N, 258Q and 273S, where the amino acid numbering is as set forth in SEQ ID NO:129. In some embodiments, a subject light-activated anion channel polypeptide comprises the amino acid sequence set forth in SEQ ID NO:129. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1V1 (SEQ ID NO:80), wherein the amino acid sequence has been modified by replacing the first 50 N-terminal amino acids of C1V1 with amino acids 1-11 from the protein ChR2 (MDYGGALSAVG) (SEQ ID NO:82). In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:130; and comprises 1, 2, 3, 4, 5, 6, 7, 8, 9 or 10 of: 59S, 83N, 90Q, 101S, 117R, 123S, 242R, 246N, 258Q and 273S, and comprises 156N, where the amino acid numbering is as set forth in SEQ ID NO:130. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:130; and comprises 59S, 83N, 90Q, 101S, 117R, 123S, 242R, 246N, 258Q and 273S, and comprises 156N, where the amino acid numbering is as set forth in SEQ ID NO:130. In some embodiments, a subject light-activated anion channel polypeptide comprises the amino acid sequence set forth in SEQ ID NO:130. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1V1 (SEQ ID NO:80), wherein the cysteine amino acid residue at position 167 has been replaced by a threonine residue. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:131; and comprises 1, 2, 3, 4, 5, 6, 7, 8, 9 or 10 of: 98S, 122N, 129Q, 140S, 156R, 162S, 281R, 285N, 297Q, and 312S; and comprises 167T. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:131; and comprises 98S, 122N, 129Q, 140S, 156R, 162S, 281R, 285N, 297Q, and 312S; and comprises 167T, where the amino acid numbering is as set forth in SEQ ID NO:131. In some embodiments, the engineered light-activated anion channel polypeptide comprises the amino acid sequence provided in SEQ ID NO:131. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1V1, wherein the cysteine amino acid residue at position 167 has been replaced by an alanine residue. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:132; and comprises 1, 2, 3, 4, 5, 6, 7, 8, 9 or 10 of: 98S, 122N, 129Q, 140S, 156R, 162S, 281R, 285N, 297Q, and 312S; and comprises 167A, where the amino acid numbering is as set forth in SEQ ID NO:132. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:132; and comprises 98S, 122N, 129Q, 140S, 156R, 162S, 281R, 285N, 297Q, and 312S; and comprises 167A, where the amino acid numbering is as set forth in SEQ ID NO:132. In some embodiments, the engineered light-activated anion channel polypeptide comprises the amino sequence provided in SEQ ID NO:132. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1V1, wherein the cysteine amino acid residue at position 167 has been replaced by a serine residue. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:133; and comprises 1, 2, 3, 4, 5, 6, 7, 8, 9 or 10 of: 98S, 122N, 129Q, 140S, 156R, 162S, 281R, 285N, 297Q, and 312S; and comprises 167S, where the amino acid numbering is as set forth in SEQ ID NO:133. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:133; and comprises 98S, 122N, 129Q, 140S, 156R, 162S, 281R, 285N, 297Q, and 312S; and comprises 167S, where the amino acid numbering is as set forth in SEQ ID NO:133. In some embodiments, a subject engineered light-activated anion channel polypeptide comprises the amino acid sequence provided in SEQ ID NO:133. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:134; and comprises 1, 2, 3, 4, 5, 6, 7, 8, 9 or 10 of: 98S, 122N, 129Q, 140S, 156R, 162S, 281R, 285N, 297Q, and 312S; comprises 195C and comprises 167T, where the amino acid numbering is as set forth in SEQ ID NO:134. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:134; and comprises 98S, 122N, 129Q, 140S, 156R, 162S, 281R, 285N, 297Q, and 312S; comprises 167T; and comprises 195C, where the amino acid numbering is as set forth in SEQ ID NO:134. In some embodiments, a subject engineered light-activated anion channel polypeptide comprises the amino acid sequence provided in SEQ ID NO:134. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:135; and comprises 1, 2, 3, 4, 5, 6, 7, 8, 9 or 10 of: 98S, 122N, 129Q, 140S, 156R, 162S, 281R, 285N, 297Q, and 312S; comprises 195N; and comprises 167T, where the amino acid numbering is as set forth in SEQ ID NO:135. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:135; and comprises 98S, 122N, 129Q, 140S, 156R, 162S, 281R, 285N, 297Q, and 312S; comprises 167T; and comprises 195N, where the amino acid numbering is as set forth in SEQ ID NO:135. In some embodiments, a subject engineered light-activated anion channel polypeptide comprises the amino acid sequence provided in SEQ ID NO:135. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:136; and comprises 1, 2, 3, 4, 5, 6, 7, 8, 9 or 10 of: 98S, 122N, 129Q, 140S, 156R, 162S, 281R, 285N, 297Q, and 312S; comprises 195C and comprises 167A, where the amino acid numbering is as set forth in SEQ ID NO:136. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:136; and comprises 98S, 122N, 129Q, 140S, 156R, 162S, 281R, 285N, 297Q, and 312S; comprises 167A; and comprises 195C, where the amino acid numbering is as set forth in SEQ ID NO:136. In some embodiments, a subject engineered light-activated anion channel polypeptide comprises the amino acid sequence provided in SEQ ID NO:136. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:137; and comprises 1, 2, 3, 4, 5, 6, 7, 8, 9 or 10 of: 98S, 122N, 129Q, 140S, 156R, 162S, 281R, 285N, 297Q, and 312S; comprises 195N; and comprises 167A, where the amino acid numbering is as set forth in SEQ ID NO:137. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:137; and comprises 98S, 122N, 129Q, 140S, 156R, 162S, 281R, 285N, 297Q, and 312S; comprises 167A; and comprises 195N, where the amino acid numbering is as set forth in SEQ ID NO:137. In some embodiments, a subject engineered light-activated anion channel polypeptide comprises the amino acid sequence provided in SEQ ID NO:137.

In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:138; and comprises 1, 2, 3, 4, 5, 6, 7, 8, 9 or 10 of: 98S, 122N, 129Q, 140S, 156R, 162S, 281R, 285N, 297Q, and 312S; comprises 195C; and comprises 167S, where the amino acid numbering is as set forth in SEQ ID NO:138. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:138; and comprises 98S, 122N, 129Q, 140S, 156R, 162S, 281R, 285N, 297Q, and 312S; comprises 167S; and comprises 195C, where the amino acid numbering is as set forth in SEQ ID NO:138. In some embodiments, a subject engineered light-activated anion channel polypeptide comprises the amino acid sequence provided in SEQ ID NO:138. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:139; and comprises 1, 2, 3, 4, 5, 6, 7, 8, 9 or 10 of: 98S, 122N, 129Q, 140S, 156R, 162S, 281R, 285N, 297Q, and 312S; comprises 195N; and comprises 167S, where the amino acid numbering is as set forth in SEQ ID NO:139. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:139; and comprises 98S, 122N, 129Q, 140S, 156R, 162S, 281R, 285N, 297Q, and 312S; comprises 167S; and comprises 195N, where the amino acid numbering is as set forth in SEQ ID NO:139. In some embodiments, a subject engineered light-activated anion channel polypeptide comprises the amino acid sequence provided in SEQ ID NO:139. In some embodiments, the first 50 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein C1V1 with one or more of the modifications described above, wherein the aspartate amino acid residue at original position 195 has been replaced by an alanine residue. In certain embodiments wherein the first 50 N-terminal amino acids of the protein are replaced by amino acids 1-11 from the protein ChR2, the aspartate amino acid residue at position 156 (which corresponds to original position 195 of the C1V1 amino acid sequence set forth in SEQ ID NO:80) is replaced by an alanine residue.

In some embodiments, a subject engineered light-activated anion channel polypeptide is based on the amino acid sequence of the protein C1V1 with one or more of the modifications described above, wherein the aspartate amino acid residue at original position 195 has been replaced by an asparagine residue. In certain embodiments wherein the first 50 N-terminal amino acids of the protein are replaced by amino acids 1-11 from the protein ChR2, the aspartate amino acid residue at position 156 (which corresponds to original position 195 of the C1V1 amino acid sequence set forth in SEQ ID NO:80) is replaced by an asparagine residue.

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:140; and comprises 1, 2, 3, 4, 5, 6, 7, 8, 9 or 10 of: 59S, 83N, 90Q, 101S, 117R, 123S, 242R, 246N, 258Q and 273S; and comprises 128T, where the amino acid numbering is as set forth in SEQ ID NO:140. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:140; and comprises 59S, 83N, 90Q, 101S, 117R, 123S, 242R, 246N, 258Q and 273S; and comprises 128T, where the amino acid numbering is as set forth in SEQ ID NO:140. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:141; and comprises 1, 2, 3, 4, 5, 6, 7, 8, 9 or 10 of: 59S, 83N, 90Q, 101S, 117R, 123S, 242R, 246N, 258Q and 273S; and comprises 128A, where the amino acid numbering is as set forth in SEQ ID NO:141. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:141; and comprises 59S, 83N, 90Q, 101S, 117R, 123S, 242R, 246N, 258Q and 273S; and comprises 128A, where the amino acid numbering is as set forth in SEQ ID NO:141. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:142; and comprises 1, 2, 3, 4, 5, 6, 7, 8, 9 or 10 of: 59S, 83N, 90Q, 101S, 117R, 123S, 242R, 246N, 258Q and 273S; and comprises 128S, where the amino acid numbering is as set forth in SEQ ID NO:142. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:142; and comprises 59S, 83N, 90Q, 101S, 117R, 123S, 242R, 246N, 258Q and 273S; and comprises 128S, where the amino acid numbering is as set forth in SEQ ID NO:142. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:143; and comprises 1, 2, 3, 4, 5, 6, 7, 8, 9 or 10 of: 59S, 83N, 90Q, 101S, 117R, 123S, 242R, 246N, 258Q and 273S; and comprises 128T and 156C, where the amino acid numbering is as set forth in SEQ ID NO:143. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:143; and comprises 59S, 83N, 90Q, 101S, 117R, 123S, 242R, 246N, 258Q and 273S; and comprises 128T and 156C, where the amino acid numbering is as set forth in SEQ ID NO:143. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:144; and comprises 1, 2, 3, 4, 5, 6, 7, 8, 9 or 10 of: 59S, 83N, 90Q, 101S, 117R, 123S, 242R, 246N, 258Q and 273S; and comprises 128T and 156N, where the amino acid numbering is as set forth in SEQ ID NO:144. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:144; and comprises 59S, 83N, 90Q, 101S, 117R, 123S, 242R, 246N, 258Q and 273S; and comprises 128T and 156N, where the amino acid numbering is as set forth in SEQ ID NO:144. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:145; and comprises 1, 2, 3, 4, 5, 6, 7, 8, 9 or 10 of: 59S, 83N, 90Q, 101S, 117R, 123S, 242R, 246N, 258Q and 273S; and comprises 128A and 156C, where the amino acid numbering is as set forth in SEQ ID NO:145. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:145; and comprises 59S, 83N, 90Q, 101S, 117R, 123S, 242R, 246N, 258Q and 273S; and comprises 128A and 156C, where the amino acid numbering is as set forth in SEQ ID NO:145. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:146; and comprises 1, 2, 3, 4, 5, 6, 7, 8, 9 or 10 of: 59S, 83N, 90Q, 101S, 117R, 123S, 242R, 246N, 258Q and 273S; and comprises 128A and 156N, where the amino acid numbering is as set forth in SEQ ID NO:146. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:146; and comprises 59S, 83N, 90Q, 101S, 117R, 123S, 242R, 246N, 258Q and 273S; and comprises 128A and 156N, where the amino acid numbering is as set forth in SEQ ID NO:146. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:147; and comprises 1, 2, 3, 4, 5, 6, 7, 8, 9 or 10 of: 59S, 83N, 90Q, 101S, 117R, 123S, 242R, 246N, 258Q and 273S; and comprises 128S and 156C, where the amino acid numbering is as set forth in SEQ ID NO:147. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:147; and comprises 59S, 83N, 90Q, 101S, 117R, 123S, 242R, 246N, 258Q and 273S; and comprises 128S and 156C, where the amino acid numbering is as set forth in SEQ ID NO:147. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:148; and comprises 1, 2, 3, 4, 5, 6, 7, 8, 9 or 10 of: 59S, 83N, 90Q, 101S, 117R, 123S, 242R, 246N, 258Q and 273S; and comprises 128S and 156N, where the amino acid numbering is as set forth in SEQ ID NO:148. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:148; and comprises 59S, 83N, 90Q, 101S, 117R, 123S, 242R, 246N, 258Q and 273S; and comprises 128S and 156N, where the amino acid numbering is as set forth in SEQ ID NO:148. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In certain embodiments, a subject engineered light-activated anion channel polypeptide is based on the amino acid sequence of the protein C1V1, wherein the amino acid sequence is at least about 90%, 91%, 92%, 93%, 94%, 95%, 96%, 97%, 98%, 99%, or 100% identical to the sequence provided in one of SEQ ID NOS: 127-148.

Anion Channel Polypeptides Based on ReaChR

In some embodiments, a subject engineered light-activated anion channel polypeptide is based on the amino acid sequence of the protein ReaChR. The amino acid sequence of ReaChR is set forth in SEQ ID NO:81. In some embodiments, the amino acid sequence of the ReaChR protein has been modified by introducing one or more of the following mutations into the amino acid sequence: T99S, E130S, E141S, E163S, V157K, H174R, A286N, P282K and/or N298Q. In some embodiments, a subject engineered light-activated anion channel polypeptide comprises the amino acid sequence of the protein ReaChR with all 9 of the above-listed amino acid substitutions, such that the amino acid sequence of the polypeptide is provided in SEQ ID NO:56.

In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:56; and comprises 1, 2, 3, 4, 5, 6, 7, 8, or 9 amino acid substitutions selected from T99S, E130S, E141S, E163S, V157K, H174R, A286N, P282K and/or N298Q, relative to the amino acid sequence of ReaChR (SEQ ID NO:81).

In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:56; and comprises 1, 2, 3, 4, 5, 6, 7, 8, or 9 of: S99, S130, S141, S163, K157, R174, N286, K281, and Q298, where the amino acid numbering is as set forth in SEQ ID NO:56. In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:56; and comprises S99, S130, S141, S163, K157, R174, N286, K281, and Q298, where the amino acid numbering is as set forth in SEQ ID NO:56. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:57; and comprises 1, 2, 3, 4, 5, 6, 7, 8, or 9 of: S99, S130, S141, S163, K157, R174, N286, K281, and Q298, and comprises N196, where the amino acid numbering is as set forth in SEQ ID NO:57. In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:57; and comprises S99, S130, S141, S163, K157, R174, N286, K281, and Q298, and comprises N196, where the amino acid numbering is as set forth in SEQ ID NO:57. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ReaChR (SEQ ID NO:81), wherein the amino acid sequence has been modified by replacing the first 51 N-terminal amino acids of ReaChR with amino acids 1-11 from the protein ChR2 (MDYGGALSAVG) (SEQ ID NO:82). In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:58; and comprises 1, 2, 3, 4, 5, 6, 7, 8, or 9 of: S59, S90, S101, S123, K117, R134, N246, K242, and Q258, where the amino acid numbering is as set forth in SEQ ID NO:58. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:58; and comprises S59, S90, S101, S123, K117, R134, N246, K242, and Q258, where the amino acid numbering is as set forth in SEQ ID NO:58. In some embodiments, a subject light-activated anion channel polypeptide comprises the amino acid sequence set forth in SEQ ID NO:58. In any one of these embodiments, a subject anion channel polypeptide comprises a membrane trafficking signal (e.g., KSRIT-SEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ReaChR (SEQ ID NO:81), wherein the amino acid sequence has been modified by replacing the first 51 N-terminal amino acids of ReaChR with amino acids 1-11 from the protein ChR2 (MDYGGALSAVG) (SEQ ID NO:82). In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:59; and comprises 1, 2, 3, 4, 5, 6, 7, 8, or 9 of: S59, S90, S101, S123, K117, R134, N246, K242, and Q258, and comprises N156, where the amino acid numbering is as set forth in SEQ ID NO:59. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:59; and comprises S59, S90, S101, S123, K117, R134, N246, K242, and Q258, and comprises N156, where the amino acid numbering is as set forth in SEQ ID NO:59. In some embodiments, a subject light-activated anion channel polypeptide comprises the amino acid sequence set forth in SEQ ID NO:59. In any one of these embodiments, a subject anion channel polypeptide comprises a membrane trafficking signal (e.g., KSRIT-SEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ReaChR (SEQ ID NO:81), wherein the cysteine amino acid residue at position 168 has been replaced by a threonine residue. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:60; and comprises 1, 2, 3, 4, 5, 6, 7, 8, or 9 of: S99, 5130, S141, 5163, K157, R174, N286, K281, and Q298; and comprises T168. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:60; and comprises S99, S130, S141, S163, K157, R174, N286, K281, and Q298; and comprises T168, where the amino acid numbering is as set forth in SEQ ID NO:60. In some embodiments, the engineered light-activated anion channel polypeptide comprises the amino acid sequence provided in SEQ ID NO:60. In some embodiments, the first 51 amino acids are replaced with MDYG-GALSAVG (SEQ ID NO:82). In any one of these embodiments, a subject anion channel polypeptide comprises a membrane trafficking signal (e.g., KSRITSEGEYIPLDQID-INV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRIT-SEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ReaChR, wherein the cysteine amino acid residue at position 168 has been replaced by an alanine residue. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:61; and comprises 1, 2, 3, 4, 5, 6, 7, 8, or 9 of: S99, S130, S141, S163, K157, R174, N286, K281, and Q298; and comprises A168, where the amino acid numbering is as set forth in SEQ ID NO:61. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:61; and comprises S99, S130, S141, S163, K157, R174, N286, K281, and Q298; and comprises A168, where the amino acid numbering is as set forth in SEQ ID NO:61. In some embodiments, the engineered light-activated anion channel polypeptide comprises the amino sequence provided in SEQ ID NO:61. In some embodiments, the first 51 amino acids are replaced with MDYG-GALSAVG (SEQ ID NO:82). In any one of these embodiments, a subject anion channel polypeptide comprises a membrane trafficking signal (e.g., KSRITSEGEYIPLDQID-INV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRIT-SEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ReaChR, wherein the cysteine amino acid residue at position 168 has been replaced by a serine residue. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:62; and comprises 1, 2, 3, 4, 5, 6, 7, 8, or 9 of: S99, S130, S141, S163, K157, R174, N286, K281, and Q298; and comprises S168, where the amino acid numbering is as set forth in SEQ ID NO:62. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:62; and comprises S99, S130, S141, S163, K157, R174, N286, K281, and Q298; and comprises S168, where the amino acid numbering is as set forth in SEQ ID NO:62. In some embodiments, a subject engineered light-activated anion channel polypeptide comprises the amino acid sequence provided in SEQ ID NO:62. In some embodiments, the first 51 amino acids are replaced with MDYG-GALSAVG (SEQ ID NO:82). In any one of these embodiments, a subject anion channel polypeptide comprises a membrane trafficking signal (e.g., KSRITSEGEYIPLDQID-INV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRIT-SEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:63; and comprises 1, 2, 3, 4, 5, 6, 7, 8, or 9 of: S99, S130, S141, S163, K157, R174, N286, K281, and Q298; comprises A196; and comprises T168, where the amino acid numbering is as set forth in SEQ ID NO:63. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:63; and comprises S99, S130, S141, S163, K157, R174, N286, K281, and Q298; comprises T168; and comprises A196, where the amino acid numbering is as set forth in SEQ ID NO:63. In some embodiments, a subject engineered light-activated anion channel polypeptide comprises the amino acid sequence provided in SEQ ID NO:63. In some embodiments, the first 51 amino acids are replaced with MDYGGALSAVG (SEQ ID NO:82). In any one of these embodiments, a subject anion channel polypeptide comprises a membrane trafficking signal (e.g., KSRIT-SEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:64; and comprises 1, 2, 3, 4, 5, 6, 7, 8, or 9 of: S99, S130, S141, S163, K157, R174, N286, K281, and Q298; comprises N196; and comprises T168, where the amino acid numbering is as set forth in SEQ ID NO:64. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:64; and comprises S99, S130, S141, S163, K157, R174, N286, K281, and Q298; comprises T168; and comprises N196, where the amino acid numbering is as set forth in SEQ ID NO:64. In some embodiments, a subject engineered light-activated anion channel polypeptide comprises the amino acid sequence provided in SEQ ID NO:64. In some embodiments, the first 51 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:65; and comprises 1, 2, 3, 4, 5, 6, 7, 8, or 9 of: S99, S130, S141, S163, K157, R174, N286, K281, and Q298; comprises A196; and comprises A168, where the amino acid numbering is as set forth in SEQ ID NO:65. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:65; and comprises S99, S130, S141, S163, K157, R174, N286, K281, and Q298; comprises A168; and comprises A196, where the amino acid numbering is as set forth in SEQ ID NO:65. In some embodiments, a subject engineered light-activated anion channel polypeptide comprises the amino acid sequence provided in SEQ ID NO:65. In some embodiments, the first 51 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:66; and comprises 1, 2, 3, 4, 5, 6, 7, 8, or 9 of: S99, S130, S141, S163, K157, R174, N286, K281, and Q298; comprises N196; and comprises A168, where the amino acid numbering is as set forth in SEQ ID NO:66. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:66; and comprises S99, S130, S141, S163, K157, R174, N286, K281, and Q298; comprises A168; and comprises N196, where the amino acid numbering is as set forth in SEQ ID NO:66. In some embodiments, a subject engineered light-activated anion channel polypeptide comprises the amino acid sequence provided in SEQ ID NO:66. In some embodiments, the first 51 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:67; and comprises 1, 2, 3, 4, 5, 6, 7, 8, or 9 of: S99, S130, S141, S163, K157, R174, N286, K281, and Q298; comprises A196; and comprises S168, where the amino acid numbering is as set forth in SEQ ID NO:67. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:67; and comprises S99, S130, S141, S163, K157, R174, N286, K281, and Q298; comprises S168; and comprises A196, where the amino acid numbering is as set forth in SEQ ID NO:67. In some embodiments, a subject engineered light-activated anion channel polypeptide comprises the amino acid sequence provided in SEQ ID NO:67. In some embodiments, the first 51 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:68; and comprises 1, 2, 3, 4, 5, 6, 7, 8, or 9 of: S99, S130, S141, S163, K157, R174, N286, K281, and Q298; comprises N196; and comprises S168, where the amino acid numbering is as set forth in SEQ ID NO:68. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:68; and comprises S99, S130, S141, S163, K157, R174, N286, K281, and Q298; comprises S168; and comprises N196, where the amino acid numbering is as set forth in SEQ ID NO:68. In some embodiments, a subject engineered light-activated anion channel polypeptide comprises the amino acid sequence provided in SEQ ID NO:68. In some embodiments, the first 51 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ReaChR with one or more of the modifications described above, wherein the aspartate amino acid residue at original position 196 has been replaced by an alanine residue. In certain embodiments wherein the first 51 N-terminal amino acids of the protein are replaced by amino acids 1-11 from the protein ChR2, the aspartate amino acid residue at position 156 (which corresponds to original position 196 of the ReaChR amino acid sequence set forth in SEQ ID NO:81) is replaced by an alanine residue.

In some embodiments, a subject engineered light-activated anion channel polypeptide is based on the amino acid sequence of the protein ReaChR with one or more of the modifications described above, wherein the aspartate amino acid residue at original position 196 has been replaced by an asparagine residue. In certain embodiments wherein the first 51 N-terminal amino acids of the protein are replaced by amino acids 1-11 from the protein ChR2, the aspartate amino acid residue at position 156 (which corresponds to original position 196 of the ReaChR amino acid sequence set forth in SEQ ID NO:81) is replaced by an asparagine residue.

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:69; and comprises 1, 2, 3, 4, 5, 6, 7, 8, or 9 of: S59, S90, S101, S123, K117, R134, N246, K242, and Q258; and comprises T128, where the amino acid numbering is as set forth in SEQ ID NO:69. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:69; and comprises S59, S90, S101, S123, K117, R134, N246, K242, and Q258; and comprises T128, where the amino acid numbering is as set forth in SEQ ID NO:69. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:70; and comprises 1, 2, 3, 4, 5, 6, 7, 8, or 9 of: S59, S90, S101, S123, K117, R134, N246, K242, and Q258; and comprises A128, where the amino acid numbering is as set forth in SEQ ID NO:70. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:70; and comprises S59, S90, S101, S123, K117, R134, N246, K242, and Q258; and comprises A128, where the amino acid numbering is as set forth in SEQ ID NO:70. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:71; and comprises 1, 2, 3, 4, 5, 6, 7, 8, or 9 of: S59, S90, S101, S123, K117, R134, N246, K242, and Q258; and comprises S128, where the amino acid numbering is as set forth in SEQ ID NO:71. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:71; and comprises S59, S90, S101, S123, K117, R134, N246, K242, and Q258; and comprises S128, where the amino acid numbering is as set forth in SEQ ID NO:71. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:72; and comprises 1, 2, 3, 4, 5, 6, 7, 8, or 9 of: S59, S90, S101, S123, K117, R134, N246, K242, and Q258; and comprises T128 and A156, where the amino acid numbering is as set forth in SEQ ID NO:72. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:72; and comprises S59, S90, S101, S123, K117, R134, N246, K242, and Q258; and comprises T128 and A156, where the amino acid numbering is as set forth in SEQ ID NO:72. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:73; and comprises 1, 2, 3, 4, 5, 6, 7, 8, or 9 of: S59, S90, S101, S123, K117, R134, N246, K242, and Q258; and comprises T128 and N156, where the amino acid numbering is as set forth in SEQ ID NO:73. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:73; and comprises S59, S90, S101, S123, K117, R134, N246, K242, and Q258; and comprises T128 and N156, where the amino acid numbering is as set forth in SEQ ID NO:73. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:74; and comprises 1, 2, 3, 4, 5, 6, 7, 8, or 9 of: S59, S90, S101, S123, K117, R134, N246, K242, and Q258; and comprises A128 and A156, where the amino acid numbering is as set forth in SEQ ID NO:74. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:74; and comprises S59, S90, S101, S123, K117, R134, N246, K242, and Q258; and comprises A128 and A156, where the amino acid numbering is as set forth in SEQ ID NO:74. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:75; and comprises 1, 2, 3, 4, 5, 6, 7, 8, or 9 of: S59, S90, S101, S123, K117, R134, N246, K242, and Q258; and comprises A128 and N156, where the amino acid numbering is as set forth in SEQ ID NO:75. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:75; and comprises S59, S90, S101, S123, K117, R134, N246, K242, and Q258; and comprises A128 and N156, where the amino acid numbering is as set forth in SEQ ID NO:75. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:76; and comprises 1, 2, 3, 4, 5, 6, 7, 8, or 9 of: S59, S90, S101, S123, K117, R134, N246, K242, and Q258; and comprises S128 and A156, where the amino acid numbering is as set forth in SEQ ID NO:76. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:76; and comprises S59, S90, S101, S123, K117, R134, N246, K242, and Q258; and comprises S128 and A156, where the amino acid numbering is as set forth in SEQ ID NO:76. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:77; and comprises 1, 2, 3, 4, 5, 6, 7, 8, or 9 of: S59, S90, S101, S123, K117, R134, N246, K242, and Q258; and comprises S128 and N156, where the amino acid numbering is as set forth in SEQ ID NO:77. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:77; and comprises S59, S90, S101, S123, K117, R134, N246, K242, and Q258; and comprises S128 and N156, where the amino acid numbering is as set forth in SEQ ID NO:77. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQ-IDINV (SEQ ID NO:83)) and an ER export signal (e.g., FCYENEV (SEQ ID NO:84)).

In certain embodiments, a subject engineered light-activated anion channel polypeptide is based on the amino acid sequence of the protein ReaChR, wherein the amino acid sequence is at least about 90%, 91%, 92%, 93%, 94%, 95%, 96%, 97%, 98%, 99%, or 100% identical to the sequence provided in one of SEQ ID NOS: 56-77.

In some embodiments, the amino acid sequence of the ReaChR protein has been modified by introducing one or more of the following mutations into the amino acid sequence: T99S, E123N, E130Q, E141S, V157R, E163S, P282R, A286N, N298Q and/or E313S. In some embodiments, a subject engineered light-activated anion channel polypeptide comprises the amino acid sequence of the protein ReaChR with all 10 of the above-listed amino acid substitutions, such that the amino acid sequence of the polypeptide is provided in SEQ ID NO:149.

In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:149; and comprises 1, 2, 3, 4, 5, 6, 7, 8, 9 or 10 amino acid substitutions selected from T99S, E123N, E130Q, E141S, V157R, E163S, P282R, A286N, N298Q and/or E313S, relative to the amino acid sequence of ReaChR (SEQ ID NO:81).

In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:149; and comprises 1, 2, 3, 4, 5, 6, 7, 8, 9 or 10 of: 99S, 123N, 130Q, 141S, 157R, E163S, 282R, 286N, 298Q and 313S, where the amino acid numbering is as set forth in SEQ ID NO:149. In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:149; and comprises 99S, 123N, 130Q, 141S, 157R, E163S, 282R, 286N, 298Q and 313S, where the amino acid numbering is as set forth in SEQ ID NO:149. In any one of these embodiments, a subject anion channel polypeptide comprises a membrane trafficking signal (e.g., KSRITSEGEYI-PLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:150; and comprises 1, 2, 3, 4, 5, 6, 7, 8, 9 or 10 of: 99S, 123N, 130Q, 141S, 157R, E163S, 282R, 286N, 298Q and 313S, and comprises 196N, where the amino acid numbering is as set forth in SEQ ID NO:150. In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:150; and comprises 99S, 123N, 130Q, 141S, 157R, E163S, 282R, 286N, 298Q and 313S, and comprises 196N, where the amino acid numbering is as set forth in SEQ ID NO:150. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRIT-SEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ReaChR (SEQ ID NO:81), wherein the amino acid sequence has been modified by replacing the first 51 N-terminal amino acids of ReaChR with amino acids 1-11 from the protein ChR2 (MDYGGALSAVG) (SEQ ID NO:82). In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:151; and comprises 1, 2, 3, 4, 5, 6, 7, 8, 9 or 10 of: 59S, 83N, 90Q, 101S, 117R, 123S, 242R, 246N, 258Q and 273S, where the amino acid numbering is as set forth in SEQ ID NO:151. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:151; and comprises 59S, 83N, 90Q, 101S, 117R, 123S, 242R, 246N, 258Q and 273S, where the amino acid numbering is as set forth in SEQ ID NO:151. In some embodiments, a subject light-activated anion channel polypeptide comprises the amino acid sequence set forth in SEQ ID NO:151. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQ-IDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ReaChR (SEQ ID NO:81), wherein the amino acid sequence has been modified by replacing the first 51 N-terminal amino acids of ReaChR with amino acids 1-11 from the protein ChR2 (MDYGGALSAVG) (SEQ ID NO:82). In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:152; and comprises 1, 2, 3, 4, 5, 6, 7, 8, 9 or 10 of: 59S, 83N, 90Q, 101S, 117R, 123S, 242R, 246N, 258Q and 273S, and comprises 156N, where the amino acid numbering is as set forth in SEQ ID NO:152. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:152; and comprises 59S, 83N, 90Q, 101S, 117R, 123S, 242R, 246N, 258Q and 273S, and comprises 156N, where the amino acid numbering is as set forth in SEQ ID NO:152. In some embodiments, a subject light-activated anion channel polypeptide comprises the amino acid sequence set forth in SEQ ID NO:152. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQ-IDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ReaChR (SEQ ID NO:81), wherein the cysteine amino acid residue at position 168 has been replaced by a threonine residue. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:153; and comprises 1, 2, 3, 4, 5, 6, 7, 8, 9 or 10 of: 99S, 123N, 130Q, 141S, 157R, 163S, 282R, 286N, 298Q and 313S; and comprises 168T. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:153; and comprises 99S, 123N, 130Q, 141S, 157R, 163S, 282R, 286N, 298Q and 313S; and comprises 168T, where the amino acid numbering is as set forth in SEQ ID NO:153. In some embodiments, the engineered light-activated anion channel polypeptide comprises the amino acid sequence provided in SEQ ID NO:153. In some embodiments, the first 51 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQ-IDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ReaChR, wherein the cysteine amino acid residue at position 168 has been replaced by an alanine residue. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:154; and comprises 1, 2, 3, 4, 5, 6, 7, 8, 9 or 10 of: 99S, 123N, 130Q, 141S, 157R, 163S, 282R, 286N, 298Q and 313S; and comprises 168A, where the amino acid numbering is as set forth in SEQ ID NO:154. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:154; and comprises 99S, 123N, 130Q, 141S, 157R, 163S, 282R, 286N, 298Q and 313S; and comprises 168A, where the amino acid numbering is as set forth in SEQ ID NO:154. In some embodiments, the engineered light-activated anion channel polypeptide comprises the amino sequence provided in SEQ ID NO:154. In some embodiments, the first 51 amino acids are replaced with MDYG-GALSAVG (SEQ ID NO:82). In any one of these embodiments, a subject anion channel polypeptide comprises a membrane trafficking signal (e.g., KSRITSEGEYIPLDQID-INV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRIT-SEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ReaChR, wherein the cysteine amino acid residue at position 168 has been replaced by a serine residue. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:155; and comprises 1, 2, 3, 4, 5, 6, 7, 8, 9 or 10 of: 99S, 123N, 130Q, 141S, 157R, 163S, 282R, 286N, 298Q and 313S; and comprises 168S, where the amino acid numbering is as set forth in SEQ ID NO:155. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:155; and comprises 99S, 123N, 130Q, 141S, 157R, 163S, 282R, 286N, 298Q and 313S; and comprises 168S, where the amino acid numbering is as set forth in SEQ ID NO:155. In some embodiments, a subject engineered light-activated anion channel polypeptide comprises the amino acid sequence provided in SEQ ID NO:155. In some embodiments, the first 51 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:156; and comprises 1, 2, 3, 4, 5, 6, 7, 8, 9 or 10 of: 99S, 123N, 130Q, 141S, 157R, 163S, 282R, 286N, 298Q and 313S; comprises 196C; and comprises 168T, where the amino acid numbering is as set forth in SEQ ID NO:156. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:156; and comprises 99S, 123N, 130Q, 141S, 157R, 163S, 282R, 286N, 298Q and 313S; comprises 168T; and comprises 196C, where the amino acid numbering is as set forth in SEQ ID NO:156. In some embodiments, a subject engineered light-activated anion channel polypeptide comprises the amino acid sequence provided in SEQ ID NO:156. In some embodiments, the first 51 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:157; and comprises 1, 2, 3, 4, 5, 6, 7, 8, 9 or 10 of: 99S, 123N, 130Q, 141S, 157R, 163S, 282R, 286N, 298Q and 313S; comprises 196N; and comprises 168T, where the amino acid numbering is as set forth in SEQ ID NO:157. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:157; and comprises 99S, 123N, 130Q, 141S, 157R, 163S, 282R, 286N, 298Q and 313S; comprises 168T; and comprises 196N, where the amino acid numbering is as set forth in SEQ ID NO:157. In some embodiments, a subject engineered light-activated anion channel polypeptide comprises the amino acid sequence provided in SEQ ID NO:157. In some embodiments, the first 51 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:158; and comprises 1, 2, 3, 4, 5, 6, 7, 8, 9 or 10 of: 99S, 123N, 130Q, 141S, 157R, 163S, 282R, 286N, 298Q and 313S; comprises 196C; and comprises 168A, where the amino acid numbering is as set forth in SEQ ID NO:158. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:158; and comprises 99S, 123N, 130Q, 141S, 157R, 163S, 282R, 286N, 298Q and 313S; comprises 168A; and comprises 196C, where the amino acid numbering is as set forth in SEQ ID NO:158. In some embodiments, a subject engineered light-activated anion channel polypeptide comprises the amino acid sequence provided in SEQ ID NO:158. In some embodiments, the first 51 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:159; and comprises 1, 2, 3, 4, 5, 6, 7, 8, 9 or 10 of: 99S, 123N, 130Q, 141S, 157R, 163S, 282R, 286N, 298Q and 313S; comprises 196N; and comprises 168A, where the amino acid numbering is as set forth in SEQ ID NO:159. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:159; and comprises 99S, 123N, 130Q, 141S, 157R, 163S, 282R, 286N, 298Q and 313S; comprises 168A; and comprises 196N, where the amino acid numbering is as set forth in SEQ ID NO:159. In some embodiments, a subject engineered light-activated anion channel polypeptide comprises the amino acid sequence provided in SEQ ID NO:159. In some embodiments, the first 51 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:160; and comprises 1, 2, 3, 4, 5, 6, 7, 8, 9 or 10 of: 99S, 123N, 130Q, 141S, 157R, 163S, 282R, 286N, 298Q and 313S; comprises 196C; and comprises 168S, where the amino acid numbering is as set forth in SEQ ID NO:160. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:160; and comprises 99S, 123N, 130Q, 141S, 157R, 163S, 282R, 286N, 298Q and 313S; comprises 168S; and comprises 196C, where the amino acid numbering is as set forth in SEQ ID NO:160. In some embodiments, a subject engineered light-activated anion channel polypeptide comprises the amino acid sequence provided in SEQ ID NO:160. In some embodiments, the first 51 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:161; and comprises 1, 2, 3, 4, 5, 6, 7, 8, 9 or 10 of: 99S, 123N, 130Q, 141S, 157R, 163S, 282R, 286N, 298Q and 313S; comprises 196N; and comprises 168S, where the amino acid numbering is as set forth in SEQ ID NO:161. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:161; and comprises 99S, 123N, 130Q, 141S, 157R, 163S, 282R, 286N, 298Q and 313S; comprises 168S; and comprises 196N, where the amino acid numbering is as set forth in SEQ ID NO:161. In some embodiments, a subject engineered light-activated anion channel polypeptide comprises the amino acid sequence provided in SEQ ID NO:161. In some embodiments, the first 51 amino acids are replaced with MDYGGALSAVG (SEQ ID NO:82). In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ReaChR with one or more of the modifications described above, wherein the aspartate amino acid residue at original position 196 has been replaced by an alanine residue. In certain embodiments wherein the first 51 N-terminal amino acids of the protein are replaced by amino acids 1-11 from the protein ChR2, the aspartate amino acid residue at position 156 (which corresponds to original position 196 of the ReaChR amino acid sequence set forth in SEQ ID NO:81) is replaced by an alanine residue.

In some embodiments, a subject engineered light-activated anion channel polypeptide is based on the amino acid sequence of the protein ReaChR with one or more of the modifications described above, wherein the aspartate amino acid residue at original position 196 has been replaced by an asparagine residue. In certain embodiments wherein the first 51 N-terminal amino acids of the protein are replaced by amino acids 1-11 from the protein ChR2, the aspartate amino acid residue at position 156 (which corresponds to original position 196 of the ReaChR amino acid sequence set forth in SEQ ID NO:81) is replaced by an asparagine residue.

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:162; and comprises 1, 2, 3, 4, 5, 6, 7, 8, 9 or 10 of: 59S, 83N, 90Q, 101S, 117R, 123S, 242R, 246N, 258Q and 273S; and comprises 128T, where the amino acid numbering is as set forth in SEQ ID NO:162. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:162; and comprises 59S, 83N, 90Q, 101S, 117R, 123S, 242R, 246N, 258Q and 273S; and comprises 128T, where the amino acid numbering is as set forth in SEQ ID NO:162. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:163; and comprises 1, 2, 3, 4, 5, 6, 7, 8, 9 or 10 of: 59S, 83N, 90Q, 101S, 117R, 123S, 242R, 246N, 258Q and 273S; and comprises 128A, where the amino acid numbering is as set forth in SEQ ID NO:163. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:163; and comprises 59S, 83N, 90Q, 101S, 117R, 123S, 242R, 246N, 258Q and 273S; and comprises 128A, where the amino acid numbering is as set forth in SEQ ID NO:163. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:164; and comprises 1, 2, 3, 4, 5, 6, 7, 8, 9 or 10 of: 59S, 83N, 90Q, 101S, 117R, 123S, 242R, 246N, 258Q and 273S; and comprises 128S, where the amino acid numbering is as set forth in SEQ ID NO:164. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:164; and comprises 59S, 83N, 90Q, 101S, 117R, 123S, 242R, 246N, 258Q and 273S; and comprises 128S, where the amino acid numbering is as set forth in SEQ ID NO:164. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:165; and comprises 1, 2, 3, 4, 5, 6, 7, 8, 9 or 10 of: 59S, 83N, 90Q, 101S, 117R, 123S, 242R, 246N, 258Q and 273S; and comprises 128T and 156C, where the amino acid numbering is as set forth in SEQ ID NO:165. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:165; and comprises 59S, 83N, 90Q, 101S, 117R, 123S, 242R, 246N, 258Q and 273S; and comprises 128T and 156C, where the amino acid numbering is as set forth in SEQ ID NO:165. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:166; and comprises 1, 2, 3, 4, 5, 6, 7, 8, 9 or 10 of: 59S, 83N, 90Q, 101S, 117R, 123S, 242R, 246N, 258Q and 273S; and comprises 128T and 156N, where the amino acid numbering is as set forth in SEQ ID NO:166. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:166; and comprises 59S, 83N, 90Q, 101S, 117R, 123S, 242R, 246N, 258Q and 273S; and comprises 128T and 156N, where the amino acid numbering is as set forth in SEQ ID NO:166. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:167; and comprises 1, 2, 3, 4, 5, 6, 7, 8, 9 or 10 of: 59S, 83N, 90Q, 101S, 117R, 123S, 242R, 246N, 258Q and 273S; and comprises 128A and 156C, where the amino acid numbering is as set forth in SEQ ID NO:167. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:167; and comprises 59S, 83N, 90Q, 101S, 117R, 123S, 242R, 246N, 258Q and 273S; and comprises 128A and 156C, where the amino acid numbering is as set forth in SEQ ID NO:167. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:168; and comprises 1, 2, 3, 4, 5, 6, 7, 8, 9 or 10 of: 59S, 83N, 90Q, 101S, 117R, 123S, 242R, 246N, 258Q and 273S; and comprises 128A and 156N, where the amino acid numbering is as set forth in SEQ ID NO:168. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:168; and comprises 59S, 83N, 90Q, 101S, 117R, 123S, 242R, 246N, 258Q and 273S; and comprises 128A and 156N, where the amino acid numbering is as set forth in SEQ ID NO:168. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:169; and comprises 1, 2, 3, 4, 5, 6, 7, 8, 9 or 10 of: 59S, 83N, 90Q, 101S, 117R, 123S, 242R, 246N, 258Q and 273S; and comprises 128S and 156C, where the amino acid numbering is as set forth in SEQ ID NO:169. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:169; and comprises 59S, 83N, 90Q, 101S, 117R, 123S, 242R, 246N, 258Q and 273S; and comprises 128S and 156C, where the amino acid numbering is as set forth in SEQ ID NO:169. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:170; and comprises 1, 2, 3, 4, 5, 6, 7, 8, 9 or 10 of: 59S, 83N, 90Q, 101S, 117R, 123S, 242R, 246N, 258Q and 273S; and comprises 128S and 156N, where the amino acid numbering is as set forth in SEQ ID NO:170. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:170; and comprises 59S, 83N, 90Q, 101S, 117R, 123S, 242R, 246N, 258Q and 273S; and comprises 128S and 156N, where the amino acid numbering is as set forth in SEQ ID NO:170. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In certain embodiments, a subject engineered light-activated anion channel polypeptide is based on the amino acid sequence of the protein ReaChR, wherein the amino acid sequence is at least about 90%, 91%, 92%, 93%, 94%, 95%, 96%, 97%, 98%, 99%, or 100% identical to the sequence provided in one of SEQ ID NOS: 149-170.

Anion Channel Proteins Based on ChR2

In some embodiments, a subject engineered light-activated anion channel polypeptide is based on the amino acid sequence of the protein ChR2. The amino acid sequence of ChR2 is set forth in SEQ ID NO:79. In some embodiments, the amino acid sequence of the ChR2 protein has been modified by introducing one or more of the following mutations into the amino acid sequence: A59S, E90S, E101S, E123S, Q117K, H134R, V242K, T246N and/or N258Q. In some embodiments, a subject engineered light-activated anion channel polypeptide comprises the amino acid sequence of the protein ChR2 with all 9 of the above-listed amino acid substitutions, such that the amino acid sequence of the polypeptide is provided in SEQ ID NO:23.

In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:23; and comprises 1, 2, 3, 4, 5, 6, 7, 8, or 9 amino acid substitutions selected from A59S, E90S, E101S, E123S, Q117K, H134R, V242K, T246N and/or N258Q, relative to the amino acid sequence of ChR2 (SEQ ID NO:79).

In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:23; and comprises 1, 2, 3, 4, 5, 6, 7, 8, or 9 of: S59, S90, S101, S123, K117, R134, K242, N246 and Q258, where the amino acid numbering is as set forth in SEQ ID NO:23. In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:23; and comprises S59, S90, S101, S123, K117, R134, K242, N246 and Q258, where the amino acid numbering is as set forth in SEQ ID NO:23. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:24; and comprises 1, 2, 3, 4, 5, 6, 7, 8, or 9 of: S59, S90, S101, S123, K117, R134, K242, N246 and Q258, and comprises N156, where the amino acid numbering is as set forth in SEQ ID NO:24. In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:24; and comprises S59, S90, S101, S123, K117, R134, K242, N246 and Q258, and comprises N156, where the amino acid numbering is as set forth in SEQ ID NO:24. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ChR2 (SEQ ID NO:79), wherein the cysteine amino acid residue at position 128 has been replaced by a threonine residue. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:25; and comprises 1, 2, 3, 4, 5, 6, 7, 8, or 9 of: S59, S90, 5101, S123, K117, R134, K242, N246 and Q258; and comprises T128. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:25; and comprises S59, S90, S101, S123, K117, R134, K242, N246 and Q258; and comprises T128, where the amino acid numbering is as set forth in SEQ ID NO:25. In some embodiments, the engineered light-activated anion channel polypeptide comprises the amino acid sequence provided in SEQ ID NO:25. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ChR2, wherein the cysteine amino acid residue at position 128 has been replaced by an alanine residue. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:26; and comprises 1, 2, 3, 4, 5, 6, 7, 8, or 9 of: S59, S90, S101, S123, K117, R134, K242, N246 and Q258; and comprises A128, where the amino acid numbering is as set forth in SEQ ID NO:26. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:26; and comprises S59, S90, S101, S123, K117, R134, K242, N246 and Q258; and comprises A128, where the amino acid numbering is as set forth in SEQ ID NO:26. In some embodiments, the engineered light-activated anion channel polypeptide comprises the amino sequence provided in SEQ ID NO:26. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ChR2, wherein the cysteine amino acid residue at position 128 has been replaced by a serine residue. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:27; and comprises 1, 2, 3, 4, 5, 6, 7, 8, or 9 of: S59, S90, S101, S123, K117, R134, K242, N246 and Q258; and comprises S128, where the amino acid numbering is as set forth in SEQ ID NO:27. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:27; and comprises S59, S90, S101, S123, K117, R134, K242, N246 and Q258; and comprises S128, where the amino acid numbering is as set forth in SEQ ID NO:27. In some embodiments, a subject engineered light-activated anion channel polypeptide comprises the amino acid sequence provided in SEQ ID NO:27. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:28; and comprises 1, 2, 3, 4, 5, 6, 7, 8, or 9 of: S59, S90, S101, S123, K117, R134, K242, N246 and Q258; comprises A156; and comprises T128, where the amino acid numbering is as set forth in SEQ ID NO:28. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:28; and comprises S59, S90, S101, S123, K117, R134, K242, N246 and Q258; comprises T128; and comprises A156, where the amino acid numbering is as set forth in SEQ ID NO:28. In some embodiments, a subject engineered light-activated anion channel polypeptide comprises the amino acid sequence provided in SEQ ID NO:28. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:29; and comprises 1, 2, 3, 4, 5, 6, 7, 8, or 9 of: S59, S90, S101, S123, K117, R134, K242, N246 and Q258; comprises N156; and comprises T128, where the amino acid numbering is as set forth in SEQ ID NO:29. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:29; and comprises S59, S90, S101, S123, K117, R134, K242, N246 and Q258; comprises T128; and comprises N156, where the amino acid numbering is as set forth in SEQ ID NO:29. In some embodiments, a subject engineered light-activated anion channel polypeptide comprises the amino acid sequence provided in SEQ ID NO:29. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:30; and comprises 1, 2, 3, 4, 5, 6, 7, 8, or 9 of: S59, S90, S101, S123, K117, R134, K242, N246 and Q258; comprises A128; and comprises A156, where the amino acid numbering is as set forth in SEQ ID NO:30. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:30; and comprises S59, S90, S101, S123, K117, R134, K242, N246 and Q258; comprises A128; and comprises A156, where the amino acid numbering is as set forth in SEQ ID NO:30. In some embodiments, a subject engineered light-activated anion channel polypeptide comprises the amino acid sequence provided in SEQ ID NO:30. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:31; and comprises 1, 2, 3, 4, 5, 6, 7, 8, or 9 of: S59, S90, S101, S123, K117, R134, K242, N246 and Q258; comprises A128; and comprises N156, where the amino acid numbering is as set forth in SEQ ID NO:31. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:31; and comprises S59, S90, S101, S123, K117, R134, K242, N246 and Q258; comprises A128; and comprises N156, where the amino acid numbering is as set forth in SEQ ID NO:31. In some embodiments, a subject engineered light-activated anion channel polypeptide comprises the amino acid sequence provided in SEQ ID NO:31.

In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:32; and comprises 1, 2, 3, 4, 5, 6, 7, 8, or 9 of: S59, S90, S101, S123, K117, R134, K242, N246 and Q258; comprises A156; and comprises S128, where the amino acid numbering is as set forth in SEQ ID NO:32. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:32; and comprises S59, S90, S101, S123, K117, R134, K242, N246 and Q258; comprises S128; and comprises A156, where the amino acid numbering is as set forth in SEQ ID NO:32. In some embodiments, a subject engineered light-activated anion channel polypeptide comprises the amino acid sequence provided in SEQ ID NO:32. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:33; and comprises 1, 2, 3, 4, 5, 6, 7, 8, or 9 of: S59, S90, S101, S123, K117, R134, K242, N246 and Q258; comprises N156; and comprises S128, where the amino acid numbering is as set forth in SEQ ID NO:33. In some embodiments, a subject engineered light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:33; and comprises S59, S90, S101, S123, K117, R134, K242, N246 and Q258; comprises S128; and comprises N156, where the amino acid numbering is as set forth in SEQ ID NO:33. In some embodiments, a subject engineered light-activated anion channel polypeptide comprises the amino acid sequence provided in SEQ ID NO:33. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises a membrane trafficking signal (e.g., KSRITSEGEYIPLDQIDINV (SEQ ID NO:83)) and an ER export signal (e.g., FCYENEV (SEQ ID NO:84)).

In certain embodiments, a subject engineered light-activated anion channel polypeptide is based on the amino acid sequence of the protein ChR2, wherein the amino acid sequence is at least about 90%, 91%, 92%, 93%, 94%, 95%, 96%, 97%, 98%, 99%, or 100% identical to the sequence provided in one of SEQ ID NOS:23-33.

In some embodiments, the amino acid sequence of the ChR2 protein has been modified by introducing one or more of the following mutations into the amino acid sequence: A59S, E83N, E90Q, E101S, Q117R, E123S, V242R, T246N, N258Q, and/or E273S. In some embodiments, a subject engineered light-activated anion channel polypeptide comprises the amino acid sequence of the protein ChR2 with all 10 of the above-listed amino acid substitutions, such that the amino acid sequence of the polypeptide is provided in SEQ ID NO:116.

In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:116; and comprises 1, 2, 3, 4, 5, 6, 7, 8, 9 or 10 amino acid substitutions selected from A59S, E83N, E90Q, E101S, Q117R, E123S, V242R, T246N, N258Q, and/or E273S, relative to the amino acid sequence of ChR2 (SEQ ID NO:79).

In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:116; and comprises 1, 2, 3, 4, 5, 6, 7, 8, 9 or 10 of: 59S, 83N, 90Q, 101S, 117R, 123S, 242R, 246N, 258Q, and 273S, where the amino acid numbering is as set forth in SEQ ID NO:116. In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:116; and comprises 59S, 83N, 90Q, 101S, 117R, 123S, 242R, 246N, 258Q, and 273S, where the amino acid numbering is as set forth in SEQ ID NO:116. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:117; and comprises 1, 2, 3, 4, 5, 6, 7, 8, 9 or 10 of: 59S, 83N, 90Q, 101S, 117R, 123S, 242R, 246N, 258Q, and 273S, and comprises 156N, where the amino acid numbering is as set forth in SEQ ID NO:117. In some embodiments, a subject light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:117; and comprises 59S, 83N, 90Q, 101S, 117R, 123S, 242R, 246N, 258Q, and 273S, and comprises 156N, where the amino acid numbering is as set forth in SEQ ID NO:117. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ChR2 (SEQ ID NO:79), wherein the cysteine amino acid residue at position 128 has been replaced by a threonine residue. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:118; and comprises 1, 2, 3, 4, 5, 6, 7, 8, 9 or 10 of: 59S, 83N, 90Q, 101S, 117R, 123S, 242R, 246N, 258Q, and 273S; and comprises 128T. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:118; and comprises 59S, 83N, 90Q, 101S, 117R, 123S, 242R, 246N, 258Q, and 273S; and comprises 128T, where the amino acid numbering is as set forth in SEQ ID NO:118. In some embodiments, the engineered light-activated anion channel polypeptide comprises the amino acid sequence provided in SEQ ID NO:118. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ChR2, wherein the cysteine amino acid residue at position 128 has been replaced by an alanine residue. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:119; and comprises 1, 2, 3, 4, 5, 6, 7, 8, 9 or 10 of: 59S, 83N, 90Q, 101S, 117R, 123S, 242R, 246N, 258Q, and 273S; and comprises 128A, where the amino acid numbering is as set forth in SEQ ID NO:119. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:119; and comprises 59S, 83N, 90Q, 101S, 117R, 123S, 242R, 246N, 258Q, and 273S; and comprises 128A, where the amino acid numbering is as set forth in SEQ ID NO:119. In some embodiments, the engineered light-activated anion channel polypeptide comprises the amino sequence provided in SEQ ID NO:119. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide is based on the amino acid sequence of the protein ChR2, wherein the cysteine amino acid residue at position 128 has been replaced by a serine residue. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:120; and comprises 1, 2, 3, 4, 5, 6, 7, 8, 9 or 10 of: 59S, 83N, 90Q, 101S, 117R, 123S, 242R, 246N, 258Q, and 273S; and comprises 128S, where the amino acid numbering is as set forth in SEQ ID NO:120. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:120; and comprises 59S, 83N, 90Q, 101S, 117R, 123S, 242R, 246N, 258Q, and 273S; and comprises 128S, where the amino acid numbering is as set forth in SEQ ID NO:120. In some embodiments, a subject engineered light-activated anion channel polypeptide comprises the amino acid sequence provided in SEQ ID NO:120. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:121; and comprises 1, 2, 3, 4, 5, 6, 7, 8, 9 or 10 of: 59S, 83N, 90Q, 101S, 117R, 123S, 242R, 246N, 258Q, and 273S; comprises 156C; and comprises 128T, where the amino acid numbering is as set forth in SEQ ID NO:121. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:121; and comprises 59S, 83N, 90Q, 101S, 117R, 123S, 242R, 246N, 258Q, and 273S; comprises 128T; and comprises 156C, where the amino acid numbering is as set forth in SEQ ID NO:121. In some embodiments, a subject engineered light-activated anion channel polypeptide comprises the amino acid sequence provided in SEQ ID NO:121. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:122; and comprises 1, 2, 3, 4, 5, 6, 7, 8, 9 or 10 of: 59S, 83N, 90Q, 101S, 117R, 123S, 242R, 246N, 258Q, and 273S; comprises 156N; and comprises 128T, where the amino acid numbering is as set forth in SEQ ID NO:122. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:122; and comprises 59S, 83N, 90Q, 101S, 117R, 123S, 242R, 246N, 258Q, and 273S; comprises 128T; and comprises 156N, where the amino acid numbering is as set forth in SEQ ID NO:122. In some embodiments, a subject engineered light-activated anion channel polypeptide comprises the amino acid sequence provided in SEQ ID NO:122. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:123; and comprises 1, 2, 3, 4, 5, 6, 7, 8, 9 or 10 of: 59S, 83N, 90Q, 101S, 117R, 123S, 242R, 246N, 258Q, and 273S; comprises 128A; and comprises 156C, where the amino acid numbering is as set forth in SEQ ID NO:123. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:123; and comprises 59S, 83N, 90Q, 101S, 117R, 123S, 242R, 246N, 258Q, and 273S; comprises 128A; and comprises 156C, where the amino acid numbering is as set forth in SEQ ID NO:123. In some embodiments, a subject engineered light-activated anion channel polypeptide comprises the amino acid sequence provided in SEQ ID NO:123. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:124; and comprises 1, 2, 3, 4, 5, 6, 7, 8, 9 or 10 of: 59S, 83N, 90Q, 101S, 117R, 123S, 242R, 246N, 258Q, and 273S; comprises 128A; and comprises 156N, where the amino acid numbering is as set forth in SEQ ID NO:124. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:124; and comprises 59S, 83N, 90Q, 101S, 117R, 123S, 242R, 246N, 258Q, and 273S; comprises 128A; and comprises 156N, where the amino acid numbering is as set forth in SEQ ID NO:124. In some embodiments, a subject engineered light-activated anion channel polypeptide comprises the amino acid sequence provided in SEQ ID NO:124. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:125; and comprises 1, 2, 3, 4, 5, 6, 7, 8, 9 or 10 of: 59S, 83N, 90Q, 101S, 117R, 123S, 242R, 246N, 258Q, and 273S; comprises 156C; and comprises 128S, where the amino acid numbering is as set forth in SEQ ID NO:125. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:125; and comprises 59S, 83N, 90Q, 101S, 117R, 123S, 242R, 246N, 258Q, and 273S; comprises 128S; and comprises 156C, where the amino acid numbering is as set forth in SEQ ID NO:125. In some embodiments, a subject engineered light-activated anion channel polypeptide comprises the amino acid sequence provided in SEQ ID NO:125.

In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:126; and comprises 1, 2, 3, 4, 5, 6, 7, 8, 9 or 10 of: 59S, 83N, 90Q, 101S, 117R, 123S, 242R, 246N, 258Q, and 273S; comprises 156N; and comprises 128S, where the amino acid numbering is as set forth in SEQ ID NO:126. In some embodiments, a subject engineered light-activated anion channel polypeptide comprises an amino acid sequence having at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:126; and comprises 59S, 83N, 90Q, 101S, 117R, 123S, 242R, 246N, 258Q, and 273S; comprises 128S; and comprises 156N, where the amino acid numbering is as set forth in SEQ ID NO:126. In some embodiments, a subject engineered light-activated anion channel polypeptide comprises the amino acid sequence provided in SEQ ID NO:126. In any one of these embodiments, a subject anion channel polypeptide comprises a membrane trafficking signal (e.g., KSRITSEGEYIPLDQIDINV (SEQ ID NO:83)). In any one of these embodiments, a subject anion channel polypeptide comprises an ER export signal (e.g., FCYENEV (SEQ ID NO:84)). In any one of these embodiments, a subject anion channel polypeptide comprises both a membrane trafficking signal (e.g., KSRITSEGEYIPLDQIDINV (SEQ ID NO:83)) and an ER export signal (e.g., FCYENEV (SEQ ID NO:84)).

In certain embodiments, a subject engineered light-activated anion channel polypeptide is based on the amino acid sequence of the protein ChR2, wherein the amino acid sequence is at least about 90%, 91%, 92%, 93%, 94%, 95%, 96%, 97%, 98%, 99%, or 100% identical to the sequence provided in one of SEQ ID NOS:116-126.

Enhanced Intracellular Transport Amino Acid Motifs

The present disclosure provides for the modification of proteins expressed in a cell by the addition of one or more amino acid sequence motifs that enhance transport of the proteins to the plasma membranes of mammalian cells. Light-activated proteins having components derived from evolutionarily simpler organisms may not be expressed or tolerated by mammalian cells, or may exhibit impaired subcellular localization when expressed at high levels in mammalian cells. Consequently, in some embodiments, the subject light-activated anion channel proteins that are expressed in a cell can be fused to one or more amino acid sequence motifs selected from the group consisting of a signal peptide, an endoplasmic reticulum (ER) export signal, a membrane trafficking signal, and/or an N-terminal golgi export signal. The one or more amino acid sequence motifs that enhance protein transport to the plasma membranes of mammalian cells can be fused to the N-terminus, the C-terminus, or to both the N- and C-terminal ends of a protein in order to facilitate optimal expression and/or localization of the protein in the plasma membrane of a cell. Optionally, the subject light-activated anion channel proteins and the one or more amino acid sequence motifs may be separated by a linker. In some embodiments, the light-activated anion channel protein can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:83).

Trafficking sequences that are suitable for use can comprise an amino acid sequence having 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:83)).

A trafficking sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Signal sequences that are suitable for use can comprise an amino acid sequence having 90%, 91%, 92%, 93%, 94%, 95%, 96%, 97%, 98%, 99%, or 100%, amino acid sequence identity to an amino acid sequence such as one of the following:

1) the signal peptide of hChR2 (e.g., MDYGGALSAVGRELLFVTNPVVVNGS (SEQ ID NO:85))

2) the β2 subunit signal peptide of the neuronal nicotinic acetylcholine receptor (e.g., MAGHSNSMALFSFSLLWLCSGVLGTEF (SEQ ID NO:86));

3) a nicotinic acetylcholine receptor signal sequence (e.g., MGLRALMLWLLAAAGLVRESLQG (SEQ ID NO:87)); and 4) a nicotinic acetylcholine receptor signal sequence (e.g., MRGTPLLLVVSLFSLLQD (SEQ ID NO:88)).

A signal sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Endoplasmic reticulum (ER) export sequences that are suitable for use with a light-activated anion channel protein of the present disclosure include, e.g., VXXSL (where X is any amino acid) (e.g., VKESL (SEQ ID NO:89); VLGSL (SEQ ID NO:90); etc.); NANSFCYENEVALTSK (SEQ ID NO:91); FXYENE (SEQ ID NO:92) (where X is any amino acid), e.g., FCYENEV (SEQ ID NO:93); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

In some embodiments, the signal peptide sequence in the protein can be deleted or substituted with a signal peptide sequence from a different protein.

Polynucleotides and Vectors

Aspects of the present disclosure include nucleic acids, such as polynucleotides, that comprise a nucleotide sequence that encodes one or more of the subject proteins described herein (e.g., one or more light-activated anion channel proteins as described above). In some embodiments, a subject polynucleotide comprises an expression cassette, wherein the expression cassette contains a plurality of components (e.g., a plurality of coding sequences) that are utilized to express one or more proteins encoded by the polynucleotide in a target cell.

In some embodiments, a portion of a polynucleotide encoding a subject protein is operably linked to a promoter sequence. Any suitable promoter that functions in a target cell can be used for expression of the subject polynucleotides. In certain embodiments, a promoter sequence can be a promoter that is specific to a particular target cell type or to a particular tissue type, such as a particular neuron or a pan-neuronal promoter. Initiation control regions of promoters, which are useful to drive expression of polynucleotides in a specific animal cell, are numerous and familiar to those skilled in the art. Virtually any promoter capable of driving expression of the subject polynucleotides can be used. In some embodiments, the promoter used to drive expression of a subject protein can be the Thy1 promoter (See, e.g., Llewellyn, et al., 2010, Nat. Med., 16(10):1161-1166). In some embodiments, the promoter used to drive expression of a subject protein can be a human synapsin (hSyn) promoter, a human elongation factor 1-α (EF1α) promoter, a cytomegalovirus (CMV) promoter, a CMV early enhancer/chicken β actin (CAG) promoter, a synapsin-I promoter (e.g., a human synapsin-I promoter), a human synuclein 1 promoter, a human Thy1 promoter, a calcium/calmodulin-dependent kinase II alpha (CAMKIIα) promoter, or any other promoter capable of driving expression of the a subject nucleic acid sequence in a target cell.

In some embodiments, a promoter may be an inducible promoter. For example, the promoter may be induced by a trans-acting factor that responds to an exogenously administered drug. Examples of inducible promoters include, but are not limited to, tetracycline-on or tetracycline-off promoters, or tamoxifen-inducible CreER.

In some embodiments, a subject polynucleotide may comprise a ribosomal skip sequence that can be used to generate two separate proteins from the same transcript. In such embodiments, a subject polynucleotide will typically include a coding sequence that encodes a light-activated protein as well as a response protein. In these embodiments, a ribosomal skip sequence may be placed between the two coding sequences to produce two distinct proteins (namely, the light-activated protein and the response protein) from the same transcript.

Also provided herein are recombinant expression vectors comprising the subject polynucleotides or any variant thereof as described herein. Vectors according to the present disclosure also include vectors comprising a nucleotide sequence that encodes an RNA (e.g., an mRNA) that when transcribed from the polynucleotides of the vector will result in the accumulation of a subject protein on the plasma membranes of target cells. Vectors which may be used include, without limitation, lentiviral, HSV, adenoviral, and adeno-associated viral (AAV) vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art.

In some embodiments, a vector may be a recombinant AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome that contains the rep gene involved in viral replication and expression of the viral genes; and the right-hand part of the genome that contains the cap gene encoding the capsid proteins of the virus.

AAV vectors may be prepared using standard methods in the art. Adeno-associated viruses of any serotype are suitable (see, e.g., Blacklow, pp. 165-174 of "Parvoviruses and Human Disease" J. R. Pattison, ed. (1988); Rose, Comprehensive Virology 3:1, 1974; P. Tattersall "The Evolution of Parvovirus Taxonomy" In Parvoviruses (J R Kerr, S F Cotmore. M E Bloom, R M Linden, C R Parrish, Eds.) p 5-14, Hudder Arnold, London, U K (2006); and D E Bowles, J E Rabinowitz, R J Samulski "The Genus Dependovirus" (J R Kerr, S F Cotmore. M E Bloom, R M Linden, C R Parrish, Eds.) p 15-23, Hudder Arnold, London, UK (2006), the disclosures of each of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Methods of preparing AAV vectors in a baculovirus system are described in, e.g., WO 2008/024998. AAV vectors can be self-complementary or single-stranded. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication-defective recombinant AAVs according to the present disclosure can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the methods of the present disclosure are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the present disclosure includes a recombinant virus particle (recombinant because it contains a recombinant polynucleotide) comprising any of the vectors described herein. Methods of producing such particles are known in the art and are described in U.S. Pat. No. 6,596,535, the disclosure of which is hereby incorporated by reference in its entirety.

In some embodiments, the subject anion channel proteins can be combined with various promoters and/or fluorescent proteins (XFP) for targeting specific neuronal populations in mammalian brains. For example, the following adeno associated vectors (AAVs) and components thereof may be used without limitation: AAV-CamKII-iChR-XFP, AAV-hSyn-iChR-XFP, AAV-mThy1-iChR-XFP, AAVmThy1-iChR-XFP, AAV-GFAP-iChR-XFP, AAV-VGAT-iChR-XFP, AAV-PET1-iChR-XFP, AAV-NPY-iChR-XFP, AAV-SST-iChR-XFP, AAV-AVP5.5-iChR-XFP, AAV-Ef1a-iChR-XFP, AAV-FLEX-rev-iChR-XFP, AAV-CAG-iChR-XFP, AAV-CAG-FLEX-iChR-XFP. Other AAV vectors that may be used in association with the polynucleotides include those with double floxed inverted reading frames (DIO) which allow expression of proteins under the control of recombinases such as as Cre and Flp: AAV-Ef1a-DIO(Cre)-iChR-XFP (Cre-dependent expression), AAV-Ef1a-DIO(Flp)-iChR-XFP (Hp-dependent expression), AAV-Ef1a-DIO(Cre)-DIO(Flp)-iChR-XFP (Cre and Flp dependent expression).

Another major viral transduction system utilizes lentivirus including the following potential expression vectors: pLenti-CamKII-iChR-XFP, pLenti-Ef1a-iChR-XFP, pLenti-mThy1-iChR-XFP, pLenti-hThy1-iChR-XFP, pLenti-hSyn-iChR-XFP, pLenti-VGAT-iChR-XFP, pLenti-Hcrt-iChRXFP. Herpes simplex virus (HSV) can be utilized to transport proteins of interest over synapses (anterograde) which includes the following expression vectors: HSV-EF1a-iChR-XFP and HSVEF1a-DIO-iChR-XFP. Rabies and pseudorabies virus can be utilized for retrograde transports over synapses using the following expression vector: SAD(delta)G-iChR-XFP and SAD(delta)G-DIOiChR-XFP. Other mammalian expression vectors include: pcDNA3.1-CMV-iChR-XFP and pCAGGS-iChR-XFP.

Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956; see also, e.g., U.S. Pat. No. 6,649,811, U.S. Pat. No. 5,387,742); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn et al. (2010) Nat. Med. 16:1161); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; a CMV enhancer/platelet-derived growth factor-β promoter (see, e.g., Liu et al. (2004) Gene Therapy 11:52-60); a motor neuron-specific gene Hb9 promoter (see, e.g., U.S. Pat. No. 7,632,679; and Lee et al. (2004) Development 131:3295-3306); and an alpha subunit of $Ca^{2+}$-calmodulin-dependent protein kinase II (CaMKIIα) promoter (see, e.g., Mayford et al. (1996) Proc. Natl. Acad. Sci. USA 93:13250).

Host Cells

The present disclosure provides isolated genetically modified host cells (e.g., in vitro cells) that are genetically modified with a subject nucleic acid. In some embodiments, a subject isolated genetically modified host cell can produce an opsin of the present disclosure.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. In some cases, the mammalian cell is a neuron, e.g., a non-immortalized (primary) neuron. In other cases, the mammalian cell is an immortalized cell line.

Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some embodiments, the cell is a neuronal cell or a neuronal-like cell. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S(ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) J. Immunol. 148:1176-1181; U.S. Pat. No. 6,447,784; and Sizemore et al. (1995) Science 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the host cell is *Escherichia coli*.

Pharmaceutical Compositions

Aspects of the disclosure include pharmaceutical compositions that comprise the subject polynucleotides, vectors, or components thereof. The subject pharmaceutical compositions may be administered to a subject for purposes of genetically modifying a target cell so that the target cell expresses one or more of the subject proteins. A subject pharmaceutical composition may, in some embodiments, comprise a pharmaceutically acceptable excipient. In some embodiments, a pharmaceutical composition may comprise components to facilitate delivery of the subject polynucleotides or vectors to a target cell, including but not limited to transfection reagents or components thereof, such as lipids, polymers, and the like.

In some embodiments, a subject pharmaceutical composition will be suitable for injection into a subject, e.g., will be sterile. For example, in some embodiments, a subject pharmaceutical composition will be suitable for injection into a subject, e.g., where the composition is sterile and is free of detectable pyrogens and/or other toxins.

Pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public as well, and may be incorporated into the pharmaceutical compositions of the present disclosure without limitation.

Target Cells and Tissues

As summarized above, aspects of the present disclosure include delivering the subject polynucleotides, or components thereof, to target cells. Target cells are generally cells that carry or transmit electrical impulses, such as nerve cells. In some embodiments, a target cell may be, e.g., a sensory neuron, a motor neuron, or an interneuron. Target cells of the disclosure may include cells of the central nervous system and/or cells of the peripheral nervous system. In some embodiments, a target tissue may include a plurality of nerve fibers, a nerve, a nerve cell ganglion, a neuromuscular junction, a tissue that is innervated by nerves, including but not limited to muscle, skin, or endocrine tissue, or an anatomical region, such as a portion or sub-portion of the brain or spinal cord. In some embodiments, a target tissue may be a portion of an individual cell, such as specific axon of a nerve cell.

Once the subject polynucleotides have been delivered to a target cell or tissue, the polynucleotides enter the target cells and are expressed. In some embodiments, the subject polynucleotides may contain tissue-specific promoters so that expression only occurs in target cells wherein the tissue-specific promoter is active. In this way, if a subject polynucleotide is delivered to cells other than a target cell, the polynucleotide will not be expressed in the non-target cells because the tissue-specific promoter will be inactive in those cells. In some embodiments, a subject polynucleotide may contain an inducible promoter, such that expression of the polynucleotide only takes place when an exogenously administered drug is present is a sufficient concentration within the cell to activate the promoter.

Systems and Devices

Aspects of the present disclosure include systems and devices that can be used to carry out aspects of the subject methods. The subject systems generally include an engineered light-activated anion channel protein, as described above, and one or more devices for delivering light of an activating wavelength to a target tissue or cell. Devices that find use in the subject methods include delivery devices that can be used to deliver the subject polynucleotides to target cells and tissues, light-generating devices that can be used to illuminate target cells that express the subject light-activated proteins, and control devices that can be used to control the delivery of light to specific target cells or tissues. Each of these components is further described below.

Delivery Devices

Aspects of the present disclosure include delivery devices that can be used to deliver a subject pharmaceutical composition to a target cell. The subject delivery devices may provide regular, irregular, programmed, or clinician- or patient-activated doses of the subject pharmaceutical compositions to one or more target cells to ensure that the target cells continue to express the subject protein(s) for a desired period of time.

The subject delivery devices may generally include various components, such as reservoirs, pumps, actuators, tubing components, needles, catheters, and any other suitable components for delivering the subject pharmaceutical compositions to a target cell or tissue of a patient. Delivery devices may also include components that facilitate computerized operation, such as a power source, a processor comprising a memory, a user input device, and/or a graphical user interface. In some embodiments, a delivery device may be completely or partially implantable within a patient. In some embodiments, a delivery device may be operated by a caregiver, wherein the device is introduced into a portion of the patient's body, e.g., into the patient's brain, and a subject pharmaceutical composition is delivered to a target tissue, e.g., a portion of the patient's brain. In some embodiments, following delivery of the pharmaceutical composition, the device may be removed. In other embodiments, the device may be kept in place for later delivery of additional pharmaceutical compositions.

Light-Generating Devices

Aspects of the present disclosure include light-generating devices that can be used to deliver light to target cells that express one or more of the subject proteins. Light-generating devices in accordance with embodiments of the present disclosure can generally produce light of a variety of different wavelengths from one or more light sources on the device. In some embodiments, a light-generating device may include a light cuff or sleeve that can be placed around or near target cells expressing one or more of the subject proteins. In some embodiments, a portion of the light source or the entire light source may be implantable. The subject light-generating devices may be of any useful configuration for stimulating the light-activated proteins disclosed herein. In some embodiments, for example, a light-generating device may comprise components that facilitate exclusive illumination of a target cell or tissue. For example, in some embodiments, a light-generating device may exclusively direct light to a target cell, a portion of a target cell, e.g., a particular axon of a nerve cell, or a specific anatomical structure, such as, e.g. a bundle of nerve fibers, a target tissue, or a portion of the spinal cord. By "exclusively direct light" is meant that the light-generating device only delivers light to the specific target structure, and does not illuminate other structures. For example, in some embodiments, a light-generating device may be configured to illuminate an axon of a nerve cell, but not to illuminate any other portion of the nerve cell. In this way, the light from the light-generating device only affects light-activated proteins in the specific target structure that is illuminated.

Aspects of the disclosure include light delivery devices that include one or more optical sources that are configured to deliver light in one or more 2-dimensional and/or 3-dimensional patterns to one or more target locations, including but not limited to one or more portions (e.g., multiple layers) of a target tissue and/or anatomical structure. In certain embodiments, a light delivery device may include a plurality of light sources (e.g., a plurality of laser light sources, LEDs, and the like), as well as any suitable number of light guides that are configured to bend or shape light in a desired manner. Examples of light delivery devices are provided in U.S. Pat. No. 8,545,543, the disclosure of which is hereby incorporated by reference in its entirety.

In some embodiments, a light-generating device may not completely surround the region containing a target cell expressing a light-activated protein, but, rather, can have a U-shape. In some embodiments, a light-generating device can have an attachment arm that can be used to guide the light-generating device to a specific region or target structure, e.g., a specific neuronal region. The attachment arm can be removed following implantation of the light-generating device or can be left in place to fix the position of the light-generating device in proximity to the target cells of interest.

In some embodiments, the subject light-generating devices may comprise an inner body, the inner body having at least one means for generating light which is connected to a power source. In some embodiments, the power source can be an internal battery for powering the light-generating device. In some embodiments, an implantable light-generating device may comprise an external antenna for receiving wirelessly transmitted electromagnetic energy from an external source for powering the device. The wirelessly transmitted electromagnetic energy can be a radio wave, a microwave, or any other electromagnetic energy source that can be transmitted from an external source to power the light-generating device. In some embodiments, the light-generating device is controlled by, e.g., an integrated circuit produced using semiconductor or other processes known in the art.

In some embodiments, the light-generating device may comprise a light emitting diode (LED). In some embodiments, the LED can generate blue and/or green light. In other embodiments, the LED can generate amber and/or yellow light. In some embodiments, several micro LEDs are embedded into the inner body of the light-generating device. In other embodiments, the light-generating device is a solid state laser diode or any other means capable of generating light. The light-generating device can generate light having a wavelength and intensity sufficient to activate a subject light-activated protein. In some embodiments, a light-generating device produces light having an intensity of any of about 0.05 mW/mm$^2$, 0.1 mW/mm$^2$, 0.2 mW/mm$^2$, 0.3 mW/mm$^2$, 0.4 mW/mm$^2$, 0.5 mW/mm$^2$, about 0.6 mW/mm$^2$, about 0.7 mW/mm$^2$, about 0.8 mW/mm$^2$, about 0.9 mW/mm$^2$, about 1.0 mW/mm$^2$, about 1.1 mW/mm$^2$, about 1.2 mW/mm$^2$, about 1.3 mW/mm$^2$, about 1.4 mW/mm$^2$, about 1.5 mW/mm$^2$, about 1.6 mW/mm$^2$, about 1.7 mW/mm$^2$, about 1.8 mW/mm$^2$, about 1.9 mW/mm$^2$, about 2.0 mW/mm$^2$, about 2.1 mW/mm$^2$, about 2.2 mW/mm$^2$, about 2.3 mW/mm$^2$, about 2.4 mW/mm$^2$, about 2.5 mW/mm$^2$, about 3 mW/mm$^2$, about 3.5 mW/mm$^2$, about 4 mW/mm$^2$, about 4.5 mW/mm$^2$, about 5 mW/mm$^2$, about 5.5 mW/mm$^2$, about 6 mW/mm$^2$, about 7 mW/mm$^2$, about 8 mW/mm$^2$, about 9 mW/mm$^2$, or about 10 mW/mm$^2$, inclusive, including values in between these numbers. In some embodiments, the light-generating device produces light having an intensity of at least about 10 Hz, such as up to about 25 Hz, such as up to about 50 Hz, such as up to about 75 Hz, such as up to about 100 Hz.

The subject light-generating devices are generally capable of generating light having a wavelength ranging from about 350 nm, up to about 360 nm, up to about 370 nm, up to about 380 nm, up to about 390 nm, up to about 400 nm, up to about 410 nm, up to about 420 nm, up to about 430 nm, up to about 440 nm, up to about 450 nm, up to about 460 nm, up to about 470 nm, up to about 475 nm, up to about 480 nm, up to about 490 nm, up to about 500 nm, up to about 510 nm, up to about 520 nm, up to about 530 nm, up to about 540 nm, up to about 550 nm, up to about 560 nm, up to about 570 nm, up to about 580 nm, up to about 590 nm, up to about 600 nm, up to about 610 nm, up to about 620 nm, up to about 630 nm, up to about 635 nm, up to about 640 nm, up to about 650 nm, up to about 660 nm, up to about 670 nm, up to about 680 nm, up to about 690 nm, up to about 700 nm, up to about 710 nm, up to about 720 nm, up to about 730 nm, up to about 740 nm, and/or up to about 750 nm.

In some embodiments, a light generating device may generate violet light having a wavelength ranging from about 400 nm to about 475 nm. In some embodiments, a light generating device may generate blue light having a wavelength ranging from about 475 nm to about 500 nm. In some embodiments, a light generating device may generate green light having a wavelength ranging from about 500 nm to about 560 nm. In some embodiments, a light generating device may generate yellow light having a wavelength ranging from about 560 nm to about 590 nm. In some embodiments, a light generating device may generate orange light having a wavelength ranging from about 590 nm to about 620 nm. In some embodiments, a light generating device may generate red light having a wavelength ranging from about 620 nm to about 650 nm.

In some embodiments, a subject light-generating device may include one or more optical fibers that can transmit light from a light source and deliver the light to a target structure. The optical fibers may comprise plastic or glass materials, and in some embodiments may be suitably flexible to facilitate placement of the light-generating device in locations that could not be accommodated by rigid structures. For example, in some embodiments, a light-generating device may comprise a light source that generates light, as well as one or more optical fibers that can be placed in various locations on or in the patient's body. Light from the light source can pass through the optical fiber, passing around corners and bends in the optical fiber, and emerge at the end of the optical fiber to deliver light to a target structure.

In some embodiments, the subject light-generating devices may comprise a plurality of light sources that can be used to illuminate a target tissue with different wavelengths of light. For example, in some embodiments, a light-generating device may comprise a first light source that generates light of a first wavelength, e.g., red light, and a second light source that generates light of a second wavelength, e.g., blue light. Such light-generating devices may be used to simultaneously illuminate the same target tissue with light of both wavelengths, or may alternately illuminate the target tissue with light of the first wavelength and light of the second wavelength. In some embodiments, such light generating devices may be used to deliver light from the same light source to different target tissues. For example, in some embodiments a light-generating device may deliver light of a first wavelength to a first target tissue, and may deliver light of a second wavelength to a different target tissue.

Control Devices

Aspects of the disclosure include a controller, processor (e.g., a computer) and computer readable medium that are configured or adapted to control or operate one or more components of the subject systems. In some embodiments, a system includes a controller that is in communication with one or more components of the systems, as described herein, and is configured to control aspects of the systems and/or execute one or more operations or functions of the subject systems. In some embodiments, a system includes a processor and a computer-readable medium, which may include memory media and/or storage media. Applications and/or operating systems embodied as computer-readable instructions on computer-readable memory can be executed by the processor to provide some or all of the functionalities described herein.

In some embodiments, a system includes a user interface, such as a graphical user interface (GUI), that is adapted or configured to receive input from a user, and to execute one or more of the methods as described herein. In some embodiments, a GUI is configured to display data or information to a user.

Aspects of the present disclosure include control devices that can control, or modulate, the amount of light that is emitted from the subject light-generating devices. In some embodiments, a control device may be configured to modulate the wavelength and/or the intensity of light that is delivered to a target tissue from a light-generating device. In some embodiments, a control device may be configured to modulate the frequency and/or duration of light that is delivered to a target tissue from a light-generating device. For example, in some embodiments, a control device may be configured to deliver pulses of light from the light-generating device to a target tissue. The control device can modulate the frequency and/or duration of the light pulses such that the target tissue is illuminated with light from the light-generating device, e.g., at a regular or irregular rate, according to a user input, etc. In some embodiments, a control device can produce pulses of light from the light-generating device that have a duration ranging from about 1 millisecond or less, up to about 1 second, up to about 10 seconds, up to about 20 seconds, up to about 30 seconds, up to about 40 seconds, up to about 50 seconds, up to about 60 seconds or more. In some embodiments, a control device can produce pulses of light from the light-generating device that have a frequency of 1 pulse per millisecond, up to about 1 pulse per second, up to about 1 pulse per minute, up to about 1 pulse per 10 minutes, up to about 1 pulse per 20 minutes, up to about 1 pulse per 30 minutes.

In some embodiments, a subject control device may comprise a power source that can be mounted to a transmitting coil. In some embodiments, a battery can be connected to the power source for providing power thereto. A switch can be connected to the power source, allowing an operator (e.g., a patient or caregiver) to manually activate or deactivate the power source. In some embodiments, upon activation of the switch, the power source can provide power to the light-generating device through electromagnetic coupling between the transmitting coil on the control device and an external antenna of an implantable light-generating device (such as a light cuff or sleeve). The transmitting coil can establish an electromagnetic coupling with the external antenna of the implantable light-generating device when in proximity thereof, for supplying power to the light-generating device and for transmitting one or more control signals to the light-generating device. In some embodiments, the electromagnetic coupling between the transmitting coil of the control device and the external antenna of the implantable light-generating device can be radio-frequency magnetic inductance coupling. When radio-frequency magnetic inductance coupling is used, the operational frequency of the radio wave can be between about 1 and 20 MHz, inclusive, including any values in between these numbers (for example, about 1 MHz, about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, about 15 MHz, about 16 MHz, about 17 MHz, about 18 MHz, about 19 MHz, or about 20 MHz). However, other coupling techniques may be used, such as an optical receiver, infrared, or a biomedical telemetry system (See, e.g., Kiourti, "Biomedical Telemetry: Communication between Implanted Devices and the External World, Opticon1826, (8): Spring, 2010).

Figure 8:
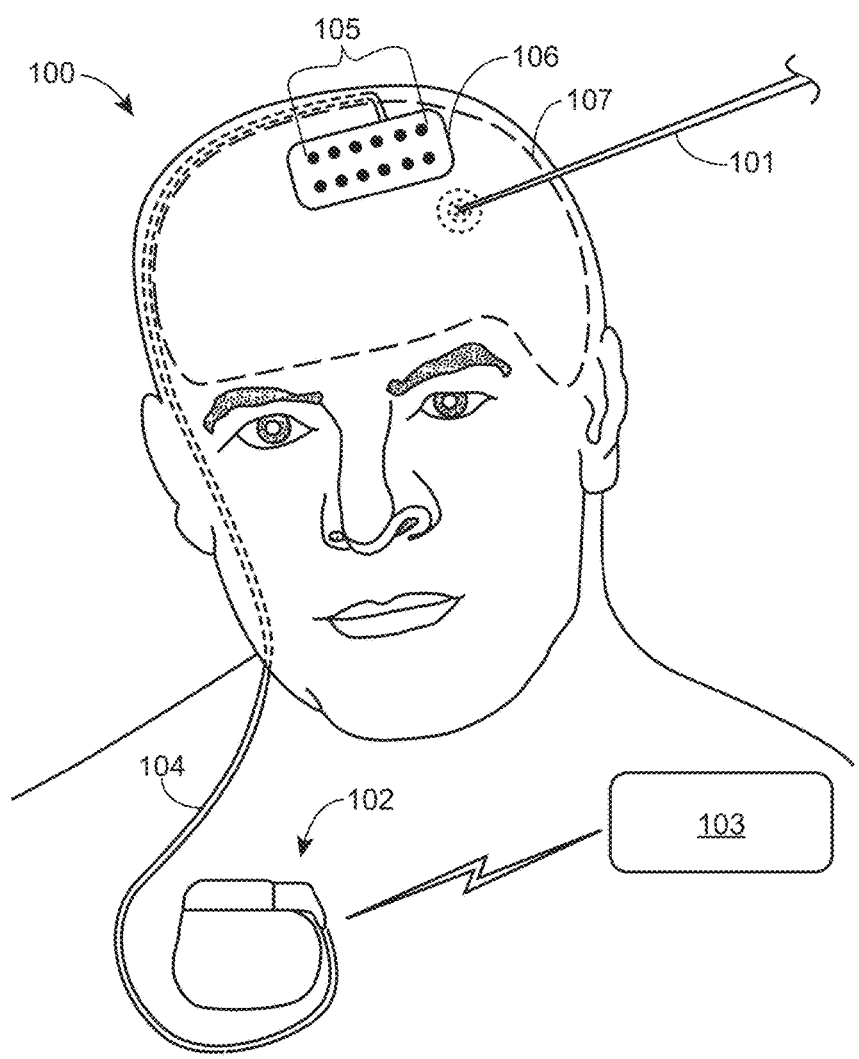
FIG. 8 shows a first example of an optical stimulation system in accordance with embodiments of the disclosure.

Turning now to FIG. 8, a first example of an optical stimulation system 100 is depicted. The optical stimulation system 100 comprises a delivery device 101 for delivering a subject polynucleotide to a target tissue, e.g., brain tissue 107 of a patient. Also provided are a light-generating device 102, a control device 103, and optical fibers 104 for conveying light generated by the light-generating device 102 to a light array 105 positioned on a light cuff 106.

Figure 9:
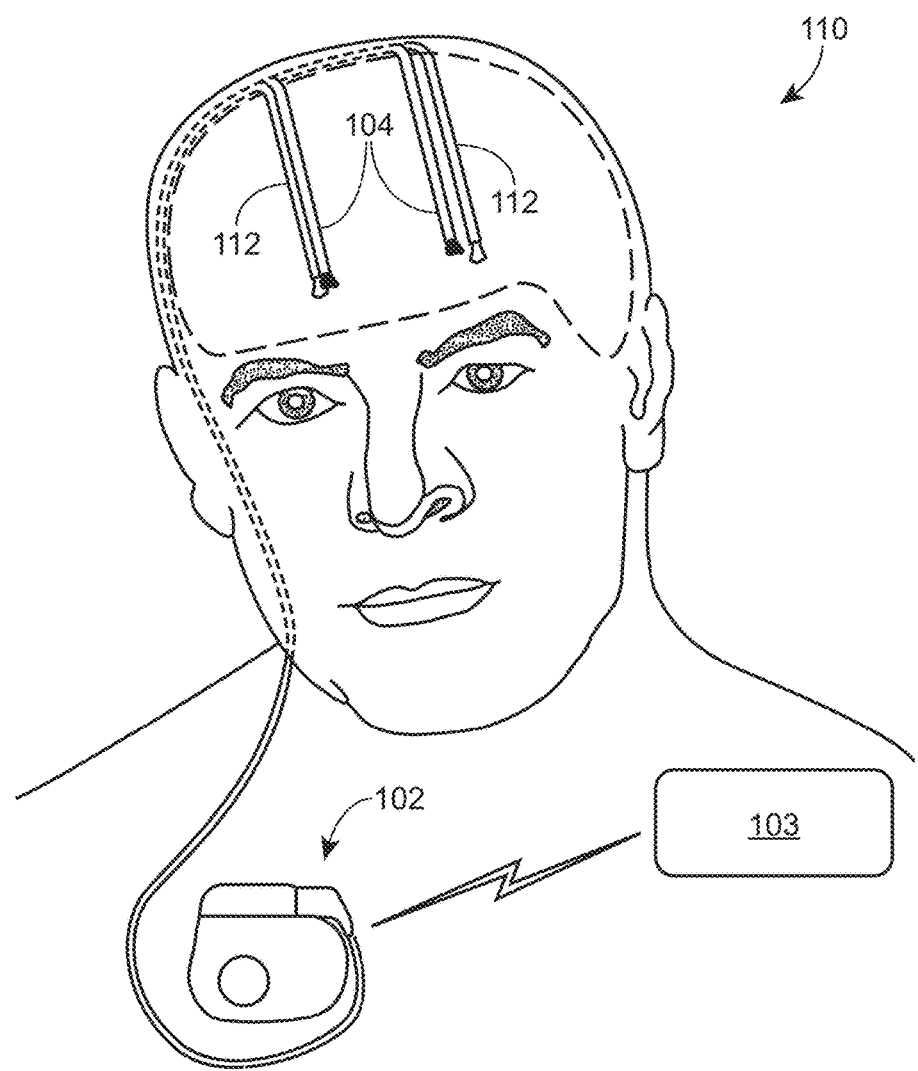
FIG. 9 shows a second example of an optical stimulation system in accordance with embodiments of the disclosure.

Turning now to FIG. 9, a second example of an optical stimulation system 110 is depicted. The optical stimulation system 110 comprises a catheter 112 for delivering a subject polynucleotide to a target tissue, e.g., brain tissue 107 of a patient. Also provided are a light-generating device 102, a control device 103, and optical fibers 104 for conveying light generated by the light-generating device 102 to the end of the optical fibers 104.

Figure 10:
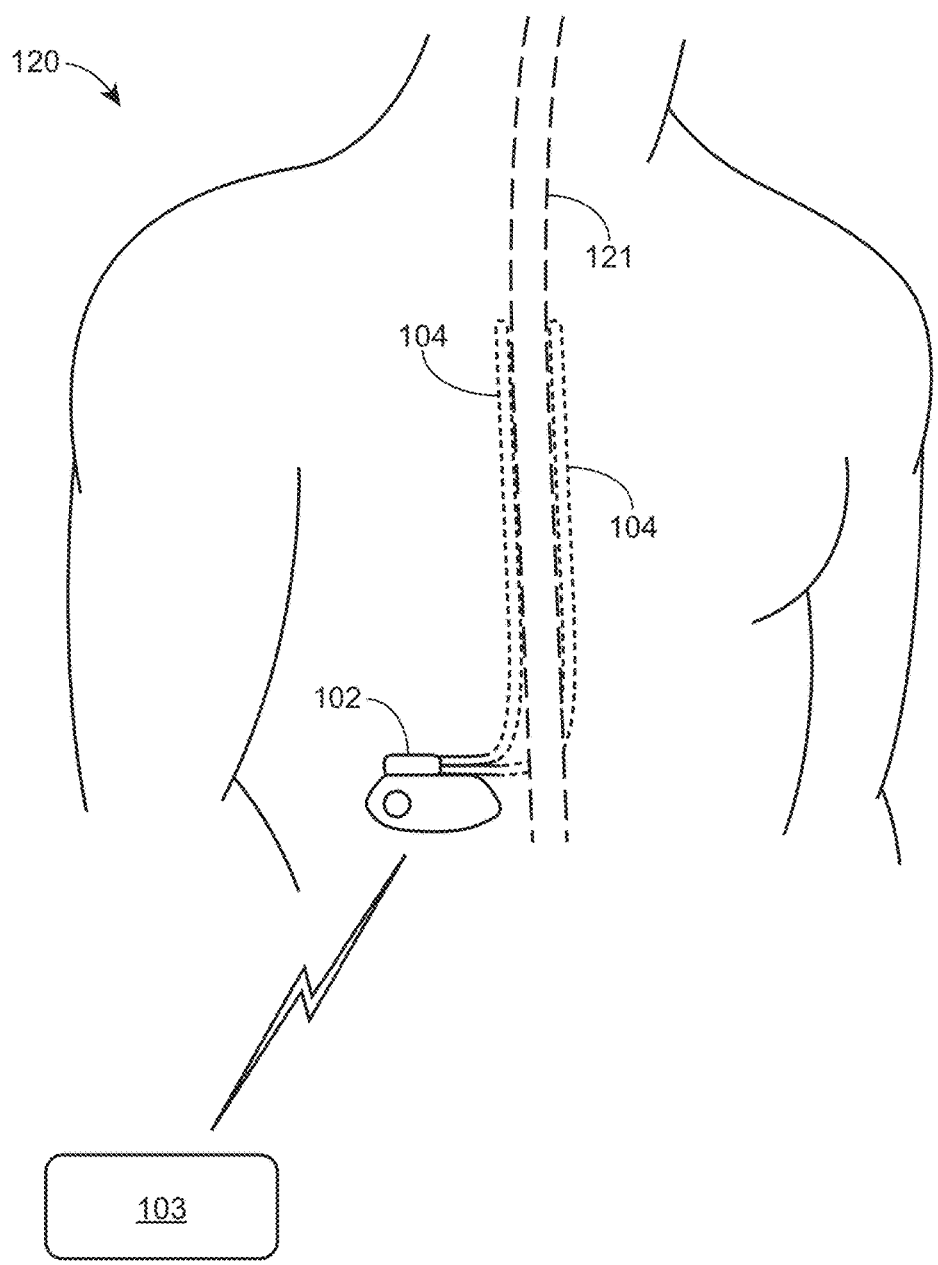
FIG. 10 shows a third example of an optical stimulation system in accordance with embodiments of the disclosure.
Figure 11:
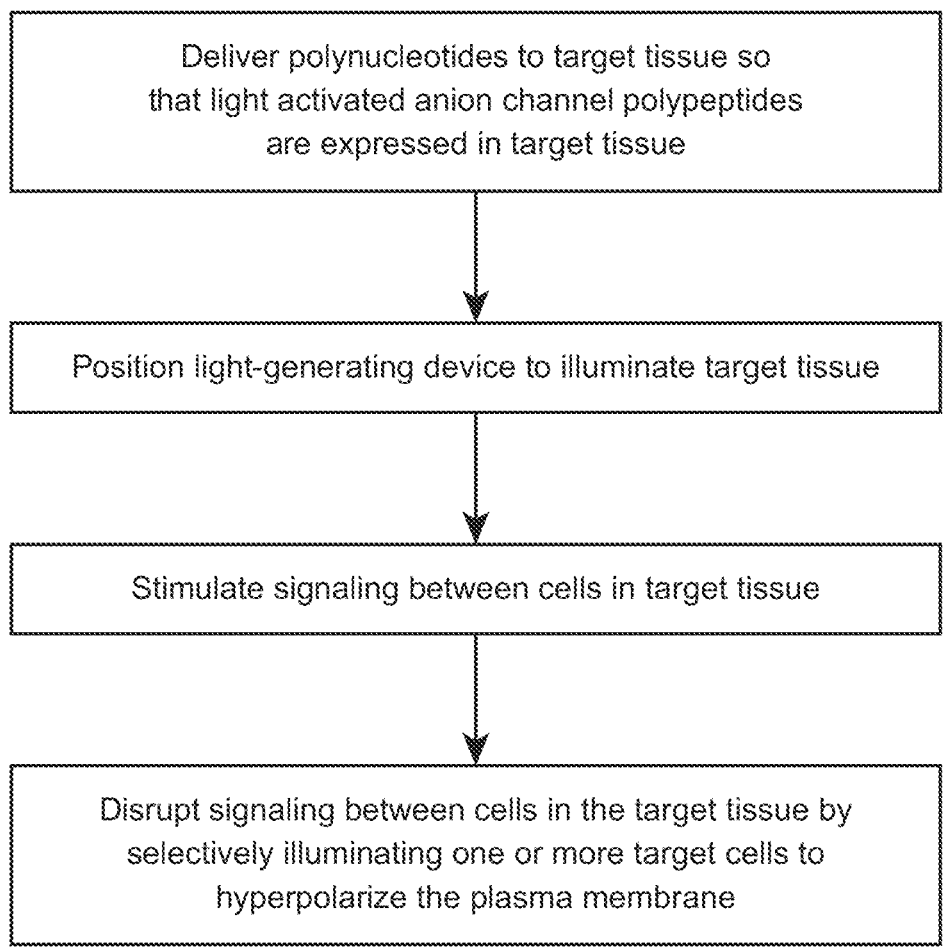
FIG. 11 shows a flow diagram that illustrates the steps of an example method in accordance with embodiments of the disclosure.

Turning now to FIG. 10, a third example of an optical stimulation system 120 is depicted. The optical stimulation system 120 comprises a light-generating device 102, a control device 103, and optical fibers 104 for conveying light generated by the light generating device 102 to various positions along the spinal cord 121 of the patient.

Methods

Aspects of the present disclosure include methods for optogenetic modulation of action potentials in target cells. The subject methods generally involve introducing a light-activated anion channel protein into a target cell and illuminating the target cell with light of an activating wavelength. Illumination of the target cell with light of an activating wavelength causes the light-activated anion channel protein to allow one or more anions to pass through the plasma membrane of the target cell. The passage of the anions through the plasma membrane of the target cell has a desired effect, such as, e.g., modulating the membrane potential of the plasma membrane. In some embodiments, the passage of the anion species through the plasma membrane may be used to modulate one or more neurological responses or processes in a patient, and may therefore by used to treat a disease or condition in the patient. As such, in some embodiments, the subject methods involve treating a patient for a condition, such as a neurological condition, using the systems and devices provided herein. The subject methods are now described in greater detail below.

Modulating Membrane Potentials in Target Cells

In some embodiments, the subject methods involve modulating membrane potentials in target cells using the subject systems and devices. In some embodiments, a nucleic acid encoding a subject light-activated anion channel protein is introduced into a target cell such that the target cell expresses the protein. The target cell is then illuminated with light of an activating wavelength using a light-generating device. Illumination of the light-activated anion channel protein results in the movement of one or more anions through the plasma membrane of the cell in response to light. In some embodiments, for example, the light-activated anion channel protein is a chloride anion channel protein, and in response to light the anion channel protein allows chloride ions to flow from the external side of the plasma membrane to the internal side of the plasma membrane. In certain embodiments, the activation of a light-activated chloride anion channel results in hyperpolarization of a cell. In certain embodiments, the activation of a light-activated chloride anion channel results in hyperpolarization of a nerve cell membrane and inhibition of action potentials without depolarizing the nerve cell to or beyond an action potential generation threshold.

Specific Inhibition of Activity Along an Axonal Projection

In some embodiments, the subject methods involve inhibiting and/or blocking activity along a portion of a nerve cell (e.g., along an axon of a nerve cell, or at the termination of an axonal projection of a nerve cell) using the subject systems and devices. For example, in some embodiments, the subject methods involve introducing into a nerve cell a subject light-activated anion channel protein. Polynucleotides encoding the proteins are introduced into the nerve cell, and the proteins are expressed by the nerve cell and inserted into the plasma membrane of the nerve cell.

Next, a light-generating device is positioned such that a target portion of the nerve cell (e.g., the axon, or a portion of the axon of the nerve cell) is illuminated with light of an activating wavelength when the light-generating device is activated. Next, the light-generating device is activated to deliver light to the desired nerve cell or portion thereof to cause the light-activated anion channel protein to allow anions to flow through the plasma membrane of the nerve cell. In some embodiments, the light-activated anion channel protein is a chloride anion channel protein that allows chloride anions to flow from the external side of the nerve cell membrane to the internal side of the nerve cell membrane. This results in hyperpolarization of the plasma membrane of the nerve cell without depolarizing the nerve cell membrane to or beyond an action potential generation threshold.

Hyperpolarization of the plasma membrane of the nerve cell inhibits action potentials by increasing the stimulus that is required to depolarize the membrane to an action potential threshold. Accordingly, the subject methods may be used to block or inhibit action potentials in a particular nerve cell or in a portion thereof (e.g., an axon or a portion thereof) by delivering light of an activating wavelength to the nerve cell or to a specific portion of the nerve cell. Importantly, action potentials may still propagate through other portions of the nerve cell or axon that are not illuminated with light of a wavelength that activates the subject light-activated anion channel protein. In this way, specificity is achieved for inhibiting action potentials in specific target cells or specific portions thereof.

Modeling of Diseases or Conditions Involving Action Potentials

In some embodiments, the subject methods may be used for studying and/or modeling certain diseases or conditions in a subject, such as conditions that involve or result from improper formation of action potentials and/or an improper blockade of action potential formation within a cell. For example, the subject methods may be used to specifically inhibit the formation of action potentials in target cells, such as specific target nerve cells, to study the effects of blocking action potential formation in those cells. In some embodiments, the subject methods may be used to selectively inhibit the formation of action potentials in certain portions of a target cell, such as an axon of a target nerve cell, to study the effects of inhibiting action potential formation in the selected portion of the target cell. Such methods may be used as models of diseases or conditions in which action potentials fail to properly form in a target cell or a portion thereof, or wherein action potentials are erroneously formed in a target cell or a portion thereof.

In some embodiments, the subject methods may be used, e.g., for screening compounds that may be effective in treating diseases or conditions involving the formation of action potentials in target cells, or the failure of action potentials to form in target cells. In some embodiments, the screening methods involve culturing cells in vitro and contacting the cultured cells with a nucleic acid encoding one or more of the subject engineered light-activated anion channel proteins such that the cultured cells express the anion channel protein. A cultured cell expressing the anion channel protein is contacted with a test compound, and the cell is then exposed to light of an activating wavelength to inhibit the formation of action potentials within the cell or a portion thereof. The ability of the test compound to elicit a desired effect or response from the cell while action potential formation is being inhibited may be useful in the treatment of a particular disease or condition.

In some embodiments, the subject methods may be used in animal models (including but not limited to transgenic animal models) of diseases of conditions associated with improper formation of action potentials within target cells, or portions thereof, or associated with the blockade of the formation of action potentials within target cells, or portions thereof. For example, in some embodiments, a target cell of an animal (such as a nerve cell, e.g., a brain cell of a rodent) may be contacted with a nucleic acid encoding a subject engineered light-activated anion channel protein so that the anion channel protein is expressed by the target cell. Next, the target cell is illuminated with light of an activating wavelength to inhibit the formation of action potentials in the target cell. The effect of the inhibition of action potential formation within the target cell, or a portion thereof, on the animal can then be examined. The use of transgenic animals that overexpress one or more gene products, or the use of "knock-out" transgenic animals that fail to express one or more gene products, may be used to investigate the role of specific gene products in the formation of action potentials in target cells.

Methods of Treatment

In some cases, a subject method involves modulating the activity of a target cell in vivo. A nucleic acid comprising a nucleotide sequence encoding a subject light-responsive anion channel polypeptide is introduced into a target cell, where the encoded light-responsive anion channel polypeptide is produced in the cell; and the light-responsive anion channel polypeptide is activated by exposure to light of an activating wavelength.

In some embodiments, the subject methods are used to treat a patient for a condition or disorder, such as a neurological condition or disorder, by optogenetically modulating the action potentials of target cells within the patient. In some embodiments, the subject methods involve introducing an engineered light-activated anion channel protein into a target tissue within the patient. In some embodiments, introduction of the subject anion channel proteins into the target tissue is accomplished using a subject delivery device. The polynucleotides encoding the subject anion channel proteins are introduced into the target tissue, and the proteins are expressed by target cells (e.g., nerve cells) in the target tissue and inserted into the plasma membrane of the target cells.

Next, a light-generating device is positioned to illuminate the target tissue with light of an activating wavelength when the light-generating device is activated. The light-generating device is activated (either by the patient, or by a caregiver (e.g., medical personnel)) to deliver light to the target tissue to cause the light-activated anion channel proteins to allow anions (e.g., chloride anions) to pass through the plasma membrane and hyperpolarize the plasma membrane, thus inhibiting the formation of action potentials within the cell(s) of the target tissue.

As such, the formation of action potentials within the cell is blocked for the duration of the effect of the light pulse and the resulting hyperpolarization of the plasma membrane. Accordingly, the subject methods may be used to block the formation of an action potential in a nerve cell by introducing the subject anion channel proteins into the nerve cell and illuminating the nerve cell with light of an activating wavelength from a light-generating device. As the duration of the action potential blockade can be tailored to outlast the duration of a light pulse, inhibition of action potential formation may be achieved using pulsed light delivery, rather than continuous light delivery.

In some embodiments, the subject methods involve treating a subject for a disorder by inhibiting the formation of action potentials in a target tissue. Accordingly, in some embodiments, the subject methods involve treating a subject by introducing into a target cell a light-activated anion channel protein. Polynucleotides encoding these proteins are introduced into the target cell, and the proteins are expressed by the target cell and inserted into the plasma membrane of the target cell. Next, the target cell is illuminated with light of an activating wavelength from a light-generating device to cause the light-activated anion channel protein to allow anions (e.g., chloride anions) to flow through the plasma membrane from outside of the cell to the inside of the cell.

Once inside the cell, the chloride anions hyperpolarize the membrane to inhibit the formation of an action potential. The hyperpolarization of the membrane prevents the formation of an action potential and therefore prevents the cell from, e.g., generating action potentials in surrounding cells, e.g., neighboring nerve cells; mediating the release of neurotransmitters, modulators, or hormones; mediating muscle contraction; and the like until the effect of the membrane hyperpolarization dissipates. Accordingly, the subject methods may be used to treat a subject for a disorder by blocking the formation of action potentials within a target cell. Since the duration of the membrane hyperpolarization can be tailored to outlast the duration of the light pulse, inhibition of action potential formation may be achieved using pulsed light delivery, rather than continuous light delivery.

Accordingly, the subject methods may be used to treat any disease or condition in which blocking or inhibiting the formation of an action potential a target cell, or along a particular portion of a target cell, would have a therapeutic effect for the patient. Examples of therapeutic applications of the subject methods include, without limitation, therapy for cardiac rhythm disorders, such as pacing, cardioversion, defibrillation, resynchronization, or other cardiac-related conditions; gastrointestinal therapy, such as therapy to address obesity, motility disorders (e.g., gastroparesis), dyspepsia, or other therapies, therapy for pelvic floor tissue (e.g., sacral or pudendal nerve tissue) to support pelvic floor therapy such as pain therapy, urinary or fecal incontinence therapy, sexual dysfunction, or other therapies; cranial nerve therapy, such as therapy to relieve occipital neuralgia, trigeminal neuralgia, facial pain, migraine headaches; therapy for the treatment of pain, such as nociceptive pain or neuropathic pain; therapy for neurological and/or psychiatric conditions; therapy for endocrine conditions; or the like. Specificity can be achieved as above by inhibiting action potential formation in specific subdomains or portions of the axonal arborization or cell.

Kits

Also provided are kits that at least include the subject systems and devices or components thereof, e.g., as described above, and instructions for how to use the subject systems and/or devices to optogenetically modulate action potentials in a target tissue. In some embodiments, a kit may include one or more of the subject polynucleotides, vectors, or pharmaceutical compositions. Kits in accordance with embodiments of the present disclosure may also include one or more devices, such as one or more delivery devices, one or more light-generating devices, and/or one or more control devices.

The instructions for using the systems and devices as discussed above are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or sub-packaging) etc. In other embodiments, the instructions are present as an electronic storage data file present on a suitable computer-readable storage medium, e.g., a digital storage medium, e.g., a CD-ROM, diskette, etc. The instructions may take any form, including complete instructions for how to use the systems and devices or as a website address with which instructions posted on the Internet may be accessed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Materials and Methods

The following materials and methods were used in the examples below.

Structural Representations

Figures of the C1C2 structure were generated using the PyMOL Molecular Graphics System, Version 1.7.0.1 (Schrodinger, LLC; PNAS 98:10037-41, 2001).

Point Mutagenesis of C1C2

C1C2 mutations were introduced using the Quick-Change™ Site-Directed mutagenesis kit (Agilent) and purified with QIAprep™ Spin Miniprep Kits (Qiagen) after transformation and amplification in *E. coli*. AAV vectors bearing the CaMKIIα promoter were used for protein expression in neurons, and a pcDNA3.1 vector bearing the CMV promoter was used for expression in HEK cells. All clones were fused to the eYFP (enhanced yellow fluorescent protein) gene for fluorescence microscopy.

Neuronal Culture Preparation and Imaging

Primary hippocampal neurons were cultured from postnatal day 0 (P0) Sprague-Dawley rat pups (Charles River). The CA1 and CA3 regions were isolated, digested with 0.4 mg/mL papain (Worthington), and plated onto 12 mm glass coverslips pre-coated with 1:30 Matrigel (Beckton Dickinson Labware), at a density of 65,000 cells per well in 24-well plates. The cultured cells were maintained in Neurobasal-A medium (Invitrogen) containing 1.25% FBS (HyClone), 4% B-27 supplement (Gibco), 2 mM Glutamax (Gibco) and 2 mg/ml fluorodeoxyuridine (FUDR, Sigma), and kept in a humid culture incubator with 5% $CO_2$ at 37° C.

Cells were transfected at 6-10 days in vitro (DIV). A $DNA$-$CaCl_2$ mix containing the following was prepared per each well to be transfected: 2 μg of DNA (prepared using an endotoxin-free preparation kit (Qiagen)) 1.875 μl 2M $CaCl_2$, and sterile water to a total volume of 15 μl. An additional 15 μl of 2× filtered HEPES-buffered saline (HBS, in mM: 50 HEPES, 1.5 $Na_2HPO_4$, 280 NaCl, pH 7.05 with NaOH) was added per $DNA$-$CaCl_2$ mix, and the resulting $DNA$-$CaCl_2$-HBS mix was incubated at room temperature for 20 minutes. During this time, the neuronal growth medium was removed from the wells and saved at 37° C., and replaced with 400 μl pre-warmed minimal essential medium (MEM). Once the $DNA$-$CaCl_2$-HBS mix incubation was complete, the mix was then added dropwise into each well, and the plates were kept in the culture incubator for 45-60 minutes. Afterwards, each well was washed three times with 1 ml of pre-warmed MEM, and then the MEM was replaced with the original neuronal growth medium. The transfected cells were then returned to the culture incubator until recordings.

For confocal images of opsin-eYFP-expressing neurons, coverslips of transfected cells expressing were fixed for 15 minutes in 4% paraformaldehyde and mounted with PVA-DABCO. Images were acquired with a Leica DM600B confocal microscope, and the same settings were used across images.

Electrophysiological Recordings in Hippocampal Neurons

The Spectra X Light engine (Lumencor) was coupled to the fluorescence port of an Olympus BX61WI microscope to detect eYFP expression and to deliver light for opsin activation. 475/15 and 632/22 filters were used for blue light and red light respectively, and light power density through a 40× objective was measured with a power meter (ThorLabs). Whole-cell recordings were obtained with patch pipettes (4-6 MΩ) pulled from glass capillaries (Sutter Instruments) with a horizontal puller (P-2000, Sutter Instruments). The external recording solution contained (in mM): 135 NaCl, 4 KCl, 10 HEPES, 2 $CaCl_2$, 2 $MgCl_2$, 30 D-glucose, pH 7.3 with synaptic transmission blockers 25 μM D-APV, 10 μM NBQX. The internal solution recording solution contained (in mM): 140 K-gluconate, 10 HEPES, 10 EGTA, 2 MgCl2, pH 7.3. Measurements were corrected for the liquid junction potential of +16 mV. We used 3 M CsCl agar bridges for the reference electrode at all recordings. Series resistance was monitored throughout recordings for stability. Recordings were made using a MultiClamp700B amplifier (Molecular Devices). pClamp10.3 (Molecular Devices), OriginLab8 (OriginLab), and Sigmaplot (SPSS) software was used to record and analyze data.

The stationary photocurrent upon light activation was used as the measure of photocurrent amplitude at different membrane potentials. The reversal potential (Vrev) was defined as the point where the stationary photocurrent amplitude was 0 pA. Action potential threshold was measured at the voltage deflection point at which the first-order derivative of the membrane potential (dV/dt) exhibited a sharp transition, typically >10 mV/ms. The resting membrane potential of the cell was measured in current-clamp after attaining whole-cell configuration. Input resistance was calculated from the steady-state current responses evoked by 20 mV hyperpolarizing steps in voltage-clamp. To investigate action potential inhibition, we tested opsin-expressing cells under two different spike induction protocols. Spikes were electrically evoked with intracellular current injections, either with short electrical pulses (30 ms pulse width, 50-280 pA) 10 Hz, or with a continuous 3 s electrical pulse. Light was applied for 1 s (during the 10 Hz train) or 0.5 s (during the continuous pulse) during the middle of the electrical current injection. Spike inhibition probability was calculated as the fraction of electrically-evoked spikes that were blocked during the light pulse epoch of the electrical stimulation.

HEK Cell Culture Preparation

Human embryonic kidney cell cultures (HEK-293: ATCC® CRL-1573™) were maintained in 50 ml Dulbecco's Modified Eagle Medium (Life Technologies) containing 100 units/mL of penicillin and 100 μg/mL of streptomycin as well as fetal bovine serum at a dilution of 1:10. HEK cells were grown in incubators at 37° C./5% $CO_2$ and were transferred to a new 225 $cm^2$ culture flask (Thermo) every 3 to 4 days at passaging dilutions ranging from 1:5 to 1:8. 24 h prior to DNA transfections cells were plated on 2 cm poly-D-lysine coated glass cover slips and maintained in 24 well culture plates (Thermo) with 500 μl growth medium. 24 h prior to recordings, HEK cells were transfected with 1.6 μl plasmid DNA per well using 2 μl Lipofectamine 2000 (Life Technologies).

HEK Cell Electrophysiology

ChR-expressing cells were identified by eYFP fluorescence and recorded ~18 to 30 hours after transfection. The same equipment and methods as for neurons was used. Measurements were conducted in voltage clamp at membrane potentials between −75 and +55 mV. An external 3M CsCl agar bridge was used in all recordings. All constructs were characterized using the same internal and external recordings. All constructs were first characterized using the same internal and external solution as in neurons and were corrected for the corresponding junction potential, and stationary photocurrents were used for data analysis. The activation spectra for C1C2, iC1C2 and NpHR was determined by measuring stationary photocurrents at −75 mV in response to low light intensities at 0.65 $mW/mm^2$ in order to prevent saturation. 20 nm bandbass filters (Thorlabs) were used to apply light at different wavelengths (in nm): 400, 420, 440, 460, 470, 480, 490, 500, 520, 540, 560, 570, 580, 590, 600, 620, 630, 650. All photocurrents were normalized to reference values at 470 nm (C1C2 and iC1C2) or 570 nm (NpHR). Kinetics of channel closure were quantified by fitting photocurrents after light-off with mono-exponential functions in order to obtain corresponding $\tau_{off}$ values. Light sensitivity measurements were carried out at 470 nm (C1C2, iC1C2) or 560 nm (NpHR). Light was applied at intensities from 0.0021 to 5 mW/mm² and normalized corresponding photocurrents to the value at maximum light intensity.

Ion selectivities were determined by varying ion composition and pH of the internal and external solutions. External solutions contained (in mM) 2 CaCl$_2$, 2 MgCl$_2$, 120 NaCl, 120 CsCl or 120 Na-gluconate, 10 Citric acid/Na-citrate (pH 6) or 10 HEPES (pH 7.3) or 10 Tris (pH 9). Internal solutions contained (in mM) 2 CaCl$_2$, 2 MgCl$_2$, 120 KCl, 120 CsCl or 120 K-gluconate, 10 Citric acid/Na-citrate (pH 6) or 10 HEPES (pH 7.3) or 10 Tris (pH 9). Junction potential was corrected for under each condition (in mV): $KCl_{int}/NaCl_{ext}$=4, $KCl_{int}/CsCl_{ext}$=−0.6, $KCl_{int}/NaGluc_{ext}$=−6.2, $KGluc_{int}/NaCl_{ext}$=15.8, $CsCl_{int}/NaCl_{ext}$=4.6. The Nernst equation was used to determine the Nernst potential for cations, Cl— and protons under each external and internal ion composition and pH. An adapted Goldman-Hodgkin-Katz equation was used to calculate the ratio of proton to Cl⁻ permeability in iC1C2. Permeability for Na+ and K+ was assumed to be zero, which resulted in:

$$V_{rev} = \frac{RT}{F} \ln \frac{P_H[H^+]_{ext} + P_{Na}[Na^+]_{ext} + P_K[K^+]_{ext} + P_{Cl}[Cl^-]_{int}}{P_H[H^+]_{int} + P_{Na}[Na^+]_{int} + P_K[K^+]_{int} + P_{Cl}[Cl^-]_{ext}}$$

$$V_{rev} = \frac{RT}{F} \ln \frac{P_H[H^+]_{ext} + P_{Cl}[Cl^-]_{int}}{P_H[H^+]_{int} + P_{Cl}[Cl^-]_{ext}}$$

$$\alpha = \frac{P_{Cl}}{P_H}$$

$$V_{rev} = \frac{RT}{F} \ln \frac{[H^+]_{ext} + \alpha[Cl^-]_{int}}{[H^+]_{int} + \alpha[Cl^-]_{ext}}$$

R=Gas constant, F=Faraday constant, T=absolute temperature.

Statistical analysis was performed with a t-test or a two-way ANOVA, and a Mann-Whitney test for non-parametric data, using Origin8 (OriginLab) and Sigmaplot (SPSS) software. Data is presented as mean±s.e.m., and error bars indicate s.e.m. $p<0.05$ is defined to be statistically significant.

Example 1: Structure-Guided Screen for Light-Activated Anion Channel Proteins

Figure 1B:
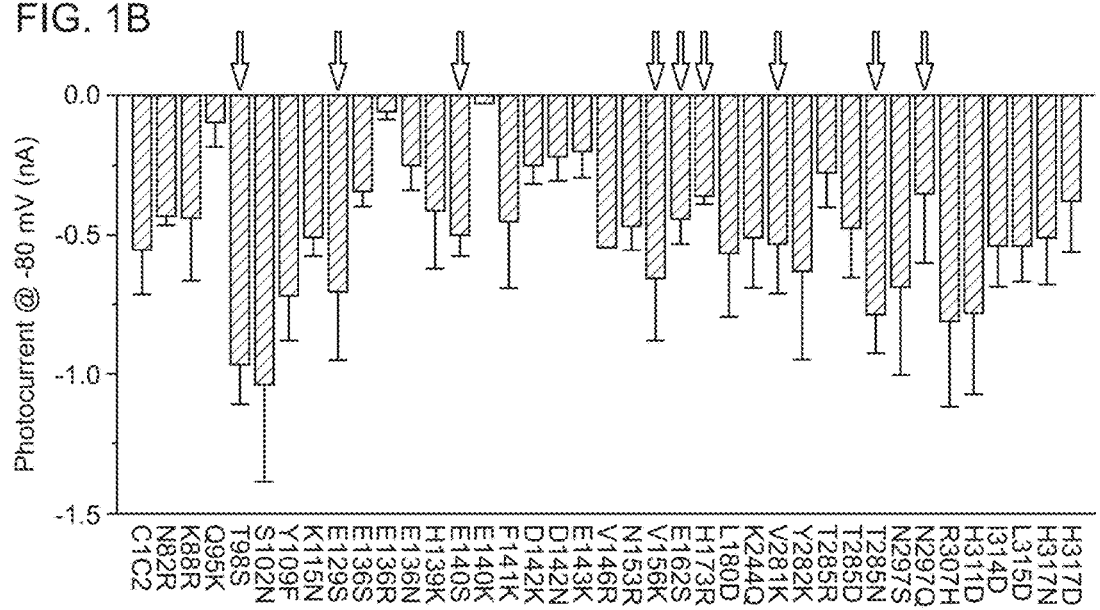
Figure 1C:
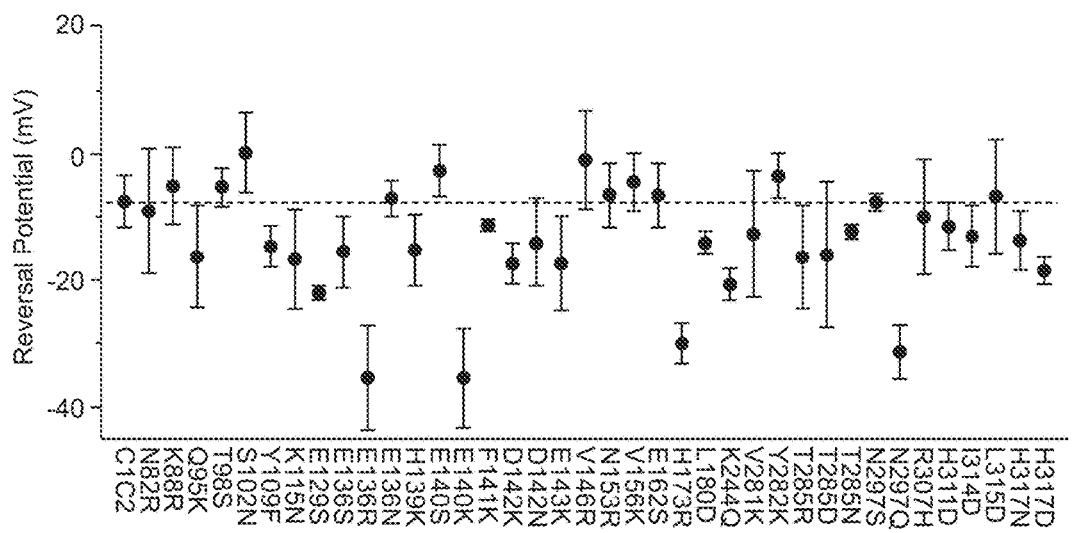
Figure 1D:
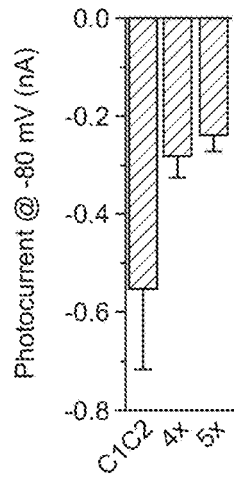
Figure 1E:
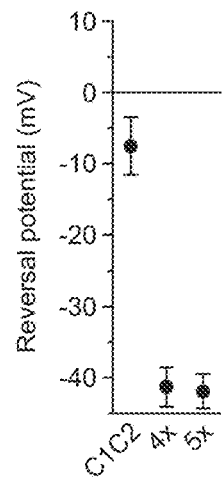

A structure-guided screen was conducted by introducing single site-directed mutations into C1C2 (FIG. 1A). All variants were expressed in cultured rat hippocampal neurons and photocurrents were tested using a whole-cell patch-clamp to ensure proper function in neurons (external/internal [Cl⁻]: 147 mM/4 mM). Stationary photocurrent amplitudes were quantified across a range of holding potentials (FIG. 1B), with particular attention to $V_{rev}$, to identify permeability variants (FIG. 1C). C1C2 exhibited $V_{rev}$ of −7 mV under these conditions, typical for non-specific cation channels. Certain mutations with powerful effects on $V_{rev}$ displayed concomitant adverse effects on photocurrent sizes (e.g. E136R and E140K; FIG. 1B), and were not studied further. More promising mutations, such as N297Q and H173R, exhibited both potent currents and altered $V_{rev}$ (FIG. 1C), and were combined in a series of increasingly integrated mutations. The 5-fold mutation T98S/E129S/E140S/E162S/T285N and 4-fold mutation V156K/H173R/V281K/N297Q both displayed prominently-shifted $V_{rev}$ (in the range of −40 mV) while maintaining functionality (FIG. 1D-1E).

Figure 2A:
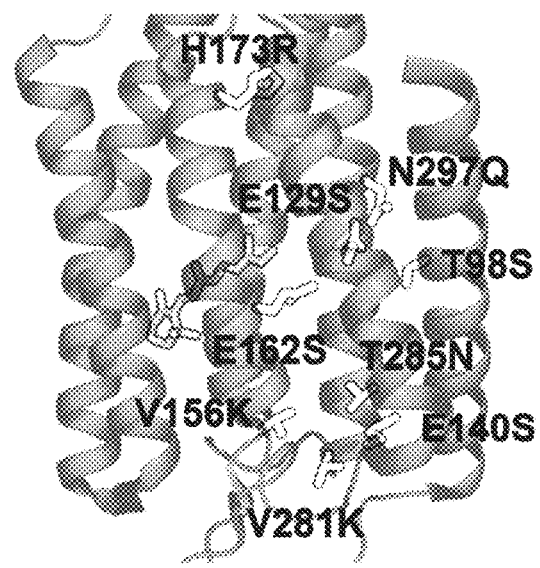
FIG. 2A-2J show biophysical properties of iC1C2.
Figure 2B:
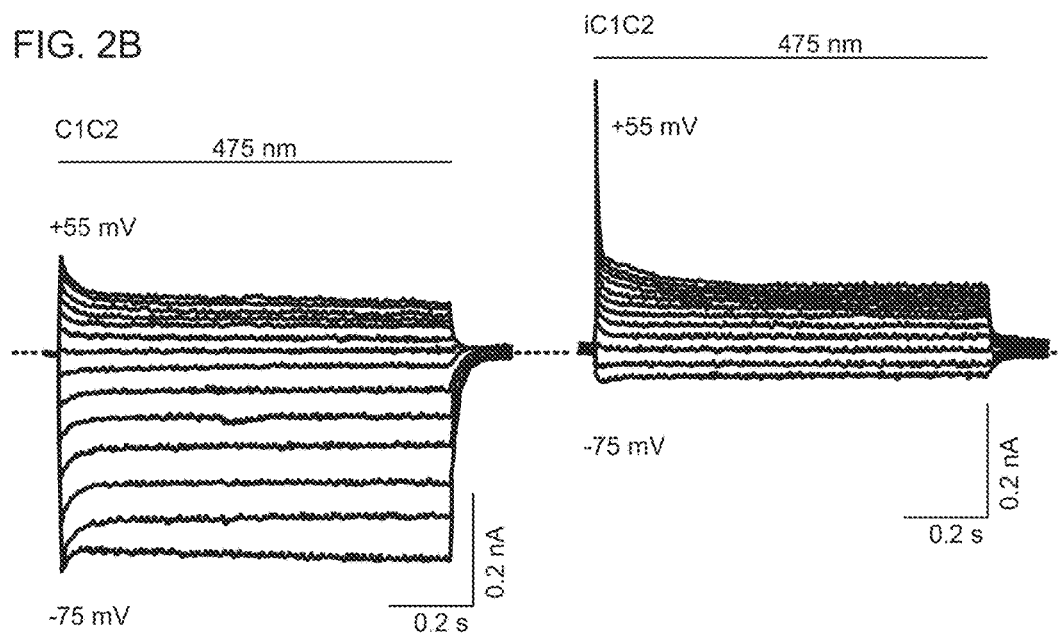
Figure 2C:
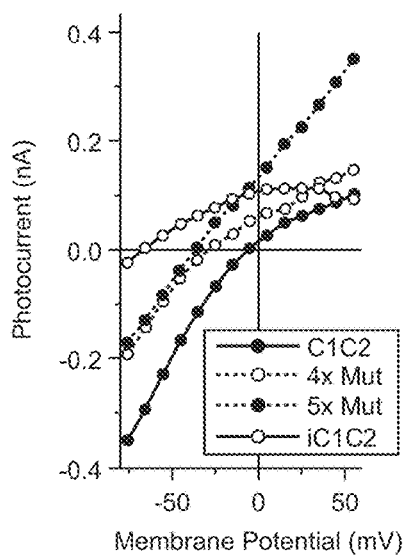
Figure 2D:
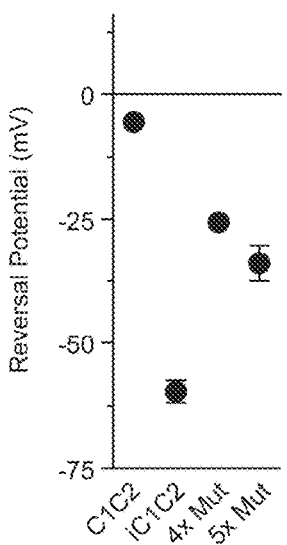
Figure 2E:
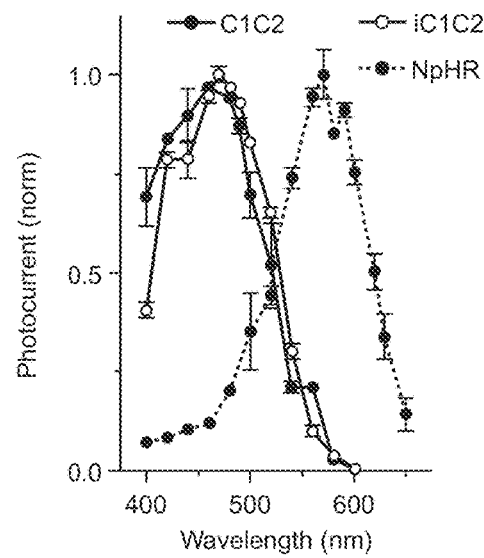

These constructs were combined to generate a 9-fold mutated variant with contiguous shifts in expected electrostatic potential distribution (FIG. 2A, FIG. 5). The 9-fold variant was expressed in HEK-293 cells to test both $V_{rev}$ and permeability under controlled ion composition and optimized voltage clamp settings (FIG. 2B). Photocurrents were mapped over a broad range of membrane potentials (FIG. 2C) (from −75 mV to +55 mV; Methods). Under these conditions (external/internal [Cl⁻]: 147 mM/4 mM), the combined 9-fold mutation exhibited $V_{rev}$ of −61 mV, far more negatively shifted than the C1C2 backbone or either parental 4× or 5× construct (FIG. 2D). Despite this major change in functionality, both peak and stationary photocurrents remained fast and robust (predicting suitability for optogenetics, especially since this channel could also recruit a reduced-membrane resistance mechanism for spiking inhibition), and the original blue light-activation spectrum of C1C2 was maintained, compared with the red-activation capability of the Cl⁻ pump eNpHR3.0 (thus maintaining a separable channel for inhibitory control in optogenetic applications; FIG. 2D). This 9-fold variant was termed "iC1C2".

Figure 2F:
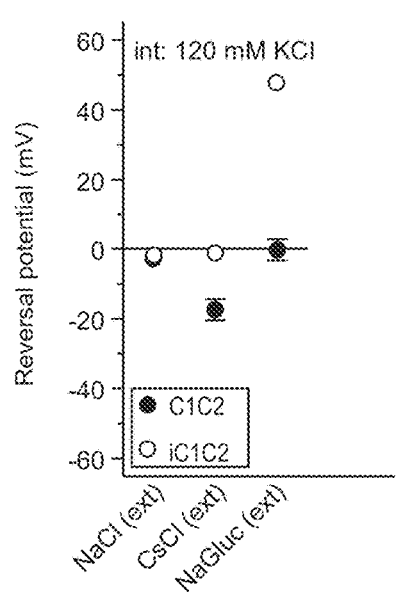
Figure 2G:
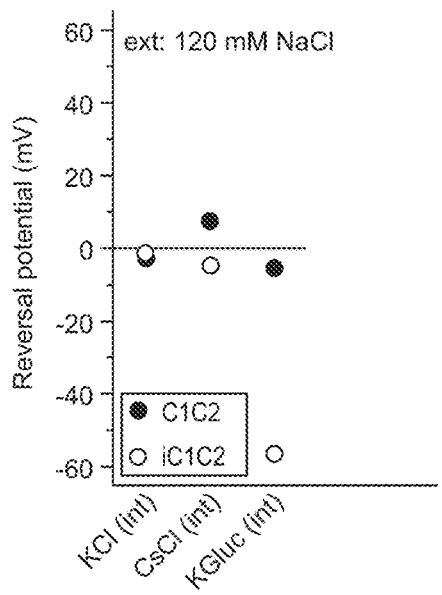

As the shifted $V_{rev}$ could be attributable to increased K⁺ selectivity or a new Cl⁻ conductance, $V_{rev}$ was measured under varying ion compositions (corrected for the calculated junction potential arising from each condition; Methods) in order to determine the specific ion selectivity of iC1C2. ChRs are highly permeable for protons and typically show no selectivity between K⁺ and Na⁺. Therefore, with a pipette solution composition of 120 mM KCl at pH 7.3 and a bath solution of 120 mM NaCl also at pH 7.3, virtually no chemical gradient for permeant ions would be expected, and indeed under these conditions $V_{rev}$ for both C1C2 and iC1C2 was ~0 mV (FIG. 2F). Replacement of external KCl by CsCl would create a strong outward-directed gradient for K⁺ ions, and, as expected under this condition, $V_{rev}$ of C1C2 dropped to −17.4 mV consistent with K⁺ as a major charge carrier. However, there was no such $V_{rev}$ shift for iC1C2 ($V_{rev}$=−1 mV). These data do not support a hypothesis that iC1C2 achieves shifted $V_{rev}$ by increased K⁺ conductance, and, in fact, iC1C2 does not appreciably conduct K⁺ under these conditions (FIG. 2F). To test the other possibility of new Cl⁻ conductivity, external Cl⁻ was replaced with gluconate (for a chemical Cl⁻ gradient of 8 mM$_{ext}$/128 mM$_{int}$ and shifting its Nernst potential to +71 mV). Despite this strong outward-directed Cl⁻ gradient, C1C2 showed no shift in $V_{rev}$ (0 mV), as expected since the native C1C2 does not conduct Cl⁻. In contrast, iC1C2 exhibited a positively shifted $V_{rev}$ of +48 mV, revealing a strong contribution of Cl⁻ to the photocurrent (FIG. 2F). Finally, internal Cl⁻ was replaced with gluconate to create a strong inward-directed Cl⁻ gradient (128 mM [Cl⁻]$_{ext}$/8 mM [Cl⁻]$_{int}$; $V_{Nernst-Cl}$=−71 mV). The resulting $V_{rev}$ was −6 mV for C1C2 but −57 mV for iC1C2, confirming a potent contribution from conducted Cl⁻ ions to iC1C2 photocurrents (FIG. 2G).

Figure 2H:
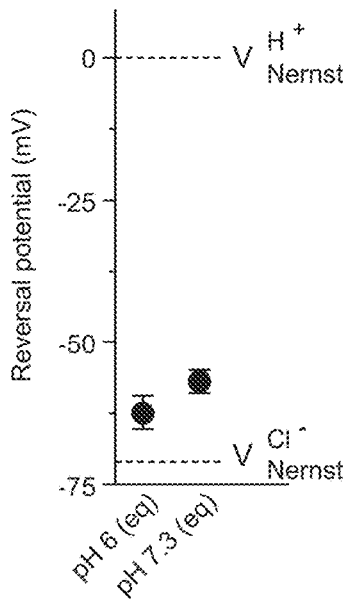
Figure 2I:
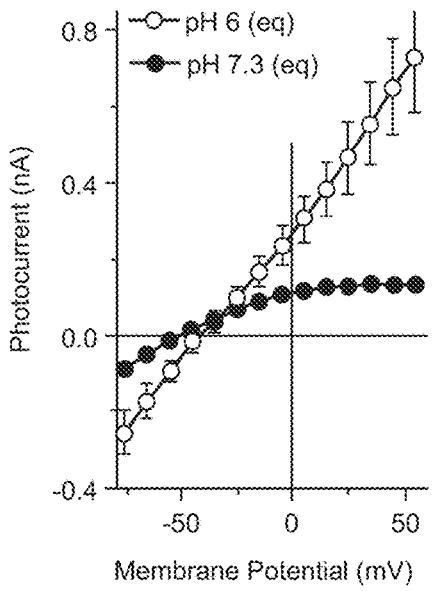
Figure 2J:
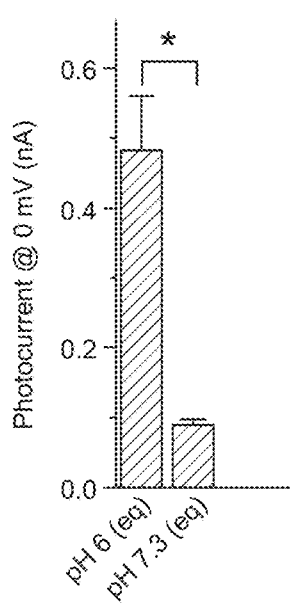

Since the $V_{rev}$ for iC1C2 was not identical to the calculated $V_{Nernst-Cl}$, other ions, such as protons could be conducted as well. To explore this possibility in physiological Cl⁻ gradients, the proton concentrations of internal and external solutions were altered while maintaining the inward-directed Cl⁻ chemical gradient (128 mM$_{ext}$/8 mM$_{int}$; $V_{Nernst-Cl}$=−71 mV) (FIG. 2H). The pH of external and internal solutions was varied together (no proton chemical gradient; $V_{Nernst-H+}$=0 mV), and iC1C2 responses at physiological (7.3) and low (6.0) pH were measured, with matched internal/external proton concentrations. The expectation was that at lower pH and more negative membrane potential protons would contribute more to the iC1C2 photocurrent, and thus positively shift $V_{rev}$ towards the 0 mV Nernst potential for protons. Surprisingly, the iC1C2 $V_{rev}$ was more negatively shifted at pH 6 compared to pH 7.3 (FIG. 2H), suggesting that iC1C2 conducts Cl⁻ even more robustly and maintains a prominently negative $V_{rev}$ at lower pH values. Total iC1C2 photocurrents were greater at lower pH values (FIG. 2I-2J), consistent with a proton-enhanced Cl⁻ permeability. The ratio of Cl— to proton permeability was calculated at the different pH values ($\alpha$=PCl/PH, see Methods). Indeed, at pH 6, the contribution of Cl⁻ to the overall current was 35 times higher than at pH 7.3, suggesting that even excursions to lower pH as can happen during extreme neural activity will not impair the important Cl⁻ conductance.

Figure 3A:
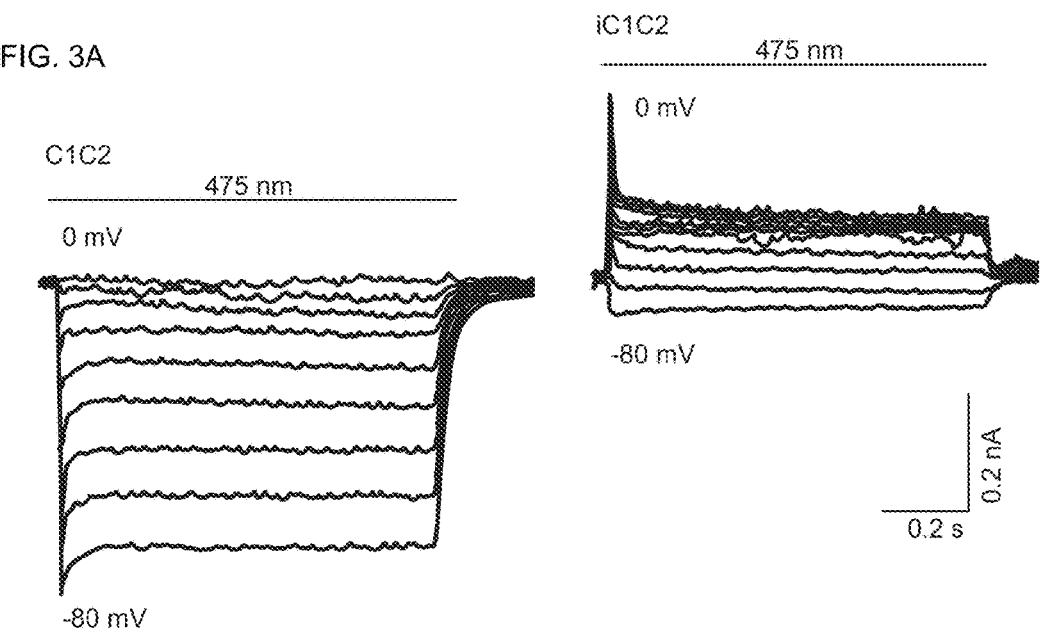
Figure 3B:
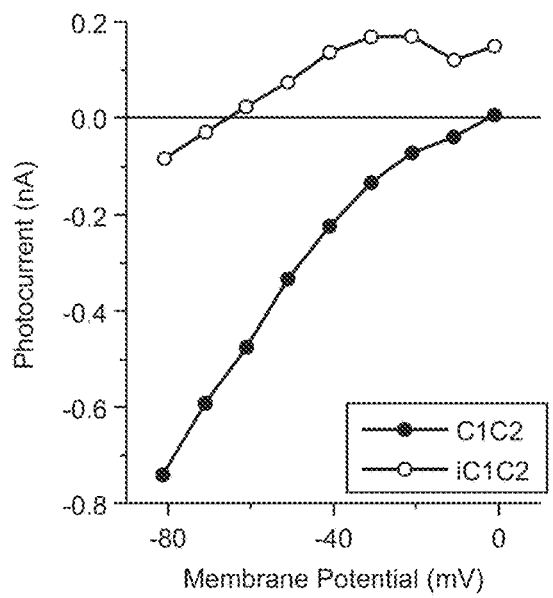
Figure 3C:
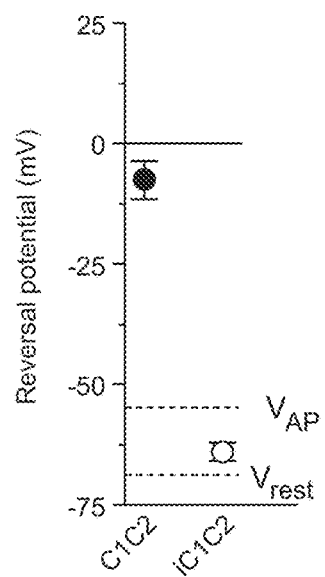

Example 2: Expression of Light-Activated Anion Channel Proteins in Cultured Neurons C1C2 and iC1C2 were expressed, each fused to enhanced yellow fluorescent protein (eYFP), in cultured hippocampal neurons (FIG. 5). Mean resting potentials were not different (C1C2: −65 mV; iC1C2: −69 mV) and input resistances were in the expected range (above 200 MΩ) for both constructs. $V_{rev}$ was determined (FIG. 3A), which for iC1C2 ($V_{rev}$=−64 mV) was negatively shifted by 56 mV compared to C1C2 ($V_{rev}$=−7 mV) (FIG. 3B). This $V_{rev}$ of iC1C2 lies more negative than the measured threshold for AP generation (VAP=−55 mV) (FIG. 3C). Consequently at $V_{AP}$, in voltage clamp C1C2 generated an inward-directed photocurrent of −475 pA, while iC1C2 produced an outward-directed photocurrent of +42 pA; in current clamp, C1C2 depolarized neurons by +20 mV while iC1C2 hyperpolarized neurons by −3 mV (FIG. 3D). In addition, input resistance dropped by about 50% during light in cells expressing iC1C2, indicating increased ion flux through membrane pores, and after light-off recovered to original levels (FIG. 3E).

Figure 4A:
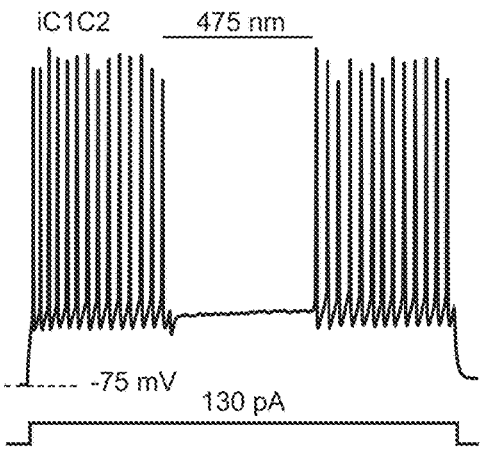
Figure 4B:
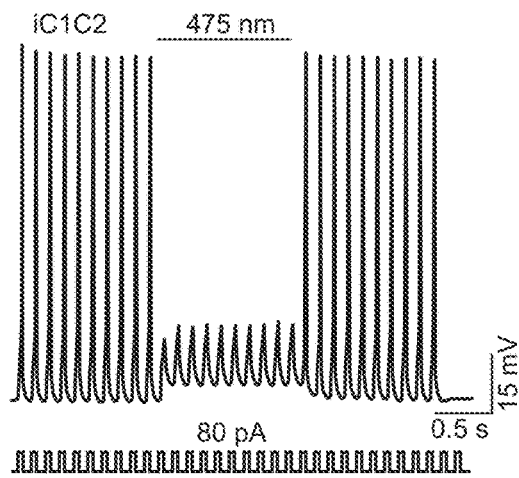
Figure 4D:
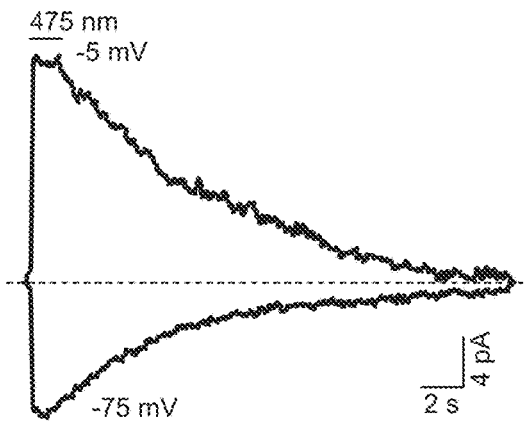
Figure 4C:
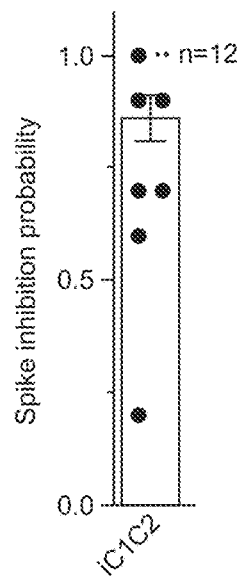
Figure 4E:
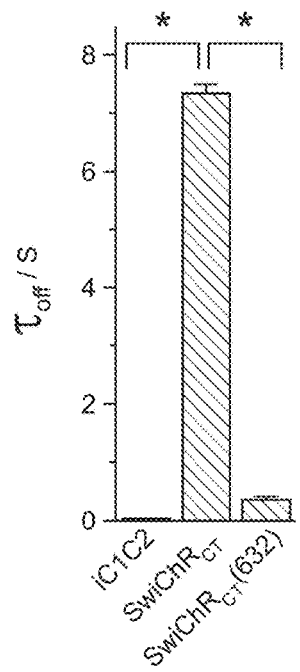
Figure 6:
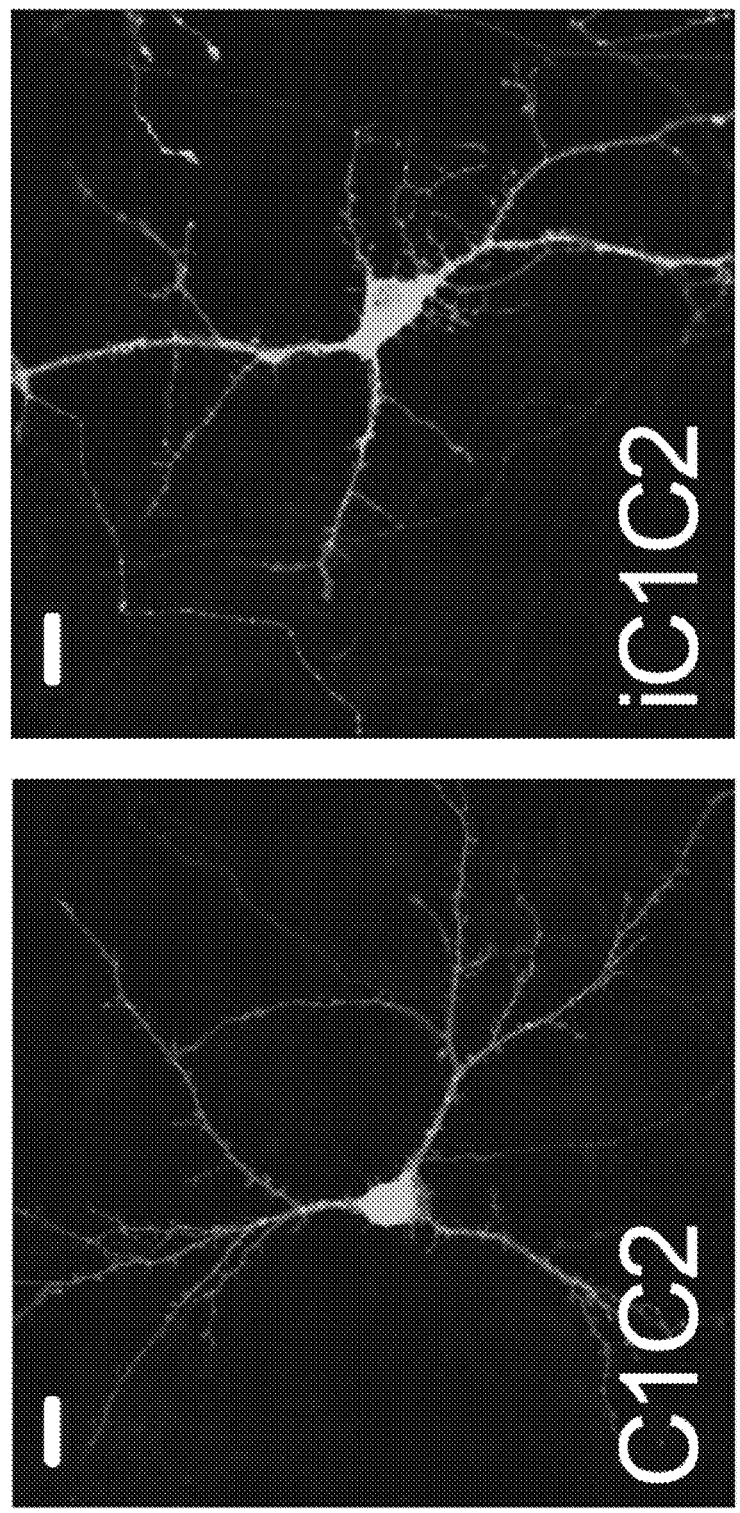
FIG. 6 shows confocal microscope images of cultured neurons expressing C1C2-eYFP (left panel) and iC1C2-eYFP (right panel). Scale bar: 20 µm.
Figure 7A:
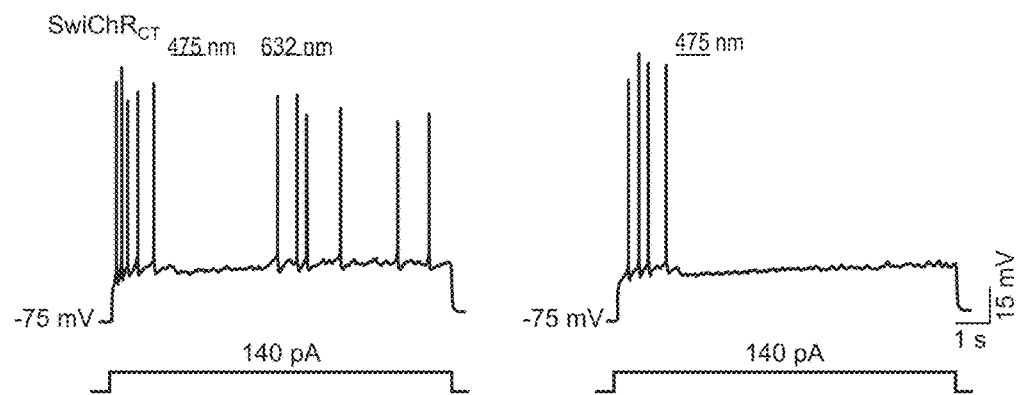
FIG. 7A-7D show bistable inhibition with SwiChRs.
Figure 7B:
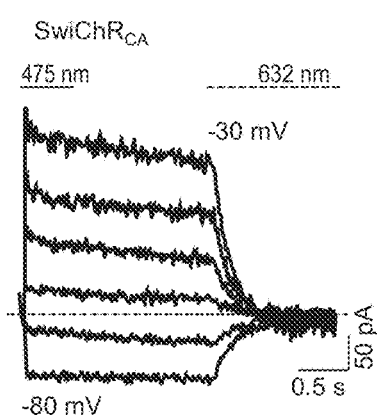
Figure 7C:
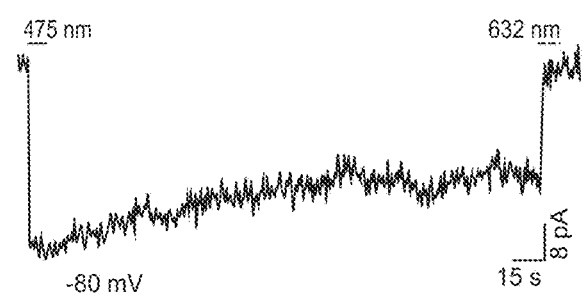
Figure 7D:
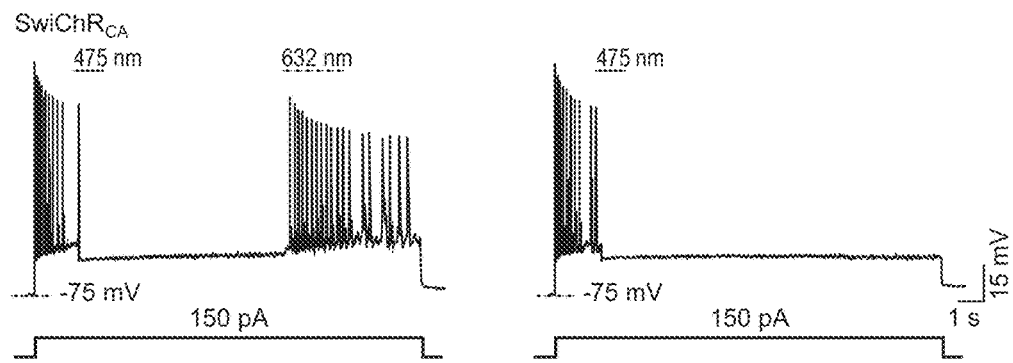

The iC1C2 input-resistance effects and iC1C2 membrane polarization effects that together would tend to maintain membrane potential below spike-firing threshold (FIG. 3F), suggested utility in optogenetic control of spiking Indeed, optical activation of iC1C2 sufficed to inhibit electrically-evoked spikes without exerting a depolarizing effect (FIG. 4A-4C). To further explore the properties of iC1C2, cysteine-167 was mutated to mimic step-function mutations of channelrhodopsin, which decelerate channel closure and extend lifetime of the ion-conducting state; as a result, brief light stimulation induces prolonged depolarization, and light sensitivity of cells expressing these variants is greatly increased. The inhibitory versions here define the SwiChR variants (for Step-waveform inhibitory ChR), including C167T (SwiChR$_{CT}$) and C167A (SwiChR$_{CA}$). SwiChR$_{CT}$ was first expressed in HEK cells to determine channel kinetics and sensitivity. Both inward and outward-directed photocurrents were stabilized by orders-of-magnitude after light-off (FIG. 4D). The time-constant of channel closure ($\tau$ off) for SwiChR$_{CT}$ was 7.3 s, compared to 24 ms for the parent iC1C2 (FIG. 4E). Beyond stability, another feature of step-function variants is the ability to quickly convert to the closed state upon red-shifted light application, and indeed, SwiChR$_{CT}$ channel closure was accelerated by application of 632 nm light (SwiChR$_{CT}$ $\tau$ off-632=375 ms) (FIG. 4E). Another feature of step-function variants is increased light sensitivity of expressing cells, which effectively become photon integrators for long light pulses. Indeed, SwiChR$_{CT}$-expressing cells showed a 25-fold increase in light sensitivity compared to iC1C2, and a 200-fold increase compared to the pump-based inhibitor NpHR (FIG. 4F). Similar results were observed in neurons; SwiChR$_{CT}$ generated outward current at AP threshold in neurons with reversal potential of −61 mV and −67 mV for SwiChR$_{CA}$ (FIG. 4G; FIG. 7). This sufficed to stably and reversibly inhibit spiking (FIG. 4H; FIG. 7) with minimal directly-driven current (FIG. 4G; FIG. 7) or membrane potential change (FIG. 4H; FIG. 7), presenting desirable properties for optogenetic investigation.

Structure-guided conversion of a cation-selective ChR into a light-activated Cl⁻ channel was demonstrated. The iC1C2 mechanism provides more physiological inhibition that does not require a major membrane potential change, and variants enable improvement of stability and light-sensitivity by orders of magnitude over existing inhibitory tools. Depolarization-block strategies with excitatory tools, while useful in some settings, may not reliably inhibit all targeted cells, since light intensities are highly variable in scattering tissue; in contrast, iC1C2-based tools can only depolarize membranes to $V_{rev}$ of ∼−64 mV (well below $V_{AP}$) and hyperpolarize when membrane potential is above $V_{rev}$ (FIG. 3F).

While aspects of final functionality arose by design (for example, removal of acidic residues and introduction of basic residues; FIG. 2A), other properties remain to be fully explored. The new Cl⁻ permeability of iC1C2 not only provides an unexpectedly effective illustration of cation-channel to anion-channel conversion, but also demonstrates structure-guided design of ChRs for new classes of functionality.

Example 3: Selective Interruption of Signaling Between Neurons

A network comprising two or more neurons that communicate with one another is identified. A target neuron in the network is identified and a nucleic acid encoding a subject light-activated anion channel polypeptide is introduced into the target neuron. The introduction of the nucleic acid into the target neuron causes the light-activated anion channel polypeptide to be expressed by the neuron and localized to the plasma membrane of the neuron. Subsequently, the target neuron, or a portion thereof, is illuminated with light of an activating wavelength. The illumination causes the light-activated anion channel polypeptide to open its anion channel pore, which allows chloride anions to enter the neuron and hyperpolarize the plasma membrane. The hyperpolarization of the plasma membrane of the neuron inhibits signaling between two or more neurons in the network by inhibiting the formation of an action potential in the target neuron.

Example 4: Treatment of Acute and Chronic Pain

One or more neurons that are associated with pain sensation by a subject are identified. A nucleic acid encoding a subject light-activated anion channel polypeptide is introduced into the one or more neurons associated with pain sensation. The introduction of the nucleic acid into the one or more neurons causes the light-activated anion channel polypeptide to be expressed by the neuron(s) and localized to the plasma membrane of the neuron(s). Subsequently, the neuron(s), or a portion thereof, is illuminated with light of an activating wavelength. The illumination causes the light-activated anion channel polypeptide to open its anion channel pore, which allows chloride anions to enter the neuron and hyperpolarize the plasma membrane. The hyperpolarization of the plasma membrane of the neuron inhibits the formation of an action potential in the neuron, thereby blocking or alleviating the sensation of pain in the subject.

Example 5: Treatment of Cough by Inhibiting the Phrenic Nerve

A nucleic acid encoding a subject light-activated anion channel polypeptide is introduced into the phrenic nerve of a subject having an urge to cough. The introduction of the nucleic acid into the phrenic nerve causes the light-activated anion channel polypeptide to be expressed by the phrenic nerve and localized to the plasma membrane of the phrenic nerve. Subsequently, the phrenic nerve, or a portion thereof, is illuminated with light of an activating wavelength. The illumination causes the light-activated anion channel polypeptide to open its anion channel pore, which allows chloride anions to enter the phrenic nerve and hyperpolarize the plasma membrane. The hyperpolarization of the plasma membrane of the phrenic nerve inhibits the formation of an action potential in the phrenic nerve, thereby blocking or reducing the subject's urge to cough.

Figure 17A:
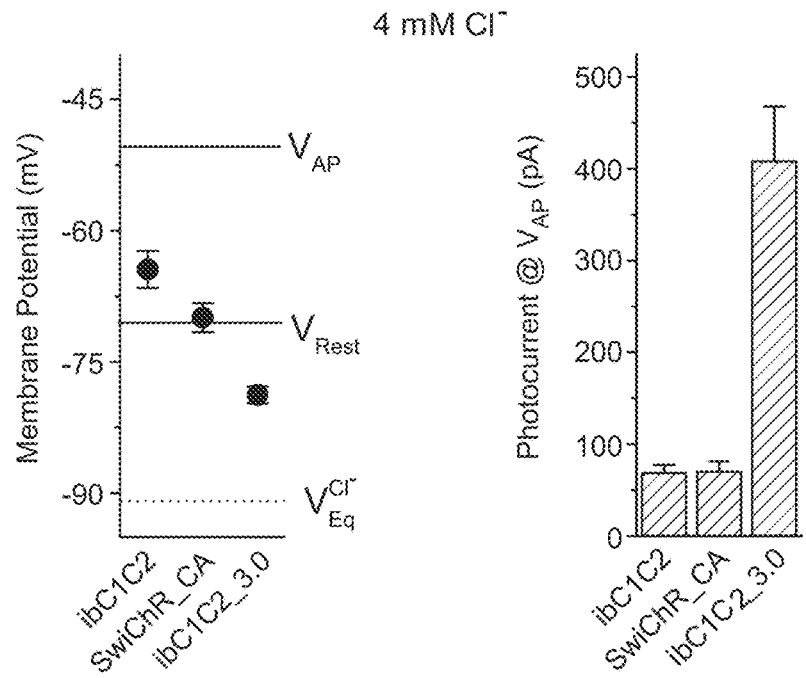
FIG. 17A-17B show four graphs that demonstrate the reversal potential and activity of improved inhibitory channelrhodopsins measured in cultured neurons.
Figure 17B:
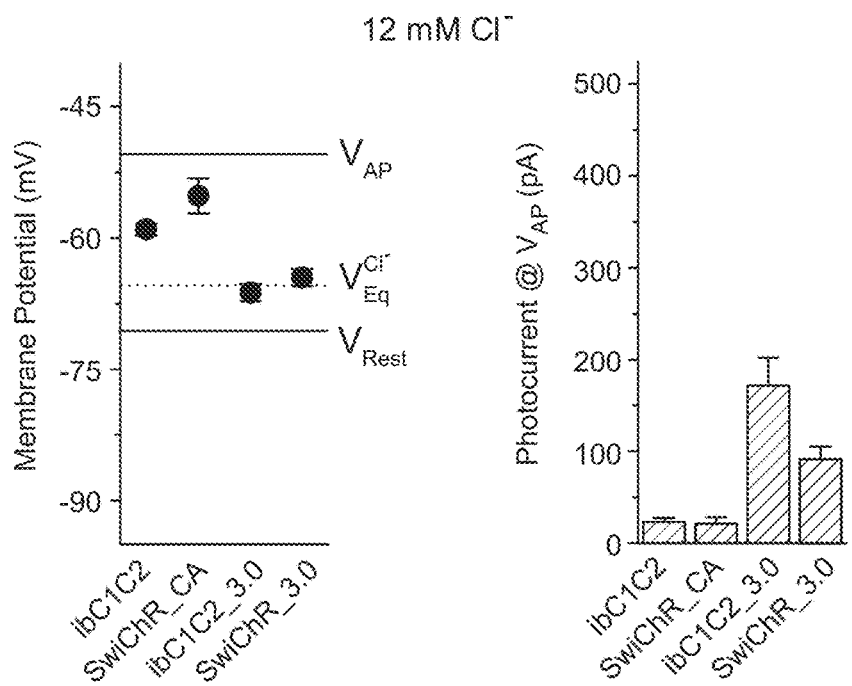
Figure 18A:
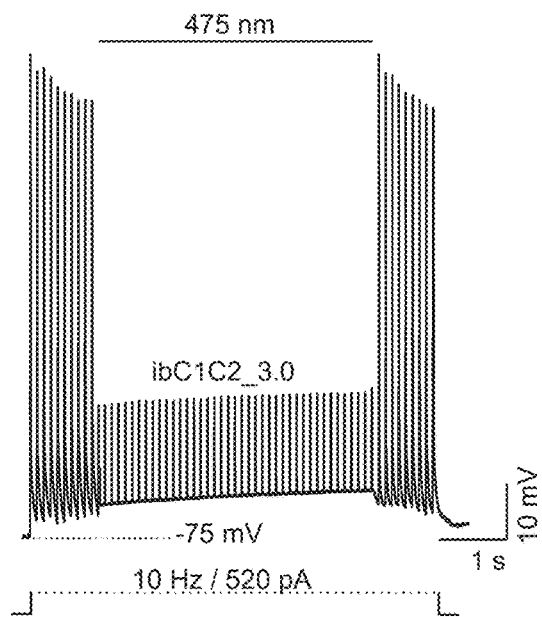
FIG. 18A-18C show three graphs that demonstrate inhibition of cultured neurons.
Figure 18B:
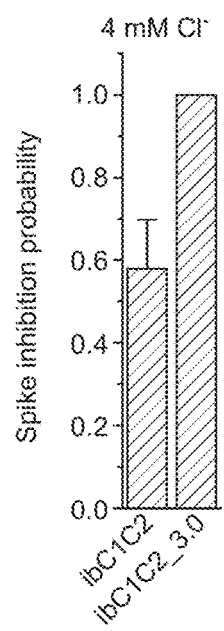
Figure 18C:
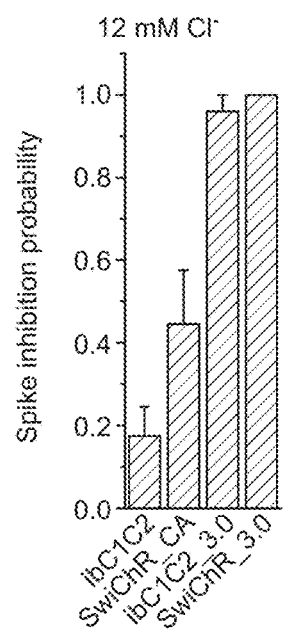
Figure 20:
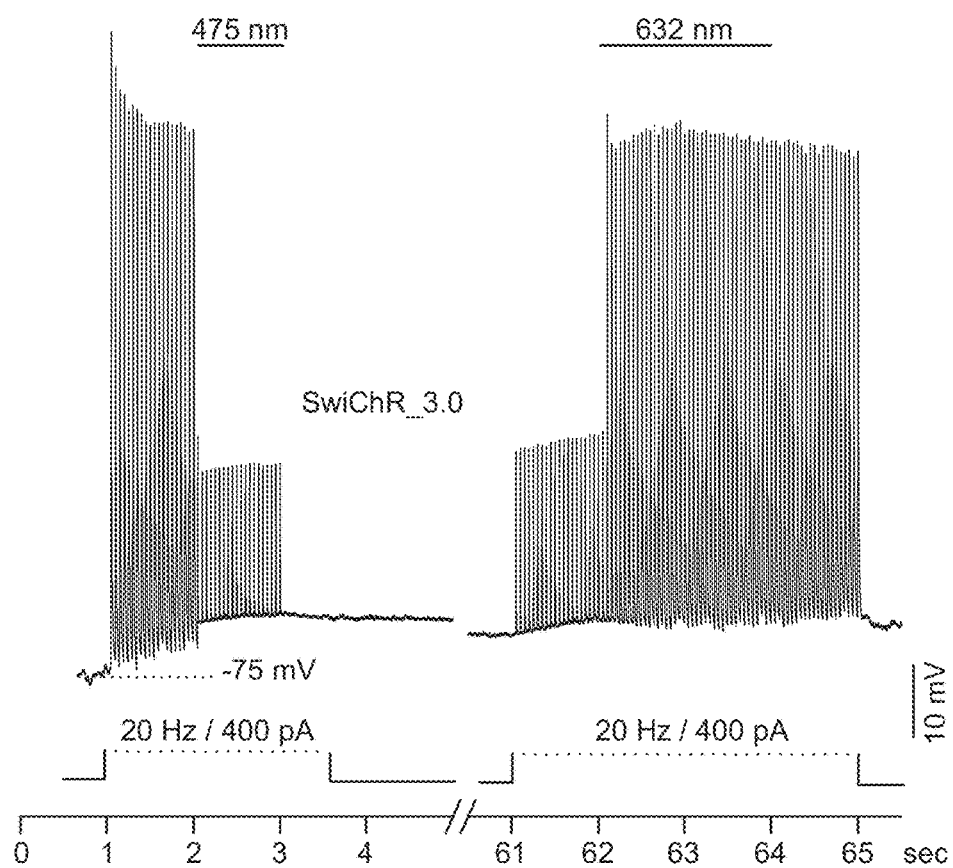
FIG. 20 shows a collection of graphs that demonstrate inhibition of a SwiChR_3.0 (SEQ ID NO: 108)-expressing neuron for 1 min at 12 mM internal chloride concentration.

Example 6: Expression of Light-Activated Anion Channel Proteins in Cultured Neurons ibC1C2_3.0 (SEQ ID NO: 96) and SwiChR_3.0 (SEQ ID NO: 108) constructs were tested in cultured neurons under physiological conditions with 4 mM and 12 mM internal chloride concentrations and compared to ibC1C2 (SEQ ID NO: 3) and SwiChR_CA (ibC1C2-C128A, SEQ ID NO: 15). At 4 mM internal chloride the reversal potential of ibC1C2_3.0 was −79 mV (±1 mV, standard error of the mean (s.e.m.)) compared to −64 mV (±2 mV, s.e.m.) for ibC1C2 (SEQ ID NO: 3) (FIG. 17A). This reflects an increased selectivity for chloride ions in ibC1C2_3.0 (SEQ ID NO: 96). Furthermore, the photocurrents at the threshold for action potential generation (VAP=−55 mV) are 408 pA (±60 pA, s.e.m.) for ibC1C2_3.0 (SEQ ID NO: 96) compared to 68 pA (±9 pA, s.e.m.) in ibC1C2 (SEQ ID NO: 3), which reflects an increased transport rate for chloride ions. At 12 mM internal chloride concentration the reversal potentials were −66 mV (±1 mV, s.e.m.) for ibC1C2_3.0 (SEQ ID NO: 96), −59 mV (±1 mV, s.e.m.) for ibC1C2 (SEQ ID NO: 3), −65 mV (±1 mV, s.e.m.) for SwiChR_3.0 (SEQ ID NO: 108) and −55 mV (±1 mV, s.e.m.) for SwiChR_CA (SEQ ID NO: 15) (FIG. 17B). The photocurrents at VAP were 171 pA (±31 pA, s.e.m.) for ibC1C2_3.0 (SEQ ID NO: 96), 23 pA (±4 pA, s.e.m.) for ibC1C2 (SEQ ID NO: 3), 91 pA (±14 pA, s.e.m.) for SwiChR_3.0 (SEQ ID NO: 108) and 21 pA for SwiChR_CA (SEQ ID NO: 15) (±7 pA, s.e.m.). Both measurements reflect that the improved constructs have a higher chloride selectivity and conductivity at high internal chloride concentrations. As a result, ibC1C2_3.0 (SEQ ID NO: 96) and SwiChR_3.0 (SEQ ID NO: 108) have a significantly higher probability to inhibit electrically evoked action potentials in neurons at low and high internal chloride concentrations. Cultured neurons were recorded in current clamp mode and action potentials were evoked by 30 ms long electrical pulses at 10 Hz for 6 seconds. 1 s after the start of the stimulation, blue light (475 nm, 5 mW/mm$^2$) was applied for 4 seconds (FIG. 18A). At 4 mM chloride concentration, ibC1C2_3.0 (SEQ ID NO: 96) inhibited 100% of all action potentials whereas ibC1C2 (SEQ ID NO: 3) inhibited 58% (±12%, s.e.m.) (FIG. 18B). At 12 mM internal chloride the inhibition probability was 96% (±4%, s.e.m.) for ibC1C2_3.0 (SEQ ID NO: 96), 18% (±7%, s.e.m.) for ibC1C2 (SEQ ID NO: 3), 100% for SwiChR_3.0 (SEQ ID NO: 108) and 45% for SwiChR_CA (SEQ ID NO: 15) (±13%, s.e.m.) (FIG. 18C). To demonstrate the capabilities of the improved constructs, even stronger inhibition protocols were applied. For example, ibC1C2_3.0 (SEQ ID NO: 96)-expressing cultured neurons were stimulated for 12 seconds at 20 Hz with 2 ms long electrical pulses to evoke action potentials (FIG. 19A). Blue light was applied for 10 s to inhibit spiking. At 12 mM chloride, the inhibition probability was 86% (±13%, s.e.m.) (FIG. 19C). Constructs which contain mutations at position 128, such as SwiChR_CA (SEQ ID NO: 15) and SwiChR_3.0 (SEQ ID NO: 108) have a decelerated channel closure, i.e., the channel pore stays open and conducts chloride ions for an extended period of time after blue light excitation has stopped. The channel can be immediately closed by the application of red light (>600 nm). This allows for extended inhibition of neuronal activities upon brief blue light applications, which can be immediately recovered by red light pulses. This feature was demonstrated by inhibiting electrically evoked action potentials for up to 1 minute between the blue and red light pulses in cultured neurons at 12 mM internal chloride (FIG. 18B-18C, FIG. 19, FIG. 20).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A light-activated polypeptide comprising an amino acid sequence that is at least 95% identical to SEQ ID NO:1, wherein the polypeptide functions as a light-activated anion channel, wherein the polypeptide comprises 1, 2, 3, 4, 5, 6, 7, 8, or 9 amino acid substitutions selected from the group consisting of T98S, E129S, E140S, E162S, V156K, H173R, T285N, V281K and N297Q, relative to the amino acid sequence of C1C2 (SEQ ID NO:78).

2. The polypeptide of claim 1, wherein the polypeptide comprises an amino acid sequence having at least 98% amino acid sequence identity to the amino acid sequence set forth in SEQ ID NO:1.

3. The polypeptide of claim 1, comprising an endoplasmic reticulum (ER) export polypeptide.

4. The polypeptide of claim 3, wherein the ER export polypeptide comprises the amino acid sequence FXYENE (SEQ ID NO:92), where X is any amino acid.

5. The polypeptide of claim 1, comprising a membrane trafficking polypeptide.

6. The polypeptide of claim 5, wherein the membrane trafficking polypeptide comprises the amino acid sequence KSRITSEGEYIPLDQIDINV (SEQ ID NO:83).

7. The light-activated polypeptide of claim 1, wherein the polypeptide further comprises a C167T, C167A, or C167S substitution, relative to the amino acid sequence of C1C2 (SEQ ID NO:78).

8. The light-activated polypeptide of claim 1, wherein the polypeptide further comprises a D195A or a D195N substitution, relative to the amino acid sequence of C1C2 (SEQ ID NO:78).

9. The light-activated polypeptide of claim 1, wherein the polypeptide comprises T98S, E129S, E140S, E162S, and T285N substitutions, relative to the amino acid sequence of C1C2 (SEQ ID NO:78).

10. The light-activated polypeptide of claim 1, wherein the polypeptide comprises V156K, H173R, V281K and N297Q substitutions, relative to the amino acid sequence of C1C2 (SEQ ID NO:78).

11. The light-activated polypeptide of claim 1, wherein the polypeptide comprises T98S, E129S, E140S, E162S, V156K, H173R, T285N, V281K and N297Q substitutions, relative to the amino acid sequence of C1C2 (SEQ ID NO:78).

12. The light-activated polypeptide of claim 11, wherein the polypeptide further comprises a C167T substitution, relative to the amino acid sequence of C1C2 (SEQ ID NO:78).

13. The light-activated polypeptide of claim 11, wherein the polypeptide further comprises a C167A substitution, relative to the amino acid sequence of C1C2 (SEQ ID NO:78).

14. The light-activated polypeptide of claim 1, wherein the first 50 N-terminal amino acid residues are replaced by a peptide having the amino acid sequence MDYGGAL-SAVG (SEQ ID NO:82), relative to the amino acid sequence of C1C2 (SEQ ID NO:78).

15. A nucleic acid comprising a nucleotide sequence encoding a light-activated polypeptide comprising an amino acid sequence that is at least 95% identical to SEQ ID NO:1, wherein the polypeptide functions as a light-activated anion channel, wherein the polypeptide comprises 1, 2, 3, 4, 5, 6, 7, 8, or 9 amino acid substitutions selected from the group consisting of T98S, E129S, E140S, E162S, V156K, H173R, T285N, V281K and N297Q, relative to the amino acid sequence of C1C2 (SEQ ID NO:78).

16. A recombinant expression vector comprising the nucleic acid of claim 15.

17. A pharmaceutical composition comprising:
a) the recombinant expression vector of claim 16; and
b) a pharmaceutically acceptable carrier.

18. A cell comprising the nucleic acid of claim 15.

19. A cell comprising the recombinant expression vector of claim 16.

20. A system for modulating the membrane potential of a cell, the system comprising:
a) the recombinant vector of claim 16; and
b) a device configured to illuminate a target location with light.

21. The system of claim 20, wherein the device is configured to illuminate the target location with light having a wavelength ranging from about 350 nm to about 750 nm, or from about 450 nm to about 500 nm.

22. The system of claim 20, wherein the device is configured to:
a) constantly illuminate the target location with light;
b) illuminate the target location with pulses of light;
c) modulate the wavelength and/or the intensity of the light;
d) modulate the frequency and/or the duration of the pulses of light; or
e) illuminate the target location in response to a user input.

23. The system of claim 20, wherein the device is configured to illuminate the target location in response to a user input, and wherein the user input comprises: the wavelength of light, the intensity of light, the duration of a light pulse, the frequency of a light pulse, and/or the target location.

24. The system of claim 20, wherein the device is adapted to be implanted in a subject.

25. The system of claim 20, wherein the target location is: a cell, a portion of a cell, a plurality of cells, a bundle of nerve fibers, a neuromuscular junction, a central nervous system (CNS) tissue, a peripheral nervous system (PNS) tissue, or an anatomical region.

26. A method for modulating the membrane potential of a cell in response to light, the method comprising exposing a cell to light of an activating wavelength, wherein the cell is genetically modified with the recombinant vector of claim 16.

27. The method of claim 26, wherein the cell is a neuron.

* * * * *